(12) United States Patent
Davis et al.

(10) Patent No.: US 6,265,564 B1
(45) Date of Patent: *Jul. 24, 2001

(54) EXPRESSED LIGAND-VASCULAR INTERCELLULAR SIGNALLING MOLECULE

(75) Inventors: Samuel Davis, New York; George D. Yancopoulos, Yorktown Heights, both of NY (US)

(73) Assignee: Regeneron Pharmaceuticals, Inc., Tarrytown, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/740,223

(22) Filed: Oct. 25, 1996

Related U.S. Application Data

(60) Provisional application No. 60/022,999, filed on Aug. 2, 1996.

(51) Int. Cl.[7] .................................................. C07H 21/04
(52) U.S. Cl. ............................................................ 536/23.5
(58) Field of Search ................................ 536/23.1, 23.2, 536/23.5

(56) References Cited

U.S. PATENT DOCUMENTS 5,070,192 * 12/1991 Earnshaw et al. .

FOREIGN PATENT DOCUMENTS

WO 9611269 * 4/1996 (WO) .

OTHER PUBLICATIONS

Rudinger, J. in Peptide Hormones, Parson, J. A. (Ed.), University Park Press, Baltimore, MD, pp. 1–7, 1976.*

Zhou et al. PNAS 95(5):2492–7, 1998.*

* cited by examiner

Primary Examiner—David Saunders
Assistant Examiner—Amy DeCloux
(74) Attorney, Agent, or Firm—Robert J. Cobert; Linda O. Palladino

(57) ABSTRACT

The present invention provides for a modified TIE-2 ligand which has been altered by addition, deletion or substitution of one or more amino acids, or by way of tagging, with for example, the Fc portion of human IgG-1, but which retains its ability to bind the TIE-2 receptor. The invention further provides for a modified TIE-2 ligand which is a chimeric TIE-2 ligand comprising at least a portion of a first TIE-2 ligand and a portion of a second TIE-2 ligand which is different from the first. In a specific embodiment, the invention further provides for a chimeric TIE ligand comprising at least a portion of TIE-2 Ligand-1 and a portion of TIE-2 Ligand-2. In addition the present invention provides for isolated nucleic acid molecule encoding the modified TIE-2 ligands described. The invention also provides for therapeutic compositions as well as a method of blocking blood vessel growth, a method of promoting neovascularization, a method of promoting the growth or differentiation of a cell expressing the TIE receptor, a method of blocking the growth or differentiation of a cell expressing the TIE receptor and a method of attenuating or preventing tumor growth in a human.

8 Claims, 47 Drawing Sheets r EHK-1 ecto/h IgG1 Fc
Gelfoam (6ug)

r TIE-2 ecto/h IgG1 Fc
Gelfoam (6ug)

Fig. 4A

```
         10              20              30              40              50              60              70              80
          .               .               .               .               .               .               .               .
CAGCTGACTCAGGCAGGCTCCATCGTGAACGGTCACACAGAGAGAAACATAAATCTCAGCTACTATGCAATAAATATC 90             100             110             120             130             140             150             160
          .               .               .               .               .               .               .               .
TCAAGTTTTAACGANGAAAAACATCATTGCAGTGAAATAAAATTTTAAAATTTTAGAACAAGCTAACAAATGGCTAG 170             180             190             200             210             220             230             240
          .               .               .               .               .               .               .               .
TTTTCTATGATTCTCTTCAAACGCTTTCTTTGAGGGGGAAAGAGTAGTCAAACAAACAGCAGTTTTACCTGAAATAAAGAA 250             260             270             280             290             300             310
          .               .               .               .               .               .               .
CTAGTTTTAGAGGTCAAGAAGAAGGAGCAAGTTTTGCAGAGGCACGGAGAGGAGTGCTGGCAGTACA ATG ACA
                                                                           M   T >

320             330             340             350             360             370
          .               .               .               .               .               .
GTT TTC CTT TCC TTT GCT TTC CTC GCT GCC ATT CTG ACT CAC ATA GGG TGC AGC AAT CAG
 V   F   L   S   F   A   F   L   A   A   I   L   T   H   I   G   C   S   N   Q >

380             390             400             410             420             430
          .               .               .               .               .               .
CGC CGA AGT CCA GAA AAC AGT GGG AGA AGA TAT AAC CGG ATT CAA CAT GGG CAA TGT GCC
 R   R   S   P   E   N   S   G   R   R   Y   N   R   I   Q   H   G   Q   C   A >

440             450             460             470             480             490
          .               .               .               .               .               .
TAC ACT TTC ATT CTT CCA GAA CAC GAT GGC AAC TGT CGT GAG AGT ACG ACA GAC CAG TAC
 Y   T   F   I   L   P   E   H   D   G   N   C   R   E   S   T   T   D   Q   Y >

500             510             520             530             540             550
          .               .               .               .               .               .
AAC ACA AAC GCT CTG CAG AGA GAT GCT CCA CAC GTG GAA CCG GAT TTC TCT TCC CAG AAA
 N   T   N   A   L   Q   R   D   A   P   H   V   E   P   D   F   S   S   Q   K >
```

Fig. 4B

```
    560             570             580             590             600             610
     .               .               .               .               .               .
CTT CAA CAT CTG GAA CAT GTG ATG GAA AAT TAT ACT CAG TGG CTG CAA AAA CTT GAG AAT
 L   Q   H   L   E   H   V   M   E   N   Y   T   Q   W   L   Q   K   L   E   N>

620             630             640             650             660             670
     .               .               .               .               .               .
TAC ATT GTG GAA AAC ATG AAG TCG GAG ATG GCC CAG ATA CAG CAG AAT GCA GTT CAG AAC
 Y   I   V   E   N   M   K   S   E   M   A   Q   I   Q   Q   N   A   V   Q   N>

680             690             700             710             720             730
     .               .               .               .               .               .
CAC ACG GCT ACC ATG CTG GAG ATA GGA ACC AGC CTC CTC TCT CAG ACT GCA GAG CAG ACC
 H   T   A   T   M   L   E   I   G   T   S   L   L   S   Q   T   A   E   Q   T>

740             750             760             770             780             790
     .               .               .               .               .               .
AGA AAG CTG ACA GAT GTT TCA AAT CAC CAG GTA CTA ACT TCT CGA CTT GAG ATA CAG
 R   K   L   T   D   V   S   N   T   Q   V   L   N   T   S   R   L   E   I   Q>

800             810             820             830             840             850
     .               .               .               .               .               .
CTG CTG GAG AAT TCA TTA TCC ACC TAC AAG CTA GAG AAG CAA CTT CAA CAG ACA AAT
 L   L   E   N   S   L   S   T   Y   K   L   E   K   Q   L   Q   Q   T   N>

860             870             880             890             900             910
     .               .               .               .               .               .
GAA ATC TTG AAG ATC CAT GAA AAA AAC AGT TTA TTA GAA CAT AAA ATC TTA GAA ATG GAA
 E   I   L   K   I   H   E   K   N   S   L   L   E   H   K   I   L   E   M   E>

920             930             940             950             960             970
     .               .               .               .               .               .
GGA AAA CAC AAG GAA GAG TTG GAC ACC TTA AAG GAA GAG AAA CTT CAA GGC TTG
 G   K   H   K   E   E   L   D   T   L   K   E   E   K   E   N   L   Q   G   L>

980             990            1000            1010            1020            1030
     .               .               .               .               .               .
GAA ATC CGT CAA ACA TAT ATA ATC CAG GAG CTG GAA AAG CAA TTA AAC AGA GCT ACC
 V   T   R   Q   T   Y   I   I   Q   E   L   E   K   Q   L   N   R   A   T>

1040            1050            1060            1070            1080            1090
     .               .               .               .               .               .
AAC AAC AGT GTC CTT CAG AAG CAG CAA CTG GAG CTG ATG GAC ACA GTC CAC AAC CTT GTC
 N   N   S   V   L   Q   K   Q   Q   L   E   L   M   D   T   V   H   N   L   V>
```

Fig. 4 C

```
      1100                  1110                  1120                  1130                  1140                  1150
       •                     •                     •                     •                     •                     •
AAT   CTT   TGC   ACT   AAA   GAA   GGT   GTT   TTA   CTA   AAG   GGA   GGA   AAA   AGA   GAG   GAG   AAA   CCA
 N     L     C     T     K     E     G     V     L     L     K     G     G     K     R     E     E     K     P 1160                  1170                  1180                  1190                  1200                  1210
       •                     •                     •                     •                     •                     •
TTT   AGA   GAC   TGT   GCA   GAT   GTA   TAT   CAA   GCT   GGT   TTT   AAT   AAA   AGT   GGA   ATC   TAC   ACT   ATT
 F     R     D     C     A     D     V     Y     Q     A     G     F     N     K     S     G     I     Y     T     I 1220                  1230                  1240                  1250                  1260                  1270
       •                     •                     •                     •                     •                     •
TAT   ATT   AAT   AAT   ATG   CCA   GAA   CCC   AAA   AAG   GTG   TTT   TGC   AAT   ATG   GAT   GTC   AAT   GGG   GGA
 Y     I     N     N     M     P     E     P     K     K     V     F     C     N     M     D     V     N     G     G 1280                  1290                  1300                  1310                  1320                  1330
       •                     •                     •                     •                     •                     •
GGT   TGG   ACT   GTA   ATA   CAA   CAT   CGT   GAA   GAT   GGA   AGT   CTA   GAT   TTC   CAA   AGA   GGC   TGG   AAG
 G     W     T     V     I     Q     H     R     E     D     G     S     L     D     F     Q     R     G     W     K 1340                  1350                  1360                  1370                  1380                  1390
       •                     •                     •                     •                     •                     •
GAA   TAT   AAA   ATG   GGT   TTT   GGA   AAT   CCC   TCC   GGT   GAA   TAT   TGG   CTG   GGG   AAT   GAG   TTT   ATT
 E     Y     K     M     G     F     G     N     P     S     G     E     Y     W     L     G     N     E     F     I 1400                  1410                  1420                  1430                  1440                  1450
       •                     •                     •                     •                     •                     •
TTT   GCC   ATT   ACC   AGT   CAG   AGG   CAG   TAC   ATG   CTA   AGA   ATT   GAG   TTA   ATG   GAC   TGG   GAA   GGG
 F     A     I     T     S     Q     R     Q     Y     M     L     R     I     E     L     M     D     W     E     G 1460                  1470                  1480                  1490                  1500                  1510
       •                     •                     •                     •                     •                     •
AAC   CGA   GCC   TAT   TCA   CAG   TAT   GAC   AGA   TTC   CAC   ATA   GGA   AAT   GAA   AAG   CAA   AAC   TAT   AGG
 N     R     A     Y     S     Q     Y     D     R     F     H     I     G     N     E     K     Q     N     Y     R
```

Fig. 4D

```
     1580          1590          1600          1610          1620          1630
       .             .             .             .             .             .
     GCT GAT TTC AGC ACT AAA GAT GCT GAT AAT GAC AAC TGT ATG TCC AAA TGT GCC CTC ATG
      A   D   F   S   T   K   D   A   D   N   D   N   C   M   S   K   C   A   L   M 1640          1650          1660          1670          1680          1690
       .             .             .             .             .             .
     TTA ACA GGA GGA TGG TGG TTT GAT GCT TGT GGC CCC TCC AAT CTA AAT GGA ATG TTC TAT
      L   T   G   G   W   W   F   D   A   C   G   P   S   N   L   N   G   M   F   Y 1700          1710          1720          1730          1740          1750
       .             .             .             .             .             .
     ACT GCG GGA CAA AAC CAT GGA AAA CTG AAT GGG ATA AAG TGG CAC TAC TTC AAA GGG CCC
      T   A   G   Q   N   H   G   K   L   N   G   I   K   W   H   Y   F   K   G   P 1760          1770          1780          1790          1800          1810
       .             .             .             .             .             .
     AGT TAC TCC TTA CGT TCC ACA ACT ATG ATT CGA CCT TTA GAT TTT TGA AAG CGCAATGT
      S   Y   S   L   R   S   T   T   M   I   R   P   L   D   F   *

1820          1830          1840          1850          1860          1870          1880          1890
       .             .             .             .             .             .             .             .
     CAGAAGCGATTATGAAAGAACAAAGAAATCCGGAGAAGCTGCCAGGTGAGAAGCTGTTTGAAAACTCAGAAGCAAACA 1900          1910          1920          1930          1940          1950          1960          1970
       .             .             .             .             .             .             .             .
     ATATTGTCTCCCTTCAGCAATAGTGGTAGTTATGTGAAGTCACCAAGGTTCTTGACCGTGAATCTGGAGCCGTTTGAG 1980          1990          2000          2010          2020          2030          2040          2050
       .             .             .             .             .             .             .             .
     TTCAAGAGTCTCTACTTGGGGTGACAGTGCCTCAGTGCTCGACTATGAAAAACTCCACTGTGCGGCTTTAAAA 2060          2070          2080          2090          2100          2110          2120          2130
       .             .             .             .             .             .             .             .
     AGGGAAGAAACTGCTGAGCTTGCTGTGTTCAAACTACTACTGGACCTTATTTTGGAACTATGGTAGCCAGATGATAAAT

2140
       .
     ATGGTAATTTC
```

Fig. 5A

```
         10         20         30         40         50         60         70         80
          •          •          •          •          •          •          •          •
CAGTGACTCGAGGCAGGCTCCATGCTGAACGGTCCACACAGAGAGGAACAATAAATCTCAGTACTACTATCCAATAAATATC 90        100        110        120        130        140        150        160
          •          •          •          •          •          •          •          •
TCAAGTTTTAACGAAGAAAACATCATTGCAGTGAAATAAAAATTTAAATTTAGAACAAAGCTAACAAATGGCTAG 170        180        190        200        210        220        230        240
          •          •          •          •          •          •          •          •
TTTTCTATGATTCTTCTCAAACGCTTCTTTGAGGGGAAAGAGTCAAACAACAAGCAGTTTTACCTGAAATAAGAA 250        260        270        280        290        300        310
          •          •          •          •          •          •          •
CTAGTTTTAGAGTCAGAAGAAGGACCAAGTTTTGCGAGGCACGGAAGGAGTGCTGGCCAGTACA ATG ACA
                                                                   M   T >

320        330        340        350        360        370
          •          •          •          •          •          •
GTT TTC CTT TCC TTT GCT TTC CTC GCC ATT CTG ACT CAC ATA GGG TGC AGC AAT CAG
 V   F   L   S   F   A   F   L   A   I   L   T   H   I   G   C   S   N   Q >

380        390        400        410        420        430
          •          •          •          •          •          •
CGC CGA AGT CCA GAA AAC AGT GGG AGA AGA TAT AAC CGG ATT CAA CAT GGG CAA TGT GCC
 R   R   S   P   E   N   S   G   R   R   Y   N   R   I   Q   H   G   Q   C   A >

440        450        460        470        480        490
          •          •          •          •          •          •
TAC ACT TTC ATT CCA GAA CAC GAT GGC AAC TGT CCT GAG AGT ACG ACA GAC CAG TAC
 Y   T   F   I   L   P   E   H   D   G   N   C   R   E   S   T   T   D   Q   Y >

500        510        520        530        540        550
          •          •          •          •          •          •
AAC ACA AAC GCT CTG CAG AGA GAT GCT CCA CAC GTG GAA CCG GAT TTC TCT TCC CAG AAA
 N   T   N   A   L   Q   R   D   A   P   H   V   E   P   D   F   S   S   Q   K >
```

Fig. 5B

```
560            570            580            590            600            610
 .              .              .              .              .              .
CTT CAA CAT CTG GAA CAT GTG ATG GAA AAT TAT ACT CAG TGG CTG CAA AAA CTT GAG AAT
 L   Q   H   L   E   H   V   M   E   N   Y   T   Q   W   L   Q   K   L   E   N 620            630            640            650            660            670
 .              .              .              .              .              .
TAC ATT GTG GAA AAC ATG AAG TCG GAG ATG GCC CAG ATA CAG CAG CAG AAT GCA GTT CAG AAC
 Y   I   V   E   N   M   K   S   E   M   A   Q   I   Q   Q   Q   N   A   V   Q   N 680            690            700            710            720            730
 .              .              .              .              .              .
CAC ACG GCT ACC ATG CTG GAG ATA GGA ACC CTC TCT CAG ACT GCA GAG GAG ACC
 H   T   A   T   M   L   E   I   G   T   L   S   Q   T   A   E   E   T 740            750            760            770            780            790
 .              .              .              .              .              .
AGA AAG CTG ACA GAT GTT GAG ACC TAC AAG CTA CTA AAT CAA ACT CAG CTT GAG ATA CAG
 R   K   L   T   D   V   E   T   Y   K   L   L   N   Q   T   Q   L   E   I   Q 800            810            820            830            840            850
 .              .              .              .              .              .
CTG CTG GAG AAT TCA TTA TCC ACC TAC AAA CTA GAG AAG CAA CTT CTT CGA CAG ACA AAT
 L   L   E   N   S   L   S   T   Y   K   L   E   K   Q   L   L   R   Q   T   N 860            870            880            890            900            910
 .              .              .              .              .              .
GAA ATC TTG AAG ATC CAT GAA AAA AAC AGT TTA GAA CAT CTT AAA ATC TTA GAA ATG GAA
 E   I   L   K   I   H   E   K   N   S   L   E   H   L   K   I   L   E   M   E 920            930            940            950            960            970
 .              .              .              .              .              .
GGA AAA CAC AAG GAA GAG TTG GAC ACC TTA AAG GAG GAG AAG GAA AAC CTT CAA GGC TTG
 G   K   H   K   E   E   L   D   T   L   K   E   E   K   E   N   L   Q   G   L 980            990            1000           1010           1020           1030
 .              .              .              .              .              .
GTT ACT CGT CAA ACA TAT ATA ATC CAG GAG CTG GAA AAG CAA TTA AAC AGA GCT ACC ACC
 V   T   R   Q   T   Y   I   I   Q   E   L   E   K   Q   L   N   R   A   T   T 1040           1050           1060           1070           1080           1090
 .              .              .              .              .              .
AAC AAC AGT GTC CTT CAG AAG CAG CAA CTG GAG CTG ATG ATC ACA GTC CAC AAC CTT GTC
 N   N   S   V   L   Q   K   Q   Q   L   E   L   M   I   T   V   H   N   L   V
```

Fig. 5C

```
      1580         1590         1600         1610         1620         1630
       .            .            .            .            .            .
GAT TTC AGC ACT AAA CAT GCT GAT AAT GAC AAC TGT ATG TGC AAA TGT GCC CTC ATG TTA
 D   F   S   T   K   H   A   D   N   D   N   C   M   C   K   C   A   L   M   L >

1640         1650         1660         1670         1680         1690
       .            .            .            .            .            .
ACA GGA GGA TGG TGG TTT GAT GCT TGT GGC CCC TCC AAT CTA AAT GGA ATG TTC TAT ACT
 T   G   G   W   W   F   D   A   C   G   P   S   N   L   N   G   M   F   Y   T >

1700         1710         1720         1730         1740         1750
       .            .            .            .            .            .
GCG GGA CAA AAC CAT GGA AAA CTG AAT GGG ATA AAG TGG CAC TAC TTC AAA GGG CCC AGT
 A   G   Q   N   H   G   K   L   N   G   I   K   W   H   Y   F   K   G   P   S >

1760         1770         1780         1790         1800         1810
       .            .            .            .            .            .
TAC TCC TTA CGT TCC ACA ACT ATG ATG ATT CGA CCT TTA GAT TTT TGA AAGGGCAATGTCAGAA
 Y   S   L   R   S   T   T   M   M   I   R   P   L   D   F   * >

1820         1830         1840         1850         1860         1870         1880         1890
       .            .            .            .            .            .            .            .
CCGATTATGAAAGCAACAAAGAAATCCGAGAAGCTGCCAGGTCAGAAACTGTTTGAAAACTTCAGAAGCAAACAATATT 1900         1910         1920         1930         1940         1950         1960         1970
       .            .            .            .            .            .            .            .
GTCTCCCTTCCAGCAATAAGTGTAGTTATGTGAAGTCACCAAGGTTCTTGACCGTGAATCTGGAGCCGTTTGAGTTCAC 1980         1990         2000         2010         2020         2030         2040         2050
       .            .            .            .            .            .            .            .
AAGAGTCTCTACTTGGGGTGACAGTGCCTCGACTATAGAAAACTCCACTTGACTGTCGGGCTTTAAAAGGGA 2060         2070         2080         2090         2100         2110         2120         2130
       .            .            .            .            .            .            .            .
AGAAACTGCTGAGCTTGCTGTGCTTCAAACTACTACTGGACCTTATTTTGGAACTATGCTAGCCAGATGATAAATATCGT

2140
       .
TAATTTC
```

Fig. 5D

```
         1100        1110        1120        1130        1140        1150
          .           .           .           .           .           .
     AAT CTT TGC ACT AAA GAA GTT TTA CTA AAG GGA GGA AAA AGA GAG GAA GAG AAA CCA TTT
      N   L   C   T   K   E   V   L   L   K   G   G   K   R   E   E   E   K   P   F 1160        1170        1180        1190        1200        1210
          .           .           .           .           .           .
     AGA GAC TGT GCA GAT GTA TAT CAA GCT GGT TTT AAT AGT GGA ATC TAC ACT ATT TAT
      R   D   C   A   D   V   Y   Q   A   G   F   N   S   G   I   Y   T   I   Y 1220        1230        1240        1250        1260        1270
          .           .           .           .           .           .
     ATT AAT AAT ATG CCA GAA CCC AAA AAG GTG TTT TGC AAT ATG GAT GTC AAT GGG GGA GGT
      I   N   N   M   P   E   P   K   K   V   F   C   N   M   D   V   N   G   G   G 1280        1290        1300        1310        1320        1330
          .           .           .           .           .           .
     TGG ACT GTA ATA CAT CGT GAA GAT GGA AGT CTA GAT TTC CAA AGA GGC TGG AAG GAA
      W   T   V   I   H   R   E   D   G   S   L   D   F   Q   R   G   W   K   E 1340        1350        1360        1370        1380        1390
          .           .           .           .           .           .
     TAT AAA ATG GGT TTT GGA AAT CCC TCC GGT GAA TAT TGG CTG GGG AAT GAG TTT ATT TTT
      Y   K   M   G   F   G   N   P   S   G   E   Y   W   L   G   N   E   F   I   F 1400        1410        1420        1430        1440        1450
          .           .           .           .           .           .
     GCC ATT ACC AGT CAG AGG CAG TAC ATG CTA AGA ATT GAG TTA CAT GAC TGG GAA GGG AAC
      A   I   T   S   Q   R   Q   Y   M   L   R   I   E   L   H   D   W   E   G   N 1460        1470        1480        1490        1500        1510
          .           .           .           .           .           .
     CGA GCC TAT TCA CAG TAT GAC AGA TTC CAC ATA GGA AAT GAA AAG CAA AAC TAT AGG TTG
      R   A   Y   S   Q   Y   D   R   F   H   I   G   N   E   K   Q   N   Y   R   L 1520        1530        1540        1550        1560        1570
          .           .           .           .           .           .
     TAT TTA AAA GGT CAC ACT GGG ACA GCA GGA AAA CAG AGC CTG ATC TTA CAC GGT GCT
      Y   L   K   G   H   T   G   T   A   G   K   Q   S   L   I   L   H   G   A
```

Fig. 6A

```
         10        20        30        40        50        60        70        80
         *         *         *         *         *         *         *         *
GAATTCCTGGGTTGGTTGTGTTTATCTCCCCCAGCCTTGAGGGAGGAGGAACAACACTGTAGGATCTGGGAGAGGAGGAACAAA 90       100       110       120       130       140       150       160
         *         *         *         *         *         *         *         *
GGACCGTGAAAGCTGCTCTGTAAAGCTGACACAGAGCCCTCCCAAGTGTCAGCAGGACTGTCTTCCCACTGAATCTGACAG 170       180       190       200       210       220       230       240
         *         *         *         *         *         *         *         *
TTTACTGCATGCCTGGAGAGAACACAGCAGTAAAAACCAGGTTTGCTACTGAAAAAGAGGAAAGAGAAGACTTTCATTG 250       260       270       280       290       300       310       320
         *         *         *         *         *         *         *         *
ACGGACCCCAGCCATGCAGCGTAGCAGCCCCTGCGTTTCAGACGGCAGCAGCTCGGGACTCTGGACGTGTGTTTGCCCTCA 330       340       350       360       370       380
         *         *         *         *         *         *
AGTTTGCTAAGCTGCCTGGTTATTACTGAAGAAAGA ATG TGG CAG ATT GTT TTC TTT ACT CTG AGC TGT
                                      M   W   Q   I   V   F   F   T   L   S   C>

390       400       410       420       430       440
         *         *         *         *         *         *
GAT CTT GTC TTG GCC GCA GCC TAT AAC AAC TTT CGG AAG AGC ATG GAC AGC ATA GGA AAG
 D   L   V   L   A   A   A   Y   N   N   F   R   K   S   M   D   S   I   G   K>

450       460       470       480       490       500
         *         *         *         *         *         *
AAG CAA TAT CAG GTC CAG CAT GGG TCC TGC AGC TAC ACT TTC CTC CTG CCA GAG ATG GAC
 K   Q   Y   Q   V   Q   H   G   S   C   S   Y   T   F   L   L   P   E   M   D>

510       520       530       540       550       560
         *         *         *         *         *         *
AAC TGC CGC TCT TCC TCC AGC CCC TAC GTG TCC AAT GCT GTG CAG AGG GAC GCG CCG CTC
 N   C   R   S   S   S   S   P   Y   V   S   N   A   V   Q   R   D   A   P   L>
```

Fig. 6B

```
570        580        590        600        610        620
  *          *          *          *          *          *
GAA TAC GAT GAC TCG GTG CAG AGG CTG CAA GTG CTG GAG AAC ATC ATG GAA AAC ACT
 E   Y   D   D   S   V   Q   R   L   Q   V   L   E   N   I   M   E   N   T >

630        640        650        660        670        680
  *          *          *          *          *          *
CAG TGG CTA ATG AAG CTT GAG AAT TAT ATC CAG GAC AAC ATG AAG AAA GAA ATG GTA GAG
 Q   W   L   M   K   L   E   N   Y   I   Q   D   N   M   K   K   E   M   V  E>

690        700        710        720        730        740
  *          *          *          *          *          *
ATA CAG CAG AAT GCA GTA CAG AAC CAG ACG GCT GTG ATG ATA GAA ATA GGG ACA AAC CTG
 I   Q   Q   N   A   V   Q   N   Q   T   A   V   M   I   E   I   G   T   N  L>

750        760        770        780        790        800
  *          *          *          *          *          *
TTG AAC ACA GCT GAG CAG CAA ACG CGG AAG TTA ACT GAT GTG GAA GCC CAA GTA TTA AAT
 L   N   T   A   E   Q   Q   T   R   K   L   T   D   V   E   A   Q   V   L  N>

810        820        830        840        850        860
  *          *          *          *          *          *
CAG ACC ACG AGA CTT GAA CTT CAG CTC TTG GAA CAC TCC CTC TCG ACA AAC AAA TTG GAA
 Q   T   T   R   L   E   L   Q   L   L   E   H   S   L   S   T   N   K   L  E>

870        880        890        900        910        920
  *          *          *          *          *          *
AAA CAG ATT TTG GAC CAG ACC AGT GAA ATA AAC AAG TTG CAA GAT AAG CTA CAG AGT TTC CTA
 K   Q   I   L   D   Q   T   S   E   I   N   K   L   Q   D   K   L   Q   S  F  L>

930        940        950        960        970        980
  *          *          *          *          *          *
GAA AAG AAG GTG CTA GCT ATG GAA GAC AAG CAC ATC ATC CAG CTA CAG TCA ATA AAA GAA
 E   K   K   V   L   A   M   E   D   K   H   I   I   Q   L   Q   S   I   K  E>

990        1000       1010       1020       1030       1040
  *          *          *          *          *          *
CAG AAA GAT CAG CTA CAG GTG CTT GTA TCC AAG CAA AAT TCC ATC ATT GAA GAA CTA GAA
 E   K   D   Q   L   Q   V   L   V   S   K   Q   N   S   I   I   E   E   L  E>

1050       1060       1070       1080       1090       1100
  *          *          *          *          *          *
AAA AAA ATA GTG ACT GCC ACG GTG AAT AAT TCA GTT CTT CAA AAG CAG CAA CAT GAT CTC
 K   K   I   V   T   A   T   V   N   N   S   V   L   Q   K   Q   Q   H   D  L>
```

Fig. 6C

```
1110                1120            1130            1140            1150            1160
ATG GAG ACA GTT AAT AAC TTA CTG ACT ATG TCC ACA AAC TCA AGC GCT AAG GAC CCC
 M   E   T   V   N   N   L   L   T   M   S   T   N   S   A   K   D   P>

1170                1180            1190            1200            1210            1220
ACT GTT GCT AAA GAA GAA CAA ATC AGC TTC AGA GAC TGT GCT GAA GTA TTC AAA TCA GGA
 T   V   A   K   E   E   Q   I   S   F   R   D   C   A   E   V   F   K   S   G>

1230                1240            1250            1260            1270            1280
CAC ACC ACA AAT GGC ATC TAC ACG TTA ACA TTC CCT AAT TCT ACA GAA GAG ATC AAG GCC
 H   T   T   N   G   I   Y   T   L   T   F   P   N   S   T   E   E   I   K   A>

1290                1300            1310            1320            1330            1340
TAC TGT GAC ATG GAA GCT GGA GGA GGG ACA ATT ATT CAG CGT GAG GAT GGC
 Y   C   D   M   E   A   G   G   G   T   I   I   Q   R   R   E   D   G>

1350                1360            1370            1380            1390            1400
AGC GTT GAT TTT CAG AGG ACT TGG AAA GAA TAT AAA GTG GGA TTT GGT AAC CCT TCA GGA
 S   V   D   F   Q   R   T   W   K   E   Y   K   V   G   F   G   N   P   S   G>

1410                1420            1430            1440            1450            1460
GAA TAT TGG CTG GGA AAT GAG TTT GTT TCG CAA CTG ACT AAT CAG CAA CGC TAT GTG CTT
 E   Y   W   L   G   N   E   F   V   S   Q   L   T   N   Q   Q   R   Y   V   L>

1470                1480            1490            1500            1510            1520
AAA ATA CAC CTT AAA GAC TGG GAA GGG AAT GAG GCT TAC TCA TTG TAT GAA CAT TTC TAT
 K   I   H   L   K   D   W   E   G   N   E   A   Y   S   L   Y   E   H   F   Y>

1530                1540            1550            1560            1570            1580
CTC TCA AGT GAA GAA CTC AAT TAT AGG ATT CAC CTT AAA GGA CTT ACA GGG ACA GCC GGC
 L   S   S   E   E   L   N   Y   R   I   H   L   K   G   L   T   G   T   A   G>
```

Fig. 6D

```
1590        1600        1610        1620        1630        1640
  .           .           .           .           .           .
AAA ATA AGC AGC ATC AGC CAA CCA GGA AAT GAT TTT AGC ACA AAG GAT GGA GAC AAC GAC
 K   I   S   S   I   S   Q   P   G   N   D   F   S   T   K   D   G   D   N   D>

1650        1660        1670        1680        1690        1700
  .           .           .           .           .           .
AAA TGT ATT TGC AAA TGT TCA CAA ATG CTA ACA GGA GGC TGG TGG TTT GAT GCA TGT GGT
 K   C   I   C   K   C   S   Q   M   L   T   G   G   W   W   F   D   A   C   G>

1710        1720        1730        1740        1750        1760
  .           .           .           .           .           .
CCT TCC AAC TTG AAC GGA ATG TAC TAT CCA CAG AGG CAG AAC ACA AAT AAG TTC AAC GGC
 P   S   N   L   N   G   M   Y   Y   P   Q   R   Q   N   T   N   K   F   N   G>

1770        1780        1790        1800        1810        1820
  .           .           .           .           .           .
ATT AAA TGG TAC TAC TGG AAA GGC TCA GGC TAT TCG CTC AAG GCC ACA ACC ATG ATG ATC
 I   K   W   Y   Y   W   K   G   S   G   Y   S   L   K   A   T   T   M   M   I>

1830        1840        1850        1860        1870        1880        1890        1900
  .           .           .           .           .           .           .           .
CGA CCA GCA GAT TTC TAAACATCCAGTCCACTGAGGAACTGTCTCAACTATTTTCAAAGACTTAAGCCCAGT
 R   P   A   D   F  *>

1910        1920        1930        1940        1950        1960        1970        1980
          .           .           .           .           .           .           .           .
GCACTGAAAGTCACGGCTGCGCACTGTCCTCTTCCACCACAGAGGGGTGTGCTCGGTGCTCGGTGACGGGACCACATGCT 1990        2000        2010        2020        2030        2040        2050        2060
          .           .           .           .           .           .           .           .
CCAGATTAGAGACAGAACACCTATGCAAAGATGAACCCGAGGCTGAGAATCAGACTGACAGTTTACAGACGCTAAACATCCATAATT 2070        2080        2090        2100        2110        2120        2130        2140
          .           .           .           .           .           .           .           .
GTGATTAGAGACAGAACACCTATGCAAAGATGAACCCGAGGCTGAGAATCAGACTGACAGTTTACAGACGCTGCTGTCACA 2150        2160        2170        2180        2190        2200        2210        2220
          .           .           .           .           .           .           .           .
CCAAGAATGTTATGTGCAAGTTTATCAGTAAATAACTGAAAACAGAAACACTTATGTTATACAATACAGATCATCTTGA 2230        2240        2250        2260        2270        2280
          .           .           .           .           .           .
ACTGCATTCTTCTGAGCACTGTTTATACACTGTGTAATACCCATATGTCCTGAATTC
```

Fig. 10
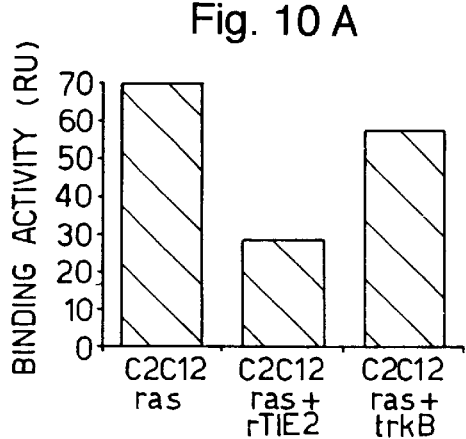
Fig. 10 A
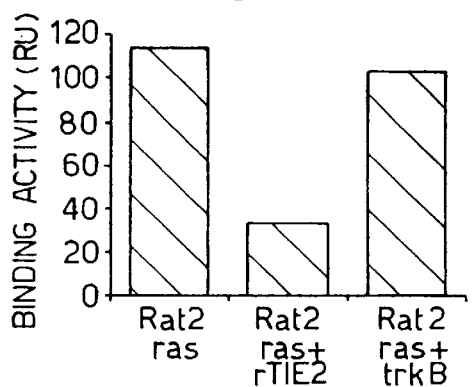
Fig. 10 B
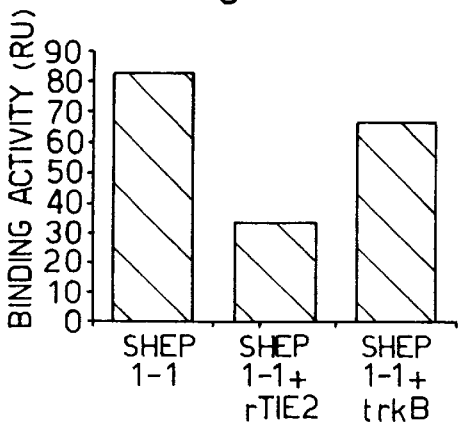
Fig. 10 C
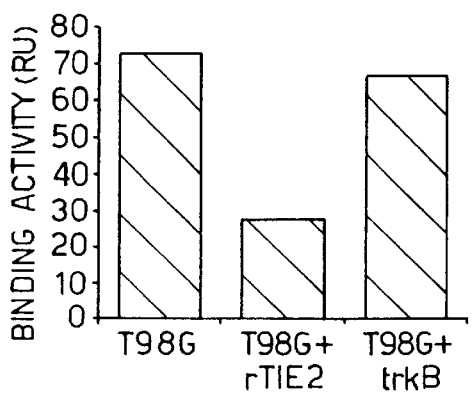
Fig. 10 D Fetal Thymus E17.5

CDR1+ : Cortical stromal cells

A2B5+ : Medulla stromal cells

Fig. 21A

```
        10         20         30         40         50         60         70         80         90
         *          *          *          *          *          *          *          *          *
CTGTCCTGGT ACCTGACAAG ACCACCTCAC CACCACTTGG TCTCAG ATG CTC TGC CAG CCA GCT ATG CTA CTA GAT GGC CTC CTC CTG
                                                        M   L   C   Q   P   A   M   L   L   D   G   L   L   L  L>

100        110        120        130        140        150        160        170
         *          *          *          *          *          *          *          *
GCC ACC ATG GCT GCA GCC CAG CAC AGA GGG CCA GAA GCC GGT GGG CAC CGC CAG ATT CAC CAG GTC CGG GGC CAG TGC AGC
 A   T   M   A   A   A   Q   H   R   G   P   E   A   G   G   H   R   Q   I   H   Q   V   R   G   Q   C   S>

180        190        200        210        220        230        240        250
         *          *          *          *          *          *          *          *
TAC ACC TTT GTG GTG CCG GAG CCT GAT ATC TGC CAG CTG CCG GCG ACA GCG GCG CCT GAG GCT TTG GGG GGC TCC AAT AGC CTC
 Y   T   F   V   V   P   E   P   D   I   C   Q   L   P   A   T   A   A   P   E   A   L   G   G   S   N   S  L>

260        270        280        290        300        310        320        330        340
 *          *          *          *          *          *          *          *          *
CAG AGG GAC TTG CCT GCC TCG AGG CTG CAC CTA ACA GAC TGG CGA AGG GCG CCT GAG TCC ATC AAG GTG TCA CTG GTG CAG
 Q   R   D   L   P   A   S   R   L   H   L   T   D   W   R   R   A   P   E   S   I   K   V   S   L   V  Q>

350        360        370        380        390        400        410        420
 *          *          *          *          *          *          *          *
GAG AAG ATA CTA GAG AAT ACT CAG TGG CTG CTG AAG CTG GAG CAG TCC ATC AAG GTG TTG AAC CAC CAG CTG CAG
 E   K   I   L   E   N   T   Q   W   L   L   K   L   E   Q   S   I   K   V   L   N   H   Q   L   V  Q>

430        440        450        460        470        480        490        500        510
 *          *          *          *          *          *          *          *          *
GCC CAG CAG GAC ACA ATC CAG AAC CAG ATG CTG GCA CTG CTG GGA GCT AAC CTC ATG CAA AAT CTG CAT CAC AAA GCT CAG ACC
 A   Q   Q   D   T   I   Q   N   Q   M   L   A   L   L   G   A   N   L   M   Q   N   L   H   H   K   A   Q  T>

520        530        540        550        560        570        580        590
 *          *          *          *          *          *          *          *
CAC AAG CTG ACT GCT GTG GAG GCA CAG CAG AGC AAG ATG CTG AAC CAG ACA TTG CAC CAG CAT CTG CAG AAC TCA CTG TCC ACC
 H   K   L   T   A   V   E   A   Q   Q   S   K   M   L   N   Q   T   L   H   Q   H   L   E   N   S   L  T>

600        610        620        630        640        650        660        670
 *          *          *          *          *          *          *          *
AAC AAG CTG GAG AGG CAG CGA GGG GCA CAG CAG GCA CAG CTA CTA AAT CAG AGC CGA GAG CTG CAA CGG AAC AGG GCC CTG AGG CTG
 N   K   L   E   R   Q   R   G   A   Q   Q   A   Q   L   L   N   Q   S   R   E   L   Q   R   N   R   A   L   E   T   R  L>

680        690        700        710        720        730        740        750        760
 *          *          *          *          *          *          *          *          *
CAG GCA CTG GAA GCA CAA CAT CAT CAA GCC CAG CTT AAC AGC CTC CAA GAG AAG AGG GAA CAA CTG CAC AGT CTC CTG GGC CAT CAG
 Q   A   L   E   A   Q   H   H   Q   A   Q   L   N   S   L   Q   E   K   R   E   Q   L   H   S   L   L   G   H  Q>
```

Fig. 21B

```
                    770         780         790         800         810         820         830         840
                      *           *           *           *           *           *           *           *
             ACC GGG ACC CTG GCT AAC CTG AAG CAC AAT CTG CAC GCT CTC AGC AGC AAT TCC AGC TCC CTG CAG CAG CAG CAG CAA CTG
              T   G   T   L   A   N   L   K   H   N   L   H   A   L   S   S   N   S   S   S   L   Q   Q   Q   Q   Q   L >

850         860         870         880         890         900         910         920         930
                *           *           *           *           *           *           *           *           *
             ACG GAG TTT GTA CAG CGC CTG GTA CGG ATT GTA GCC CAG CAT CCG CAG GTT TCC TTA AAG ACA CCT AAG CCA GTG TTC CAG
              T   E   F   V   Q   R   L   V   R   I   V   A   Q   H   P   Q   V   S   L   K   T   P   K   P   V   F   Q >

940         950         960         970         980         990        1000        1010
                *           *           *           *           *           *           *           *
             GAC TGT GCA GAG ATC AAG CGC TCC GGG GTT AAT ACC AGC GGT GTC TAT ACC ATC TAT GAG ACC ATG AAG ACA CCT CTC AAG
              D   C   A   E   I   K   R   S   G   V   N   T   S   G   V   Y   T   I   Y   E   T   M   K   T   P   L   K >

1020        1030        1040        1050        1060        1070        1080        1090
                *           *           *           *           *           *           *           *
             GTG TTC TGT GAC ATG GAG ACT GAT GGA GGT GGG TGG ACC CTC ATC CAG CAC CGG GAG GAT GGA AGC GTA AAT TTC CAG AGA
              V   F   C   D   M   E   T   D   G   G   G   W   T   L   I   Q   H   R   E   D   G   S   V   N   F   Q   R >

1100        1110        1120        1130        1140        1150        1160        1170        1180
                *           *           *           *           *           *           *           *           *
             TGG GAA GAA TAC AAA GAG GGT TTT GGT AAT GTG GCC AGA GAG CAC TGG CTG GGC AAT GAG GCT GTG CAC CGC CTC ACC AGC
              W   E   E   Y   K   E   G   F   G   N   V   A   R   E   H   W   L   G   N   E   A   V   H   R   L   T   S >

1190        1200        1210        1220        1230        1240        1250        1260
                *           *           *           *           *           *           *           *
             ACG GCC TAC TTG CTA CGC ATG GAA CTG GAA GAC TGG CAT GAC CAC AGT TCC TCC ATC CAG TAT GAG AAC TTC CAG CTG GGC AGC
              T   A   Y   L   L   R   V   E   L   E   D   W   H   D   H   S   S   S   I   Q   Y   E   N   F   Q   L   G   S >

1270        1280        1290        1300        1310        1320        1330        1340        1350
                *           *           *           *           *           *           *           *           *
             GAG AGG CAG CGG TAC AGC CTC TCT GTG AAT GAC AGC AGT GGG AGT GCA CGC AAG AAC AGC CTG GCT CCT CAG GGC ACC AAG
              E   R   Q   R   Y   S   L   S   V   N   D   S   S   G   S   A   G   R   K   N   S   L   A   P   Q   G   T   K >

1360        1370        1380        1390        1400        1410        1420        1430
                *           *           *           *           *           *           *           *
             TTC AGC ACC AAA GAC GCC AAT AAC GAC ATG AAA TGT GCT CAG GGG TGG TGG TTT GAT GCC TGT
              F   S   T   K   D   A   N   N   D   M   K   C   A   Q   G   W   W   F   D   A   C >
```

Fig. 21C

```
      1440        1450        1460        1470        1480        1490        1500        1510
        *           *           *           *           *           *           *           *
GGC CTC TCC AAC CTC TAC TAT TCA GTT CAT CAG CAC TTG CAC AAG ATC AAT GGC ATC CGC TGG CAC TAC TTC CGA
 G   L   S   N   L   Y   Y   S   V   H   Q   H   L   H   K   I   N   G   I   R   W   H   Y   F   R>

1520        1530        1540        1550        1560        1570        1580        1590        1600
        *           *           *           *           *           *           *           *           *
GGC CCC AGC TAC TCA CTG CAC GGC ACA CGC ATG ATG CTG AGG GCC ATG GGT GCC TGA CACA CAGCCCTGCA GAGACTGATG
 G   P   S   Y   S   L   H   G   T   R   M   M   L   R   P   H   G   A   *>

1610        1620        1630        1640        1650        1660        1670        1680        1690        1700
        *           *           *           *           *           *           *           *           *           *
CCGTAGGAGG ATTCTCAACC CAGGTGACTC TGTGCACGCT GGGCCCTGCC CAGAAATCAG TGCCCAGGGC TCATCTTGAC ATTCTGGAAC ATCGGAACCA 1710        1720        1730        1740        1750        1760        1770        1780        1790        1800
        *           *           *           *           *           *           *           *           *           *
CCTTACCTTG CCCCTGAATT ACAAGAATTC ACCTGCCTCC CTGTTGCCCT CTAATGTGA AATTGCTGGG TGCTTGAAGG CACCTGCCTC TGTTGGAACC 1810        1820        1830        1840
        *           *           *           *
ATACTCTTTC CCCCTCCTGC TGCATGCCCG GGAATCCCTG CCATGAACT
```

Fig. 22 A

```
              10         20         30         40         50         60         70         80
mTL3   MLLDGLLLLA TMAAAQHRGP EAGGHRQIHQ VRRGQCSYTF VVPEPDICQL APTAAPEALG GSNSLQRDLP ASRLHIADWR
hTL1.  af.aai.thi -gcsn.r.s. .ns.r-rynr iqh...a... il.h-dg-n crestdq-y nt.a.....a- ---p.-v--e->
chTL1  af.aa..ahi -gctt.r... ..s.r-rfnr iqh..t.... il..q-dg-n crestdq-y nt.a.....a- ---p.-v-e->
mTL1.  mtvflsfaffaailthigcsn.r.n. .n..r.-ynr iqh...a... il..h.-gn- cres.t.qy- nt.a.....a. ---.,v-e-->
mTL2.  mwqiifltfgwd.v.. saysnfrksv dst.r..-y. .qn.p..... ll..t.s.r- -ssss.-ym- -..av...-a. ---dy.---->
hTL2   mwqivffrlscd.v.. aaynnfrksm dsi.kk.-y. .qh.s..... ll..m.n.r- -ssss.-yv- -..av...-a. ---ey.---->

90        100        110        120        130        140        150        160
mTL3   AQRQRAQRV  SQLEKILENN TQWLLKLEQS IKVNLRSHLV QAQQDTIQNQ TTTMLALGAN LMNQTKAQTH KLTAVEAQVL
hTL1.  pdf--ss.kl qh..hvm..y .....q....y .ve.mk.ema .i..nav..h .a....ei.ts .ls..ae..r ...d..t...>
chTL1  qdf--sf.kl qh..hvm..y .....q...sy .ve.mk.em. .l..nav..h .a....ei.ts .ls..ae..r ...d..t...>
mTL1.  pdfs--s.kl qh..hvm..y .....q...ny .ve.mk.ema .i..nav..h .a....ei.ts .ls..ae..r ...d..t...>
mTL2.  -dsv.l.-.  -..n... -..m...ny .qd.mkkem. ei..nvv... av.iei.ts l...a..r .....d.....>
hTL2   -dsv.l.-.  -..n.m... -..m...ny .qd.mkkem. ei..nav... av.iei.t. l.....ae..r .....d.....>

170        180        190        200        210        220        230        240
mTL3   NQTHHKTQM  LENSLSTNKL EROMLMQSRE LQRLQGRNRA LETRLQALEA QHQAQLNSLQ EKREQLHSLL GHQTGTLANL
hTL1.  ...srlei.l ........y. .k.l.q.tn. ilkihek.sl ..hkilem.g k.kee.dt.k .ex.n.qg.v tr..yiiqe.>
chTL1  ...srlei.l ........y. .k.l.q.tn. ilkihek.sl ..hkilem.e r.keemdt.k .ex.n.q..v tr..syiiqe.>
mTL1.  ...srlei.l ........y. .k.l.q.tn. ilkihek.sl ..hkilem.g k.kee.dt.k .ex.n.qg.v sr..fiiqe.>
mTL2.  ...trlel.l .qh.i..... .k.i.d.ts. ink..nk.sf .qkv1dm.g k.se..q.mk .qkde.qv.v sk..ssvide.>
hTL2   ...trlel.l .h....... .k.i.d.ts. ink..dk.sf .kkv1.m.d k.ii.q.ik .ekd.qv.v sk..nsiiee.>

250        260        270        280        290        300        310        320
mTL3   KHNDLHALSSN SSSLQQQQQQ LTEFVQRLVR IV---AQ-DQHP--V--S L-KTPKPVFQD CAEIKRSGVN TSGVYTYET NMTKPLKVFC
hTL1.  ekq.nratt. n.v..k..le .mdt.hn..n lc---tkevllk-g--g k.-reeekp.r. .dvyqa.f. k..i....in ..pe.k....>
chTL1  ekq.nkatt. n.v..k..le .mdt.ht.it lc---sk-egvllkn--a k-.eeekp.r. .dvyq.f. k........in .vsd.k....>
mTL1.  ekq.sratn. n.i..k..le .mdt.hn..s lc---tk-egvl--1kgg k-reeekp.r. .dvyqa.f. k..i......fn ..pe.k....>
mTL2.  ekk.vtatv. n.l..k..hd .m.t.ns.lt mnss-pn-skss--.--a ir.eeqtt.r. ...fk.lt ...i..ltfp .s.eei.ay.>
hTL2   ekkivtatv. n.v..k..hd .m.t.nn.lt mnstsns-akd.--t--v a-.eeqis.r. ...vfk.ht .n.i..ltfp .s.eei.ay.>
```

Fig. 22 B

```
              330        340        350        360        370        380        390        400
       DMETDGGWT LIQHREDGSV NFQRTWEEYK EGFGNVAREH WLGNEAVHRL TSRTAYLLRV ELHDWEGRQT SIQYENFQLG
mTL3
hTL1.  n.dvn..... v......... d...g.k... m.....psg.y ......fifai ..qrg.m..i ..m....nra ys..dr.hi.>
chTL1. n..vn..... v......... d..kg.k... m.....spsg. ......fifai ..qrg.s..i ..m....nra ys..dr.hi.>
mTL1.  n.dvn..... v......... d...g.k... m.....psg.y ......fifai ..qrg.m..i ..m....nra ys..dr.hi.>
mTL2.  ..dvg..... v......... d......k.. ......plg.y ......f.sq. .gqhr.v.ki q.k.....nea hsl.dh.y.a>
hTL2.  ...ag..... i..r...... d......... v.....psg.. ......f.sq. .nqqr.v.ki h.k.....nea ysl..h.y.s>

410        420        430        440        450        460        470        480
       SERQRYSLSV NDSSSSAGRK NSLAPQGTKF STKDMDNDNC MCKCAQMLSG GWWFDACGLS NLNGIYYSVH QHLKINGIR
mTL3
hTL1.  n.k.n.r.yl kghtgt..kq s..ilh.ad. .....a.... .....l..t. ..........p. ....mf.tag .nhg.l...k>
chTL1. n.k.n.r.yl kgh.gt..kq s..ilh.ae. .....a.... .....l..t. ..........p. ....mf..ag .nhg.l...k>
mTL1.  n.k.n.r.yl kghtgt..kq s..ilh.ad. .....a.... .....l..t. ..........p. ....mf.tag .nhg.l...k>
mTL2.  g.esn.rihl tgltgt.aki s.isqp.sd. .....s...k. i....s.... .....l..... ..........p. ....q..pqk .ntn.f...k>
hTL2.  ..eln.rihl kgltgt..ki s.isqp.nd. .....g..... i....s...t. ..........p. ....m..pqr .ntn.f...k>

490        500
       WHYFRGPSYS IHGTRMMLRP MGA*
mTL3
hTL1.  .......... .rs.t..i.. ldf>
chTL1. ...k...... .rs.r..... ldf>
mTL1.  .......k.. .rs.t..i.. ldf>
mTL2.  .y.wk.sg.. .ka.t..i.. adf>
hTL2.  .y.wk.sg.. .ka.t..i.. adf>
```

Fig. 23 A

```
          10                  20                  30                  40                  50                  60
ATG CTC TCC CAG CTA GCC ATG CTG CAG GGC AGC CTC CTT GTG GTT GCC ACC ATG TCT GTG GCT
 M   L   S   Q   L   A   M   L   Q   G   S   L   L   V   V   A   T   M   S   V   A
          70                  80                  90                 100                 110                 120                 130
CAA CAG ACA AGG CAG GAG GCG GAT AGG GGC TGC GAG ACA CTT GTA GTC CAG CAC GGC CAC TGT AGC
 Q   Q   T   R   Q   E   A   D   R   G   C   E   T   L   V   V   Q   H   G   H   C   S
         140                 150                 160                 170                 180                 190
TAC ACC TTC TTG CTG CCC AAG TCT GAG CCT TGC CCT CCG GGG CCT GAG GTC TCC AGG GAC TCC AAC
 Y   T   F   L   L   P   K   S   E   P   C   P   P   G   P   E   V   S   R   D   S   N
         200                 210                 220                 230                 240                 250                 260
ACC CTC CAG AGA GAA TCA CTG GCC AAC CCA CAC CTG CAC GGG AAG TTG CCC ACC CAG CAG GTG AAA
 T   L   Q   R   E   S   L   A   N   P   H   L   H   G   K   L   P   T   Q   Q   V   K
         270                 280                 290                 300                 310                 320                 330
CAG CTG GAG CAG GCA CTG CAG AAC AAC ACG CAG TGG CTG CAG AAG CTA GAG AGG GCC ATC AAG ACG
 Q   L   E   Q   A   L   Q   N   N   T   Q   W   L   Q   K   L   E   R   A   I   K   T
         340                 350                 360                 370                 380                 390
ATC TTG AGG TCG AAG CTC CTG GAG CAG CAG ACC ACT GCC CAG ATC CGC AAG CTG ACC CCC ATG CTA
 I   L   R   S   K   L   L   E   Q   Q   T   T   A   Q   I   R   K   L   T   P   M   L
         400                 410                 420                 430                 440                 450                 460
GAG CTG GGC ACC AGC CTC CTG AAC CAG ACA TCA AGA ATG GAT GCC CAG ATC CGC ACC AGG ACC ATG GAG GCT
 E   L   G   T   S   L   L   N   Q   T   S   R   M   D   A   Q   I   R   T   R   T   M   E   A
         470                 480                 490                 500                 510                 520
CAG CTC CTG AAC CAG ACA TCA AGA ATG GAT GCC CAG ATG CCA GAG ACC TTT CTG TCC ACC AAC AAG
 Q   L   L   N   Q   T   S   R   M   D   A   Q   M   P   E   T   F   L   S   T   N   K
         530                 540                 550                 560                 570                 580                 590
CTG GAG AAC CAG CTG CTA CAG CAG AGG CAG AAG CTC CAG CTT CAG GGC CAA AAC AGC GCG CTC
 L   E   N   Q   L   L   Q   Q   R   Q   K   L   Q   L   Q   G   Q   N   S   A   L
                                                             ← 
```

Fig. 23 B

```
     600              610              620              630              640              650              660
GAG AAG CGG TTG CAG GCC CTG GAG ACC AAG CAG CAG GAG CTG GAG GCC AGC ATC CTC AGC AAG AAG
 E   K   R   L   Q   A   L   E   T   K   Q   Q   E   L   E   A   S   I   L   S   K   K
          670              680              690              700              710              720
GCG AAG CTG CTG AAC ACG CTG AGC CGC CAG AGC GCC GCC CTC ACC AAC ATC GAG CGC GGC CTG CGC
 A   K   L   L   N   T   L   S   R   Q   S   A   A   L   T   N   I   E   R   G   L   R
     730              740              750              760              770              780              790
GGT GTC AGG CAC CTG CTG AAC TCC AGC CTC CAG CAG GAC CAG CAC AGC CGC CAG CTG CTG GTG TTG
 G   V   R   H   L   L   N   S   S   L   Q   Q   D   Q   H   S   R   Q   L   L   V   L
          800              810              820              830              840              850
TTG CGG CAC CTG GTG CAA GAA AGG GCT AAC GCC TCG GCC CCG GCC TTC ATA ATG GCA GGT GAG CAG
 L   R   H   L   V   Q   E   R   A   N   A   S   A   P   A   F   I   M   A   G   E   Q
     860              870              880              890              900              910              920
GTG TTC CAG GAC TGT GCA GAG ATC CAG CGC TCT GGG GCC AGT GCC AGT GTC TAC ACC ATC CAG
 V   F   Q   D   C   A   E   I   Q   R   S   G   A   S   G   V   Y   T   I   Q
          930              940              950              960              970              980              990
GTG TCC AAT GCA ACG AAG CCC AGG AAG GTG TTC TGT GAC CTG CAG AGC AGT GGA GGG AGG TGG ACC
 V   S   N   A   T   K   P   R   K   V   F   C   D   L   Q   S   S   G   G   R   W   T
     1000             1010             1020             1030             1040             1050
CTC ATC CAG CGC CGT GAG GAT AAT GGC ACC GTG CAG CGG AAC TGG AAG GAT TAC AAA CAG GGC
 L   I   Q   R   R   E   D   N   G   T   V   Q   R   N   W   K   D   Y   K   Q   G
          1060             1070             1080             1090             1100             1110             1120
TTC GGA GAC CCA GCT GGG GAG CAC TGG CTG GGC AAT GAA GTG GTG CAC CAG CTC ACC AGA AGG GCA
 F   G   D   P   A   G   E   H   W   L   G   N   E   V   V   H   Q   L   T   R   R   A
     1130             1140             1150             1160             1170             1180
GCC TAC TCT CTG CGT GTG GAG CTG CAA GAC TGG GAA GGC AAC GAG GCC TAT GCC CAG TAC GAA CAT
 A   Y   S   L   R   V   E   L   Q   D   W   E   G   N   E   A   Y   A   Q   Y   E   H
```

Fig. 23C

```
1190                1200                1210                1220                1230                1240                1250
TTC CAC CTG GGC AGT GAG AAC CAG CTA TAC AGG CTT TCT GTG GTC GGG TAC AGC GGC TCA GCA GGG
 F   H   L   G   S   E   N   Q   L   Y   R   L   S   V   V   G   Y   S   G   S   A   G 1260                1270                1280                1290                1300                1310                1320
CGC CAG AGC AGC CTG GTC CTG CAG AAC ACC AGC TTT AGC ACC CTT GAC TCA GAC AAC GAC CAC TGT
 R   Q   S   S   L   V   L   Q   N   T   S   F   S   T   L   D   S   D   N   D   H   C 1330                1340                1350                1360                1370                1380
CTC TGC AAG TGT GCC CAG GTG ATG TCT GGA GGG TGG TGG TTT GAC GCC TGT GGC CTG TCA AAC CTC
 L   C   K   C   A   Q   V   M   S   G   G   W   W   F   D   A   C   G   L   S   N   L 1390                1400                1410                1420                1430                1440                1450
AAC GGC GTC TAC TAC CAC GCT CCC GAC AAC AAG TAC AAG ATG GAC GGC ATC CGC TGG CAC TAC TTC
 N   G   V   Y   Y   H   A   P   D   N   K   Y   K   M   D   G   I   R   W   H   Y   F 1460                1470                1480                1490                1500                1510
AAG GGC CCC AGC TAC TCA CTG CGT GCC TCT CGC ATG ATG ATA CGG CCT TTG GAC ATC TAA
 K   G   P   S   Y   S   L   R   A   S   R   M   M   I   R   P   L   D   I   *
```

```
          550       560       570       580       590       600       610       620       630
            *         *         *         *         *         *         *         *         *
ACA AAT GAA ATC TTG AAG ATC CAT GAA CTT TTA GAA CAT GTA AAT CTT TTA GAA ATG GAA GGA AAA CAC AAG GAG TTG GAC
TGT TTA CTT TAG AAC TTC TAG GTA CTT GAA AAT CTT GTA CAT TTA GAA AAT CTT TAC CTT CCT TTT GTG TTC CTC AAC CTG
 T   N   E   I   L   K   I   H   E   L   L   E   H   V   N   L   L   E   M   E   G   K   H   K   E   L   D 640       650       660       670       680       690       700       710       720
            *         *         *         *         *         *         *         *         *
ACC TTA AAG GAG AAC AGT GTC TTC CAG AAG AAC CTT CAG GAG TTG GTT ACT CGT CAA CTG ATC ATA TAT CAA TTA AAC AGA GCT
TGG AAT TTC CTC TTG TCA CAG AAG GTC TTC TTG GAA CCG AAC CAA CCA TGA GCA GTT GAC TAG TAT ATA GTT AAT TTG TCT CGA
 T   L   K   E   N   S   V   F   Q   K   N   L   Q   E   L   V   T   R   Q   L   I   I   Y   Q   L   N   R   A 730       740       750       760       770       780       790       800       810
            *         *         *         *         *         *         *         *         *
ACC ACC AAC AGT GTC CTT CAG AAG CTT GTC CTC GAG CTG ATG GAC CTG ATG AAC CTT GTC AAT CTT GAA CAG TTT CTT CCA CAA
TGG TGG TTG TCA CAG GAA GTC TTC GAA CAG GAG CTC GAC TAC CTG GAC TTG GAA CAG TTA GAA CTT GTC AAA GAA GGT GTT
 T   T   N   S   V   L   Q   K   L   V   L   E   L   M   D   L   M   N   L   V   N   L   E   Q   F   L   P   Q 820       830       840       850       860       870       880       890       900
            *         *         *         *         *         *         *         *         *
TTA CTA AAG GGA GGA AAA GAG CTC CTT CAG GAG CTC TTT GCT GAA TGT GCT GAA CTT GTC AAA TCA GGA CAC ACC AAT GGC ATC TAC
AAT GAT CCT CCT TTT CTC GAG GAA GTC CTC GAG AAA CGA CTT ACA CGA CTT CAT AGT CCT AGT TGG TGT CCG TAG ATG
 L   L   K   G   G   K   E   L   L   Q   E   L   F   A   E   C   A   E   V   F   K   S   G   H   T   N   G   I   Y 910       920       930       940       950       960       970       980       990
            *         *         *         *         *         *         *         *         *
AAT GAT TGT AAG GGA TTA TGT ACA GAA GAG CTC CTC ACA GAA GCC AAG ATC ATT ATT AGA GCT ATG GAC TGT GGA CCT GGA GGC GGG CCC TGT TAA GTC GCT GCA
TGC AAT TGT AAG GGA TTA TGT ACA TGT AGA GAC CTT CGG AAA TAG TCT AGT ACC TGT TGG GAG CCT CCC GGG
 L   L   T   F   P   N   S   T   E   E   L   L   T   E   A   K   I   I   I   R   A   M   D   C   G   P   G   G   G   P   W   T   T   I   Q   R 1000      1010      1020      1030      1040      1050      1060      1070      1080
            *         *         *         *         *         *         *         *         *
GAG GAT GGC AGC GTT GAT TTT GAT CTA CAA AGG ACT TGG GGA GAA TAT AAA GAA AAG ATA TTT AAA CCT TCA GGA AAT GAG CTG CTG GGA AAT GAG
CTC CTA CCG TCG CAA CTA AAA CTA GAT GTC TCC TGA ACC TTT ATA TTT CTT TTC TAT AAA TTT GGA AGT CCT TTA CTC GAC CCT TTA
 E   D   G   S   V   D   F   D   L   Q   R   T   W   T   V   R   Y   K   E   K   I   F   K   P   S   G   E   Y   W   L   G   N   E 1090      1100      1110      1120      1130      1140      1150      1160      1170
            *         *         *         *         *         *         *         *         *
TTT GTT TCG CAA ACT CTG CAA AAT CAG CGC TAT GTG AAA CTT CAC ATA TAT TAT ATC CTT AAA CAC CTT AAA AAG GAT TGG ACC CGA GTT CTC GAA AAT GAG GCT TAT TCA TAC TTG TAT AAC ATA CTT
AAA CAA AGC GTT GAC GTT GCA GTA CAC CCT GAA GTG TAT ATA
 F   V   S   Q   T   L   Q   N   Q   R   Y   V   K   L   H   I   Y   Y   I   L   K   H   L   K   K   D   W   E   N   E   A   Y   S   Y   L   Y   N   I   L
```

Fig. 24C

```
          1180        1190        1200        1210        1220        1230        1240        1250        1260
            *           *           *           *           *           *           *           *           *
CAT TTC TAT CTC TCA AGT GAA GAA CTC AAT TAT AGG ATT CAC CTT AAA GGA CTT ACA GGG ACA GCC AAA ATA AGC ATC AGC AGC CAA
GTA AAG GAG AGT TCA AAA TCG GAG CTT ATA TCC TAA GTG CAC TTT CCT GAA TGT CCC CGG TTT TAT TCG TAG TCG GTT
 H   F   Y   L   S   S   E   E   L   N   Y   R   I   H   L   K   G   L   T   G   T   A   G   K   I   S   S   S   Q>

1270        1280        1290        1300        1310        1320        1330        1340        1350
            *           *           *           *           *           *           *           *           *
CCA GAA AAT GAT TTT AGC ACA AAG GAT GGA GAC AAC TTG CTG AAA TGT ATT TGC AAA GAC TCA CAA ATG CTA ACA GGA GGC TGG TGG TTT GAT
GGT CCT TTA CTA AAA TCG TGT TTC CTA CCT CTG TTG AAC GAC TTT ACA TAA ACG TTT CTG AGT GTT TAC GAT TGT CCT CCG ACC AAA CTA
 P   G   N   D   F   S   T   K   D   G   D   N   L   L   K   C   I   C   K   D   S   Q   M   L   T   G   G   W   F   D>

1360        1370        1380        1390        1400        1410        1420        1430        1440
            *           *           *           *           *           *           *           *           *
GCA TGT CCT CCT TCC AAC TTG AAC GGA ATG TAC TAT ATA TCC CAG AGG CAG AAC ACA AAT AAG TTC AAG GGC ATT AAA TGG TAC TAC TGG AAA
CGT ACA CCA'GGA AGG TTG AAC TTG CCT TAC ATG TAC TAT AGG GTC TCC GTC TTG TGT TTA TTC AAG TTC CCG TAA TTT ACC ATG ATG ACC TTT
 A   C   P   P   S   N   L   N   G   M   Y   Y   I   P   Q   R   Q   N   T   N   K   F   K   N   G   I   K   W   Y   Y   W   K>

1450        1460        1470        1480        1490
            *           *           *           *           *
GGC TCA GGC TAT TCG CTC AAG GAG TTC AAG GCC ACA ACC ATG ATG ATC CGA CCA GCA GAT TTC TAA
CCG AGT CCG ATA AGC GAG CTC AAG TTC CGG TGT TGG TAC TAC TAG GCT CGT CTA AAG ATT
 G   S   G   Y   S   L   K   E   F   K   A   T   T   M   M   I   R   P   A   D   F   *>
```

Fig. 25A

```
                    10              20              30              40              50              60              70              80              90
                    *               *               *               *               *               *               *               *               *
ATG TGG CAG ATT GTT TTC ACT CTG TGT GAT CTT GTC TTG GCC TAT AAC AAC TTT CGG AAG AGC ATG GAC AGC ATA GGA
TAC ACC GTC TAA CAA AAG TGA GAC ACA CTA GAA CAG AAC CGG CGT ATA TTG TTG AAA GCC TTC TCG TAC CTG TCG TAT CCT
 M   W   Q   I   V   F   T   L   C   D   L   V   L   A   Y   N   N   F   R   K   S   M   D   S   I   G>

100             110             120             130             140             150             160             170             180
                    *               *               *               *               *               *               *               *               *
AAG AAG CAA TAT CAG GTC CAG CAT GGG TCC TGC AGC TAC ACT TTC CTC CCA GAG CTC ATG GAC AAC TGC CGC TCT TCC AGC TCG TAC
TTC TTC GTT ATA GTC CAG GTC GTA CCC AGG ACG TCG ATG TGA AAG GAG GGT CTC GAG TAC CTG TTG ACG GCG AGA AGG TCG AGC ATG
 K   K   Q   Y   Q   V   Q   H   G   S   C   S   Y   T   F   L   P   E   L   M   D   N   C   R   S   S   Y>

190             200             210             220             230             240             250             260             270
                    *               *               *               *               *               *               *               *               *
GTG TCC AAT GCT CTG CAG AGG GAC GCG CTC GAA TAC GAT GAT CTA CTG ATG CAA AGG CAG GTG CTG CTG GAG AAC ATC ATG GAA AAC
CAC AGG TTA CGA GTC TCC CTG CGC GAG CTT ATG CTA GAT GAC TAC GTT TCC GTC CAC GAC GAC CTC TTG TAG TAC CTT TTG TTG
 V   S   N   A   L   Q   R   D   A   L   E   Y   D   D   L   L   M   Q   R   Q   V   L   E   N   I   M   E   N>

280             290             300             310             320             330             340             350             360
                    *               *               *               *               *               *               *               *               *
ACT CAG TGG CTA ATG AAG CTT GAA AAT CTT GAG ATA TAT CAG GAC AAC CTG GTA ATG GAA GAA CTC TTT CGT GTC CAT GTC TTG GTC
TGA GTC ACC GAT TAC TTC GAA CTT TTA GAA CTC TAT ATA GTC CTG TTG GAC CAT TAC CTT CTT GAG AAA GCA CAG GTA CAG AAC CAG
 T   Q   W   L   M   K   L   E   N   L   E   I   Y   Q   D   N   L   V   M   E   E   L   F   R   V   H   V   Q>

370             380             390             400             410             420             430             440             450
                    *               *               *               *               *               *               *               *               *
ACG GCT GTG ATG ATA GAA ATA TAT CTT GAA CTT CAG AAC CTG TTG AAC CAA ACA GCT CGA ACG GAG CAA CTC GTT GAA GCC CAA GTA TTA
TGC CGA CAC TAC TAT CTT TAT ATA GAA CTT GAA GTC TTG GAC AAC TTG GTT TGT CGA GCT TGC CTC GTT GAG CAA CTT CGG CAT AAT
 T   A   V   M   I   E   I   Y   L   E   L   Q   N   L   L   N   Q   T   A   E   Q   T   R   K   L   T   D   V   E   A   Q   V   L>

460             470             480             490             500             510             520             530             540
                    *               *               *               *               *               *               *               *               *
AAT CAG ACC ACG AGA CTT GAA CTT CAG CTC CTC TTG GAA CAC CTC GTG AGG AGC TCG ACA AAC CTG GAA AAA CAG ATT TTG GAA GAA
TTA GTC TGG TGC TCT GAA CTT GAA GTC GAG GAG AAC CTT GTG GAG CAC TCC TCG AGC TGT TTG GAC CTT TTT GTC TAA AAC CTT CTT
 N   Q   T   T   R   L   E   L   Q   L   L   L   E   H   S   L   R   S   S   T   N   L   E   K   Q   I   L   E   E>
```

```
         1180      1190      1200      1210      1220      1230      1240      1250      1260
           *         *         *         *         *         *         *         *         *
CAC ATA GGA AAT GAA AAG TTC CAA AAC TAT AGG TTG TAT TTA AAA GGT CAC ACT GGG ACA GCA GGA AAA CAG AGC CTG ATC TTA CAC GGT
GTG TAT CCT TTA CTT GTT TTG ATA TCC AAC ATA AAT TTT CCA GTG TGA CCC TGT CGT AGT CTG GAC TAG AAT GTG CCA
 H   I   G   N   E   K   F   Q   N   Y   R   L   Y   L   K   G   H   T   G   T   A   G   K   Q   S   L   I   L   H   G>

1270      1280      1290      1300      1310      1320      1330      1340      1350
           *         *         *         *         *         *         *         *         *
GCT GAT TTC AGC AGG ACT AAA GAT GCT AAT GAC AAC TTG GCC CTC ATG TGT ATG TTA ACA GGA GGA TGG TGG TTT GAT GCT CGA TGT
CGA CTA AAG TCG TGA TTT CTA CGA TTA CTG TTG AAC CGG GAG TAC ACG TAC AAT TGT CCT CCT ACC ACC AAA CTA CGA ACA
 A   D   F   S   R   T   K   D   A   N   D   N   L   A   L   M   C   M   Y   T   N   C   K   G   G   W   W   F   D   A   C>

1360      1370      1380      1390      1400      1410      1420      1430      1440
           *         *         *         *         *         *         *         *         *
GGC CCC TCC AAT CTA AAT GGA ATG TTC TAT ACT GCG GGA CAA CAT GGA AAA CTG AAT GGG ATA AAG TGG CAC TAC TTC AAA GGG CCC
CCG GGG AGG TTA GAT TTA CCT TAC AAG ATA TGA CGC CCT GTT GTA CCT TTT GAC TTA CCC TAT TTC ACC GTG AAG TTT CCC GGG
 G   P   S   N   L   N   G   M   F   Y   T   A   G   Q   H   G   K   L   N   G   I   K   W   H   Y   F   K   G   P>

1450      1460      1470      1480      1490
           *         *         *         *         *
AGT TAC ATG TCC TTA CGT TCC ACA ACT ATG ATT CGA CCT TTA GAT TTT TGA
TCA ATG TAC AGG AAT GCA AGG TGT TGA TAC TAA GCT GGA AAT CTA AAA ACT
 S   Y   M   S   L   R   S   T   T   M   I   R   P   L   D   F   *>
```

```
          550            560            570            580            590            600            610            620            630
           *              *              *              *              *              *              *              *              *
ACC AGT GAA ATA AAC AAA TTG CAA GAT CTA AAG AAC AGT TCA TTC CTA GAA AAG GTG CTA GAT GCT ATG GAA GAC AAG CAC ATC ATC CAA CTA CAG
TGG TCA CTT TAT ATT TTG AAC GTT CTA GAT AAG TTG TCA AAG GAT CTT TTC TTC CAC GAT CGA TAC CTT CTG TAG GTT TAG GTT GAT GTC
 T   S   E   I   N   K   L   Q   D   L   K   N   S   S   F   L   E   K   V   L   D   A   M   E   D   K   H   I   I   Q   L  Q>

640            650            660            670            680            690            700            710            720
           *              *              *              *              *              *              *              *              *
TCA ATA AAA GAA GAG AAA GAT CAG GTC CAG CTA GTA TCC AAG AAT CAA ATT GAA GAA CTA GAA AAA ATA GTG ACT GCC
AGT TAT TTT CTT CTC TTT CTA GTC GAT GTC GAT CAT AGG TTC TTA AGT TTC CTT GAT CTT TTT TAT CAC TGA CGG
 S   I   K   E   E   K   D   Q   L   V   Q   L   V   S   K   N   Q   I   E   E   L   E   K   K   I   V   T  A>

730            740            750            760            770            780            790            800            810
           *              *              *              *              *              *              *              *              *
ACG GTG AAT AAT TCA GTT CTT CAA CAG CAT CTC ATG GAG CTC ATG CTC TTA AAC CTG ACT ATG ATG TCC ACA TCA AAC TCA
TGC CAC TTA AGT CAA GAA GTT CAA GTC GTA GAG TAC CTC GAG TAC AAT TTG GAC TGA TAC TAC AGG TGT AGT TTG
 T   V   N   N   S   V   L   Q   Q   H   L   M   E   L   M   L   L   N   L   T   M   M   S   T   S   N  S>

820            830            840            850            860            870            880            890            900
           *              *              *              *              *              *              *              *              *
GCT AAG GAC CCC ACT GTT GCT AAA GAA CTT CAA GAA ATC AGC AGA GAC TTC AAG GAT TGT GAA CTT GCT GAA GTA TCA GGA CAC ACC AAT GGC ATC
CGA TTC CTG GGG TGA CAA CGA TTT CTT GAA GTT CTT TAG TCG TCT CTG AAG TTC CTA ACA CTT GAA CGA CTT CAT GGT GTG TGG TTA CCG TAG
 A   K   D   P   T   V   A   K   E   L   Q   E   I   S   R   D   F   K   D   C   E   L   A   E   V   S   G   H   T   N   G  I>

910            920            930            940            950            960            970            980            990
           *              *              *              *              *              *              *              *              *
TAC ACG TTA ACA TTC CCT AAT TCT ACA GAA GAG ATC CTT GAC ATG GAA GCT GGA GGC CCC GGG TGG ACA ATT ATT CAG CGA
ATG TGC AAT TGT AAG GGA TTA AGA TGT CTT CTC TAG GAA CTG TAC CTT CGA CCT CCG GGG CCC ACC TGT TAA GTC GCT
 Y   T   L   T   F   P   N   S   T   E   E   I   L   D   M   E   A   G   G   P   G   W   T   I   I   Q  R>

1000           1010           1020           1030           1040           1050           1060           1070           1080
           *              *              *              *              *              *              *              *              *
CGT GAG GAT GGC AGC CTC CCG TCG CAA TTC GTT CAG AGG ACT TGG AAA GAA TAT ATA TTT CAG GGA TTT TCA GGA GAA CCT TCA GGA TAT TGG CTG GAC CCT TTA AAT
GCA CTC CTA CCG TCG GAG GCA AGT GTC TCC TGA ACC TTT CTT ATA TAT AAA GTC CCT AAA AGT CCT CTT GGA AGT CCT ATA ACC GAC CTG GGA AAT TTA
 R   E   D   G   S   V   D   F   Q   R   T   W   K   E   Y   K   V   G   F   G   N   P   S   G   E   Y   W   L   G  N>
```

Fig. 26C

```
           1090       1100       1110       1120       1130       1140       1150       1160       1170
            *          *          *          *          *          *          *          *          *
      GAG TTT GTT TCG CAA CTG ACT AAT CAG CAA CGC TAT GTG CTT AAA ATA CAC CTT AAA GAC TGG GAA GGG AAT GAG GCT TAC TCA TAT
      CTC AAA CAA AGC GTT GAC TGA TTA GTC GTT GCG ATA CAC GAA TTT TAT GTG GAA TTT CTG ACC CTT CCC TTA CTC CGA ATG AGT AAC ATA
       E   F   V   S   Q   L   T   N   Q   Q   R   Y   V   L   K   I   H   L   K   D   W   E   G   N   E   A   Y   S   L   Y>

1180       1190       1200       1210       1220       1230       1240       1250       1260
            *          *          *          *          *          *          *          *          *
      GAA CAT TTC TAT CTC TCA AGT GAA GAA CTC CTT GAG ATT AGG ATT TCC AAT TAT AAA GGA CTT ACA GGA CTT CCT GAA TTT ATA AGC AGC
      CTT GTA AAG ATA GAG AGT TCA CTT CTT GAG GAA CTC TAA TCC ATA TTT CCT GAA TGT CCT GAA GGA CTT AAA GGA CTA TAT TCG TCG
       E   H   F   Y   L   S   S   E   E   L   E   I   R   I   S   N   Y   K   G   L   T   G   L   P   E   F   I   K   S   S>

1270       1280       1290       1300       1310       1320       1330       1340       1350
            *          *          *          *          *          *          *          *          *
      CAA CCA GGA AAT GAT TTT AGC ACA GGA GAC AAG CTG GAC AAC CTT GAA ATA TGT ATT TCA CAA AAT GTT TCA ACA GGA GGC TGG TGG TTT
      GTT GGT CCT TTA CTA AAA TCG TGT CCT CTG TTC GAC CTG TTG GAA CTT TAT ACA TAA ACG AGT GTT TTA ACA AGT TGT CCT CCG ACC AAA
       Q   P   G   N   D   F   S   T   G   D   K   L   D   N   L   E   I   C   I   S   Q   N   V   S   T   G   G   W   W   F>

1360       1370       1380       1390       1400       1410       1420       1430       1440
            *          *          *          *          *          *          *          *          *
      GAT GCA TGT GGT CCT AAC TTG AAC GGA ATG TAC ATG TAT CCA CAG AGG GTC TTG AAC ACA AAT AAG TTC AAC GGC ATT AAA TGG TAC TGG
      CTA CGT ACA CCA GGA TTG AAC TTG CCT TAC ATG TAC ATA GGT GTC TCC CAG AAC TTG TGT TTA TTC AAG TTG CCG TAA TTT ACC ATG ACC
       D   A   C   G   P   N   L   N   G   M   Y   M   Y   P   Q   R   V   L   N   T   N   K   F   N   G   I   K   W   Y   W>

1450       1460       1470       1480       1490       1500
            *          *          *          *          *          *
      AAA GGC TCA GGC TAT TCG CTC AAG GCC ACC ATG ATC CGA CCA GCA GAT TTC TAA
      TTT CCG AGT CCG ATA AGC GAG TTC CGG TGG TAC TAG GCT GGT CGT CTA AAG ATT
       K   G   S   G   Y   S   L   K   A   T   M   I   R   P   A   D   F   *>
```

Fig. 27A

```
          10                  20                  30                  40                  50                  60                  70                  80                  90
           *                   *                   *                   *                   *                   *                   *                   *                   *
ATG TGG CAG ATT GTT TTC ACT CTG AGC TGT GAT CTT TTG GCC GCA TAT AAC TTG AAC AGC ATA GGA
TAC ACC GTC TAA CAA AAG TGA GAC TCG ACA CTA GAA CGG CGT CAT TTG AAC TTG TCG TAT CCT
 M   W   Q   I   V   F   T   L   S   C   D   L   L   A   A   Y   N   L   N   S   I   G>

100                 110                 120                 130                 140                 150                 160                 170                 180
           *                   *                   *                   *                   *                   *                   *                   *                   *
AAG AAG CAA TAT CAG GTC CAG CAT GGG TCC AGC TAC ACT TTC CTC CTG CCA GAG ATG AAC TTC CGC TCT TCC AGC CCC TAC
TTC TTC GTT ATA GTC CAG GTC GTA CCC AGG TCG ATG TGA AAG GAG GAC GGT CTC TAC TTG AAG GCG AGA AGG TCG GGG ATG
 K   K   Q   Y   Q   V   Q   H   G   S   S   Y   T   F   L   L   P   E   M   N   F   R   S   S   S   P   Y>

190                 200                 210                 220                 230                 240                 250                 260                 270
           *                   *                   *                   *                   *                   *                   *                   *                   *
GTG TCC AAT GCT GTG CAG AGG GAC GCG CCG CTC GAA CTT GAT TTC TCT CAG AAA CTT CAA CAT GTA GAA CAT GTG ATG TAT
CAC AGG TTA CGA CTC GTC TCC CTG CGC GGC GAG CTT GAA CTA AAG AGA GTC TTT GAA GTT GTA CAT CTT GTA CAC TAC ATA
 V   S   N   A   V   Q   R   D   A   P   L   E   L   D   F   S   Q   K   L   Q   H   V   E   H   V   M   Y>

280                 290                 300                 310                 320                 330                 340                 350                 360
           *                   *                   *                   *                   *                   *                   *                   *                   *
ACT CAG TGG CTG CAA AAA CTT TTT GAA CTT GAG ATT GTG GAA AAC ATG AAG TTC TAC AGC CAG ATA GCC GAG ATG GCA GTT CAG AAC CAC
TGA GTC ACC GAC GTT TTT GAA AAA CTT GAA CTC TAA CAC CTT TTG TAC TTC AAG ATG TCG GTC TAT CGG CTC TAC CGT CAA GTC TTG GTG
 T   Q   W   L   Q   K   L   F   E   L   E   I   V   E   N   M   K   F   Y   S   Q   I   A   E   M   A   V   Q   N   H>

370                 380                 390                 400                 410                 420                 430                 440                 450
           *                   *                   *                   *                   *                   *                   *                   *                   *
ACG GCT ACC ATG GAG CTT GAG ATA GGA ACC CTC CTC TCT CAG GCA GAG GAG ACC AGA AAG CTG ACA GAT GTT CAA GAC ACC TGG CAG CAC
TGC CGA TGG TAC CTC GAA CTC TAT CCT TGG GAG GAG AGA GTC CGT CTC CTG TGG TCT TTC GAC TGT CTA CAA GTT CTG TGG ACC GTC GTG
 T   A   T   M   E   L   E   I   G   T   L   L   S   Q   A   E   E   T   R   K   L   T   D   V   Q   D   T   W   Q   H>

460                 470                 480                 490                 500                 510                 520                 530                 540
           *                   *                   *                   *                   *                   *                   *                   *                   *
AAT CAA ACT TCT CGA CTT GAG CTT GAC CTG CTG GAG AAT TCA TTA TCC ACC TAC AAG TTC CTT GAT CTA GAG AAG CTA GAG GTA CTA AAT GAA
TTA GTT TGA AGA GCT GAA CTC GAC GAC CTC TTA AGT AAT AGG TGG ATG TTC AAG GAA CTA GAT CTC TTC GAT CTC CAT GAT TTA CTT
 N   Q   T   S   R   L   E   L   D   L   L   E   N   S   L   S   T   Y   K   L   L   E   K   Q   L   L   Q   T   N   E>
```

Fig. 27B

```
        550         560         570         580         590         600         610         620         630
         *           *           *           *           *           *           *           *           *
ATC TTG AAG ATC CAT GAA AAA AAC AGT TTA TTA GAA CAT GTA TTT AAA ATC TTA GAA ATG GAA GGA AAA CAC AAG GAA GAG TTG GAC ACC TTA AAG
TAG AAC TTC TAG GTA CTT TTT TTG TCA AAT AAT CTT GTA CAT AAA TTT TAG AAT CTT TAC CTT CCT TTT GTG TTC CTT CAC CTG TGG AAT TTC
 I   L   K   I   H   E   K   N   S   L   L   E   H   V   F   K   I   L   E   M   E   G   K   H   K   E   E   L   D   T   L   K>

640         650         660         670         680         690         700         710         720
         *           *           *           *           *           *           *           *           *
GAA GAG AAA GAG AAC CTT CAA GGC TTG GTT ACT CGT CAA ACA TAT ATA ATC CAG GAG CTG GAA AAG TTC TTA AAC AGA GCT ACC ACC AAC
CTT CTC TTT CTC TTG GAA GTT CCG AAC CAA TGA GCA GTT TGT ATA TAT TAG GTC CTC GAC CTT TTC AAT TTG TCT CGA TGG TGG TTG
 E   E   K   E   N   L   Q   G   L   V   T   R   Q   T   Y   I   I   Q   E   L   E   K   F   L   N   R   A   T   T   N>

730         740         750         760         770         780         790         800         810
         *           *           *           *           *           *           *           *           *
AAC AGT GTC CTT CAG AAG CAG CAA CTG GAG CTG ATG GAC ACA GTC CAC AAC CTT GTC AAT CTT TGC ACT AAA GAA GGT GTT TTA CTA AAG
TTG TCA CAG GAA GTC TTC GTC GTT GAC CTC GAC TAC CTG TGT CAG GTG TTG GAA CAG TTA GAA ACG TGA TTT CTT CCA CAA AAT GAT TTC
 N   S   V   L   Q   K   Q   Q   L   E   L   M   D   T   V   H   N   L   V   N   L   C   T   K   E   G   V   L   L   K>

820         830         840         850         860         870         880         890         900
         *           *           *           *           *           *           *           *           *
GGA GGA AAA AGA GAG GAG AAA CCA TTT AGA GAC GTA GCA GAT GTA CAT ATA GTT CAA GCT GGT TTT AAT AAA AGT GGA ATC TAC ACT ATT TAT
CCT CCT TTT TCT CTC CTT TTT GGT AAA TCT CTG CAT CGT CTA CAT GTA CAA GTT CGA CCA AAA TTA TTT TCA CCT TAG ATG TGA TAA ATA
 G   G   K   R   E   E   K   P   F   R   D   V   A   D   V   H   I   V   Q   A   G   F   N   K   S   G   I   Y   T   I   Y>

910         920         930         940         950         960         970         980         990
         *           *           *           *           *           *           *           *           *
CCT CCT TTT CTC CTT CTC TTT GGG TTT TTC AAA AAG CCC AAA AGT GAT GTC AAT GGG GGA GGT TGG ACT GAA TAT GTA CAT CAA GAT CGT GAA GAT GGA
GGA GGA AAA GAG GAA GAG AAA CCC AAA AAG TTT TTC GGG TTT TCA CTA CAG TTA CCC CCT CCA ACC TGA CTT ATA CAT GTA GTT CTA GCA CTT CTA CCT
 G   G   K   R   E   E   K   P   K   K   F   G   F   F   N   M   D   V   N   G   G   G   W   T   E   Y   V   H   Q   D   R   E   D   G>

1000        1010        1020        1030        1040        1050        1060        1070        1080
         *           *           *           *           *           *           *           *           *
ATT AAT ATG CCA GAA TTC CAA AGA GAG CTT GGG TTT TGC AAT GTG TTT AAA ATG GGT TGG AAG GGA TAT TGG CTG GGG AAT GAG TTT ATT TTT
TAA TTA TAC GGT CTT AAG GTT TCT CTC GAA CCC AAA ACG TTA CAC AAA TTT TAC CCA ACC TTC CCT ATA ACC GAC CCC TTA CTC AAA TAA AAA
 I   N   M   P   E   F   Q   R   E   L   G   F   C   N   V   F   K   M   G   W   K   G   Y   W   L   G   N   E   F   I   F>

AGT CTA GAT TTC CAA AGA GTT CTT GAT GTA CAT CCC TCC AGG AGG CCC TTA GGG AGG CCC TTA GCA CTT CTA CCT
TCA GAT CTA AAG GTT TCT CAA GAA CTA CAT GTA GGG AGG TCC TCC GGG AAT CCC TCC GGG AAT CGT GAA GAT GGA
 S   L   D   F   Q   R   V   L   D   V   H   P   S   R   R   P   L   G   R   P   L   A   L   L   P>
```

Fig. 27C

```
      1090        1100        1110        1120        1130        1140        1150        1160        1170
        *           *           *           *           *           *           *           *           *
GCC ATT ACC AGT CAG AGG CAG TAC ATG CTA AGA ATT GAG CTC TAA ATG GAC TGG GAA GGG AAC CGA GCC TAT TCA CAG TAT GAC AGA TTC CAC
CGG TAA TGG TCA GTC TCC GTC ATG TAC GAT TCT TAA CTC GAG ATT TAC CTG ACC CTT CCC TTG GCT CGG ATA AGT GTC ATA CTG TCT AAG GTG
 A   I   T   S   Q   R   Q   Y   M   L   R   I   E   L   *   M   D   W   E   G   N   R   A   Y   S   Q   Y   D   R   F   H>

1180        1190        1200        1210        1220        1230        1240        1250        1260
        *           *           *           *           *           *           *           *           *
ATA GGA AAT GAA AAG CAA AAC TAT TTG TAT TTA AAA GGT CAC ACT GGG CCC ACA GCA GGA AAA CAG AGC CTG ATC TTA CAC GTG GGT GCT
TAT CCT TTA CTT TTC GTT TTG ATA AAC ATA AAT TTT CCA GTG TGA CCC TGT GGT CCT TTT GTC TCG GAC TAG AAT GTG CCA CGA
 I   G   N   E   K   Q   N   Y   L   Y   L   K   G   H   T   G   P   T   A   G   K   Q   S   L   I   L   H   G   A>

1270        1280        1290        1300        1310        1320        1330        1340        1350
        *           *           *           *           *           *           *           *           *
GAT TTC AGC ACT AAA GAT GCT GAT AAT GAC ATG TGC AAA TGT ACA GGA TTA ACA GGA TGG TTT GAT GCT GGC
CTA AAG TCG TGA TTT CTA CGA CTA TTA CTG TAC ACG TTT ACA TGT CCT AAT TGT CCT ACC AAA CTA CGA CCG
 D   F   S   T   K   D   A   D   N   D   M   C   K   C   T   G   L   T   G   W   F   D   A   G>

1360        1370        1380        1390        1400        1410        1420        1430        1440
        *           *           *           *           *           *           *           *           *
CCC TCC AAT CTA AAT GGA ATG TTC TAT ACT GCG GGA CAA AAC CAT GTA CCT TTT GAC CTG AAA CTG GGA ATA AAG TGG CAC TAC TTC AAA GGG CCC AGT
GGG AGG TTA GAT TTA CCT TAC AAG ATA TGA CGC CCT GTT TTG GTA CAT GGA AAA CTG GAC TTT GAC CCT TAT TTC ACC GTG ATG AAG TTT CCC GGG TCA
 P   S   N   L   N   G   M   F   Y   T   A   G   Q   N   H   V   P   F   D   L   K   L   G   I   K   W   H   Y   F   K   G   P   S>

1450        1460        1470        1480
        *           *           *           *
TAC TCC TTA CGT TCC ACA ACT ATG ATG ATT CGA CCT TTA GAT TTT TGA
ATG AGG AAT GCA AGG TGT TGA TAC TAC TAA GCT GGA AAT CTA AAA ACT
 Y   S   L   R   S   T   T   M   M   I   R   P   L   D   F   *>
```

EXPRESSED LIGAND-VASCULAR INTERCELLULAR SIGNALLING MOLECULE

This application claims the priority of U.S. Provisional application 60/022,999 filed Aug. 2, 1996. Throughout this application various publications are referenced. The disclosures of these publications in their entireties are hereby incorporated by reference into this application.

INTRODUCTION

The present invention relates generally to the field of genetic engineering and more particularly to genes for receptor tyrosine kinases and their cognate ligands, their insertion into recombinant DNA vectors, and the production of the encoded proteins in recipient strains of microorganisms and recipient eukaryotic cells. More specifically, the present invention is directed to a novel modified TIE-2 ligand that binds the TIE-2 receptor, as well as to methods of making and using the modified ligand. The invention further provides a nucleic acid sequence encoding the modified ligand, and methods for the generation of nucleic acid encoding the modified ligand and the gene product. The modified TIE-2 ligand, as well as nucleic acid encoding it, may be useful in the diagnosis and treatment of certain diseases involving endothelial cells and associated TIE receptors, such as neoplastic diseases involving tumor angiogenesis, wound healing, thromboembolic diseases, atherosclerosis and inflammatory diseases. In addition, the modified ligand may be used to promote the proliferation and/or differentiation of hematopoietic stem cells.

More generally, the receptor activating modified TIE-2 ligands described herein may be used to promote the growth, survival, migration, and/or differentiation and/or stabilization or destabilization of cells expressing TIE receptor. Biologically active modified TIE-2 ligand may be used for the in vitro maintenance of TIE receptor expressing cells in culture. Cells and tissues expressing TIE receptor include, for example, cardiac and vascular endothelial cells, lens epithelium and heart epicardium and early hematopoietic cells. Alternatively, such human ligand may be used to support cells which are engineered to express TIE receptor. Further, modified TIE-2 ligand and its cognate receptor may be used in assay systems to identify further agonists or antagonists of the receptor.

BACKGROUND OF THE INVENTION

The cellular behavior responsible for the development, maintenance, and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long-term readjustment of cellular gene expression. Several receptors associated with various cell surfaces may bind specific growth factors.

The phosphorylation of tyrosine residues in proteins by tyrosine kinases is one of the key modes by which signals are transduced across the plasma membrane. Several currently known protein tyrosine kinase genes encode transmembrane receptors for polypeptide growth factors and hormones such as epidermal growth factor (EGF), insulin, insulin-like growth factor-I (IGF-I), platelet derived growth factors (PDGF-A and -B), and fibroblast growth factors (FGFs). (Heldin et al., Cell Regulation, 1: 555–566 (1990); Ullrich, et al., Cell, 61: 243–54 (1990)). In each instance, these growth factors exert their action by binding to the extracellular portion of their cognate receptors, which leads to activation of the intrinsic tyrosine kinase present on the cytoplasmic portion of the receptor. Growth factor receptors of endothelial cells are of particular interest due to the possible involvement of growth factors in several important physiological and pathological processes, such as vasculogenesis, angiogenesis, atherosclerosis, and inflammatory diseases. (Folkman, et al. Science, 235: 442–447 (1987)). Also, the receptors of several hematopoietic growth factors are tyrosine kinases; these include c-fms, which is the colony stimulating factor 1 receptor, Sherr, et al., Cell, 41: 665–676 (1985), and c-kit, a primitive hematopoietic growth factor receptor reported in Huang, et al., Cell, 63: 225–33 (1990).

The receptor tyrosine kinases have been divided into evolutionary subfamilies based on the characteristic structure of their ectodomains. (Ullrich, et al. Cell, 61: 243–54 (1990)). Such subfamilies include, EGF receptor-like kinase (subclass I) and insulin receptor-like kinase (subclass II), each of which contains repeated homologous cysteine-rich sequences in their extracellular domains. A single cysteine-rich region is also found in the extracellular domains of the eph-like kinases. Hirai, et al., Science, 238: 1717–1720 (1987); Lindberg, et al. Mol. Cell. Biol., 10: 6316–24 (1990); Lhotak, et al., Mol. Cell. Biol. 11: 2496–2502 (1991). PDGF receptors as well as c-fms and c-kit receptor tyrosine kinases may be grouped into subclass III; while the FGF receptors form subclass IV. Typical for the members of both of these subclasses are extracellular folding units stabilized by intrachain disulfide bonds. These so-called immunoglobulin (Ig)-like folds are found in the proteins of the immunoglobulin superfamily which contains a wide variety of other cell surface receptors having either cell-bound or soluble ligands. Williams, et al., Ann. Rev. Immunol., 6: 381–405 (1988).

Receptor tyrosine kinases differ in their specificity and affinity. In general, receptor tyrosine kinases are glycoproteins which consist of (1) an extracellular domain capable of binding the specific growth factor(s); (2) a transmembrane domain which usually is an alpha-helical portion of the protein; (3) a juxtamembrane domain where the receptor may be regulated by, e.g., protein phosphorylation; (4) a tyrosine kinase domain which is the enzymatic component of the receptor; and (5) a carboxyterminal tail which in many receptors is involved in recognition and binding of the substrates for the tyrosine kinase.

Processes such as alternative exon splicing and alternative choice of gene promoter or polyadenylation sites have been reported to be capable of producing several distinct polypeptides from the same gene. These polypeptides may or may not contain the various domains listed above. As a consequence, some extracellular domains may be expressed as separate, secreted proteins and some forms of the receptors may lack the tyrosine kinase domain and contain only the extracellular domain inserted in the plasma membrane via the transmembrane domain plus a short carboxyl terminal tail.

A gene encoding an endothelial cell transmembrane tyrosine kinase, originally identified by RT-PCR as an unknown tyrosine kinase-homologous cDNA fragment from human leukemia cells, was described by Partanen, et al., Proc. Natl. Acad. Sci. USA, 87: 8913–8917 (1990). This gene and its encoded protein are called "TIE" which is an abbreviation for "tyrosine kinase with Ig and EGF homology domains." Partanen, et al. Mol. Cell. Biol. 12: 1698–1707 (1992).

It has been reported that tie mRNA is present in all human fetal and mouse embryonic tissues. Upon inspection, tie message has been localized to the cardiac and vascular endothelial cells. Specifically, tie mRNA has been localized to the endothelia of blood vessels and endocardium of 9.5 to 18.5 day old mouse embryos. Enhanced tie expression was shown during neovascularization associated with developing ovarian follicles and granulation tissue in skin wounds. Korhonen, et al. Blood 80: 2548–2555 (1992). Thus the TIEs have been suggested to play a role in angiogenesis, which is important for developing treatments for solid tumors and several other angiogenesis-dependent diseases such as diabetic retinopathy, psoriasis, atherosclerosis and arthritis.

Two structurally related rat TIE receptor proteins have been reported to be encoded by distinct genes with related profiles of expression. One gene, termed tie-1, is the rat homolog of human tie. Maisonpierre, et al., Oncogene 8: 1631–1637 (1993). The other gene, tie-2, may be the rat homolog of the murine tek gene, which, like tie, has been reported to be expressed in the mouse exclusively in endothelial cells and their presumptive progenitors. Dumont, et al. Oncogene 8: 1293–1301 (1993). The human homolog of tie-2 is described in Ziegler, U.S. Pat. No. 5,447,860 which issued on Sep. 5, 1995 (wherein it is referred to as "ork"), which is incorporated in its entirety herein.

Both genes were found to be widely expressed in endothelial cells of embryonic and postnatal tissues. Significant levels of tie-2 transcripts were also present in other embryonic cell populations, including lens epithelium, heart epicardium and regions of mesenchyme. Maisonpierre, et al., Oncogene 8: 1631–1637 (1993).

The predominant expression of the TIE receptor in vascular endothelia suggests that TIE plays a role in the development and maintenance of the vascular system. This could include roles in endothelial cell determination, proliferation, differentiation and cell migration and patterning into vascular elements. Analyses of mouse embryos deficient in TIE-2 illustrate its importance in angiogenesis, particularly for vascular network formation in endothelial cells. Sato, T. N., et al., Nature 376:70–74 (1995). In the mature vascular system, the TIEs could function in endothelial cell survival, maintenance and response to pathogenic influences.

The TIE receptors are also expressed in primitive hematopoietic stem cells, B cells and a subset of megakaryocytic cells, thus suggesting the role of ligands which bind these receptors in early hematopoiesis, in the differentiation and/ or proliferation of B cells, and in the megakaryocytic differentiation pathway. Iwama, et al. Biochem. Biophys. Research Communications 195:301–309 (1993); Hashiyama, et al. Blood 87:93–101 (1996), Batard, et al. Blood 87:2212–2220 (1996).

SUMMARY OF THE INVENTION

The present invention provides for a composition comprising a modified TIE-2 ligand substantially free of other proteins. As used herein, modified TIE-2 ligand refers to a ligand of the TIE family of ligands, whose representatives comprise ligands TL1, TL2, TL3 and TL4 as described herein, which has been altered by addition, deletion or substitution of one or more amino acids, or by way of tagging, with for example, the Fc portion of human IgG-1, but which retains its ability to bind the TIE-2 receptor. Modified TIE-2 ligand also includes a chimeric TIE-2 ligand comprising at least a portion of a first TIE-2 ligand and a portion of a second TIE-2 ligand which is different from the first. By way of non-limiting example, the first TIE-2 ligand is TL1 and the second TIE-2 ligand is TL2. The invention envisions other combinations using additional TIE-2 ligand family members. For example, other combinations for creating a chimeric TIE-2 ligand are possible, including but not limited to those combinations wherein the first ligand is selected from the group consisting of TL1, TL2, TL3 and TL4, and the second ligand, different from the first ligand, is selected from the group consisting of TL1, TL2, TL3 and TL4.

The invention also provides for an isolated nucleic acid molecule encoding a modified TIE-2 ligand. In one embodiment, the isolated nucleic acid molecule encodes a TIE-2 ligand of the TIE family of ligands, whose representatives comprise ligands TL1, TL2, TL3 and TL4 as described herein, which has been altered by addition, deletion or substitution of one or more amino acids, or by way of tagging, with for example, the Fc portion of human IgG-1, but which retains its ability to bind the TIE-2 receptor. In another embodiment, the isolated nucleic acid molecule encodes a modified TIE-2 ligand which is a chimeric TIE-2 ligand comprising at least a portion of a first TIE-2 ligand and a portion of a second TIE-2 ligand which is different from the first. By way of non-limiting example, the first TIE-2 ligand is TL1 and the second TIE-2 ligand is TL2. The invention envisions other combinations using additional TIE-2 ligand family members. For example, other combinations are possible, including but not limited to those combinations wherein the isolated nucleic acid molecule encodes a modified TIE-2 ligand which is a chimeric TIE-2 ligand comprising a portion of a first ligand selected from the group consisting of TL1, TL2, TL3 and TL4, and a portion of a second ligand, different from the first ligand, selected from the group consisting of TL1, TL2, TL3 and TL4.

The isolated nucleic acid may be DNA, cDNA or RNA. The invention also provides for a vector comprising an isolated nucleic acid molecule encoding a modified TIE-2 ligand. The invention further provides for a host-vector system for the production in a suitable host cell of a polypeptide having the biological activity of a modified TIE-2 ligand. The suitable host cell may be bacterial, yeast, insect or mammalian. The invention also provides for a method of producing a polypeptide having the biological activity of a modified TIE-2 ligand which comprises growing cells of the host-vector system under conditions permitting production of the polypeptide and recovering the polypeptide so produced.

The invention herein described of an isolated nucleic acid molecule encoding a modified TIE-2 ligand further provides for the development of the ligand as a therapeutic for the treatment of patients suffering from disorders involving cells, tissues or organs which express the TIE-2 receptor. The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The present invention also provides for an antibody which specifically binds a modified TIE-2 ligand as described herein. The antibody may be monoclonal or polyclonal.

Thus the invention further provides for therapeutic compositions comprising an antibody which specifically binds a modified TIE-2 ligand, in a pharmaceutically acceptable vehicle. The invention also provides for a method of blocking blood vessel growth in a mammal by administering an effective amount of a therapeutic composition comprising an antibody which specifically binds a receptor activating modified TIE-2 ligand as described herein, in a pharmaceutically acceptable vehicle.

The invention further provides for therapeutic compositions comprising a modified TIE-2 ligand as described herein, in a pharmaceutically acceptable vehicle. The invention also provides for a method of promoting neovascularization in a patient by administering an effective amount of a therapeutic composition comprising a receptor activating modified TIE-2 ligand as described herein, in a pharmaceutically acceptable vehicle. In one embodiment, the method may be used to promote wound healing. In another embodiment, the method may be used to treat ischemia. In yet another embodiment, a receptor activating modified TIE-2 ligand as described herein is used, alone or in combination with other hematopoietic factors, to promote the proliferation or differentiation of hematopoietic stem cells, B cells or megakaryocytic cells.

Alternatively, the invention provides that a modified TIE-2 ligand may be conjugated to a cytotoxic agent and a therapeutic composition prepared therefrom. The invention further provides for a receptorbody which specifically binds a modified TIE-2 ligand. The invention further provides for therapeutic compositions comprising a receptorbody which specifically binds a modified TIE-2 ligand in a pharmaceutically acceptable vehicle. The invention also provides for a method of blocking blood vessel growth in a mammal by administering an effective amount of a therapeutic composition comprising a receptorbody which specifically binds a modified TIE-2 ligand in a pharmaceutically acceptable vehicle.

The invention also provides for a TIE-2 receptor antagonist as well as a method of inhibiting TIE-2 biological activity in a mammal comprising administering to the mammal an effective amount of a TIE-2 antagonist. According to the invention, the antagonist may be a modified TIE-2 ligand as described herein which binds to, but does not activate, the TIE-2 receptor.

BRIEF DESCRIPTION OF THE FIGURES

FIG. 1A: embryos treated with EHK-1 RB (rEHK-1 ecto/hIgG1 Fc) were viable and possessed normally developed blood vessels in their surrounding CAM. FIG. 1B: all embryos treated with TIE-2 RB (r TIE-2 ecto/h IgG1 Fc) were dead, diminished in size and were almost completely devoid of surrounding blood vessels.

FIGS. 4A–4D—Nucleic acid and deduced amino acid (single letter code) sequences of human TIE-2 ligand 1 from clone λgt10 encoding htie-2 ligand 1 (SEQ. ID. NO. 1 and SEQ. ID. NO. 2).

FIGS. 5A–5D—Nucleic acid and deduced amino acid (single letter code) sequences of human TIE-2 ligand 1 from T98G clone (SEQ. ID. NO. 3 and SEQ. ID. NO. 4).

FIGS. 6A–6D—Nucleic acid and deduced amino acid (single letter code) sequences of human TIE-2 ligand 2 from clone pBluescript KS encoding human TIE 2 ligand 2 (SEQ. ID. NO. 5 and SEQ. ID. NO. 6).

FIGS. 10A–10D—Histogram representation of binding to rat TIE-2 IgG immobilized surface by TIE-2 ligand in C2C12 ras (FIG. 10A), Rat2 ras (FIG. 10B), SHEP (FIG. 10C), and T98G (FIG. 10D) concentrated (10×) conditioned medium. Rat TIE-2 (rTIE2) specific binding is demonstrated by the significant reduction in the binding activity in the presence of 25 μg/ml soluble rat TIE-2 RB as compared to a minor reduction in the presence of soluble trkB RB.

FIGS. 21A–21C—Nucleotide and deduced amino acid (single letter code) sequences of TIE ligand-3 (SEQ. ID. NO. 9 and SEQ. ID. NO. 10). The coding sequence starts at position 47. The fibrinogen-like domain starts at position 929.

FIGS. 22A–22B—Comparison of Amino Acid Sequences of TIE Ligand Family Members. mTL3=mouse TIE ligand-3 (SEQ. ID. NO. 11); hTL1=human TIE-2 ligand1 (SEQ. ID. NO. 12); chTL1=chicken TIE-2 ligand1 (SEQ. ID. NO. 13); mTL1=mouse TIE-2 ligand 1 (SEQ. ID. NO. 14); mTL2= mouse TIE-2 ligand 2 (SEQ. ID. NO. 15); hTL2=human TIE-2 ligand 2 (SEQ. ID. NO. 16). The boxed regions indicate conserved regions of homology among the family members.

FIGS. 23A–23C—Nucleotide and deduced amino acid (single letter code) sequences of TIE ligand-4 (SEQ. ID. NO. 17 and SEQ. ID. NO. 18). Arrow indicates nucleotide position 569.

FIGS. 24A–24C—Nucleotide and deduced amino acid (single letter code) sequences of chimeric TIE ligand designated 1N1C2F (chimera 1) (SEQ. ID. NO. 19 and SEQ. ID. NO. 20). The putative leader sequence is encoded by nucleotides 1–60.

Figure 25B:
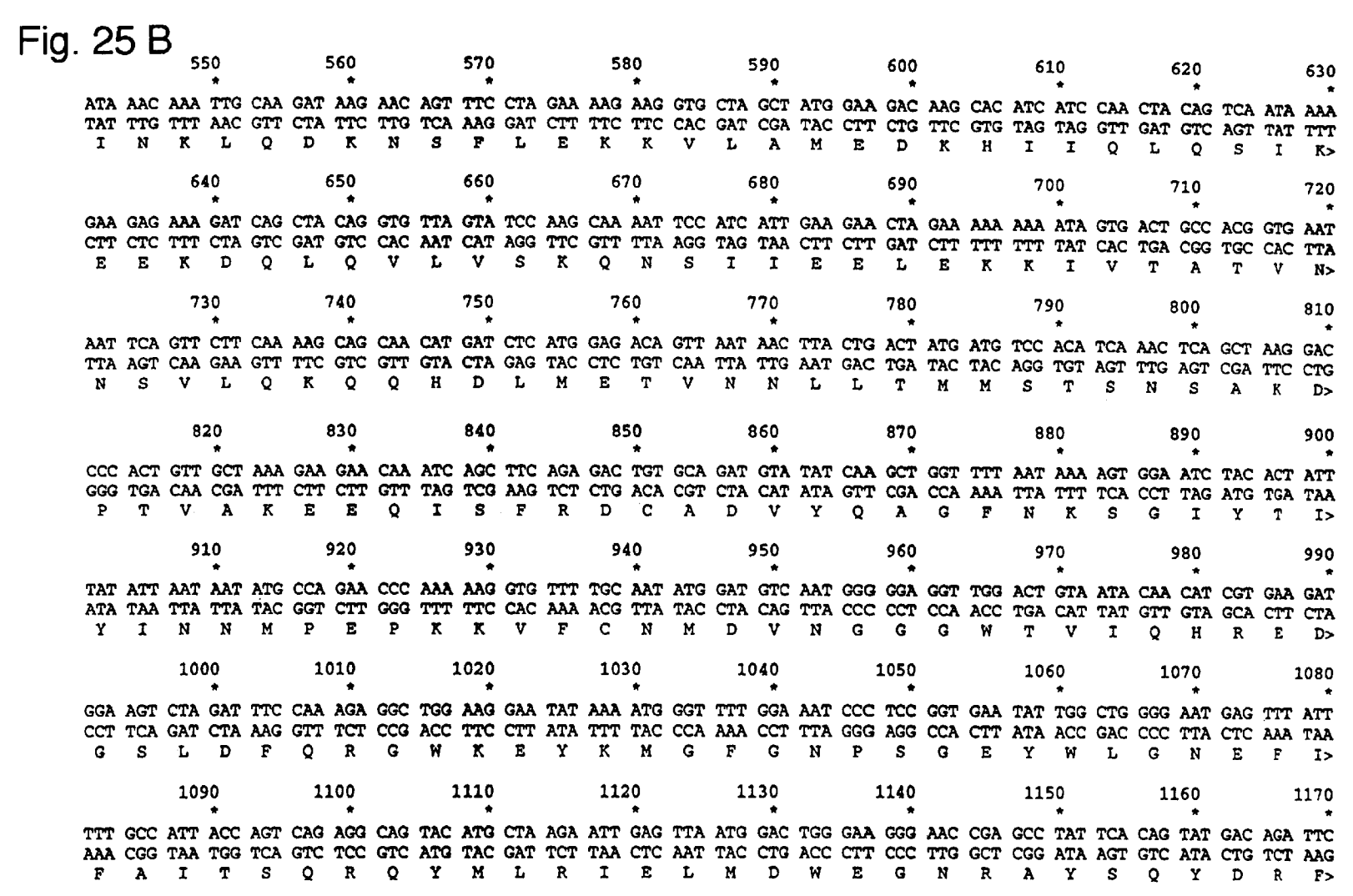

FIGS. 25A–25C—Nucleotide and deduced amino acid (single letter code) sequences of chimeric TIE ligand designated 2N2C1F (chimera 2) (SEQ. ID. NO. 21 and SEQ. ID. NO. 22). The putative leader sequence is encoded by nucleotides 1–48.

Figure 26A:
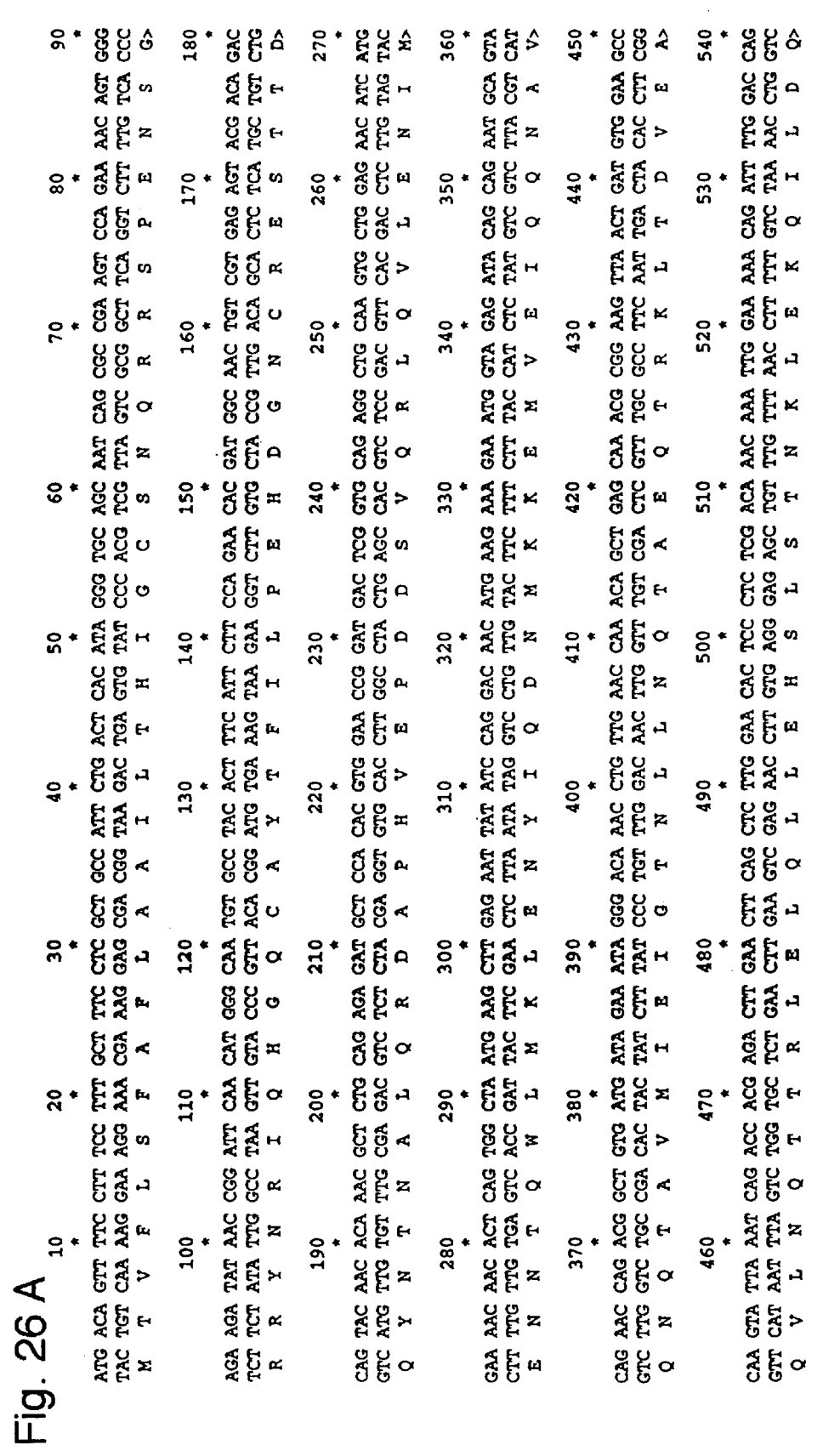

FIGS. 26A–26C—Nucleotide and deduced amino acid (single letter code) sequences of chimeric TIE ligand designated 1N2C2F (chimera 3) (SEQ. ID. NO. 23 and SEQ. ID. NO. 24). The putative leader sequence is encoded by nucleotides 1–60.

FIGS. 27A–27C—Nucleotide and deduced amino acid (single letter code) sequences of chimeric TIE ligand designated 2N1C1F (chimera 4) (SEQ. ID. NO. 25 and SEQ. ID. NO. 26). The putative leader sequence is encoded by nucleotides 1–48.

DETAILED DESCRIPTION OF THE INVENTION

Figure 1:
FIGS. 1A and 1B—TIE-2 receptorbody (TIE-2 RB) inhibits the development of blood vessels in the embryonic chicken chorioallantoic membrane (CAM). A single piece of resorbable gelatin foam (Gelfoam) soaked with 6 μg of RB was inserted immediately under the CAM of 1-day chick embryos. After 3 further days of incubation, 4 day old embryos and surrounding CAM were removed and examined.
Figure 1:
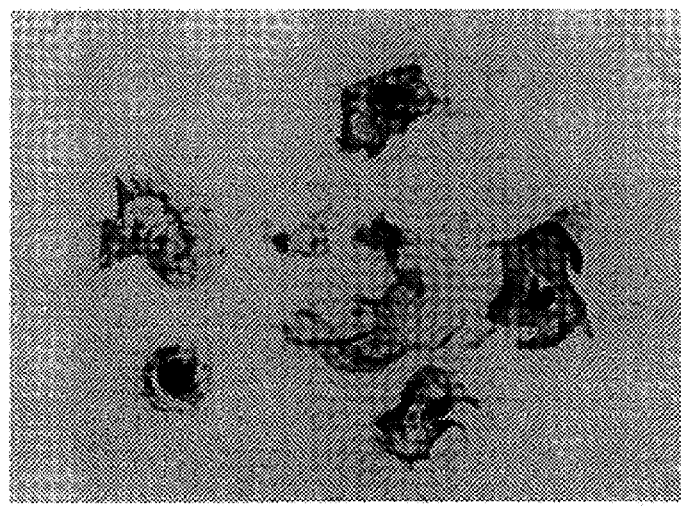

As described in greater detail below, applicants have created novel modified TIE-2 ligands that bind the TIE-2 receptor. The present invention provides for a composition comprising a modified TIE-2 ligand substantially free of other proteins. As used herein, modified TIE-2 ligand refers to a ligand of the TIE family of ligands, whose representatives comprise ligands TL1, TL2, TL3 and TL4 as described herein, which has been altered by addition, deletion or substitution of one or more amino acids, or by way of tagging, with for example, the Fc portion of human IgG-1, but which retains its ability to bind the TIE-2 receptor. Modified TIE-2 ligand also includes a chimeric TIE-2 ligand comprising at least a portion of a first TIE-2 ligand and a portion of a second TIE-2 ligand which is different from the first. By way of non-limiting example, the first TIE-2 ligand is TL1 and the second TIE-2 ligand is TL2. The invention envisions other combinations using additional TIE-2 ligand family members. For example, other combinations for creating a chimeric TIE-2 ligand are possible, including but not limited to those combinations wherein the first ligand is selected from the group consisting of TL1, TL2, TL3 and TL4, and the second ligand, different from the first ligand, is selected from the group consisting of TL1, TL2, TL3 and TL4.

The invention also provides for an isolated nucleic acid molecule encoding a modified TIE-2 ligand. In one embodiment, the isolated nucleic acid molecule encodes a TIE-2 ligand of the TIE family of ligands, whose representatives comprise ligands TL1, TL2, TL3 and TL4 as described herein, which has been altered by addition, deletion or substitution of one or more amino acids, or by way of tagging, with for example, the Fc portion of human IgG-1, but which retains its ability to bind the TIE-2 receptor. In another embodiment, the isolated nucleic acid molecule encodes a modified TIE-2 ligand which is a chimeric TIE-2 ligand comprising at least a portion of a first TIE-2 ligand and a portion of a second TIE-2 ligand which is different from the first. By way of non-limiting example, the first TIE-2 ligand is TL1 and the second TIE-2 ligand is TL2. The invention envisions other combinations using additional TIE-2 ligand family members. For example, other combinations are possible, including but not limited to those combinations wherein the isolated nucleic acid molecule encodes a modified TIE-2 ligand which is a chimeric TIE-2 ligand comprising a portion of a first ligand selected from the group consisting of TL1, TL2, TL3 and TL4, and a portion of a second ligand, different from the first ligand, selected from the group consisting of TL1, TL2, TL3 and TL4.

The present invention comprises the modified TIE-2 ligands and their amino acid sequences, as well as functionally equivalent variants thereof, as well as proteins or peptides comprising substitutions, deletions or insertional mutants of the described sequences, which bind TIE-2 receptor and act as agonists or antagonists thereof. Such variants include those in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Also included within the scope of the invention are proteins or fragments or derivatives thereof which exhibit the same or similar biological activity as the modified TIE-2 ligands described herein, and derivatives which are differentially modified during or after translation, e.g., by glycosylation, proteolytic cleavage, linkage to an antibody molecule or other cellular ligand, etc. Functionally equivalent molecules also include molecules that contain modifications, including N-terminal modifications, which result from expression in a particular recombinant host, such as, for example, N-terminal methylation which occurs in certain bacterial (e.g E. coli) expression systems.

The present invention also encompasses the nucleotide sequences that encode the proteins described herein as modified TIE-2 ligands, as well as host cells, including yeast, bacteria, viruses, and mammalian cells, which are genetically engineered to produce the proteins, by e.g. transfection, transduction, infection, electroporation, or microinjection of nucleic acid encoding the modified TIE-2 ligands described herein in a suitable expression vector. The present invention also encompasses introduction of the nucleic acid encoding modified TIE-2 ligands through gene therapy techniques such as is described, for example, in Finkel and Epstein FASEB J. 9:843–851 (1995); Guzman, et al. PNAS (USA) 91:10732–10736 (1994).

One skilled in the art will also recognize that the present invention encompasses DNA and RNA sequences that hybridize to a modified TIE-2 ligand encoding nucleotide sequence, under conditions of moderate stringency, as defined in, for example, Sambrook, et al. Molecular Cloning: A Laboratory Manual, 2 ed. Vol. 1, pp. 101–104, Cold Spring Harbor Laboratory Press (1989). Thus, a nucleic acid molecule contemplated by the invention includes one having a nucleotide sequence deduced from an amino acid sequence of a modified TIE-2 ligand prepared as described herein, as well as a molecule having a sequence of nucleotides that hybridizes to such a nucleotide sequence, and also a nucleotide sequence which is degenerate of the above sequences as a result of the genetic code, but which encodes a ligand that binds TIE-2 receptor and which has an amino acid sequence and other primary, secondary and tertiary characteristics that are sufficiently duplicative of a modified TIE-2 ligand described herein so as to confer on the molecule the same biological activity as the modified TIE-2 ligand described herein.

The present invention provides for an isolated nucleic acid molecule encoding a modified TIE-2 ligand that binds and activates TIE-2 receptor comprising a nucleotide sequence encoding TIE-2 ligand 1 wherein the portion of the nucleotide sequence that encodes the N-terminal domain of TIE-2 ligand 1 is replaced by a nucleotide sequence that encodes the N-terminal domain of TIE-2 ligand 2. The invention also provides for such a nucleic acid molecule, with a further modification such that the portion of the nucleotide sequence that encodes the coiled-coil domain of TIE-2 ligand 1 is replaced by a nucleotide sequence that encodes the coiled-coil domain of TIE-2 ligand 2.

The present invention also provides for an isolated nucleic acid molecule encoding a modified TIE-2 ligand that binds and activates TIE-2 receptor comprising a nucleotide sequence encoding TIE-2 ligand 1 wherein the portion of the nucleotide sequence that encodes the N-terminal domain of TIE-2 ligand 1 is replaced by a nucleotide sequence that encodes the N-terminal domain of TIE-2 ligand 2 and which is further modified to encode a different amino acid instead of the cysteine residue encoded by nucleotides 784–787 as set forth in FIGS. 27A–27C (SEQ. ID. NO. 25 and SEQ. ID. NO. 26). A serine residue is preferably substituted for the cysteine residue. In another embodiment, the nucleic acid molecule is further modified to encode a different amino acid instead of the arginine residue encoded by nucleotides 199–201 as set forth in FIGS. 27A–27C (SEQ. ID. NO. 25 and SEQ. ID. NO. 26). A serine residue is preferably substituted for the arginine residue.

The present invention also provides for an isolated nucleic acid molecule encoding a modified TIE-2 ligand that binds and activates TIE-2 receptor comprising a nucleotide sequence encoding TIE-2 ligand 1 which is modified to encode a different amino acid instead of the cysteine residue at amino acid position 245. A serine residue is preferably substituted for the cysteine residue.

The invention further provides for an isolated nucleic acid molecule encoding a modified TIE-2 ligand that binds but does not activate TIE-2 receptor comprising a nucleotide sequence encoding TIE-2 ligand 1 wherein the portion of the nucleotide sequence that encodes the N-terminal domain of TIE-2 ligand 1 is deleted. The invention also provides for such a nucleic acid molecule further modified so that the portion of the nucleotide sequence that encodes the coiled-coil domain of TIE-2 ligand 1 is deleted and the portion encoding the fibrinogen-like domain is fused in-frame to a nucleotide sequence encoding a human immunoglobulin gamma-1 constant region (IgG1 Fc).

The invention further provides for an isolated nucleic acid molecule encoding a modified TIE-2 ligand that binds but does not activate TIE-2 receptor comprising a nucleotide sequence encoding TIE-2 ligand 2 wherein the portion of the nucleotide sequence that encodes the N-terminal domain of TIE-2 ligand 2 is deleted. The invention also provides for such a nucleic acid molecule further modified so that the portion of the nucleotide sequence that encodes the coiled-coil domain of TIE-2 ligand 2 is deleted and the portion encoding the fibrinogen-like domain is fused in-frame to a nucleotide sequence encoding a human immunoglobulin gamma-1 constant region (IgG1 Fc).

The invention further provides for an isolated nucleic acid molecule encoding a modified TIE-2 ligand that binds but does not activate TIE-2 receptor comprising a nucleotide sequence encoding TIE-2 ligand 1 wherein the portion of the nucleotide sequence that encodes the fibrinogen-like domain of TIE-2 ligand 1 is replaced by a nucleotide sequence that encodes the fibrinogen-like domain of TIE-2 ligand 2. The invention also provides for such a nucleic acid molecule further modified so that the portion of the nucleotide sequence that encodes the coiled-coil domain of TIE-2 ligand 1 is replaced by a nucleotide sequence that encodes the coiled-coil domain of TIE-2 ligand 2.

The invention further provides for a modified TIE-2 ligand encoded by any of nucleic acid molecules of the invention.

The present invention also provides for a chimeric TIE-2 ligand comprising at least a portion of a first TIE-2 ligand and a portion of a second TIE-2 ligand which is different from the first, wherein the first and second TIE-2 ligands are selected from the group consisting of TIE-2 Ligand-1, TIE-2 Ligand-2, TIE Ligand-3 and TIE Ligand-4. Preferably, the chimeric TIE ligand comprises at least a portion of TIE-2 Ligand-1 and a portion of TIE-2 Ligand-2.

Figure 24A:
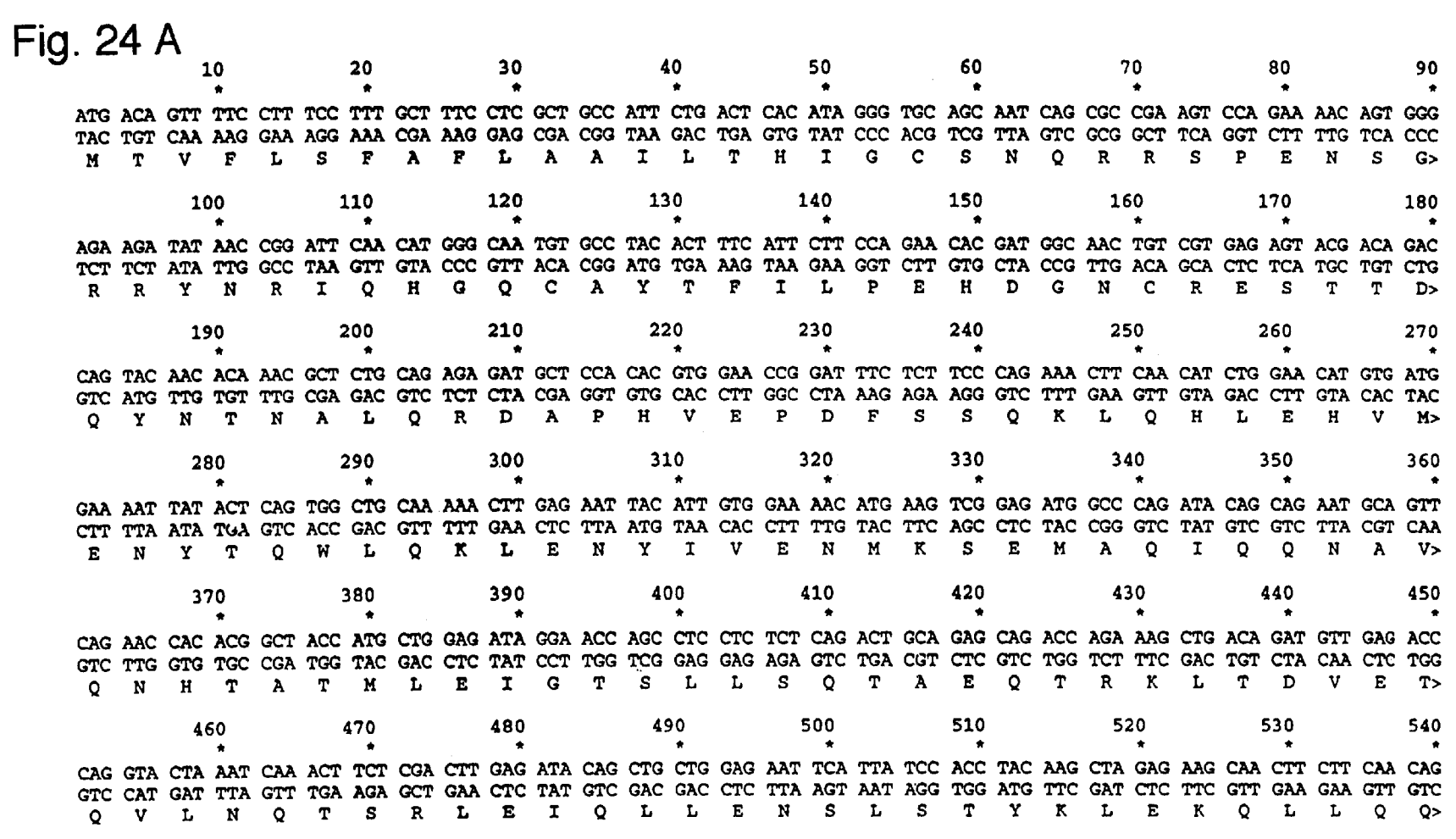

The invention also provides a nucleic acid molecule that encodes a chimeric TIE ligand as set forth in FIGS. 24A–24C (SEQ. ID. NO. 19 and SEQ. ID. NO. 20), 25A–25C (SEQ. ID. NO. 21 and SEQ. ID. NO. 22), 26A–26C (SEQ. ID. NO. 23 and SEQ. ID. NO. 24), or 27A–27C (SEQ. ID. NO. 25 and SEQ. ID. NO. 26). The invention also provides a chimeric TIE ligand as set forth in FIGS. 24A–24C (SEQ. ID. NO. 19 and SEQ. ID. NO. 20), 25A–25C (SEQ. ID. NO. 21 and SEQ. ID. NO. 22), 26A–26C (SEQ. ID. NO. 23 and SEQ. ID. NO. 24), or 27A–27C (SEQ. ID. NO. 25 and SEQ. ID. NO. 26). The invention further provides a chimeric TIE ligand as set forth in FIGS. 27A–27C (SEQ. ID. NO. 25 and SEQ. ID. NO. 26), modified to have a different amino acid instead of the cysteine residue encoded by nucleotides 784–787.

Any of the methods known to one skilled in the art for the insertion of DNA fragments into a vector may be used to construct expression vectors encoding a modified TIE-2 ligand using appropriate transcriptional/translational control signals and the protein coding sequences. These methods may include in vitro recombinant DNA and synthetic techniques and in vivo recombinations (genetic recombination). Expression of a nucleic acid sequence encoding a modified TIE-2 ligand or peptide fragments thereof may be regulated by a second nucleic acid sequence which is operably linked to the a modified TIE-2 ligand encoding sequence such that the modified TIE-2 ligand protein or peptide is expressed in a host transformed with the recombinant DNA molecule. For example, expression of a modified TIE-2 ligand described herein may be controlled by any promoter/enhancer element known in the art. Promoters which may be used to control expression of the ligand include, but are not limited to the long terminal repeat as described in Squinto et al., (Cell 65:1–20 (1991)); the SV40 early promoter region (Bernoist and Chambon, Nature 290:304–310), the CMV promoter, the M-MuLV 5' terminal repeat, the promoter contained in the 3' long terminal repeat of Rous sarcoma virus (Yamamoto, et al., Cell 22:787–797 (1980)), the herpes thymidine kinase promoter (Wagner et al., Proc. Natl. Acad. Sci. U.S.A. 78:144–1445 (1981)), the adenovirus promoter, the regulatory sequences of the metallothionein gene (Brinster et al., Nature 296:39–42 (1982)); prokaryotic expression vectors such as the β-lactamase promoter (Villa-Kamaroff, et al., Proc. Natl. Acad. Sci. U.S.A. 75:3727–3731 (1978)), or the promoter (DeBoer, et al., Proc. Natl. Acad. Sci. U.S.A. 80:21–25 (1983)), see also "Useful proteins from recombinant bacteria" in Scientific American, 242:74–94 (1980); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals; elastase I gene control region which is active in pancreatic acinar cells (Swift et al., Cell 38:639–646 (1984); Ornitz et al., Cold Spring Harbor Symp. Quant. Biol. 50:399–409 (1986); MacDonald, Hepatology 7:425–515 (1987); insulin gene control region which is active in pancreatic beta cells [Hanahan, Nature 315:115–122 (1985)]; immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocytes in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378). The invention further encompasses the production of antisense compounds which are capable of specifically hybridizing with a sequence of RNA encoding a modified TIE-2 ligand to modulate its expression. Ecker, U.S. Pat. No. 5,166,195, issued Nov. 24, 1992.

Thus, according to the invention, expression vectors capable of being replicated in a bacterial or eukaryotic host comprising a nucleic acid encoding a modified TIE-2 ligand as described herein, are used to transfect a host and thereby direct expression of such nucleic acid to produce a modified TIE-2 ligand, which may then be recovered in a biologically active form. As used herein, a biologically active form includes a form capable of binding to TIE receptor and causing a biological response such as a differentiated function or influencing the phenotype of the cell expressing the receptor. Such biologically active forms could, for example, induce phosphorylation of the tyrosine kinase domain of TIE receptor. Alternatively, the biological activity may be an effect as an antagonist to the TIE receptor. In alternative embodiments, the active form of a modified TIE-2 ligand is one that can recognize TIE receptor and thereby act as a targeting agent for the receptor for use in both diagnostics and therapeutics. In accordance with such embodiments, the active form need not confer upon any TIE expressing cell any change in phenotype.

Expression vectors containing the gene inserts can be identified by four general approaches: (a) DNA-DNA hybridization, (b) presence or absence of "marker" gene functions, (c) expression of inserted sequences and (d) PCR detection. In the first approach, the presence of a foreign gene inserted in an expression vector can be detected by DNA-DNA hybridization using probes comprising sequences that are homologous to an inserted modified TIE-2 ligand encoding gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if a nucleic acid encoding a modified TIE-2 ligand is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of a modified TIE-2 ligand gene product, for example, by binding of the ligand to TIE receptor or a portion thereof which may be tagged with, for example, a detectable antibody or portion thereof or by binding to antibodies produced against the modified TIE-2 ligand protein or a portion thereof. Cells of the present invention may transiently or, preferably, constitutively and permanently express a modified TIE-2 ligand as described herein. In the fourth approach, DNA nucleotide primers can be prepared corresponding to a tie specific DNA sequence. These primers could then be used to PCR a tie gene fragment. (PCR Protocols: A Guide To Methods and Applications, Edited by Michael A. Innis et al., Academic Press (1990)).

The recombinant ligand may be purified by any technique which allows for the subsequent formation of a stable, biologically active protein. Preferably, the ligand is secreted into the culture medium from which it is recovered. Alternatively, the ligand may be recovered from cells either as soluble: proteins or as inclusion bodies, from which it may be extracted quantitatively by 8M guanidinium hydrochloride and dialysis in accordance with well known methodology. In order to further purify the ligand, affinity chromatography, conventional ion exchange chromatography, hydrophobic interaction chromatography, reverse phase chromatography or gel filtration may be used.

In additional embodiments of the invention, as described in greater detail in the Examples, a modified TIE-2 ligand encoding gene may be used to inactivate or "knock out" an endogenous gene by homologous recombination, and thereby create a TIE ligand deficient cell, tissue, or animal. For example, and not by way of limitation, the recombinant TIE ligand-4 encoding gene may be engineered to contain an insertional mutation, for example the neo gene, which would inactivate the native TIE ligand-4 encoding gene. Such a construct, under the control of a suitable promoter, may be introduced into a cell, such as an embryonic stem cell, by a technique such as transfection, transduction, or injection. Cells containing the construct may then be selected by G418 resistance. Cells which lack an intact TIE ligand-4 encoding gene may then be identified, e.g. by Southern blotting, PCR detection, Northern blotting or assay of expression. Cells lacking an intact TIE ligand-4 encoding gene may then be fused to early embryo cells to generate transgenic animals deficient in such ligand. Such an animal may be used to define specific in vivo processes, normally dependent upon the ligand.

The present invention also provides for antibodies to a modified TIE-2 ligand described herein which are useful for detection of the ligand in, for example, diagnostic applications. For preparation of monoclonal antibodies directed toward a modified TIE-2 ligand, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–25 7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of a modified TIE-2 ligand described herein. For the production of antibody, various host animals, including but not limited to rabbits, mice and rats can be immunized by injection with a modified TIE-2 ligand, or a fragment or derivative thereof. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*Bacille Calmette-Guerin*) and *Corynebacterium parvum*.

A molecular clone of an antibody to a selected a modified TIE-2 ligand epitope can be prepared by known techniques. Recombinant DNA methodology (see e.g, Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

The present invention further encompasses an immunoassay for measuring the amount of a modified TIE-2 ligand in a biological sample by
   a) contacting the biological sample with at least one antibody which specifically binds a modified TIE-2 ligand so that the antibody forms a complex with any modified TIE-2 ligand present in the sample; and
   b) measuring the amount of the complex and thereby measuring the amount of the modified TIE-2 ligand in the biological sample.

The invention further encompasses an assay for measuring the amount of TIE receptor in a biological sample by
   a) contacting the biological sample with at least one ligand of the invention so that the ligand forms a complex with the TIE receptor; and
   b) measuring the amount of the complex and thereby measuring the amount of the TIE receptor in the biological sample.

The present invention also provides for the utilization of a modified TIE-2 ligand which activates the TIE-2 receptor as described herein, to support the survival and/or growth and/or migration and/or differentiation of TIE-2 receptor expressing cells. Thus, the ligand may be used as a supplement to support, for example, endothelial cells in culture.

Further, the creation by applicants of a modified TIE-2 ligand for the TIE-2 receptor enables the utilization of assay systems useful for the identification of agonists or antagonists of the TIE-2 receptor. Such assay systems would be useful in identifying molecules capable of promoting or inhibiting angiogenesis. For example, in one embodiment, antagonists of the TIE-2 receptor may be identified as test molecules that are capable of interfering with the interaction of the TIE-2 receptor with a modified TIE-2 ligand that binds the TIE-2 receptor. Such antagonists are identified by their ability to 1) block the binding of a biologically active modified TIE-2 ligand to the receptor as measured, for example, using BlAcore biosensor technology (BlAcore; Pharmacia Biosensor, Piscataway, N.J.); or 2) block the ability of a biologically active modified TIE-2 ligand to cause a biological response. Such biological responses include, but are not limited to, phosphorylation of the TIE receptor or downstream components of the TIE signal transduction pathway, or survival, growth or differentiation of TIE receptor bearing cells.

In one embodiment, cells engineered to express the TIE receptor may be dependent for growth on the addition of a modified TIE-2 ligand. Such cells provide useful assay systems for identifying additional agonists of the TIE receptor, or antagonists capable of interfering with the activity of the modified TIE-2 ligand on such cells. Alternatively, autocrine cells, engineered to be capable of co-expressing both a modified TIE-2 ligand and receptor, may provide useful systems for assaying potential agonists or antagonists.

Therefore, the present invention provides for introduction of a TIE-2 receptor into cells that do not normally express this receptor, thus allowing these cells to exhibit profound and easily distinguishable responses to a ligand which binds this receptor. The type of response elicited depends on the cell utilized, and not the specific receptor introduced into the cell. Appropriate cell lines can be chosen to yield a response of the greatest utility for assaying, as well as discovering, molecules that can act on tyrosine kinase receptors. The molecules may be any type of molecule, including but not limited to peptide and non-peptide molecules, that will act in systems to be described in a receptor specific manner.

One of the more useful systems to be exploited involves the introduction of a TIE receptor (or a chimeric receptor comprising the extracellular domain of another receptor tyrosine kinase such as, for example, trkC and the intracellular domain of a TIE receptor) into a fibroblast cell line (e.g., NIH3T3 cells) thus such a receptor which does not normally mediate proliferative or other responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor. Such cells may be further engineered to express a modified TIE-2 ligand, thus creating an autocrine system useful for assaying for molecules that act as antagonists/agonists of this interaction. Thus, the present invention provides for host cells comprising nucleic acid encoding a modified TIE-2 ligand and nucleic acid encoding TIE receptor.

The TIE receptor/modified TIE-2 ligand interaction also provides a useful system for identifying small molecule agonists or antagonists of the TIE receptor. For example, fragments, mutants or derivatives of a modified TIE-2 ligand may be identified that bind TIE receptor but do not induce any other biological activity. Alternatively, the characterization of a modified TIE-2 ligand enables the further characterization of active portions of the molecule. Further, the identification of a ligand enables the determination of the X-ray crystal structure of the receptor/ligand complex, thus enabling identification of the binding site on the receptor. Knowledge of the binding site will provide useful insight into the rational design of novel agonists and antagonists.

The specific binding of a test molecule to TIE receptor may be measured in a number of ways. For example, the actual binding of test molecule to cells expressing TIE may be detected or measured, by detecting or measuring (i) test molecule bound to the surface of intact cells; (ii) test molecule cross-linked to TIE protein in cell lysates; or (iii) test molecule bound to TIE in vitro. The specific interaction between test molecule and TIE may be evaluated by using reagents that demonstrate the unique properties of that interaction.

As a specific, nonlimiting example, the methods of the invention may be used as follows. Consider a case in which a modified TIE-2 ligand in a sample is to be measured. Varying dilutions of the sample (the test molecule), in parallel with a negative control (NC) containing no modified TIE-2 ligand activity, and a positive control (PC) containing a known amount of a modified TIE-2 ligand, may be exposed to cells that express TIE in the presence of a detectably labeled modified TIE-2 ligand (in this example, radioiodinated ligand). The amount of modified TIE-2 ligand in the test sample may be evaluated by determining the amount of $^{125}$I-labeled modified TIE-2 ligand that binds to the controls and in each of the dilutions, and then comparing the sample values to a standard curve. The more modified TIE-2 ligand in the sample, the less $^{125}$I-ligand that will bind to TIE.

The amount of $^{125}$I-ligand bound may be determined by measuring the amount of radioactivity per cell, or by cross-linking a modified TIE-2 ligand to cell surface proteins using DSS, as described in Meakin and Shooter, 1991, Neuron 6:153–163, and detecting the amount of labeled protein in cell extracts using, for example, SDS polyacrylamide gel electrophoresis, which may reveal a labeled protein having a size corresponding to TIE receptor/modified TIE-2 ligand. The specific test molecule/TIE interaction may further be tested by adding to the assays various dilutions of an unlabeled control ligand that does not bind the TIE receptor and therefore should have no substantial effect on the competition between labeled modified TIE-2 ligand and test molecule for TIE binding. Alternatively, a molecule known to be able to disrupt TIE receptor/modified TIE-2 ligand binding, such as, but not limited to, anti-TIE antibody, or TIE receptorbody as described herein, may be expected to interfere with the competition between $^{125}$I-modified TIE-2 ligand and test molecule for TIE receptor binding.

Detectably labeled modified TIE-2 ligand includes, but is not limited to, a modified TIE-2 ligand linked covalently or noncovalently to a radioactive substance, a fluorescent substance, a substance that has enzymatic activity, a substance that may serve as a substrate for an enzyme (enzymes and substrates associated with calorimetrically detectable reactions are preferred) or to a substance that can be recognized by an antibody molecule that is preferably a detectably labeled antibody molecule.

Alternatively, the specific binding of test molecule to TIE may be measured by evaluating the secondary biological effects of a modified TIE-2 ligand/TIE receptor binding, including, but not limited to, cell growth and/or differentiation or immediate early gene expression or phosphorylation of TIE. For example, the ability of the test molecule to induce differentiation can be tested in cells that lack tie and in comparable cells that express tie; differentiation in tie-expressing cells but not in comparable cells that lack tie would be indicative of a specific test molecule/TIE interaction. A similar analysis could be performed by detecting immediate early gene (e.g. fos and jun) induction in tie-minus and tie-plus cells, or by detecting phosphorylation of TIE using standard phosphorylation assays known in the art. Such analysis might be useful in identifying agonists or antagonists that do not competitively bind to TIE.

Similarly, the present invention provides for a method of identifying a molecule that has the biological activity of a modified TIE-2 ligand comprising (i) exposing a cell that expresses tie to a test molecule and (ii) detecting the specific binding of the test molecule to TIE receptor, in which specific binding to TIE positively correlates with TIE-like activity. Specific binding may be detected by either assaying for direct binding or the secondary biological effects of binding, as discussed supra. Such a method may be particularly useful in identifying new members of the TIE ligand family or, in the pharmaceutical industry, in screening a large array of peptide and non-peptide molecules (e.g., peptidomimetics) for TIE associated biological activity. In a preferred, specific, nonlimiting embodiment of the invention, a large grid of culture wells may be prepared that contain, in alternate rows, PC12 (or fibroblasts, see infra) cells that are either tie-minus or engineered to be tie-plus. A variety of test molecules may then be added such that each column of the grid, or a portion thereof, contains a different test molecule. Each well could then be scored for the presence or absence of growth and/or differentiation. An extremely large number of test molecules could be screened for such activity in this manner.

In additional embodiments, the invention provides for methods of detecting or measuring TIE ligand-like activity or identifying a molecule as having such activity comprising (i) exposing a test molecule to a TIE receptor protein in vitro under conditions that permit binding to occur and (ii) detecting binding of the test molecule to the TIE receptor protein, in which binding of test molecule to TIE receptor correlates with TIE ligand-like activity. According to such methods, the TIE receptor may or may not be substantially purified, may be affixed to a solid support (e.g. as an affinity column or as an ELISA assay), or may be incorporated into an artificial membrane. Binding of test molecule to TIE receptor may be evaluated by any method known in the art. In preferred embodiments, the binding of test molecule may be detected or measured by evaluating its ability to compete with detectably labeled known TIE ligands for TIE receptor binding.

The present invention also provides for a method of detecting the ability of a test molecule to function as an antagonist of TIE ligand-like activity comprising detecting the ability of the molecule to inhibit an effect of TIE ligand binding to TIE receptor on a cell that expresses the receptor. Such an antagonist may or may not interfere with TIE receptor/modified TIE-2 ligand binding. Effects of a modified TIE-2 ligand binding to TIE receptor are preferably biological or biochemical effects, including, but not limited to, cell survival or proliferation, cell transformation, immediate early gene induction, or TIE phosphorylation.

The invention further provides for both a method of identifying antibodies or other molecules capable of neutralizing the ligand or blocking binding to the receptor, as well as the molecules identified by the method. By way of nonlimiting example, the method may be performed via an assay which is conceptually similar to an ELISA assay. For example, TIE receptorbody may be bound to a solid support, such as a plastic multiwell plate. As a control, a known amount of a modified TIE-2 ligand which has been Myc-tagged may then be introduced to the well and any tagged modified TIE-2 ligand which binds the receptorbody may then be identified by means of a reporter antibody directed against the Myc-tag. This assay system may then be used to screen test samples for molecules which are capable of i) binding to the tagged ligand or ii) binding to the receptorbody and thereby blocking binding to the receptorbody by the tagged ligand. For example, a test sample containing a putative molecule of interest together with a known amount of tagged ligand may be introduced to the well and the amount of tagged ligand which binds to the receptorbody may be measured. By comparing the amount of bound tagged ligand in the test sample to the amount in the control, samples containing molecules which are capable of blocking ligand binding to the receptor may be identified. The molecules of interest thus identified may be isolated using methods well known to one of skill in the art.

Once a blocker of ligand binding is found, one of skill in the art would know to perform secondary assays to determine whether the blocker is binding to the receptor or to the ligand, as well as assays to determine if the blocker molecule can neutralize the biological activity of the ligand. For example, by using a binding assay which employs BIAcore biosensor technology (or the equivalent), in which either TIE receptorbody or a modified TIE-2 ligand or ligandbody is covalently attached to a solid support (e.g. carboxymethyl dextran on a gold surface), one of skill in the art would be able to determine if the blocker molecule is binding specifically to the ligand, ligandbody or to the receptorbody. To determine if the blocker molecule can neutralize the biological activity of the ligand, one of skill in the art could perform a phosphorylation assay (see Example 5) or alternatively, a functional bioassay, such as a survival assay, by using primary cultures of, for example, endothelial cells. Alternatively, a blocker molecule which binds to the receptorbody could be an agonist and one of skill in the art would know to how to determine this by performing an appropriate assay for identifying additional agonists of the TIE receptor.

In addition, the invention further contemplates compositions wherein the TIE ligand is the receptor binding domain of a TIE-2 ligand described herein. For example, TIE-2 ligand 1 contains a "coiled coil" domain (beginning at the 5' end and extending to the nucleotide at about position 1160 of FIGS. 4A–4D (SEQ. ID. NO. 1 and SEQ. ID. NO. 2) and about position 1157 of FIGS. 5A–5D (SEQ. ID. NO. 3 and SEQ. ID. NO. 4)) and a fibrinogen-like domain (which is encoded by the nucleotide sequence of FIGS. 4A–4D (SEQ. ID. NO. 1 and SEQ. ID. NO. 2) beginning at about position 1161 and about position 1158 of FIGS. 5A–5D (SEQ. ID. NO. 3 and SEQ. ID. NO. 4)). The fibrinogen-like domain of TIE-2 ligand 2 is believed to begin on or around the same amino acid sequence as in ligand 1 (FRDCA) which is encoded by nucleotides beginning around 1197 of FIGS. 6A–6D (SEQ. ID. NO. 5 and SEQ. ID. NO. 6). The fibrinogen-like domain of TIE ligand-3 is believed to begin on or around the amino acid sequence which is encoded by nucleotides beginning around position 929 as set forth in FIGS. 21A–21C (SEQ. ID. NO. 9 and SEQ. ID. NO. 10). Multimerization of the coiled coil domains during production of the ligand hampers purification. As described in Example 19, Applicants have discovered, however, that the fibrinogen-like domain comprises the TIE-2 receptor binding domain. The monomeric forms of the fibrinogen-like domain do not, however, appear to bind the receptor. Studies utilizing myc-tagged fibrinogen-like domain, which has been "clustered" using anti-myc antibodies, do bind the TIE-2 receptor. [Methods of production of "clustered ligands and ligandbodies are described in Davis, et al. Science 266:816–819 (1994)]. Based on these finding, applicants produced "ligandbodies" which comprise the fibrinogen-like domain of the TIE-2 ligands coupled to the Fc domain of IgG ("fFc's"). These ligandbodies, which form dimers, efficiently bind the TIE-2 receptor. Accordingly, the present invention contemplates the production of modified TIE ligandbodies which may be used as targeting agents, in diagnostics or in therapeutic applications, such as targeting agents for tumors and/or associated vasculature wherein a TIE antagonist is indicated.

The invention herein further provides for the development of the ligand, a fragment or derivative thereof, or another molecule which is a receptor agonist or antagonist, as a therapeutic for the treatment of patients suffering from disorders involving cells, tissues or organs which express the TIE receptor. Such molecules may be used in a method of treatment of the human or animal body, or in a method of diagnosis.

Because TIE receptor has been identified in association with endothelial cells and, as demonstrated herein, blocking of TIE-2 ligand 1 appears to prevent vascularization, applicants expect that a modified TIE-2 ligand described herein may be useful for the induction of vascularization in diseases or disorders where such vascularization is indicated. Such diseases or disorders would include wound healing, ischaemia and diabetes. The ligands may be tested in animal models and used therapeutically as described for other agents, such as vascular endothelial growth factor (VEGF), another endothelial cell-specific factor that is angiogenic. Ferrara, et al. U.S. Pat. No. 5,332,671 issued Jul. 26, 1994. The Ferrara reference, as well as other studies, describe in vitro and in vivo studies that may be used to demonstrate the effect of an angiogenic factor in enhancing blood flow to ischemic myocardium, enhancing wound healing, and in other therapeutic settings wherein neoangiogenesis is desired. [see Sudo, et al. European Patent Application 0 550 296 A2 published Jul. 7, 1993; Banai, et al. Circulation 89:2183–2189 (1994); Unger, et al. Am. J. Physiol. 266:H1588–H1–595 (1994); Lazarous, et al. Circulation 91:145–153 (1995)]. According to the invention, a modified TIE-2 ligand may be used alone or in combination with one or more additional pharmaceutically active compounds such as, for example, VEGF or basic fibroblast growth factor (bFGF), as well as cytokines, neurotrophins, etc.

Conversely, antagonists of the TIE receptor, such as modified TIE-2 ligands which bind but do not activate the receptor as described herein, receptorbodies as described herein in Examples 2 and 3, and TIE-2 ligand 2 as described in Example 9, would be useful to prevent or attenuate vascularization, thus preventing or attenuating, for example, tumor growth. These agents may be used alone or in combination with other compositions, such as anti-VEGF antibodies, that have been shown to be useful in treating conditions in which the therapeutic intent is to block angiogenesis. Applicants expect that a modified TIE-2 ligand described herein may also be used in combination with agents, such as cytokine antagonists such as IL-6 antagonists, that are known to block inflammation.

For example, applicants have determined that TIE ligands are expressed in cells within, or closely associated with, tumors. For example, TIE-2 ligand 2 appears to be tightly associated with tumor endothelial cells. Accordingly, it and other TIE antagonists may also be useful in preventing or attenuating, for example, tumor growth. In addition, TIE ligands or ligandbodies may be useful for the delivery of toxins to a receptor bearing cell. Alternatively, other molecules, such as growth factors, cytokines or nutrients, may be delivered to a TIE receptor bearing cell via TIE ligands or ligandbodies. TIE ligands or ligandbodies such as modified TIE-2 ligand described herein may also be used as diagnostic reagents for TIE receptor, to detect the receptor in vivo or in vitro. Where the TIE receptor is associated with a disease state, TIE ligands or ligandbodies such as a modified TIE-2 ligand may be useful as diagnostic reagents for detecting the disease by, for example, tissue staining or whole body imaging. Such reagents include radioisotopes, flurochromes, dyes, enzymes and biotin. Such diagnostics or targeting agents may be prepared as described in Alitalo, et al. WO 95/26364 published Oct. 5, 1995 and Burrows, F. and P. Thorpe, PNAS (USA) 90:8996–9000 (1993) which is incorporated herein in its entirety.

In other embodiments, the TIE ligands, a receptor activating modified TIE-2 ligand described herein are used as hematopoietic factors. A variety of hematopoietic factors and their receptors are involved in the proliferation and/or differentiation and/or migration of the various cells types contained within blood. Because the TIE receptors are expressed in early hematopoietic cells, the TIE ligands are expected to play a comparable role in the proliferation or differentiation or migration of these cells. Thus, for example, TIE containing compositions may be prepared, assayed, examined in in vitro and in vivo biological systems and used therapeutically as described in any of the following: Sousa, U.S. Pat. No. 4,810,643, Lee, et al., Proc. Natl. Acad. Sci. USA 82:4360–4364 (1985) Wong, et al. Science, 228:810–814 (1985); Yokota, et al. Proc. Natl. Acad. Sci (USA) 81:1070 (1984); Bosselman, et al. WO 9105795 published May 2, 1991 entitled "Stem Cell Factor" and Kirkness, et al. WO 95/19985 published Jul. 27, 1995 entitled "Haemopoietic Maturation Factor". Accordingly receptor activating modified TIE-2 ligand may be used to diagnose or treat conditions in which normal hematopoiesis is suppressed, including, but not limited to anemia, thrombocytopenia, leukopenia and granulocytopenia. In a preferred embodiment, receptor activating modified TIE-2 ligand may be used to stimulate differentiation of blood cell precursors in situations where a patient has a disease, such as acquired immune deficiency syndrome (AIDS) which has caused a reduction in normal blood cell levels, or in clinical settings in which enhancement of hematopoietic populations is desired, such as in conjunction with bone marrow transplant, or in the treatment of aplasia or myelosuppression caused by radiation, chemical treatment or chemotherapy.

The receptor activating modified TIE-2 ligands of the present invention may be used alone, or in combination with another pharmaceutically active agent such as, for example, ctyokines, neurotrophins, interleukins, etc. In a preferred embodiment, the ligands may be used in conjunction with any of a number of the above referenced factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF, etc.

In an alternative embodiment, TIE receptor antagonists are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the a modified TIE-2 ligand, TIE antibody, TIE receptorbody, a conjugate of a modified TIE-2 ligand, or a ligandbody or fFC as described herein.

The present invention also provides for pharmaceutical compositions comprising a modified TIE-2 ligand or ligandbodies described herein, peptide fragments thereof, or derivatives in a pharmacologically acceptable vehicle. The modified TIE-2 ligand proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The invention further provides for a therapeutic composition comprising a modified TIE-2 ligand or ligandbody and a cytotoxic agent conjugated thereto. In one embodiment, the cytotoxic agent may be a radioisotope or toxin.

The invention also provides for an antibody which specifically binds a modified TIE-2 ligand. The antibody may be monoclonal or polyclonal. The invention further provides for a method of purifying a modified TIE-2 ligand comprising:

a) coupling at least one TIE binding substrate to a solid matrix;
b) incubating the substrate of a) with a cell lysate so that the substrate forms a complex with any modified TIE-2 ligand in the cell lysate;
c) washing the solid matrix; and
d) eluting the modified TIE-2 ligand from the coupled substrate.

The substrate may be any substance that specifically binds the modified TIE-2 ligand. In one embodiment, the substrate is selected from the group consisting of anti-modified TIE-2 ligand antibody, TIE receptor and TIE receptorbody. The invention further provides for a receptorbody which specifically binds a modified TIE-2 ligand, as well as a therapeutic composition comprising the receptorbody in a pharmaceutically acceptable vehicle, and a method of blocking blood vessel growth in a human comprising administering an effective amount of the therapeutic composition.

The invention also provides for a therapeutic composition comprising a receptor activating modified TIE-2 ligand or ligandbody in a pharmaceutically acceptable vehicle, as well as a method of promoting neovascularization in a patient comprising administering to the patient an effective amount of the therapeutic composition.

In addition, the present invention provides for a method for identifying a cell which expresses TIE receptor which comprises contacting a cell with a detectably labeled modified TIE-2 ligand or ligandbody, under conditions permitting binding of the detectably labeled ligand to the TIE receptor and determining whether the detectably labeled ligand is bound to the TIE receptor, thereby identifying the cell as one which expresses TIE receptor. The present invention also provides for a therapeutic composition comprising a modified TIE-2 ligand or ligandbody and a cytotoxic agent conjugated thereto. The cytotoxic agent may be a radioisotope or toxin.

The invention also provides a method of detecting expression of a modified TIE-2 ligand by a cell which comprises obtaining mRNA from the cell, contacting the mRNA so obtained with a labeled nucleic acid molecule encoding a modified TIE-2 ligand, under hybridizing conditions, determining the presence of mRNA hybridized to the labeled molecule, and thereby detecting the expression of a modified TIE-2 ligand in the cell.

The invention further provides a method of detecting expression of a modified TIE-2 ligand in tissue sections which comprises contacting the tissue sections with a labeled nucleic acid molecule encoding a modified TIE-2 ligand, under hybridizing conditions, determining the presence of mRNA hybridized to the labelled molecule, and thereby detecting the expression of a modified TIE-2 ligand in tissue sections.

EXAMPLE 1

IDENTIFICATION OF THE ABAE CELL LINE AS REPORTER CELLS FOR THE TIE-2 RECEPTOR

Adult BAE cells are registered in the European Cell Culture Repository, under ECACC#92010601. (See PNAS 75:2621 (1978)). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and subjected to immunoprecipitation, followed by Western blot analyses of immunoprecipitated proteins with TIE-2 specific and phosphotyrosine-specific antisera. Omission or inclusion of TIE-2 peptides as specific blocking molecules during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2 \times 10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors PMSF and aprotinin. Insoluble debris was removed from the cell lysates by centrifugation at 14,000×G for 10 minutes, at 4° C. and the supernatants were subjected to immunoprecipitation with antisera specific for TIE-2 receptor, with or without the presence of blocking peptides added to ~20 µg/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2 protein was visualized by incubation of the membrane with HRP-linked secondary antisera followed by treatment with ECL reagent (Amersham).

EXAMPLE 2

CLONING AND EXPRESSION OF TIE-2 RECEPTORBODY FOR AFFINITY-BASED STUDY OF TIE-2 LIGAND INTERACTIONS

An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin, et. al. Cell 73:447–456 (1993).

Milligram quantities of TIE-2 RB were obtained by cloning the TIE-2 RB DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the TIE-2 RB was cloned as an Eco RI-Notl fragment into the baculovirus transfer plasmid pVL1393. Plasmid DNA purified by cesium chloride density gradient centrifugation was recombined into viral DNA by mixing 3 $\mu$g of plasmid DNA with 0.5 $\mu$g of Baculo-Gold DNA (Pharminigen), followed by introduction into liposomes using 30 $\mu$g Lipofectin (GIBCO-BRL). DNA-liposome mixtures were added to SF-21AE cells ($2 \times 10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, *Baculovirus Expression Vectors—A Laboratory Manual*. 1992, New York: W. H. Freeman) except that the agarose overlay contained 125 $\mu$g/mL X-gal (5-bromo-4-chloro-3-indolyl-$\beta$-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 $\mu$g/mL MTT (3-[4,5-dimethylthiazol-2-yl]2,5, diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptorbody) were produced.

SF-21AE cells were cultured in serum free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection.

Cells were grown at 27° C., with gassing to 50% dissolved oxygen, at a gas flow rate of 80 ml/min (aeration at a sparge ring). Agitation was by means of a marine impeller at a rate of 100 rpm. Cells were harvested in mid-logarithmic growth phase (~$2 \times 10^6$ cells/mL), concentrated by centrifugation, and infected with 5 plaque forming units of vTIE-2 receptorbody per cell. Cells and inoculum were brought to 400 mL with fresh medium, and virus was adsorbed for 2 hours at 27° C. in a spinner flask. The culture was then resuspended in a final volume of 8L with fresh serum-free medium, and the cells incubated in the bioreactor using the previously described conditions.

Culture medium from vTIE-2 receptorbody-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 $\mu$m, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TIE-2 receptorbody were pooled and dialyzed versus PBS.

EXAMPLE 3

DEMONSTRATION THAT TIE-2 HAS A CRITICAL ROLE IN DEVELOPMENT OF THE VASCULATURE

Insight into the function of TIE-2 was gained by introduction of "excess" soluble TIE-2 receptorbody (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extra-embryonically-derived endothelial cells, which provide the major source of endothelial cells in the embryo, originate from accretions of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intra-embryonically-derived vascular elements.

Newly fertilized chicken eggs obtained from Spafas, Inc. (Boston, Mass.) were incubated at 99.5° F., 55% relative humidity. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE-2- or EHK-1 receptorbody. EHK-1 receptorbody was made as set forth in Example 2 using the EHK-1 extracellular domain instead of the TIE-2 extracellular domain (Maisonpierre et al., Oncogene 8:3277–3288 (1993). Each Gelfoam piece absorbed approximately 6 µg of protein in 30 µl. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similarly-staged eggs were treated in parallel with RB of the unrelated, neuronally expressed receptor tyrosine kinase, EHK-1 (Maisonpierre et al., Oncogene 8:3277–3288 (1993). Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos, as shown in FIGS. 1A and 1B. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2–5 mm. in diameter, as compared with more than 10 mm in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

EXAMPLE 4

IDENTIFICATION OF A TIE-2-SPECIFIC BINDING ACTIVITY IN CONDITIONED MEDIUM FROM THE ras ONCOGENE-TRANSFORMED C2C12 MOUSE MYOBLAST CELL LINE Screening of ten-fold-concentrated cell-conditioned media (10×CCM) from various cell lines for the presence of soluble, TIE-2-specific binding activity (BIAcore; Pharmacia Biosensor, Piscataway, N.J.) revealed binding activity in serum-free medium from oncogenic-ras-transformed C2C12 cells (C2C12-ras), RAT 2-ras (which is a ras transformed fibroblast cell line), human glioblastoma T98G and the human neuroblastoma cell line known as SHEP-1.

The C2C12-ras 10×CCM originated from a stably transfected line of C2C12 myoblasts that was oncogenically transformed by transfection with the T-24 mutant of H-ras by standard calcium phosphate-based methods. An SV40 based neomycin-resistance expression plasmid was physically linked with the ras expression plasmid in order to permit selection of transfected clones. Resulting G418-resistant ras-C2C12 cells were routinely maintained as a monolayer on plastic dishes in DMEM/glutamine/penicillin-streptomycin supplemented with 10% fetal calf serum (FCS). Serum-free C2C12-ras 10×CCM was made by plating the cells at 60% confluence in a serum free defined media for 12 hours. [Zhan and Goldfarb, Mol. Cell. Biol. 6: 3541–3544 (1986)); Zhan, et al. Oncogene 1: 369–376 (1987)]. The medium was discarded and replaced with fresh DMEM/Q/P-S for 24 hours. This medium was harvested and cells were re-fed fresh DMEM/Q/P-S, which was also harvested after a further 24 hours. These CCM were supplemented with the protease inhibitors PMSF (1 mM) and aprotinin (10 µg/ml), and ten-fold concentrated on sterile size-exclusion membranes (Amicon). TIE-2-binding activity could be neutralized by incubation of the medium with an excess of TIE-2 RB, but not by incubation with EHK-1 RB, prior to BlAcore analysis.

Binding activity of the 10×CCM was measured using biosensor technology (BIAcore; Pharmacia Biosensor, Piscataway, N.J.) which monitors biomolecular interactions in real-time via surface plasmon resonance. Purified TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 µg/mL, pH 4.5) and deactivation of unreacted sites with 1.0 M ethanolamine (pH 8.5). A negative control surface of the EHK-1 receptorbody was prepared in a similar manner.

The running buffer used in the system was HBS (10 mM Hepes, 3.4 mM EDTA, 150 mM NaCl, 0.005% P20 surfactant, pH 7.4). The 10×CCM samples were centrifuged for 15 min at 4° C. and further clarified using a sterile, low protein-binding 0.45 µm filter (Millipore; Bedford, Mass.). Dextran (2 mg/ml) and P20 surfactant (0.005%) were added to each CCM sample. Aliquots of 40 µL were injected across the immobilized surface (either TIE-2 or EHK-1) at a flow rate of 5 µl/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 12-µL pulse of 3 M $MgCl_2$.

The instrument noise level is 20 RU; therefore, any binding activity with a signal above 20 RU may be interpreted as a real interaction with the receptor. For C2C12-ras conditioned media, the binding activities were in the range 60–90 RU for the TIE-2 RB immobilized surface. For the same samples assayed on a EHK-1 RB immobilized surface, the measured activities were less than 35 RU. Specific binding to the TIE-2 receptorbody was evaluated by incubating the samples with an excess of either soluble TIE-2 or EHK-1 RB prior to assaying the binding activity. The addition of soluble EHK-1 RB had no effect on the TIE-2 binding activity of any of the samples, while in the presence of soluble TIE-2 binding to the surface is two-thirds less than that measured in the absence of TIE-2. A repeat assay using >50×concentrated C2C12-ras CCM resulted in a fourfold enhancement over background of the TIE-2 specific binding signal.

EXAMPLE 5

C2C12-ras CCM CONTAINS AN ACTIVITY THAT INDUCES TYROSINE PHOSPHORYLATION OF TIE-2 RECEPTOR C2C12-ras 10×CCM was examined for its ability to induce tyrosine phosphorylation of TIE-2 in ABAE cells.

Serum-starved ABAE cells were briefly incubated with C2C12-ras CCM, lysed and subjected to immunoprecipitation and Western analyses as described above. Stimulation of serum-starved ABAE cells with serum-free C2C12-ras 10×CCM was done as follows. The medium of ABAE cells starved as described above was removed and replaced with either defined medium or 10×CCM that had been pre-warmed to 37° C. After 10 minutes, the media were removed and the cells were twice rinsed on ice with an excess of chilled PBS supplemented with orthovanadate/NaF/ benzamidine. Cell lysis and TIE-2-specific immunoprecipitation was done as described above.

ABAE cells incubated for 10 minutes with defined medium showed no induction of TIE-2 tyrosine phosphorylation, whereas incubation with C2C12-ras CCM stimulated at least a 100×increase in TIE-2 phosphorylation. This activity was almost totally depleted by pre-incubation of the C2C12-ras 10×CCM for 90 minutes at room temperature with 13 μg of TIE-2 RB coupled to protein G-Sepharose beads. Medium incubated with protein G Sepharose alone was not depleted of this phosphorylating activity.

EXAMPLE 6

EXPRESSION CLONING OF TIE-2 LIGAND

Figure 2:
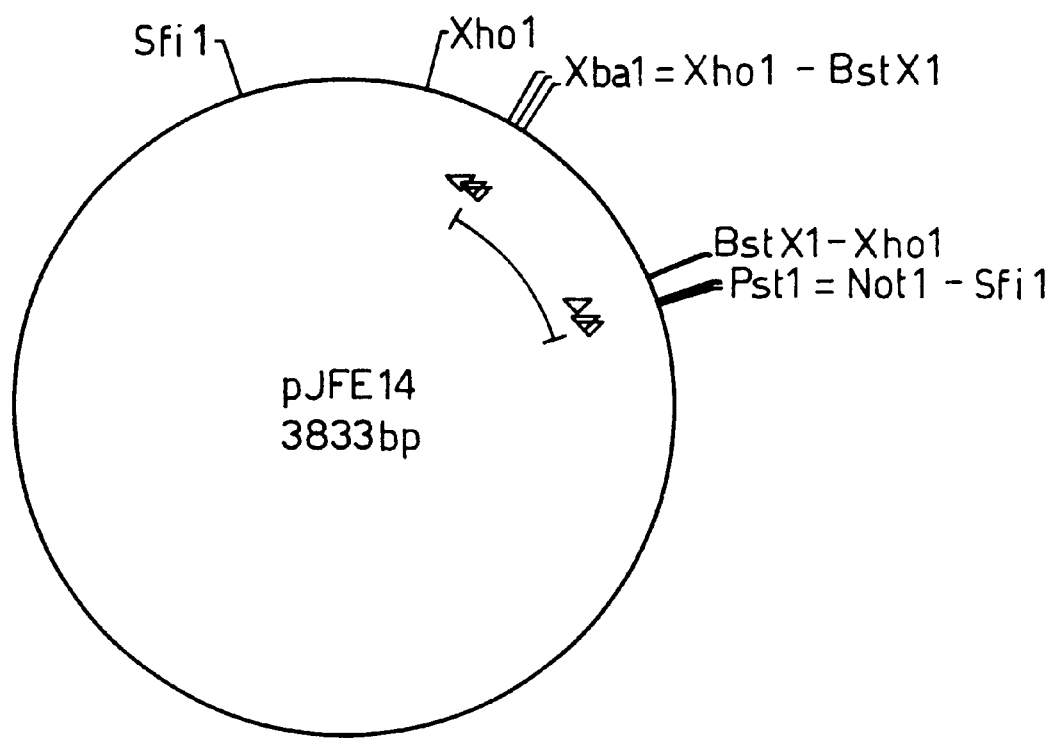
FIG. 2—Vector pJFE14.

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The mouse myoblast C2C12 ras cell line was cultured in Eagle's minimal essential medium (EMEM) with 10% FBS, (P/S) and 2 mM glutamine. Full length mouse TIE-2 ligand cDNA clones were obtained by screening a C2C12 ras cDNA library in the pJFE14 vector expressed in COS cells. This vector, as shown in FIG. 2, is a modified version of the vector $pSR_\alpha$ (Takebe, et al. 1988, Mol. Cell. Biol. 8:466–472). The library was created using the two BSTX1 restriction sites in the pJFE14 vector.

COS-7 cells were transiently transfected with either the pJFE14 library or control vector by the DEAE-dextran transfection protocol. Briefly, COS-7 cells were plated at a density of $1.0×10^6$ cells/100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with PBS with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Two days after transfection the cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody (RB), which consisted of the extracellular domain of TIE-2 fused to the IgG1 constant region. This receptorbody was prepared as set forth in Example 2. A 100 mm dish of transfected, fixed and permeabilized COS cells was probed by incubating them for 30 min with TIE-2 RB. The cells were then washed twice with PBS and incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. For each stained cell, a small area of cells including the stained cell was scraped from the dish using a plastic pipette tip and plasmid DNA was then rescued and used to electroporate bacterial cells. Single bacterial colonies resulting from the electroporation were picked and plasmid DNA prepared from these colonies was used to transfect COS-7 cells which were probed for TIE-2 ligand expression as evidenced by binding to TIE-2 receptorbodies. This allowed identification of single clones coding for TIE-2 ligand. Confirmation of TIE-2 ligand expression was obtained by phosphorylation of the TIE-2 receptor using the method set forth in Example 5. A plasmid clone encoding the TIE-2 ligand was deposited with the ATCC on Oct. 7, 1994 and designated as "pJFE14 encoding TIE-2 ligand" under ATCC Accession No. 75910.

EXAMPLE 7

ISOLATION AND SEQUENCING OF FULL LENGTH cDNA CLONE ENCODING HUMAN TIE-2 LIGAND

Figure 3:
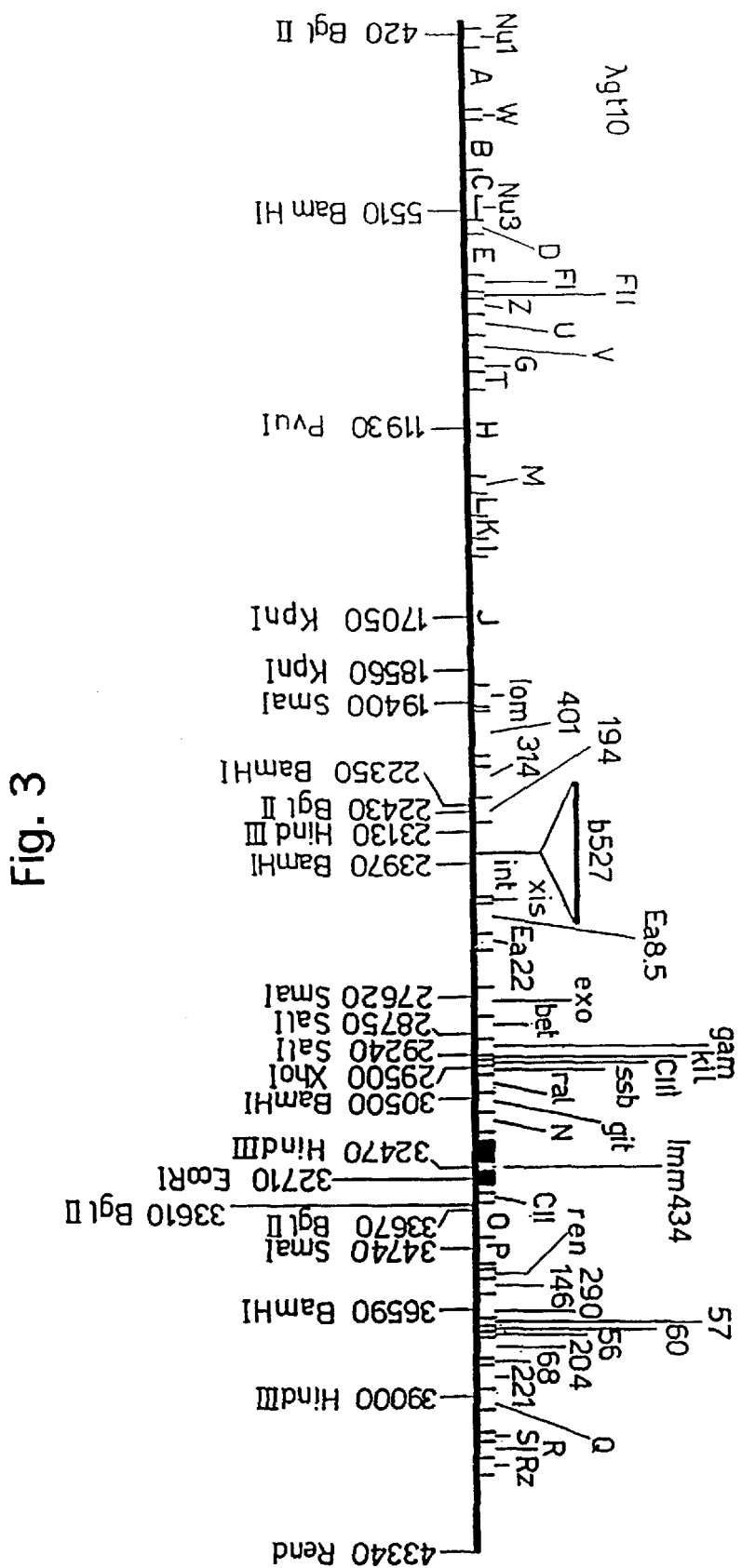
FIG. 3—Restriction map of λgt10.

A human fetal lung cDNA library in lambda gt-10 (see FIG. 3) was obtained from Clontech Laboratories, Inc. (Palo Alto, Calif.). Plaques were plated at a density of $1.25×10^6$/ 20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.).

Isolation of human tie-2 ligand clones was carried out as follows. A 2.2 kb XhoI fragment from the deposited tie-2 ligand clone (ATCC NO. 75910—see Example 6 above) was labeled by random priming to a specific activity of approximately $5×10^8$ cpm/ng. Hybridization was carried out at 65° C. in hybridization solution containing 0.5 mg/ml salmon sperm DNA. The filters were washed at 65° C. in 2×SSC, 0.1% SDS and exposed to Kodak XAR-5 film overnight at −70° C. Positive phage were plaque purified. High titre phage lysates of pure phage were used for isolation of DNA via a Qiagen column using standard techniques (Qiagen, Inc., Chatsworth, Calif., 1995 catalog, page 36). Phage DNA was digested with EcoRI to release the cloned cDNA fragment for subsequent subcloning. A lambda phage vector containing human tie-2 ligand DNA was deposited with the ATCC on Oct. 26, 1994 under the designation λgt10 encoding htie-2 ligand 1 (ATCC Accession No. 75928). Phage DNA may be subjected directly to DNA sequence analysis by the dideoxy chain termination method (Sanger, et al., 1977, Proc. Natl. Acad. Sci. U.S.A. 74: 5463–5467).

Subcloning of the human tie-2 ligand DNA into a mammalian expression vector may be accomplished as follows. The clone λgt10 encoding htie-2 ligand 1 contains an EcoRI site located 490 base pairs downstream from the start of the coding sequence for the human TIE-2 ligand. The coding region may be excised using unique restriction sites upstream and downstream of the initiator and stop codons respectively. For example, an SpeI site, located 70 bp 5' to the initiator codon, and a Bpu1102i (also known as BIpi) site, located 265 bp 3' to the stop codon, may be used to excise the complete coding region. This may then be subcloned into the pJFE14 cloning vector, using the XbaI (compatible to the Spel overhang) and the PstI sites (the PstI and Bpu1102i sites are both made blunt ended).

The coding region from the clone λgt10 encoding htie-2 ligand 1 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE-2 ligand from the clone λgt10 encoding htie-2 ligand 1 is shown in FIGS. 4A–4D (SEQ. ID. NO. 1 and SEQ. ID. NO. 2).

In addition, full length human tie-2 ligand cDNA clones were obtained by screening a human glioblastoma T98G cDNA library in the pJFE14 vector. Clones encoding human TIE-2 ligand were identified by DNA hybridization using a 2.2 kb XhoI fragment from the deposited tie-2 ligand clone (ATCC NO. 75910) as a probe (see Example 6 above). The coding region was sequenced using the ABI 373A DNA sequencer and Taq Dideoxy Terminator Cycle Sequencing Kit (Applied Biosystems, Inc., Foster City, Calif.). This sequence was nearly identical to that of clone λgt10 encoding htie-2 ligand 1. As shown in FIGS. 4A–4D (SEQ. ID. NO. 1 and SEQ. ID. NO. 2), the clone λgt10 encoding htie-2 ligand 1 contains an additional glycine residue which is encoded by nucleotides 1114–1116. The coding sequence of the T98G clone does not contain this glycine residue but otherwise is identical to the coding sequence of the clone λgt10 encoding htie-2 ligand 1. FIGS. 5A–5D (SEQ. ID. NO. 1 and SEQ. ID. NO. 4) sets forth the nucleotide and deduced amino acid sequence of human TIE-2 ligand from the T98G clone.

EXAMPLE 8

ISOLATION AND SEQUENCING OF SECOND FULL LENGTH cDNA CLONE A ENCODING HUMAN TIE-2 LIGAND

A human fetal lung cDNA library in lambda gt-10 (see FIG. 3) was obtained from Clontech Laboratories, Inc. (Palo Alto, Calif.). Plaques were plated at a density of 1.25×10⁶/20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.). Duplicate filters were screened at low stringency (2×SSC, 55° C.) with probes made to the human TIE-2 ligand 1 sequence. One of the duplicate filters was probed with a 5' probe, encoding amino acids 25–265 of human TIE-2 ligand 1 as set forth in FIGS. 4A–4D (SEQ. ID. NO. 1 and SEQ. ID. NO. 2). The second duplicate filter was probed with a 3' probe, encoding amino acids 282–498 of human TIE-2 ligand 1 sequence (see FIGS. 4A–4D (SEQ. ID. NO. 1 and SEQ. ID. NO. 2)). Both probes were hybridized at 55° C. in hybridization solution containing 0.5 mg/ml salmon sperm DNA. Filters were washed in 2×SSC at 55° C. and exposed overnight to X-ray film. In addition, duplicate filters were also hybridized at normal stringency (2×SSC, 65° C.) to the full length coding probe of mouse TIE-2 ligand 1 (F3-15, XhoI insert). Three positive clones were picked that fulfilled the following criteria: i. hybridization had not been seen to the full length (mouse) probe at normal stringency, and ii. hybridization was seen at low stringency to both 5' and 3' probes. EcoRI digestion of phage DNA obtained from these clones indicated two independent clones with insert sizes of approximately 2.2 kb and approximately 1.8 kb. The 2.2 kb EcoRI insert was subcloned into the EcoRI sites of both pBluescript KS (Stratagene) and a mammalian expression vector suitable for use in COS cells. Two orientations were identified for the mammalian expression vector. The 2.2 kb insert in pBluescript KS was deposited with the ATCC on Dec. 9, 1994 and designated as pBluescript KS encoding human TIE 2 ligand 2. The start site of the TIE-2 ligand 2 coding sequence is approximately 355 base pairs downstream of the pBluescript EcoRI site.

COS-7 cells were transiently transfected with either the expression vector or control vector by the DEAE-dextran transfection protocol. Briefly, COS-7 cells were plated at a density of 1.0×10⁶ cells/100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Transfected COS-7 cells were plated at a density of 1.0×10⁶ cells/100 mm plate. The cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites. The screening was conducted by direct localization of staining using a TIE-2 receptorbody, which consisted of the extracellular domain of TIE-2 fused to the IgG1 constant region. This receptorbody was prepared as set forth in Example 2. Transfected COS cells were probed by incubating them for 30 min with TIE-2 receptorbody. The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. Cells expressing one orientation of the clone, but not the other orientation, were seen to bind the TIE-2 receptorbody.

One of skill in the art will readily see that the described methods may be used to further identify other related members of the TIE ligand family.

The coding region from the clone pBluescript KS encoding human TIE-2 ligand 2 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE-2 ligand from the clone pBluescript KS encoding human TIE-2 ligand 2 is shown in FIG. 6 (SEQ. ID. NO. 5 and SEQ. ID. NO. 6).

EXAMPLE 9

TIE-2 LIGAND 2 IS A RECEPTOR ANTAGONIST

Conditioned media from COS cells expressing either TIE-2 ligand 2 (TL2) or TIE-2 ligand 1 (TL1) were compared for their ability to activate TIE-2 receptors naturally present in human endothelial cell lines.

Lipofectamine reagent (GIBCO-BRL, Inc.) and recommended protocols were used to transfect COS-7 cells with either the pJFE14 expression vector alone, pJFE14 vector containing the human TIE-2 ligand 1 cDNA, or with a pMT21 expression vector (Kaufman, R. J., 1985, Proc. Natl. Acad. Sci. USA 82: 689–693) containing the human TIE-2 ligand 2 cDNA. COS media containing secreted ligands were harvested after three days and concentrated 20-fold by diafiltration (DIAFLO ultrafiltration membranes, Amicon, Inc.). The quantity of active TIE-2 ligand 1 and TIE-2 ligand 2 present in these media was determined and expressed as the amount (in resonance units, R.U.) of TIE-2 receptor specific binding activity measured by a BIAcore binding assay.

Figure 7:
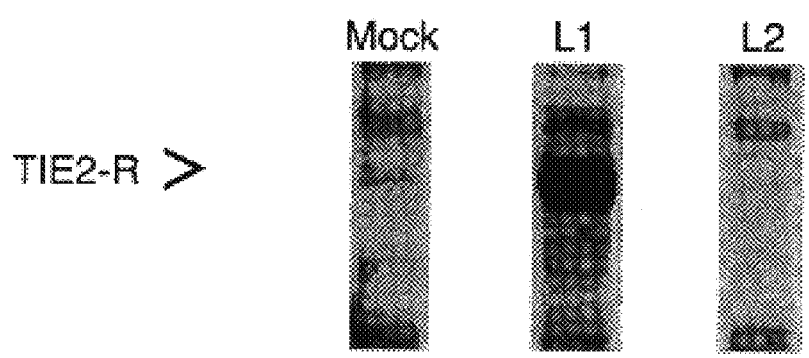
FIG. 7—Western blot showing activation of TIE-2 receptor by TIE-2 ligand 1 (Lane L1) but not by TIE-2 ligand 2 (Lane L2) or control (Mock).

Northern (RNA) analyses revealed significant levels of TIE-2 transcripts in HAEC (Human Aortic Endothelial Cell) human primary endothelial cells (Clonetics, Inc.). Therefore, these cells were used to examine whether TIE-2 receptor is tyrosine-phosphorylated when exposed to COS media containing the TIE-2 ligands. HAEC cells were maintained in a complete endothelial cell growth medium (Clonetics, Inc.) that contained 5% fetal bovine serum, soluble bovine brain extract, 10 ng/ml human EGF, 1 mg/ml hydrocortisone, 50 mg/ml gentamicin and 50 ng/ml amphotericin-B. Assessment of whether TL1 and TL2 could activate TIE-2 receptor in the HAEC cells was done as follows. Semi-confluent HAEC cells were serum-starved for two hours in high-glucose Dulbecco's MEM with added L-glutamine and penicillin-streptomycin at 37° C. followed by replacement of the starvation medium with ligand-containing conditioned COS media for 7 minutes at 37° C. in a 5% $CO_2$ incubator. The cells were subsequently lysed and TIE-2 receptor protein was recovered by immunoprecipitation of the lysates with TIE-2 peptide antiserum, followed by Western blotting with antiphosphotyrosine antiserum, exactly as described in example 1. The results are shown in FIG. 7. Phosphotyrosine levels on the TIE-2 receptor (TIE-2-R) were induced by treatment of HEAC cells with TIE-2 ligand 1 (Lane L1) but not by TIE-2 ligand 2 (Lane L2) conditioned COS media. MOCK is conditioned media from COS transfected with JFE14 empty vector.

Evidence that both TL1 and TL2 specifically bind to the TIE-2 receptor was demonstrated by using a BIAcore to assay the TIE-2 receptor specific binding activities in transfected COS media and by immunostaining of TL1- and TL2-expressing COS cells with TIE-2 receptorbodies.

Because TL2 did not activate the TIE-2 receptor, applicants set out to determine whether TL2 might be capable of serving as an antagonist of TL1 activity. HAEC phosphorylation assays were performed in which cells were first incubated with an "excess" of TL2, followed by addition of dilute TL1. It was reasoned that prior occupancy of TIE-2 receptor due to high levels of TL2 might prevent subsequent stimulation of the receptor following exposure to TL1 present at a limiting concentration.

Figure 8:
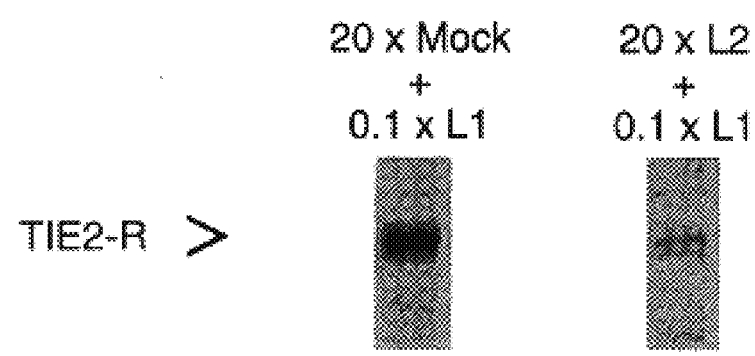
FIG. 8—Western blot showing that prior treatment of HAEC cells with excess TIE-2 ligand 2 (Lane 2) antagonizes the subsequent ability of dilute TIE-2 ligand 1 to activate the TIE-2 receptor (TIE2-R) as compared with prior treatment of HAEC cells with MOCK medium (Lane 1).

Semi-confluent HAEC cells were serum-starved as described above and then incubated for 3 min., at 37° C. with 1–2 ml. of 20×COS/JFE14-TL2 conditioned medium. Control plates were treated with 20×COS/JFE14-only medium (MOCK). The plates were removed from the incubator and various dilutions of COS/JFE14-TL1 medium were then added, followed by further incubation of the plates for 5–7 min. at 37° C. Cells were subsequently rinsed, lysed and TIE-2-specific tyrosine phosphorylation in the lysates was examined by receptor immunoprecipitation and Western blotting, as described above. TL1 dilutions were made using 20×COS/JFE14-TL1 medium diluted to 2×, 0.5×, 0.1×, or 0.02×by addition of 20×COS/JFE14-alone medium. An assay of the initial 20×TL1 and 20×TL2 COS media using BIAcore biosensor technology indicated that they contained similar amounts of TIE-2-specific binding activities, i.e., 445 R.U. and 511 R.U. for TL1 and TL2, respectively. The results of the antiphosphotyrosine Western blot, shown in FIG. 8, indicate that when compared to prior treatment of HAEC cells with MOCK medium (lane 1), prior treatment of HAEC cells with excess TIE-2 ligand 2 (lane. 2) antagonizes the subsequent ability of dilute TIE-2 ligand 1 to activate the TIE-2 receptor (TIE-2-R).

Figure 9:
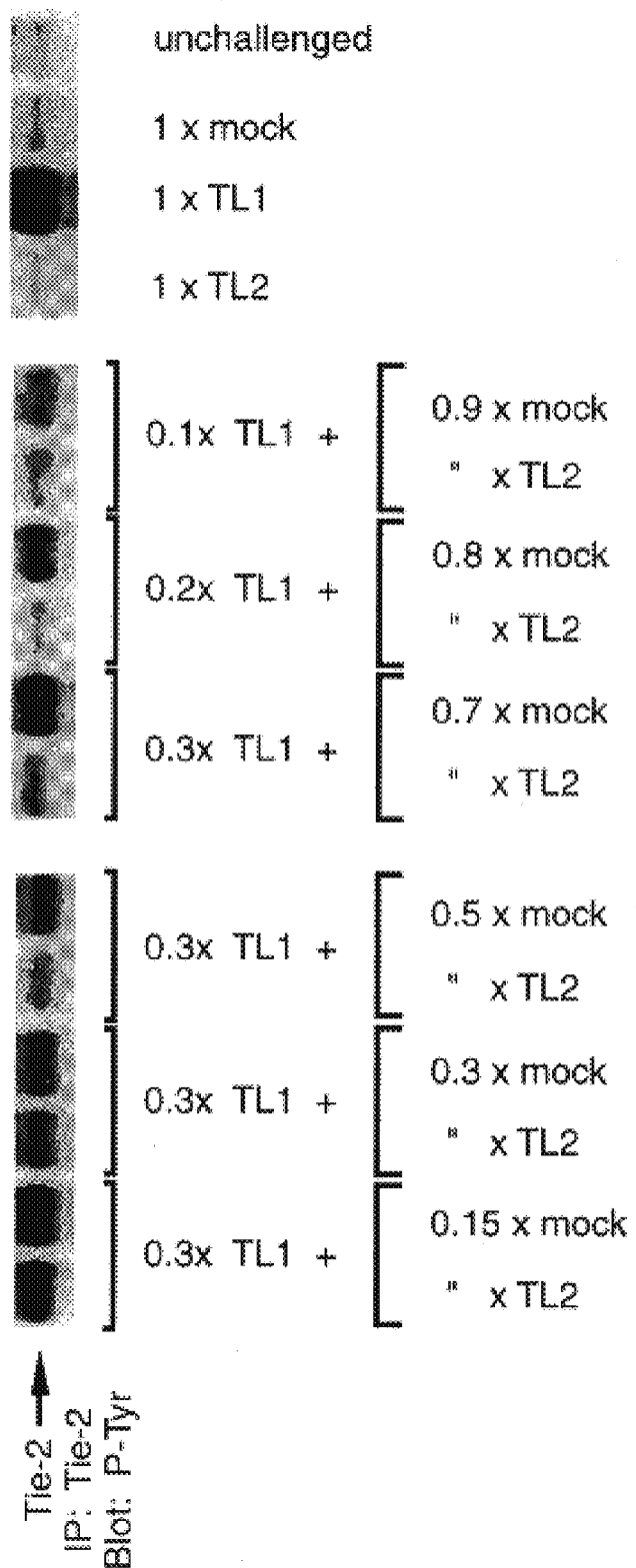
FIG. 9—Western blot demonstrating the ability of TL2 to competitively inhibit TL1 activation of the TIE-2 receptor using the human cell hybrid line, EA.hy926.
Figure 11:
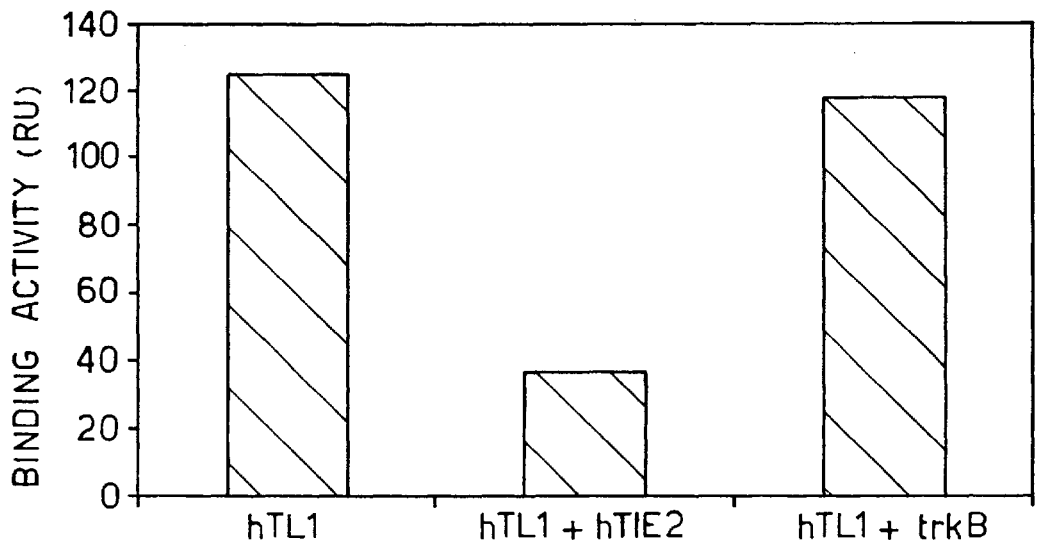
FIGS. 11A–11B—Binding of recombinant human TIE-2 ligand 1 (hTL1) (FIG. 11A) and human TIE-2 ligand 2 (hTL2) (FIG. 11B), in COS cell supernatants, to a human TIE-2 receptorbody (RB) immobilized surface. Human TIE-2-specific binding was determined by incubating the samples with 25 μg/ml of either soluble human TIE-2 RB or trkB RB; significant reduction in the binding activity is observed only for the samples incubated with human TIE-2 RB.
Figure 11:
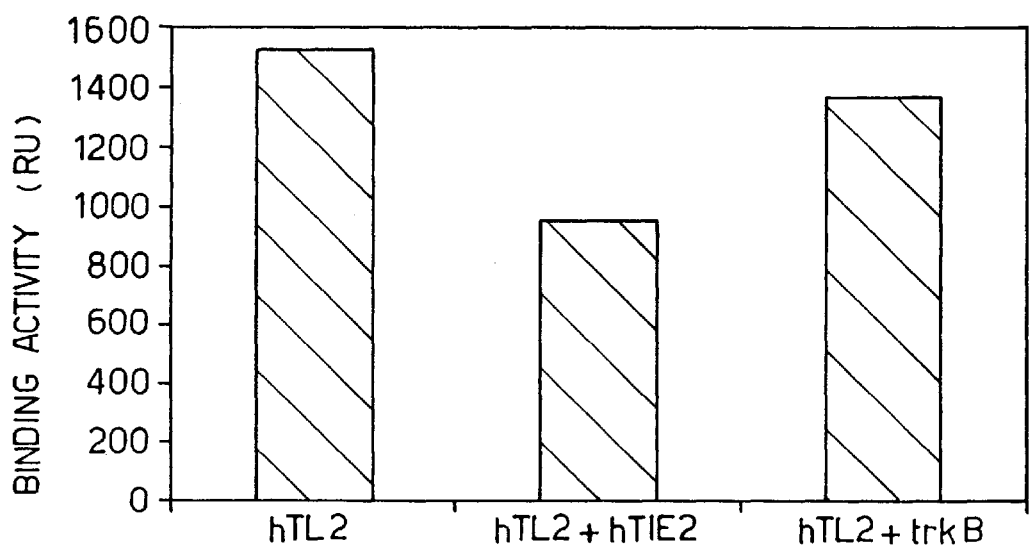

The ability of TL2 to competitively inhibit TL1 activation of the TIE-2-R was further demonstrated using the human cell hybrid line, EA.hy926 (see Example 21 for detailed description of this cell line and its maintenance). Experiments were performed in which unconcentrated COS cell media containing TL1 were mixed at varying dilutions with either MOCK- or TL2-conditioned media and placed on serum-starved EA.hy926 cell monolayers for 5 minutes at 37° C. The media were then removed, the cells were harvested by lysis and TIE-2-specific tyrosine phosphorylation was examined by Western blots, as described above. FIG. 9 shows an experiment which contains three groups of treatments, as viewed from left to right. As shown in the four lanes at the left, treatment of the EA.hy926 cells with 1×COS-TL1 alone robustly activated the endogenous TIE-2-R in these cells, whereas 1×TL2 COS medium was inactive. However, mixture of TL1 with either MOCK or TL2 demonstrated that TL2 can block the activity of TL1 in a dose-dependent fashion. In the central three pairs of lanes the ratio of TL2 (or MOCK) was decreased while the amount of TL1 in the mixture was correspondingly increased from 0.1×to 0.3×. At any of these mixture ratios the TL1:TL2 lanes showed a reduced level of TIE-2-R phosphorylation compared to that of the corresponding TL1:MOCK lanes. When the amount TL1 was held steady and the amount of TL2 (or MOCK) was decreased, however (shown in the three pairs of lanes at the right), a point was reached at which the TL2 in the sample was too dilute to effectively inhibit TL1 activity. The relative amount of each ligand present in these conditioned COS media could be estimated from their binding units as measured by the BIAcore assay and from Western blots of the COS media with ligand-specific antibodies. Consequently, we can infer that only a few-fold molar excess of TL2 is required to effectively block the activity of TL1 in vitro. This is significant because we have observed distinct examples in vivo (see Example 17 and FIG. 16) where TL2 mRNAs achieve considerable abundance relative to those of TL1. Thus, TL2 may be serving an important physiological role in effectively blocking signaling by the TIE-2-R at these sites.

Taken together these data confirm that, unlike TL1, TL2 is unable to stimulate endogenously expressed TIE-2-R on endothelial cells. Furthermore, at a few fold molar excess TL2 can block TL1 stimulation of the TIE-2 receptor, indicating that TL2 is a naturally occurring TIE-2 receptor antagonist.

EXAMPLE 10

IDENTIFICATION OF TIE-2-SPECIFIC BINDING ACTIVITY IN CONDITIONED MEDIUM AND COS CELL SUPERNATANTS

Binding activity of 10×CCM from the cell lines C2C12-ras, Rat2 ras, SHEP, and T98G, or COS cell supernatants after transfection with either human TIE-2 ligand 1 (hTL1) or human TIE-2 ligand 2 (hTL2) was measured using biosensor technology (BIAcore; Pharmacia Biosensor, Piscataway, N.J.) which monitors biomolecular interactions in real-time via surface plasmon resonance (SPR). Purified rat or human TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 µg/mL, pH 4.5) and deactivation of unreacted sites with 1.0 M ethanolamine (pH 8.5). In general, 9000–10000 RU of each receptorbody was coupled to the sensor chip.

The running buffer used in the system was HBS (10 mM Hepes, 150 mM NaCl, 0.005% P20 surfactant, pH 7.4). The samples were centrifuged for 15 min at 4° C. and further clarified using a sterile, low protein-binding 0.45 µm filter (Millipore; Bedford, Mass.). Dextran (2 mg/ml) and P20 surfactant (0.005%) were added to each sample. Aliquots of 40 µL were injected across the immobilized surface (either rat or human TIE-2) at a flow rate of 5 µL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 15-µL pulse of 3 M $MgCl_2$.

The CCM samples (C2C12-ras, Rat2-ras, SHEP, T98G) were tested on the rat TIE-2 RB immobilized surface, while the recombinant hTL1 and hTL2 were tested on the human TIE-2 RB immobilized surface. In each case, specific binding to the TIE-2 receptorbody was evaluated by incubating the samples with 25 µg/ml of either soluble TIE-2 (rat or human) RB or trkB RB prior to assaying the binding activity. As shown in FIGS. 10A–10D and FIGS. 11A–11B, the addition of soluble trkB RB causes a slight decrease in the TIE-2 binding activity, while the addition of soluble TIE-2 RB significantly reduces the binding activity as compared to that measured in the absence of TIE-2 RB.

EXAMPLE 11

TIE-2 RB SPECIFICALLY BLOCKS ACTIVATION OF THE TIE-2 RECEPTOR BY TIE-2 LIGAND 1

The applicants sought to determine whether soluble TIE-2 RB can serve as a competitive inhibitor to block activation of TIE-2 receptor by TIE-2 ligand 1 (TL1). To do this, TL1-containing COS media were preincubated with either TIE-2- or TrkB-RB and then compared for their ability to activate TIE-2 receptors naturally present in a human endothelial cell line.

Conditioned COS media were generated from COS-7 cells transfected with either the pJFE14 expression vector alone (MOCK), or pJFE14 vector containing the human TIE-2 ligand 1 cDNA (TL1) and harvested as described in Example 9 hereinabove, with the exception that the media were sterile filtered but not concentrated. The quantity of TL1 was determined and expressed as the amount (in resonance units, R.U.) of TIE-2 receptor-specific binding activity measured by BIAcore binding assay.

Figure 12:
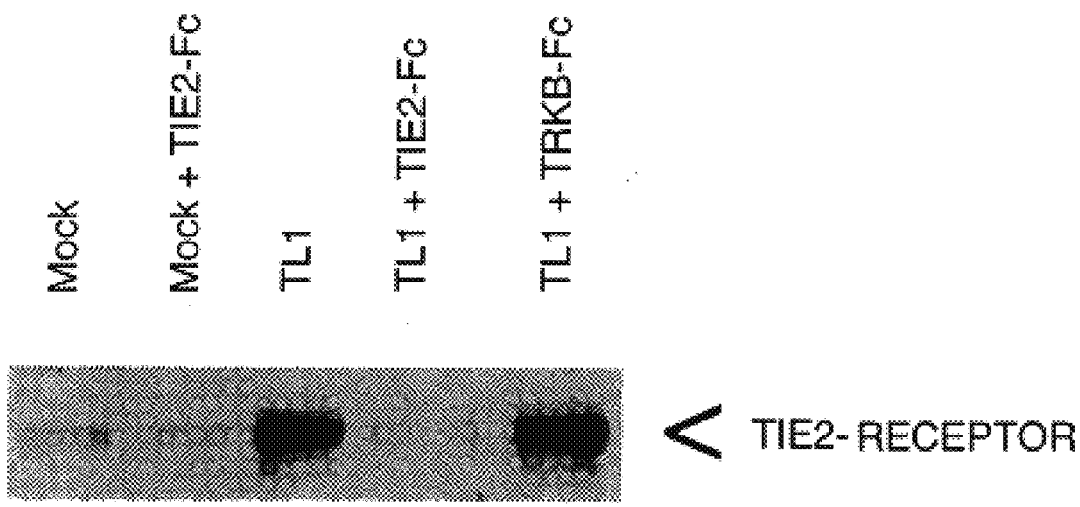
FIG. 12—Western blot showing that TIE-2 receptorbody (denoted TIE-2 RB or, as here, TIE2-Fc) blocks the activation of TIE-2 receptors by TIE-2 ligand 1 (TL1) in HUVEC cells, whereas an unrelated receptorbody (TRKB-Fc) does not block this activation.

Northern (RNA) analyses revealed significant levels of tie-2 transcripts in HUVEC (Human Umbilical Vein Endothelial Cell) human primary endothelial cells (Clonetics, Inc.). Therefore, these cells were used to examine whether TIE-2 receptor can be tyrosine-phosphorylated when exposed in the presence of TIE-2- or TrkB-RBs to COS media containing TL1. HUVEC cells were maintained at 37° C., 5% $CO_2$ in a complete endothelial cell growth medium (Clonetics, Inc.) that contained 5% fetal bovine serum, soluble bovine brain extract with 10 µg/ml heparin, 10 ng/ml human EGF, 1 ug/ml hydrocortisone, 50 µg/ml gentamicin and 50 ng/ml amphotericin-B. Assessment of whether TL1 could activate TIE-2 receptor in the HUVEC cells was done as follows. Confluent dishes of HUVEC cells were serum-starved for two-to-four hours in low-glucose Dulbecco's MEM at 37° C., 5% $CO_2$, followed by 10 minute incubation in starvation medium that included 0.1 mM sodium orthovanadate, a potent inhibitor of phosphotyrosine phosphatases. Meanwhile, conditioned COS media were preincubated 30 min. at room temperature with either TIE-2- or TrkB-RB added to 50 µg/ml. The starvation medium was then removed from the HUVEC dishes and incubated with the RB-containing COS media for 7 minutes at 37° C. HUVEC cells were subsequently lysed and TIE-2 receptor protein was recovered by immunoprecipitation with TIE-2 peptide antiserum, followed by Western blotting with an anti-phosphotyrosine antibody, as described in Example 1. The results are shown in FIG. 12. Phosphotyrosine levels on the TIE-2 receptor were induced by treatment of HUVEC cells with TIE-2 ligand 1 (TL1) relative to that seen with control medium (MOCK) and this induction is specifically blocked by prior incubation with TIE-2-RB (TIE-2-Fc) but not by incubation with TrkB-RB (TrkB-Fc). These data indicate that soluble TIE-2 RB can serve as a selective inhibitor to block activation of TIE-2 receptor by TIE-2 ligand 1.

EXAMPLE 12

CONSTRUCTION OF TIE-2 LIGANDBODIES

An expression construct was created that would yield a secreted protein consisting of the entire coding sequence of human TIE-2 ligand 1 (TL1) or TIE-2 ligand 2 (TL2) fused to the human immunoglobulin gamma-1 constant region (IgG1 Fc). These fusion proteins are called TIE-2 ligandbodies" (TL1-Fc or TL2-Fc). The Fc portion of TL1-Fc and TL2-Fc was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding full-length TL1 or TL2 and from the human IgG1 Fc plasmid were ligated on either side of a short PCR-derived fragment that was designed so as to fuse, in-frame, TL1 or TL2 with human IgG1 Fc protein-coding sequences.

Milligram quantities of TL2-Fc were obtained by cloning the TL2-Fc DNA fragment into the pVL1393 baculovirus vector and subsequently infecting the Spodoptera frugiperda SF-21AE insect cell line. Alternatively, the cell line SF-9 (ATCC Accession No. CRL-1711) or the cell line BTI-TN-5b1–4 may be used. DNA encoding the TL2-Fc was cloned as an Eco RI-NotI fragment into the baculovirus transfer plasmid pVL1393. Plasmid DNA was recombined into viral DNA by mixing 3 µg of plasmid DNA with 0.5 µg of Baculo-Gold DNA (Pharminigen), followed by introduction into liposomes using 30 µg Lipofectin (GIBCO-BRL). DNA-liposome mixtures were added to SF-21AE cells (2×106 cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, Baculovirus Expression Vectors—A Laboratory Manual. 1992, New York: W. H. Freeman) except that the agarose overlay contained 125 mg/mL X-gal (5-bromo-4-chloro-3-indolyl-b-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 mg/mL MTT (3-[4,5-dimethylthiazol-2-yl] 2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTL2-Fc Clone #7) were produced.

SF-21AE cells were cultured in serum-free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10 6 cells/mL), concentrated by centrifugation, and infected with 5 plaque forming units of vTL2-Fc per cell. Cells and inoculum were brought to 400 mL with fresh medium, and virus was adsorbed for 2 hours at 27° C. in a spinner flask. The culture was then resuspended in a final volume of 8L with fresh serum-free medium, and the cells incubated in the bioreactor using the previously described conditions.

Culture medium from vTL2-Fc-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 $\mu$m, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TL2-Fc were pooled and dialyzed versus PBS.

EXAMPLE 13

EXPRESSION OF TIE-1, TIE-2, TL1, AND TL2 IN RENAL CELL CARCINOMA

In situ hybridization experiments were performed on human renal cell carcinoma tumor tissue using TIE-1, TIE-2, TL1, and TL2 cDNA probes. TIE-2, TIE-1, TL1, and TL2 expression were all up-regulated in the tumor vasculature. Ligand expression appeared to be localized to either the vascular endothelial cells (TL2) or very near the vascular endothelial cells in the mesenchyme (TL1). VEGF has been shown to be dramatically up-regulated in this tumor tissue. Brown, et al. Am. J. Pathol. 143:1255–1262 (1993).

EXAMPLE 14

EXPRESSION OF TIE-1, TIE-2, TL1, AND TL2 IN WOUND HEALING

In situ hybridization experiments were performed on cross-sectional tissue slices obtained from a rat cutaneous wound model using TIE-1, TIE-2, TL1, and TL2 cDNA probes. The wound healing model involves pressing a small cork bore against the skin of a rat and removing a small, cylindrical plug of skin. As healing begins at the base of the wound, a vertical slice of tissue is taken and used for in situ hybridization. In the tested tissue sample, TL1 and TL2 appeared to be slightly up-regulated by four days post-injury. In contrast to the slightly up-regulated expression of TL1 and TL2 in this tissue, VEGF expression, which may precede TL1 and TL2 expression, is dramatically up-regulated.

EXAMPLE 15

EXPRESSION OF TIE LIGANDS IN FETAL LIVER AND THYMUS

Figure 13:
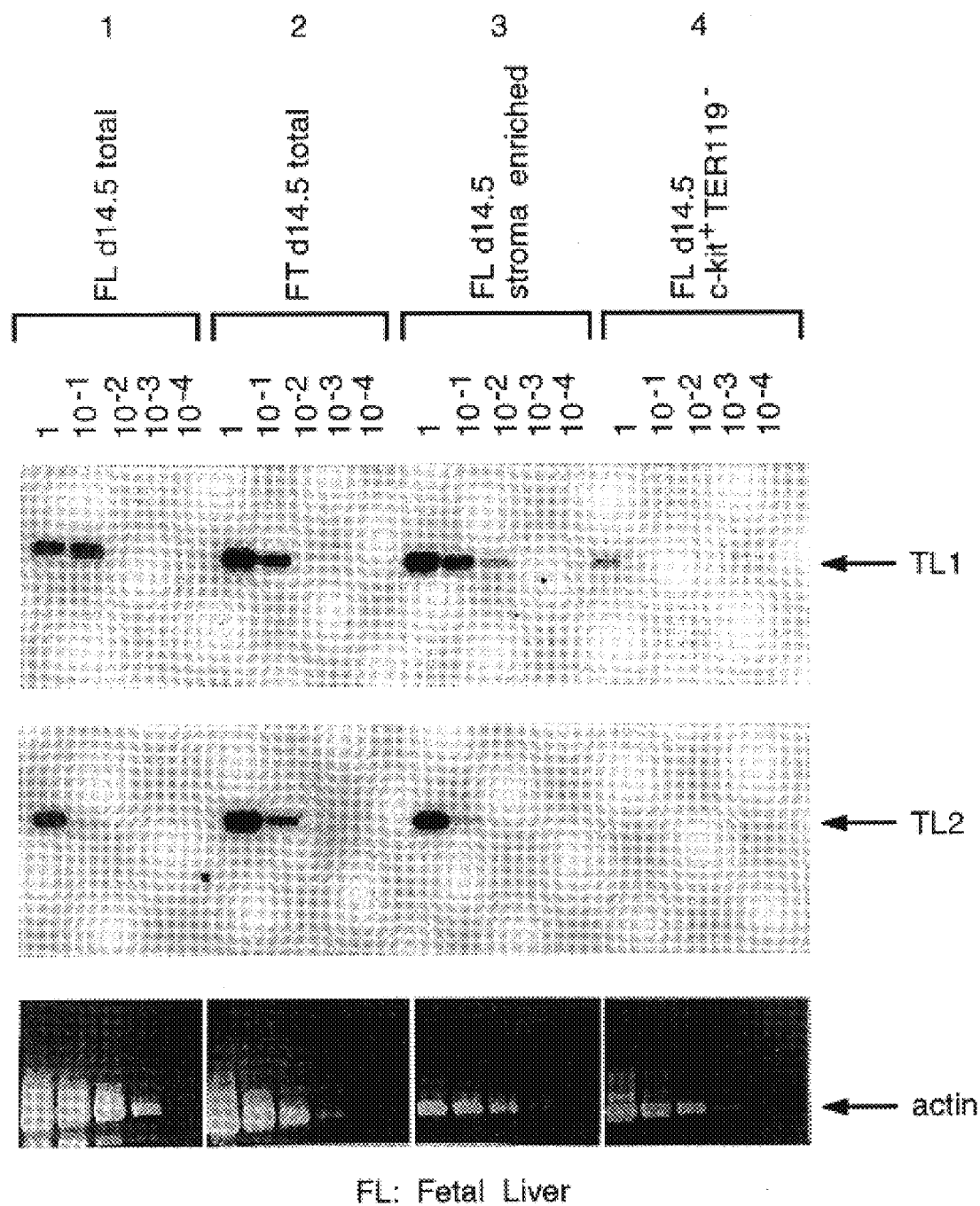
FIG. 13—Agarose gels showing serial dilutions [undiluted (1) to $10^4$] of the TL1 and TL2 RT-PCR products obtained from E14.5 mouse fetal liver (Lanes 1-total, Lanes 3-stromal enriched, and Lanes 4-c-kit$^+$TER119 hematopoietic precursor cells) and E14.5 mouse fetal thymus (Lanes 2-total).
Figure 14:
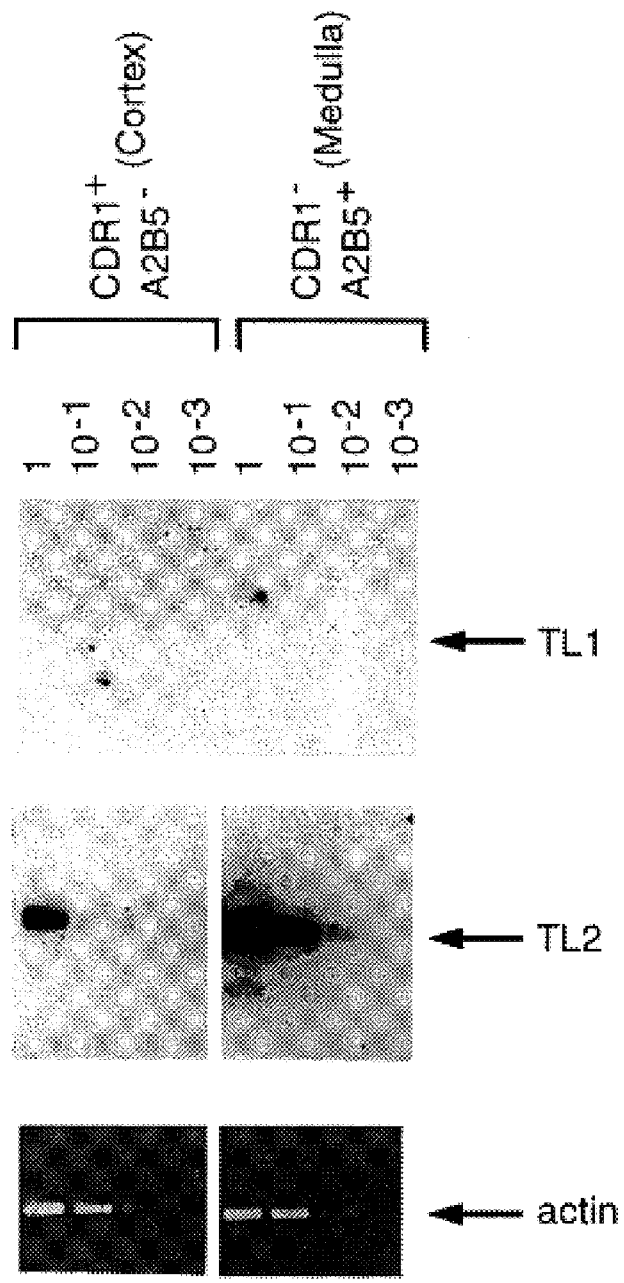
FIG. 14—Agarose gels showing serial dilutions [undiluted (1) to $10^3$] of the TL1 and TL2 RT-PCR products obtained from E17.5 mouse fetal thymus cortical stromal cells (Lanes 1-CDR1+/A2B5−−) and medullary stromal cells (Lane CDR1−/A2B5+).

Reverse transcription-PCR (RT-PCR) was performed on mouse E14.5 fetal liver and mouse E17.5 fetal thymus. Agarose gel electrophoresis of the RT-PCR products revealed that in the mouse fetal liver, TIE-2 ligand 1 (TL1) RNA is enriched in the stromal region, but is absent in c-kit$^+$TER119 hematopoietic precursor cells. In this same tissue, TIE-2 ligand 2 (TL2) RNA is enriched in the stromal cells, but absent in the hematopoietic precursor cells (FIG. 13). In the mouse fetal thymus, TL2 is enriched in the stromal cells (FIG. 14).

EXAMPLE 16

THE TIE RECEPTOR/LIGAND SYSTEM IN ANGIOGENESIS

Although the TIE-2/TIE ligand system appears to play an important role in endothelial cell biology, it has not been shown to play a significant, active role in the early to intermediate stages of vascularization (e.g. angioblast or endothelial cell proliferation and migration, tubule formation, and other early stage events in vascular modeling). In contrast to the receptors and factors known to mediate these aspects of vascular development, the temporally late pattern of expression of TIE-2 and TL1 in the course of vascularization suggests that this system plays a distinct role in the latter stages vascular development, including the structural and functional differentiation and stabilization of new blood vessels. The pattern of expression of TIE-2/TL1 also is consistent with a continuing role in the maintenance of the structural integrity and/or physiological characteristics of an established vasculature.

Figure 15:
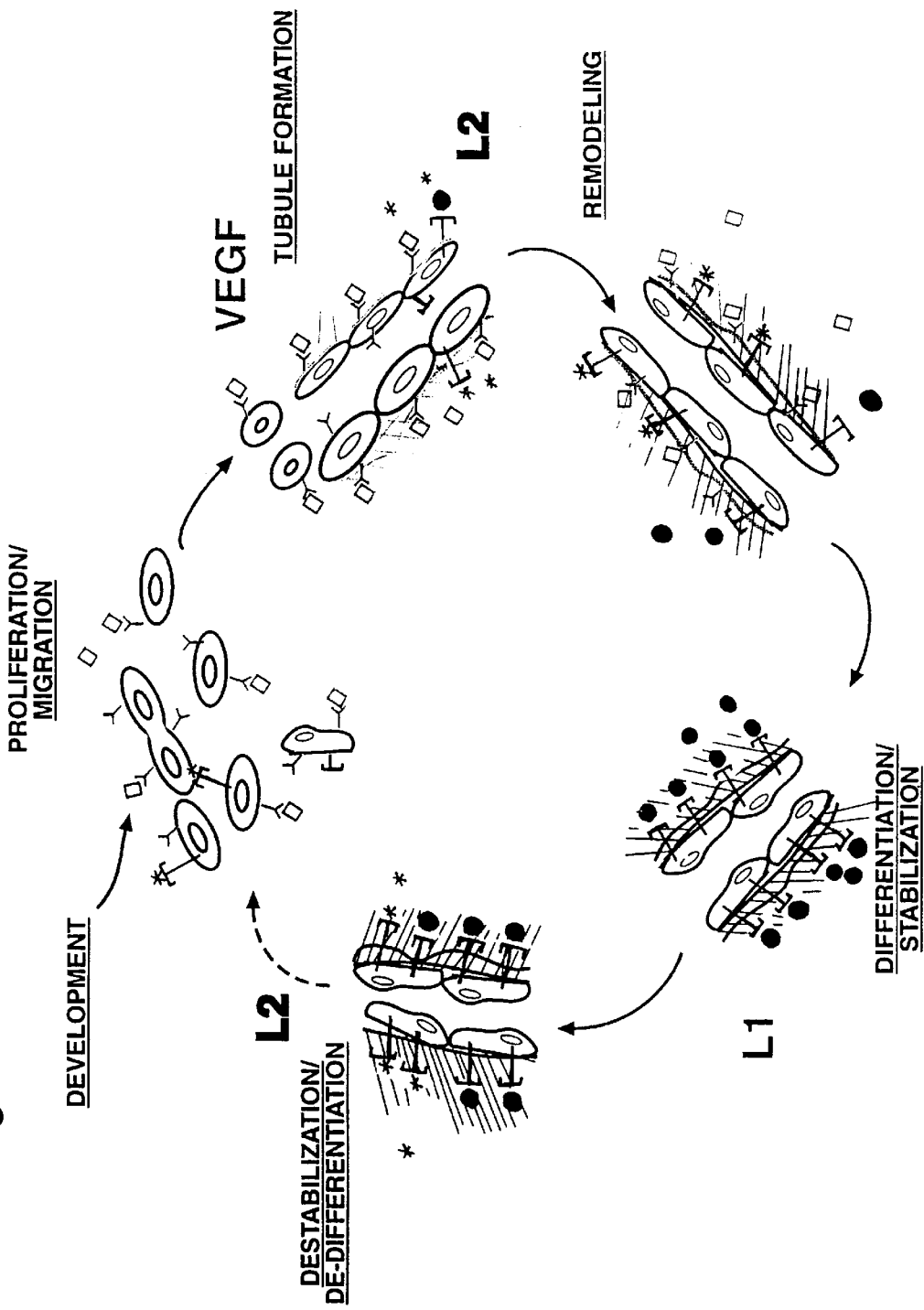
FIG. 15—A schematic representation of the hypothesized role of the TIE-2/T1E ligands in angiogenesis. TL1 is represented by (•), TL2 is represented by (*), TIE-2 is represented by (T), VEGF is represented by ([]), and flk-1 (a VEGF receptor) is represented by (Y).

TIE Ligand 2 (TL2) appears to be a competitive inhibitor of TL1. The spatiotemporal characteristics of TL2 expression suggest that this single inhibitory molecule may play multiple, context-dependent roles essential to appropriate vascular development or remodeling (e.g. de-stabilization/de-differentiation of mature endothelial cells allowing the formation of new vessels from existing vasculature, inhibition of inappropriate blood vessel formation, and regression/involution of mature blood vessels). FIG. 15 is a schematic representation of the hypothesized role of the TIE-2/TIE ligands in angiogenesis. In this figure TL1 is represented by (•), TL2 is represented by (*), TIE-2 is represented by (T), VEGF is represented by ([]), and flk-1 (a VEGF receptor) is represented by (Y).

EXAMPLE 17

EXPRESSION OF TIE LIGANDS IN THE FEMALE REPRODUCTIVE SYSTEM: EXPRESSION IN THE OVARY

Figure 16:
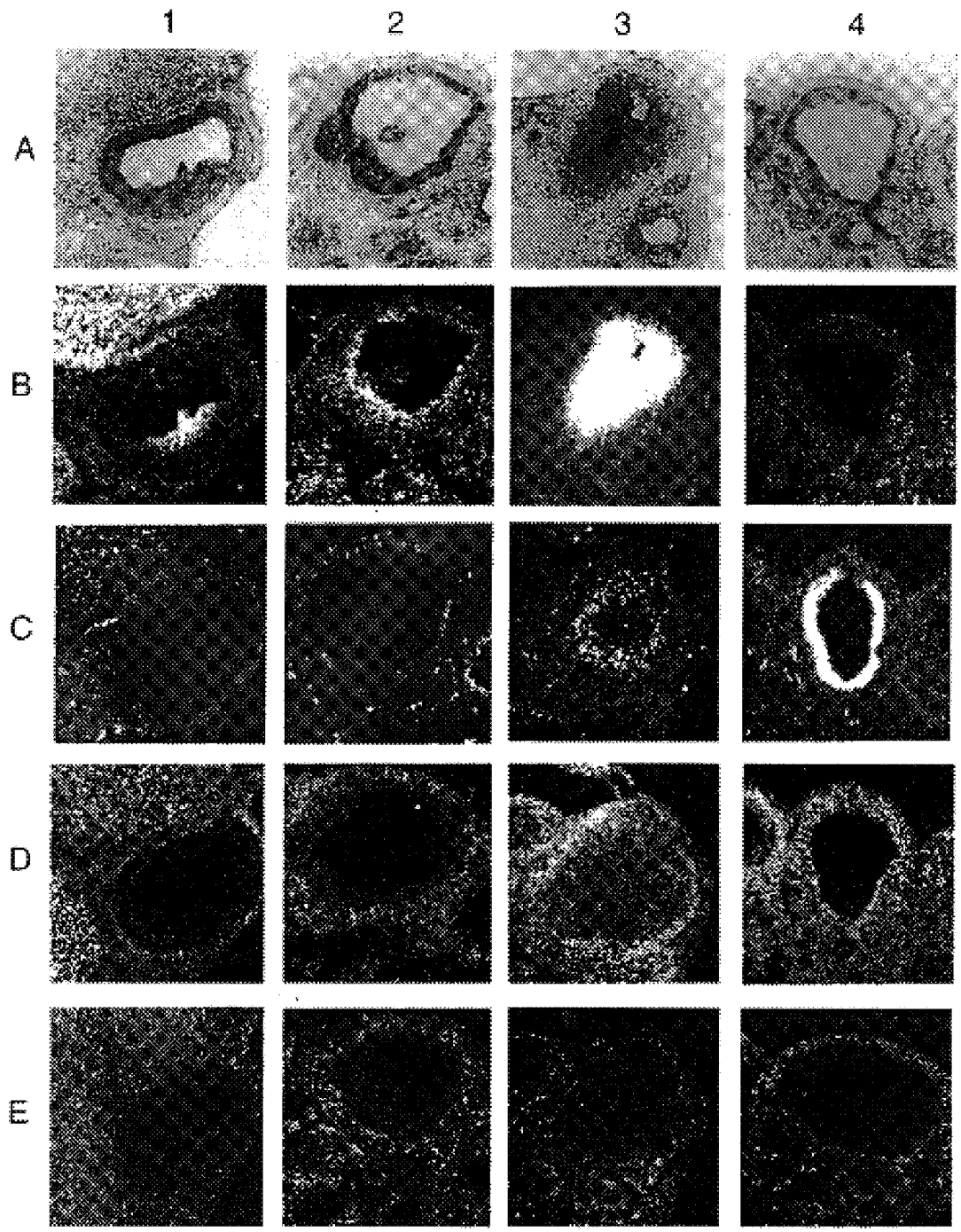
FIG. 16—In situ hybridization slides showing the temporal expression pattern of TIE-2, TL1, TL2, and VEGF during angiogenesis associated with follicular development and corpus luteum formation in the ovary of a rat that was treated with pregnant mare serum. Column 1: Early pre-ovulatory follicle; Column 2: pre-ovulatory follicle; Column 3: early corpus luteum; and Column 4: atretic follicle; Row A: bright field; Row B: VEGF; Row C: TL2; Row D: TL1 and Row E: TIE-2 receptor.

Preliminary observations made in experiments examining the expression of the TIE receptors and ligands in the female reproductive system are consistent with the hypothesis the TL1 plays a role in neovascularization which temporally follows that of VEGF. The pattern of TL2 expression is also consistent with an antagonism of the action of TL1, and a specific role in vascular regression. To verify this, expression of relevant mRNAs can be examined following experimental induction of follicular and luteal development so that their temporal relation to various aspects of neovascularization/vascular regression can be more clearly defined (e.g. in conjunction with endothelial cell staining, vascular fills). Angiogenesis associated with follicular development and corpus luteum formation in staged ovaries of mature, female rats or following induced ovulation in pre-pubertal animals was followed using in situ hybridization. FIG. 16 contains photographs of in situ hybridization slides showing the temporal expression pattern of TIE-2, TL1, TL2, and VEGF during the ovarian cycle [Column 1: Early pre-ovulatory follicle; Column 2: pre-ovulatory follicle; Column 3: early corpus luteum; and Column 4: atretic follicle; Row A:bright field; Row B:VEGF; Row C: TL2; Row D: TL1 and Row E: TIE-2 receptor]. These studies revealed that VEGF, TL1 and TL2 are expressed in a temporally and spatially coordinate fashion with respect to the development and regression of vasculature in the ovary, specifically with respect to the establishment of the vascular system which is generated in the course of the conversion of an ovarian follicle to a corpus luteum (CL).

Briefly, VEGF expression increases in the follicular granule layer prior to its vascularization during the process of luteinization. During the process of CL formation, highest levels of VEGF expression are apparent in the center of the developing CL in the vicinity of luteinizing cells which are not yet vascularized. VEGF levels remain moderately high and are diffusely distributed in the developed CL. In contrast, noticeably enhanced expression of TIE-2 ligand 1 occurs only late in process of CL formation, after a primary vascular plexus has been established. Later, TL1 expression is apparent throughout the CL at which time the definitive capillary network of the CL has been established.

TL2 exhibits a more complex pattern of expression than either VEGF or TL1. In the developing CL, TL2 is expressed at highest levels at the front of the developing capillary plexus-between the central avascular region of the CL where VEGF expression is highest, and the most peripheral portion of the CL where TL1 expression is dominant and where the luteinization process is complete and the vascular system is most mature. TL2 also appears to be expressed at high levels in the follicular layer of large follicles which are undergoing atresia. While TL1 is also apparent in atretic follicles, VEGF is not expressed.

The pattern of expression described above is most consistent with a role for VEGF in the initiation of angiogenesis, with TL1 acting late in this process-for example in modeling and/or stabilization of the definitive vascular network. In contrast, TL2 is present both in areas of active expansion of a newly forming vascular network (during CL formation), and in regions which fail to establish a new vasculature and vascular regression is in progress (atretic follicles). This suggests a more dynamic and complex role for TL2, possibly involving destabilization of existing vasculature (necessary for regression) or developing vasculature (necessary for the dynamic modeling of newly forming vessels).

EXAMPLE 18

A RECEPTORBODY BINDING ASSAY AND A LIGAND BINDING AND COMPETITION ASSAY

Figure 19:
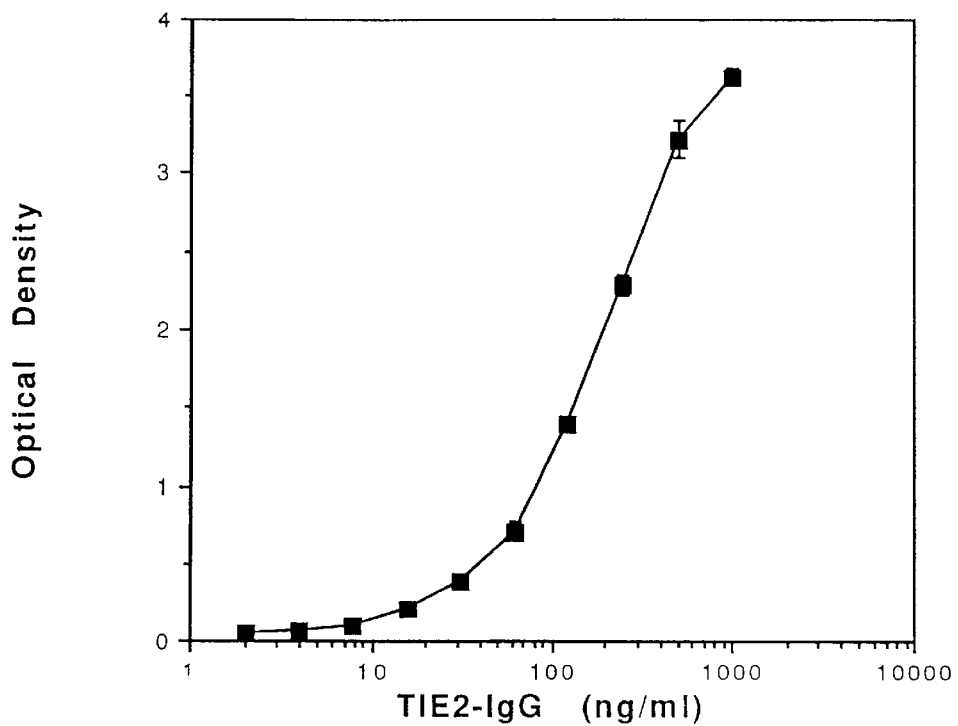
FIG. 19—A typical curve of TIE-2-IgG binding to immobilized TL1 in a quantitative cell-free binding assay.
Figure 20:
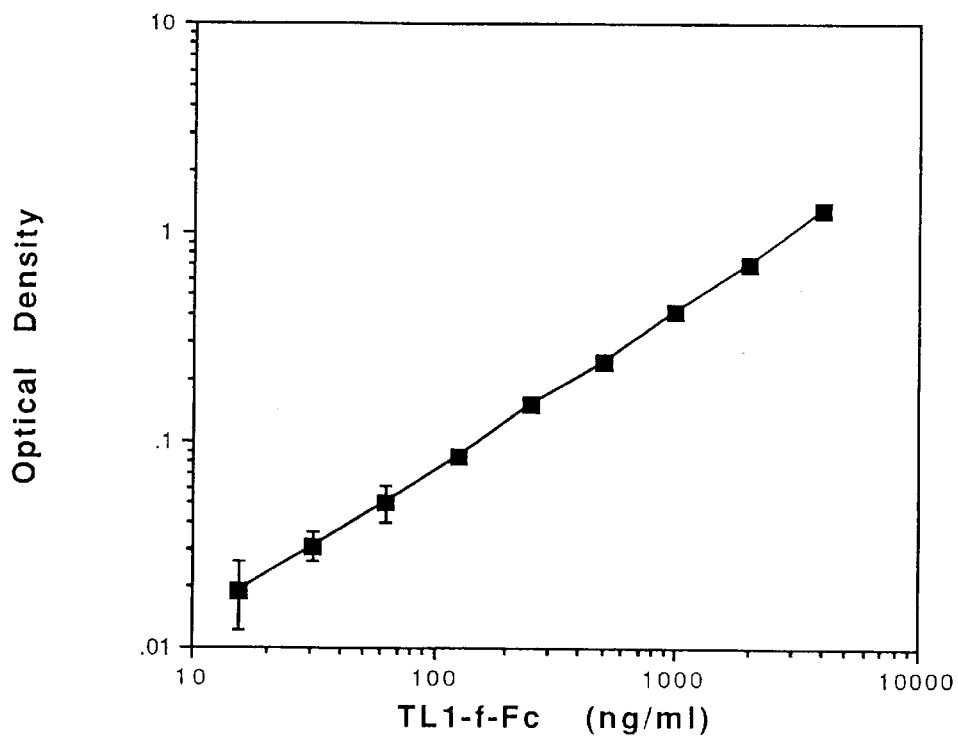
FIG. 20—A typical curve showing TIE-2 ligand 1 ligandbody comprising the fibrinogen-like domain of the ligand bound to the Fc domain of IgG (TL1-fFc) binding to immobilized TIE-2 ectodomain in a quantitative cell-free binding assay.

A quantitative cell-free binding assay with two alternate formats has been developed for detecting either TIE-2 receptorbody binding or ligand binding and competition. In the receptorbody binding version of the assay, TIE-2 ligands (purified or partially purified; either TL1 or TL2) are coated onto an ELISA plate. Receptorbody at varying concentrations is then added, which binds to the immobilized ligand in a dose-dependent manner. At the end of 2 hours, excess receptorbody is washed away, then the amount bound to the plate is reported using a specific anti-human Fc antibody which is alkaline phosphatase tagged. Excess reporter antibody is washed away, then the AP reaction is developed using a colored substrate. The assay is quantitated using a spectrophotometer. FIG. 19 shows a typical TIE-2-IgG binding curve. This assay has been used to evaluate the integrity of TIE-2-IgG after injection into rats and mice. The assay can also be used in this format as a ligand competition assay, in which purified or partially-purified TIE ligands compete with immobilized ligand for receptorbody. In the ligand binding and competition version of the binding assay, TIE-2 ectodomain is coated onto the ELISA plate. The Fc-tagged fibrinogen-like domain fragments of the TIE ligands (TL1-fFc and TL2-fFc) then bind to the ectodomain, and can be detected using the same anti-human Fc antibody as described above. FIG. 20 shows an example of TL1-fFc binding to TIE-2 ectodomain. This version of the assay can also be used to quantitate levels of TL1-fFc in serum or other samples. If untagged ligand (again, either purified or unpurified) is added at the same time as the TL1-fFc, then a competition is set up between tagged ligand fragment and full-length ligand. The full-length ligand can displace the Fc-tagged fragment, and a competition curve is generated.

EXAMPLE 19

EA.hy926 CELL LINE CAN BE USED AS A REPORTER CELL LINE FOR TIE LIGAND ACTIVITY

EA.hy926 is a cell hybrid line that was established by fusion of HUVEC with the human lung carcinoma-derived line, A549 [Edgell, et al.

Proc. Natl. Acad. Sci. (USA) 80, 3734–3737 (1983). EA.hy926 cells have been found to express significant levels of TIE-2 receptor protein with low basal phosphotyrosine levels. The density at which EA.hy926 cells are passaged prior to their use for receptor assays, as well as their degree of confluency at the time of assay, can affect TIE-2 receptor abundance and relative inducibility in response to treatment with ligand. By adopting the following regimen for growing these cells the EA.hy926 cell line can be used as a dependable system for assay of TIE-2 ligand activities.

EA.hy926 cells are seeded at $1.5 \times 10^6$ cells in T-75 flasks (Falconware) and re-fed every other day with high-glucose Dulbecco's MEM, 10% fetal bovine serum, L-glutamine, penicillin-streptomycin, and 1×hypoxanthine-aminopterin-thymidine (HAT, Gibco/BRL). After three to four days of growth, the cells are passaged once again at $1.5 \times 10^6$ cells per T-75 flask and cultured an additional three to four days. For phosphorylation assays, cells prepared as described above were serum-starved by replacement of the culture medium with high-glucose DMEM and incubation for 2–3 hours at 37° C. This medium was aspirated from the flask and samples of conditioned media or purified ligand were added to the flask in a total volume of 1.5 ml followed by incubation at 37° C. for 5 minutes. Flasks were removed from the incubator and placed on a bed of ice. The medium was removed and replaced with 1.25 ml Lysis Buffer containing 1% nonidet P-40, 0.5% sodium deoxycholate, 0.1% SDS in 20 mM Tris, pH 7.6, 150 mM NaCl, 50 mM NaF, 1 mM sodium orthovanadate, 5 mM benzamidine, and 1 mM EDTA containing the protease inhibitors PMSF, aprotinin, and leupeptin. After 10 minutes on ice to allow membrane solubilization, plates were scraped and cell lysates were clarified by microcentrifugation at top speed for 10 minutes at 4° C. TIE-2 receptor was immunoprecipitated from the clarified supernatant by incubation in the cold with an anti-TIE-2 polyclonal antiserum and Protein G-conjugated Sepharose beads. The beads were washed three times with cold cell lysis buffer and boiled 5 minutes in Laemmli sample buffer, which was then loaded on 7.5% SDS-polyacrylamide gels. Resolved proteins were electrotransferred to PVDF (Lamblia-P) membrane and then subjected to Western blot analysis using anti-phosphotyrosine antibody and the ECL reagent. Subsequent comparison of total TIE-2 protein levels on the same blots was done by stripping the anti-phosphotyrosine antibody and reincubating with a polyclonal antiserum specific to the ectodomain of TIE-2.

EXAMPLE 20

ISOLATION AND SEQUENCING OF FULL LENGTH cDNA CLONE ENCODING MAMMALIAN TIE LIGAND-3

TIE ligand-3 (TL3) was cloned from a mouse BAC genomic library (Research Genetics) by hybridizing library duplicates, with either mouse TL1 or mouse TL2 probes corresponding to the entire coding sequence of those genes. Each copy of the library was hybridized using phosphate buffer at 55° C. overnight. After hybridization, the filters were washed using 2×SSC, 0.1% SDS at 60° C., followed by exposure of X ray film to the filters. Strong hybridization signals were identified corresponding to mouse TL1 and mouse TL2. In addition, signals were identified which weakly hybridized to both mouse TL1 and mouse TL2. DNA corresponding to these clones was purified, then digested with restriction enzymes, and two fragments which hybridized to the original probes were subcloned into a bacterial plasmid and sequenced. The sequence of the fragments contained two exons with homology to both mouse TL1 and mouse TL2. Primers specific for these sequences were used as PCR primers to identify tissues containing transcripts corresponding to TL3. A PCR band corresponding to TL3 was identified in a mouse uterus cDNA library in lambda gt-11. (Clontech Laboratories, Inc., Palo Alto, Calif.).

Plaques were plated at a density of 1.25×10⁶/20×20 cm plate and replica filters taken following standard procedures (Sambrook, et al., Molecular Cloning: A Laboratory Manual, 2nd Ed., page 8.46, Cold Spring Harbor Laboratory, Cold Spring Harbor, N.Y.). Duplicate filters were screened at "normal" stringency (2×SSC, 65° C.) with a 200 bp PCR radioactive probe made to the mouse TL3 sequence. Hybridization was at 65° C. in a solution containing 0.5 mg/ml salmon sperm DNA. Filters were washed in 2×SSC at 65° C. and exposed for 6 hours to X-ray film. Two positive clones that hybridized in duplicate were picked. EcoRI digestion of phage DNA obtained from these clones indicated two independent clones with insert sizes of approximately 1.2 kb and approximately 2.2 kb. The 2.2 kb EcoRI insert was subcloned into the EcoRI site of pBluescript KS (Stratagene). Sequence analysis showed that the longer clone was lacking an initiator methionine and signal peptide but otherwise encoded a probe homologous to both mouse TL1 and mouse TL2.

Two TL3-specific PCR primers were then synthesised as follows:

US2: cctctgggctcgccagtttgttagg

US1: ccagctggcagatatcagg

The following PCR reactions were performed using expression libraries derived from the mouse cell lines C2C12ras and MG87. In the primary PCR reaction, the specific primer US2 was used in conjunction with vector-specific oligos to allow amplification in either orientation. PCR was in a total volume of 100 ml using 35 cycles of 94° C., 1 min; 42° C. or 48° C. for 1 min; 72° C., 1 min. The secondary PCR reaction included the second specific primer, US1, which is contained within the primary PCR product, in conjunction with the same vector oligos. The secondary reactions were for 30 cycles, using the same temperatures and times as previous. PCR products were gel isolated and submitted for sequence analysis. On the basis of sequences obtained from a total of four independent PCR reactions using two different cDNA libraries, the 5' end of the TL3 sequence was deduced. Northern analysis revealed moderate to low levels of mouse TL3 transcript in mouse placenta. The expression of mouse TL3 consisted of a transcript of approximately 3 kb. The full length TL3 coding sequence is set forth in FIGS. 21A–21C (SEQ. ID. NO. 9 and SEQ. ID. NO. 10).

The mouse TL3 sequence may then be used to obtain a human clone containing the coding sequence of human TL3 by hybridizing either a human genomic or cDNA library with a probe corresponding to mouse TL3 as has been described previously, for example, in Example 8 supra.

EXAMPLE 21

ISOLATION OF FULL LENGTH GENOMIC CLONE ENCODING HUMAN TIE LIGAND-4

TIE ligand-4 (TL4) was cloned from a mouse BAC genomic library (BAC HUMAN (II), Genome Systems Inc.) by hybridizing library duplicates, with either a human TL1 radioactive probe corresponding to the entire fibrinogen coding sequence of TL1 (nucleotides 1153 to 1806 of FIGS. 4A–4D (SEQ. ID. NO. 1 and SEQ. ID. NO. 2)) or a mouse TL3 radioactive probe corresponding to a segment of 186 nucleotides from the fibrinogen region of mouse TL3 (nucleotides 1307 to 1492 of FIGS. 21A–21C (SEQ. ID. NO. 9 and SEQ. ID. NO. 10)). Each probe was labeled by PCR using exact oligonucleotides and standard PCR conditions, except that dCTP was replaced by $P^{32}$dCTP. The PCR mixture was then passed through a gel filtration column to separate the probe from free $p^{32}$ dCTP. Each copy of the library was hybridized using phosphate buffer, and radioactive probe at 55° C. overnight using standard hybridization conditions. After hybridization, the filters were washed using 2×SSC, 0.1% SDS at 55° C., followed by exposure of X ray film. Strong hybridization signals were observed corresponding to human TL1. In addition, signals were identified which weakly hybridized to both human TL1 and mouse TL3. DNA corresponding to these clones was purified using standard procedures, then digested with restriction enzymes, and one fragment which hybridized to the original probes was subcloned into a bacterial plasmid and sequenced. The sequence of the fragments contained one exon with homology to both human TL1 and mouse TL3 and other members of the TIE ligand family. Primers specific for these sequences may be used as PCR primers to identify tissues containing transcripts corresponding to TL4.

The complete sequence of human TL4 may be obtained by sequencing the full BAC clone contained in the deposited bacterial cells. Exons may be identified by homology to known members of the TIE-ligand family such as TL1, TL2 and TL3. The full coding sequence of TL4 may then be determined by splicing together the exons from the TL4 genomic clone which, in turn, may be used to produce the TL4 protein. Alternatively, the exons may be used as probes to obtain a full length cDNA clone, which may then be used to produce the TL4 protein. Exons may also be identified from the BAC clone sequence by homology to protein domains such as fibrinogen domains, coiled coil domains, or protein signals such as signal peptide sequences. Missing exons from the BAC clone may be obtained by identification of contiguous BAC clones, for example, by using the ends of the deposited BAC clone as probes to screen a human genomic library such as the one used herein, by using the exon sequence contained in the BAC clone to screen a cDNA library, or by performing either 5' or 3' RACE procedure using oligonucleotide primers based on the TL4 exon sequences.

Identification of Additional TIE Ligand Family Members

The novel TIE ligand-4 sequence may be used in a rational search for additional members of the TIE ligand family using an approach that takes advantage of the existence of conserved segments of strong homology between the known family members. For example, an alignment of the amino acid sequences of the TIE ligands shows several regions of conserved sequence (see boxed regions of FIGS. 22A–22B (SEQ ID. NO. 11, SEQ. ID. NO. 12, SEQ. ID. NO. 13, SEQ, ID. NO. 14, SEQ. ID. NO. 15, and SEQ. ID. NO. 16)). Degenerate oligonucleotides essentially based on these boxes in combination with either previously known or novel TIE ligand homology segments may be used to identify new TIE ligands.

The highly conserved regions among TL1, TL2 and TL3 may be used in designing degenerate oligonucleotide primers with which to prime PCR reactions using cDNAs. cDNA templates may be generated by reverse transcription of tissue RNAs using oligo d(T) or other appropriate primers. Aliquots of the PCR reactions may then be subjected to electrophoresis on an agarose gel. Resulting amplified DNA fragments may be cloned by insertion into plasmids, sequenced and the DNA sequences compared with those of all known TIE ligands.

Size-selected amplified DNA fragments from these PCR reactions may be cloned into plasmids, introduced into *E. coli* by electroporation, and transformants plated on selective agar. Bacterial colonies from PCR transformation may be analyzed by sequencing of plasmid DNAs that are purified by standard plasmid procedures.

Cloned fragments containing a segment of a novel TIE ligand may be used as hybridization probes to obtain full length cDNA clones from a cDNA library. For example, the human TL4 genomic sequence may be used to obtain a human cDNA clone containing the complete coding sequence of human TL4 by hybridizing a human cDNA library with a probe corresponding to human TL4 as has been described previously.

EXAMPLE 22

CLONING OF THE FULL CODING SEQUENCE OF hTL4

Both 5' and 3' coding sequence from the genomic human TL-4 clone encoding human TIE ligand-4 (hTL-4 ATCC Accession No. 98095) was obtained by restriction enzyme digestion, Southern blotting and hybridization of the hTL-4 clone to coding sequences from mouse TL3, followed by subcloning and sequencing the hybridizing fragments. Coding sequences corresponding to the N-terminal and C-terminal amino acids of hTL4 were used to design PCR primers (shown below), which in turn were used for PCR amplification of TL4 from human ovary cDNA. A PCR band was identified as corresponding to human TL4 by DNA sequencing using the ABI 373A DNA sequencer and Taq Dideoxy Terminator Cycle Sequencing Kit (Applied Biosystems, Inc., Foster City, Calif.). The PCR band was then subcloned into vector pCR-script and several plasmid clones were analyzed by sequencing. The complete human TL4 coding sequence was then compiled and is shown in FIGS. 23A–23C (SEQ ID. NO. 17and SEQ. ID. NO. 18). In another embodiment of the invention, the nucleotide at position 569 is changed from A to G, resulting in an amino acid change from Q to R.

The PCR primers used as described above were designed as follows:

h T L 4 a t g
5'-gcatgctatctcgagccaccATGCTCTCCCAGCTAGCC-ATGCTGCAG-3' (SEQ. ID. NO. 27)

h T L 4 n o t
5'-gtgtcgacgcggccgctctagatcagacTTAGATGTCCAAA-GGCCGTATCATCAT-3'

Lowercase letters indicate "tail" sequences added to the PCR primers to facilitate cloning of the amplified PCR fragments.

EXAMPLE 23

CONSTRUCTION AND CHARACTERIZATION OF MODIFIED TIE LIGANDS

A genetic analysis of TIE-2 ligand-1 and TIE-2 ligand-2 (TL1 and TL2) was undertaken to gain insight into a number of their observed properties. Although TL1 and TL2 share similar structural homology, they exhibit different physical and biological properties. The most prominent feature that distinguishes the two ligands is that although they both bind to the TIE-2 receptor, TL1 is an agonist while TL2 is an antagonist. Under non-reducing electrophoretic conditions both proteins exhibit covalent, multimeric structures. TL1 is produced as a mixture of disulfide cross-linked multimers, primarily trimers and higher order species, without any dimeric species. But TL2 is produced almost exclusively as a dimeric species. Also, while TL2 is produced well in most expression systems, TL1 is expressed poorly and is difficult to produce in large quantities. Finally, production and purification conditions also appear to predispose TL1 to inactivation by proteolytic cleavage at a site near the amino terminus.

To study these differences, several modified ligands were constructed as follows.

Figure 17:
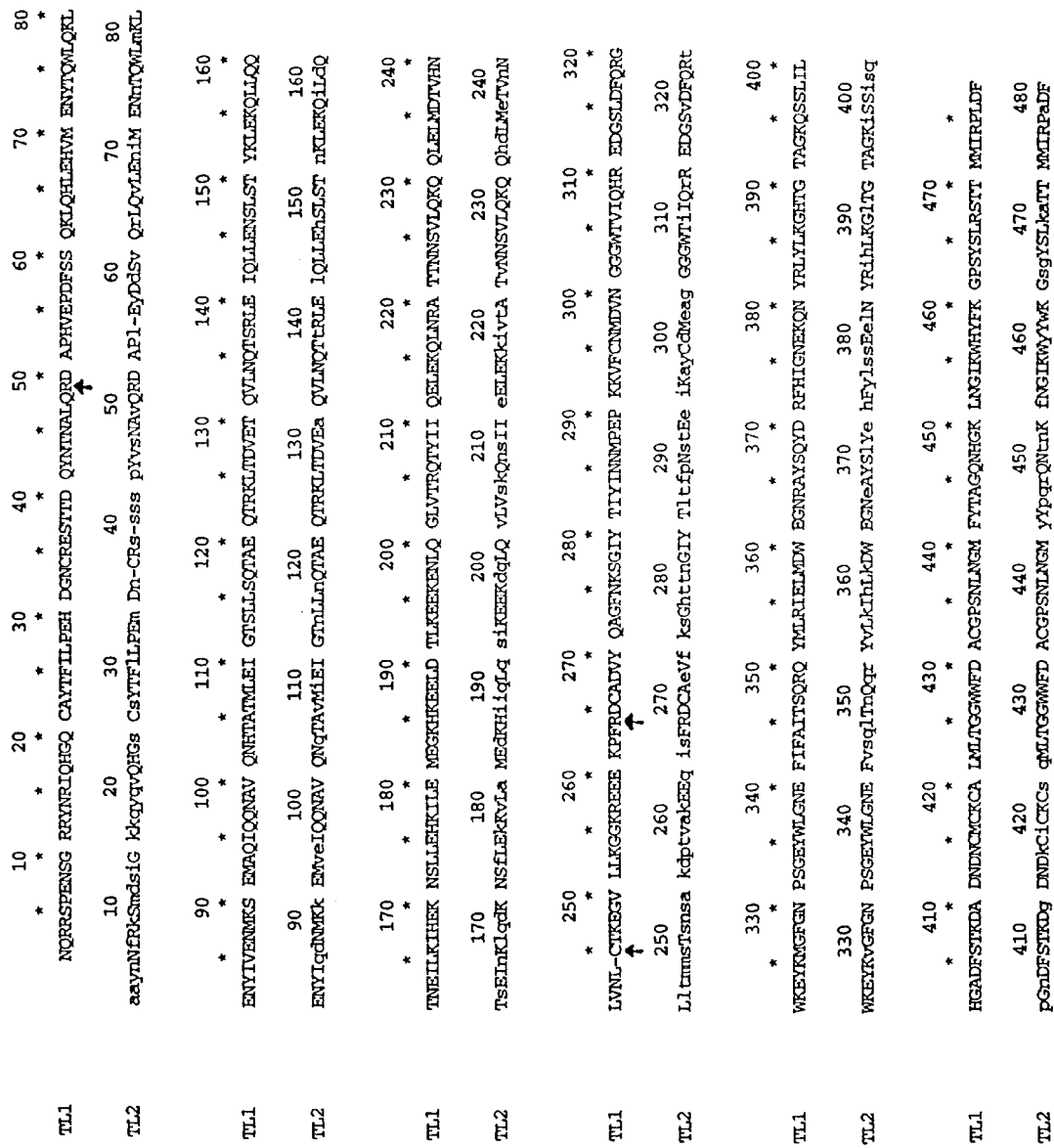
FIG. 17—Comparison of amino acid sequences of mature TL1 protein (SEQ. ID. NO. 7) and mature TL2 protein (SEQ. ID. NO. 8). The TL1 sequence is the same as that set forth in FIGS. 4A–4D (SEQ. ID. NO. 1 and SEQ. ID. NO. 2), except that the putative leader sequence has been removed. Similarly, the TL2 sequence is the same as that set forth in FIGS. 6A–6D (SEQ. ID. NO. 5 and SEQ. ID. NO. 6), except that the putative leader sequence has been removed. Arrows indicate residues Arg49, Cys245 and Arg264 of TL1, which correspond to the residues at amino acid positions 69, 265 and 284, respectively, of TL1 as set forth in FIGS. 4A–4D (SEQ. ID. NO. 1 and SEQ. ID. NO. 2).

23.1. Cysteine substitution—Investigations into what factors might be contributing to the different physical and biological properties of the two molecules revealed the presence in TL1 of a cysteine residue (CYS 265 in FIGS. 4A–4D (SEQ. ID. NO. 1 and SEQ. ID. NO. 2); CYS 245 in FIG. 17 (SEQ. ID. NO. 7 and SEQ. ID. NO. 8)) preceding the fibrinogen-like domain in TL1 but absent in TL2—i.e., there was no corresponding cysteine residue in TL2. The CYS265 residue in TL1 is encoded by TGC and is located at about nucleotides 1102–1104 (see FIGS. 4A–4D (SEQ. ID. NO. 1 and SEQ. ID. NO. 2)) at the approximate junction between the coiled-coil and fibrinogen-like domains. Because cysteine residues are generally involved in disulfide bond formation, the presence of which can contribute to both the tertiary structure and biological properties of a molecule, it was thought that perhaps the presence of the CYS265 residue in TL1 might be at least partially responsible for the different properties of the two molecules.

To test this hypothesis, an expression plasmid was constructed which contained a mutation in TL1 in which the CYS (residue 265 in FIGS. 4A–4D (SEQ. ID. NO. 1 and SEQ. ID. NO. 2); residue 245 in FIG. 17 (SEQ. ID. NO. 7 and SEQ. ID. NO. 8)) was replaced with an amino acid (serine) which does not form disulfide bonds. In addition to this TL1/CYS⁻ mutant, a second expression plasmid was constructed which mutated the approximately corresponding position in TL2 (Met247 in FIG. 17 (SEQ. ID. NO. 7 and SEQ. ID. NO. 8)) so that this residue was now a cysteine. Both non-mutated and mutated expression plasmids of TL1 and TL2 were transiently transfected into COS7 cells, cell supernatants containing the recombinant proteins were harvested, and samples were subjected to both reducing and non-reducing SDS/PAGE electrophoresis and subsequent Western blotting.

Figure 18:
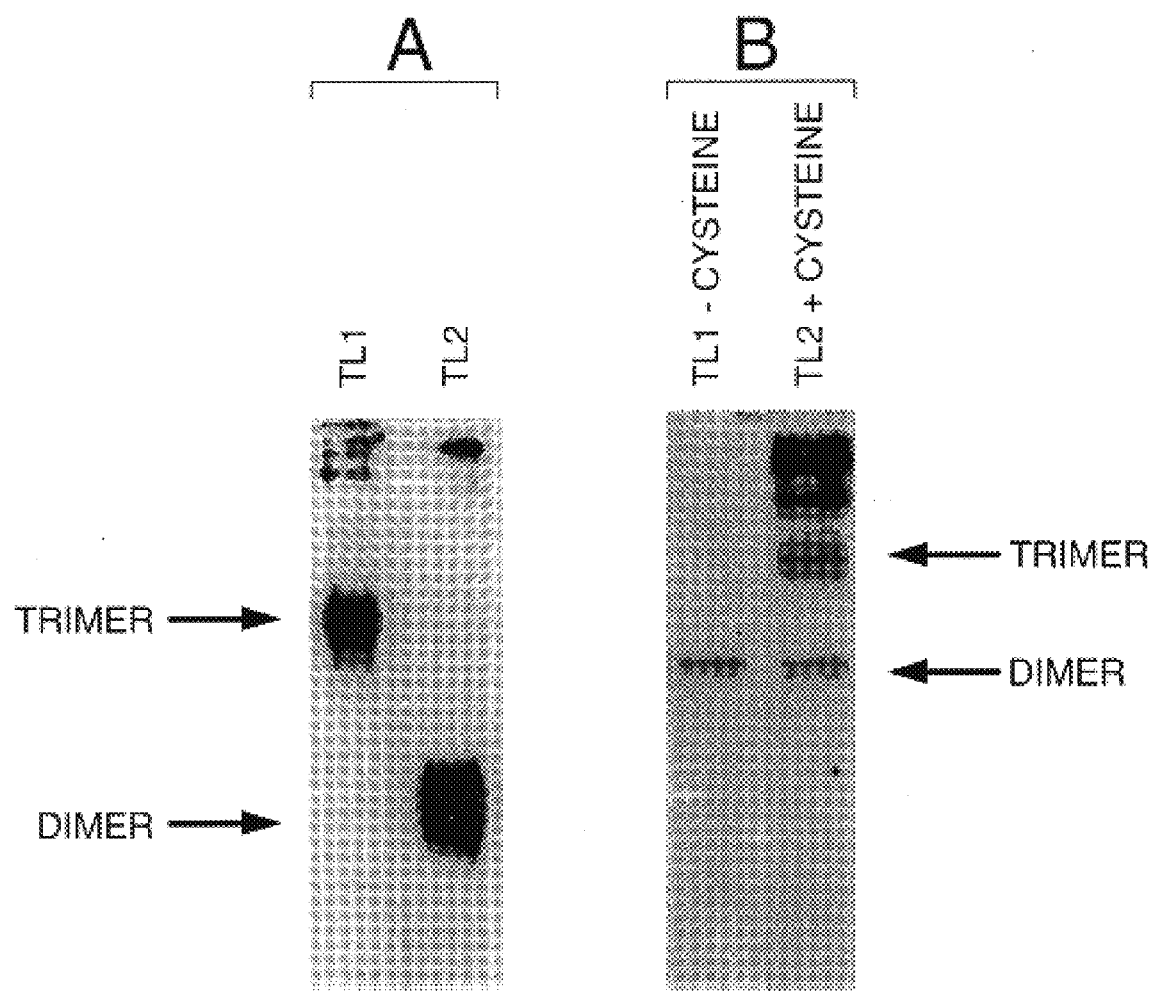
FIG. 18—Western blot of the covalent multimeric structure of TL1 and TL2 (Panel A) and the interconversion of TL1 and TL2 by the mutation of one cysteine (Panel B).

FIG. 18 shows the Western blots under non-reducing conditions of both non-mutated and mutated TL1 and TL2 proteins, revealing that the TL1/CYS⁻ mutant runs as a dimer much like TL2 and that the TL2/CYS+ mutant is able to form a trimer, as well as higher-order multimers, more like TL1. When the two mutant proteins were tested for their ability to induce phosphorylation in TIE-2 expressing cells, the TL1/CYS⁻ mutant was able to activate the TIE-2 receptor, whereas the TL2/CYS⁺ mutant was not.

Thus, when the cysteine residue (residue 265 in FIGS. 4A–4D (SEQ. ID. NO. 1 and SEQ. ID. NO. 2); residue 245 in FIG. 17 (SEQ. ID. NO. 7 and SEQ. ID. NO. 8)) of TL1 was genetically altered to a serine, it was found that the covalent structure of TL1 became similar to that of TL2, i.e., primarily dimeric. The modified TL1 molecule still behaved as an agonist, thus the trimeric and/or higher order multimeric structure was not the determining factor giving TL1 the ability to activate. Although the removal of the cysteine did make a molecule with more desirable properties, it did not improve the production level of TL1.

23.2. Domain deletions—The nucleotide sequences encoding TL1 and TL2 share a genetic structure that can be divided into three domains, based on the amino acid sequences of the mature proteins. The last approximately 215 amino acid residues of each mature protein contains six cysteines and bears strong resemblance to a domain of fibrinogen. This region was thus denoted the "fibrinogen-like" domain or "F-domain." A central region of the mature protein containing approximately 205 residues had a high probability of assuming a "coiled-coil" structure and was denoted the "coiled-coil" domain or "C-domain." The amino-terminal approximately 55 residues of the mature protein contained two cysteines and had a low probability of having a coiled-coil structure. This region was designated the "N-terminal" domain or "N-domain." The modified ligands described herein are designated using a terminology wherein N=N-terminal domain, C=coiled-coil domain, F=fibrinogen-like domain and the numbers 1 and 2 refer to TL1 and TL2 respectively. Thus 1N indicates the N-terminal domain from TL1, 2F indicates the fibrinogen-like domain of TL2, and so forth.

In order to test whether the fibrinogen-like domain (F-domain) of the TIE-2 ligands contained TIE-2 activating activity, expression plasmids were constructed which deleted the coiled-coil and N-terminal domains, leaving only that portion of the DNA sequence encoding the F-domain (for TL1, beginning in FIGS. 4A–4D (SEQ. ID. NO. 1 and SEQ. ID. NO. 2) at about nucleotide 1159, amino acid residue ARG284; for TL2, corresponding to about nucleotide 1200 in FIGS. 6A–6D (SEQ. ID. NO. 5 and SEQ. ID. NO. 6), amino acid residue 282). This mutant construct was then transiently transfected into COS cells. The supernatant containing the recombinant protein was harvested. The TL1/F-domain mutant was tested for its ability to bind the TIE-2 receptor. The results showed that, as a monomer, the TL1/F-domain mutant was not able to bind TIE-2 at a detectable level.

But when the TL1/F-domain monomer was myc-tagged and subsequently clustered with an antibody directed against the myc tag, it exhibited detectable binding to TIE-2. However, the antibody-clustered TL1/F-domain mutant was not able to induce phosphorylatioh in a TIE-2 expressing cell line.

Thus it was determined that the F-domain of the TIE-2 ligands is involved in binding the receptor but that a truncation consisting of just the F-domain alone is not sufficient for receptor binding. This raised the possibility that the coiled-coil domain was responsible for holding together several fibrinogen-like domains, which might be essential for receptor binding. In an attempt to confirm this hypothesis, the F-domain was fused with the Fc section of human antibody IgG1. Because Fc sections dimerize upon expression by mammalian cells, these recombinant proteins mimicked the theoretical configuration of the F-domains were the native ligands to dimerize. This F-domain-Fc construct bound but failed to activate the receptor. Apparently, multimerization caused by other regions of the ligands is necessary to enable the ligands to bind the TIE receptor. In addition, some other factor outside of the F-domain must contribute to phosphorylation of the receptor.

Mutants were then constructed which were missing the fibrinogen-like domain, and therefore contained only the N-terminal and coiled-coil domains. They were not capable of binding to the receptor. To assess the role of the N-terminal domain in receptor binding and activation, the ligands were truncated to just their C- and F-domains and tagged with a FLAG tag at the N-terminus, creating constructs termed FLAG-1C1F and FLAG-2C2F. Although these molecules stained robustly in COS7 cells transfected transiently to express the TIE receptor, they failed to respond in a phosphorylation assay. Thus the N-domain does contain an essential factor for receptor activation although, as disclosed infra, the ability of chimeric molecule 2N2C1F to activate the receptor shows that even the N-domain of an inactive ligand can fill that role.

The differences in behavior between the myc-tagged F-domain truncation and the Fc-tagged F-domain truncation described previously suggested that the TIE ligands can only bind in dimeric or higher multimeric forms. Indeed, non-reducing SDS-PAGE showed that the TIE ligands exist naturally in dimeric, trimeric, and multimeric forms. That the FLAG-1C1F and FLAG-2C2F truncations can bind to the TIE-2 receptor without dimerization by a synthetic tag (such as Fc), whereas the F truncations cannot, suggests that the C-region is at least partly responsible for the aggregation of the F-domains.

23.3. Swapping constructs (chimeras):

Applicants had noted that the level of production of TL1 in COS7 cells was approximately tenfold lower than production of TL2. Therefore, chimeras of TL1 and TL2 were constructed in an attempt to explain this difference and also to further characterize the agonist activity of TL1 as compared to the antagonist activity of TL2.

Four chimeras were constructed in which either the N-terminal domain or the fibrinogen domain was exchanged between TL1 and TL2 and were designated using the terminology described previously such that, for example, 1N1C2F refers to a chimera having the N-terminal and coiled-coil domains of TL1, together with the fibrinogen-like domain from TL2. The four chimeras were constructed as follows:

chimera 1—1N1C2F
chimera 2—2N2C1F
chimera 3—1N2C2F
chimera 4—2N1C1F

The nucleotide and amino acid sequences of chimeras 1–4 are shown in FIGS. 24A–24C, FIGS. 25A–25C, FIGS. 26A–26C, and FIGS. 27A–27C (SEQ. ID. NOS. 19–26) respectively.

Each chimera was inserted into a separate expression vector pJFE14. The chimeras were then transfected into COS7 cells, along with the empty pJFE14 vector, native TL1, and native TL2 as controls, and the culture supernatants were collected.

In order to determine how the swapping affected the level of expression of the ligands, a 1:5 dilution and a 1:50 dilution of the COS7 supernatants were dot-blotted onto nitrocellulose. Three ligands that contained the TL1 N-domain (i.e. native TL1, 1N2C2F and 1N1C2F) were then probed with a rabbit antibody specific to the N-terminus of TL1. Three ligands containing the TL2 N-domain, (i.e. native TL2, 2N1C1F and 2N2C1F) were probed with a rabbit antibody specific for the N-terminus of TL2. The results demonstrated that the COS7 cells were expressing any molecule containing the N-domain of TL2 at roughly ten times the level of any molecule containing the TL1 N-domain, regardless of the makeup of the rest of the protein. The conclusion was that the N-domain must principally control the level of expression of the ligand.

The next question addressed was the chimeras' ability or inability to activate the TIE-2 receptor. EAhy926 cells were challenged with the four chimeras, as well as TL1 as a positive control for phosphorylation and TL2 or an empty pJFE14-transfected COS7 cell supernatant as negative controls for phosphorylation. The cells were lysed, and the TIE-2 receptor was immunoprecipitated out of the cell lysate and run on an SDS-PAGE. The samples were Western blotted and probed with an anti-phosphotyrosine antibody to detect any receptors that had been phosphorylated. Surprisingly, only the constructs containing the TL1 fibrinogen-like domain (2N1C1F and 2N2C1F) could phosphorylate the TIE-2 receptor. Thus, although the N-terminal region of TL1 is essential for activation, it can be replaced by the N-terminal region of TL2, i.e., the information that determines whether the ligand is an agonist or an antagonist is actually contained in the fibrinogen-like domain. Thus it was determined that the F-domain, in addition to binding the TIE-2 receptor, is responsible for the phosphorylation activity of TL1. Further, when TL2, an otherwise inactive molecule, was altered by replacing its F-domain with the TL1 F-domain, the altered TL2 acted as an agonist.

The 2N1C1F construct was somewhat more potent, however. The signal caused by chimera 2N1C1F appeared slightly stronger than that of chimera 2N2C1F, leading to speculation that the C-domain of TL1, though not crucial for phosphorylation, might enhance the potency of TL1. However, since the samples used for the phosphorylation assay were not normalized in terms of the concentration of ligand, it was possible that a stronger phosphorylation signal only indicated the presence of more ligand. The phosphorylation assay was therefore repeated with varying amounts of ligand to determine whether the active chimeras displayed different potencies. The concentration of ligand in the COS7 supernatants of ligand transfections was determined through BIAcore biosenser technology according to methods previously described (Stitt, T. N., et al. (1995) Cell 80: 661–670). BIAcore measured the binding activity of a supernatant to the TIE-2 receptor in arbitrary units called resonance units (RU). Fairly good correlation between RU's and ligand concentration has been generally observed, with 400 RU of activity corresponding to about 1 μg of protein per mL of supernatant. Samples were diluted to concentrations of 100 RU, 20 RU, and 5 RU each and the phosphorylation assay was repeated. The results demonstrated that chimera 2N2C1 F was clearly more potent than either the native TL1 or chimera 1N1C2F at the same concentrations.

Another interesting aspect of these exchange constructs is in their levels of expression. Each of the four chimeras was tested for its level of production in COS cells, its ability to bind to TIE2, and its ability to phosphorylate TIE2. The results of these experiments showed that chimeras 1 and 3 were produced at levels comparable to TL1, whereas chimeras 2 and 4 were produced at levels comparable to TL2. Thus a high level of protein production was correlated with the TL2 N-terminal domain. Additionally, when tested on endothelial EAhy926 cells, chimeras 2 and 4 were active, whereas 1 and 3 were not. Thus activity (phosphorylation of the receptor) correlates with the TL1 fibrinogen-like domain. Chimeras 2 and 4 therefore each had the desirable properties of high production levels as well as agonist activity.

23.4. Proteolytic resistant constructs—Based on the observation that a large fraction of TL1 preparations was often proteolytically cleaved near the N-terminus, it was proposed that an arginine residue located at position 49 of the mature protein (see FIG. 17 (SEQ. ID. NO. 7 and SEQ. ID. NO. 8)) was a candidate cleavage site that might be involved in the regulation of the protein's activity in vivo, and that replacing the arginine with a serine (R49→S) might increase the stability of the protein without necessarily affecting its activity. Such a mutant of TL1 was constructed and was found to be about as active as the native TL1 but did not exhibit resistance to proteolytic cleavage.

23.5. Combination mutants—The most potent of the chimeric constructs, 2N1C1F, was additionally altered so that the cysteine encoded by nucleotides 784–787 as shown in FIGS. 27A–27C (SEQ. ID. NO. 25 and SEQ. ID. NO. 26) was converted to a serine. This molecule (denoted 2N1C1F (C246S)) was expressed well, potently activated the receptor, was resistant to proteolytic cleavage and was primarily dimeric, rather than higher-order multimeric. Thus the 2N domain appeared to confer protease resistance on the molecule. Finally, this molecule was further altered to eliminate the potentially protease sensitive site encoded by nucleotides 199–201 as shown in FIGS. 27A–27C (SEQ. ID. NO. 25 and SEQ. ID. NO. 26), to give a molecule (denoted 2N1C1F (R51->S,C246->S)) which was expected to be activating, well expressed, dimeric, and protease resistant.

Table 1 summarizes the modified TIE-2 ligand constructs that were made and characterizes each of them in terms of ability to bind the TIE-2 receptor, ability to activate the TIE-2 receptor, the type of structure formed (monomer, dimer, etc.) and their relative production levels. Unmodified TL1 (plain) and TL2 (striped) are shown with the three domains as boxes. Thus striped boxes indicate domains from TL2. The cysteine located at position 245 of the mature TL1 protein is indicated by a "C." An "X" through the "C" indicates that that cysteine residue was substituted for by another amino acid as in, for example, the TL1 CYS⁻ mutant. Similarly, an "X", through the "R" in the last construct indicates the substitution for an Arg residue at position 49 of the mature TL1 protein. The "C" is present in one modified TL2 construct showing the TL2 CYS⁺ mutant. Constructs having Fc tails or flag tagging are also indicated.

Based upon the teachings herein, one of skill in the art can readily see that further constructs may be made in order to create additional modified and chimeric TIE-2 ligands which have altered properties. For example, one may create a construct comprised of the N-terminal domain of TL2 and the F-domain of TL1 fused with the Fc section of human antibody IgG1. This construct would be expected to bind and activate the TIE-2 receptor. Similarly, other constructs may be created using the teachings herein and are therefore considered to be within the scope of this invention.

23.6. Materials and Methods—Construction of Chimeras

Swapping constructs were inserted into a pJFE14 vector in which the XbaI site was changed to an AscI site. This vector was then digested with AscI and NotI yielding an AscI-NotI backbone. DNA fragments for the chimeras were generated by PCR using appropriate oligonucleotides.

The FLAG-1C1F and FLAG-2C2F inserts were subcloned into a pMT21 vector backbone that had been digested with EcoRI and NotI. The "CF" truncations were obtained through PCR, and the FLAG tag and a preceding trypsin signalling sequence were constructed by annealing synthetic oligonucleotides.

Transfections

All constructs were transfected transiently into COS7 cells using either DEAE-Dextran or LipofectAMINE according to standard protocols. Cell cultures were harvested 3 days after the transfection and spun down at 1000 rpm for 1 minute, and the supernatants were transferred to fresh tubes and stored at −20° C.

Staining of FLAG-1C1F-Transfected and FLAG-2C2F-Transfected Cells 6-well dishes of COS7 cells were transfected transiently with the TIE-2 receptor. The COS7 supernatant from various ligand tansfections was incubated on the cells for 30 minutes, followed by two washes with Phosphate Buffered Saline (PBS) without magnesium or calcium. The cells were fixed in −20° C. methanol for 3 minutes, washed once with PBS, and incubated with anti-FLAG M2 antibody (IBI;1:3000 dilution) in PBS/10% Bovine Calf Serum (BCS) for 30 minutes. The cells were washed once with PBS and incubated with goat anti-mouse IgG Alkaline Phosphatase (AP) conjugated antibody (Promega;1:1000) in PBS/10% BCS. The cells were washed twice with PBS and incubated with the phosphate substrate, BCIP/NBT, with 1 mM levamisole.

Phosphorylation Assays

Dilution of COS7 supernatants for the dose response study was done in the supernatants of COS7 cells transfected with the empty vector pJFE14. EA cells that naturally express the TIE-2 receptor were starved for >2 hours in serum-free medium, followed by challenge with the appropriate COS7 supernatant for 10 minutes at 37° C. in an atmosphere of 5% CO2. The cells were then rinsed in ice-cold PBS and lysed with 1% NP40 lysis buffer containing protease inhibitors (10 µg/ml leupeptin, 10 µg/ml aprotinin, 1 mM PMSF) followed by immunoprecipitation with an antibody specific for the TIE-2 receptor. Samples were then subjected to immunoblot analysis, using anti pTyr antibodies.

Dot Blots

Samples were applied to a nitrocellulose membrane, which was blocked and probed with the appropriate antibodies.

TABLE 1

MUTATION ANALYSIS OF THE LIGANDS

| Construct (N / COILED-COIL / FIBRINOGEN-LIKE) | TIE2 Binding | TIE2 Activation | Multimeric Structure | Production Levels |
|---|---|---|---|---|
| TL1 (N, coiled-coil plain, fibrinogen-like with "c") | + | + | HIGHER ORDER | LOW |
| TL2 (N, coiled-coil hatched, fibrinogen-like plain) | + | − | DIMER | HIGH |
| (N, coiled-coil plain, fibrinogen-like with X) | + | + | DIMER | LOW |
| (N, coiled-coil hatched, fibrinogen-like hatched) | + | − | HIGHER ORDER | HIGH |
| (coiled-coil plain, fibrinogen-like with "c", no N) | − | N.D. | N.D. | LOW |
| (coiled-coil hatched only) | − | N.D. | N.D. | HIGH |
| (fibrinogen-like plain only) | − | − | MONOMER | HIGH |
| (fibrinogen-like hatched only) | − | − | MONOMER | HIGH |
| (coiled-coil plain + Fc) | + | − | DIMER | HIGH |
| (coiled-coil hatched + Fc) | + | − | DIMER | HIGH |
| (coiled-coil plain, fibrinogen-like "c", Fc) | + | + | HIGHER ORDER | LOW |
| (coiled-coil hatched, fibrinogen-like hatched, Fc) | + | − | HIGHER ORDER | LOW |
| flag- (coiled-coil plain, fibrinogen-like "c") | + | + | N.D. | LOW |
| flag- (coiled-coil hatched, fibrinogen-like hatched) | + | − | N.D. | HIGH |

TABLE 1-continued
MUTATION ANALYSIS OF THE LIGANDS

| | | | | |
|---|---|---|---|---|
| c | + | - | N.D. | HIGH |
| (hatched) | + | - | N.D. | HIGH |
| c (hatched) | + | - | N.D. | LOW |
| (hatched) | + | + | N.D. | HIGH* |
| (hatched) | + | - | N.D. | LOW |
| (hatched) c | + | +** | N.D. | HIGH |
| (hatched) X | + | +** | DIMER | HIGH |
| X c | + | + | N.D. | LOW |

DEPOSITS

The following have been deposited with the American Type Culture Collection, 12301 Parklawn Drive, Rockville, Md. 20852 in accordance with the Budapest Treaty. A plasmid clone encoding a TIE-2 ligand was deposited with the ATCC on Oct. 7, 1994 and designated as "pJFE14 encoding TIE-2 ligand" under ATCC Accession No. 75910. Recombinant *Autographa californica* baculovirus encoding TIE-2 receptorbody was deposited with the ATCC on Oct. 7, 1994 and designated as "vTIE-2 receptorbody" under ATCC Accession No. VR2484. A lambda phage vector containing human tie-2 ligand DNA was deposited with the ATCC on Oct. 26, 1994 and designated as "λgt10 encoding htie-2 ligand 1" under ATCC Accession No. 75928. A plasmid clone encoding a second TIE-2 ligand was deposited with the ATCC on Dec. 9, 1994 and designated as "pBluescript KS encoding human TIE 2 ligand 2" under ATCC Accession No. 75963. *E. coli* strain DH10B containing plasmid pBe-LoBac11 with a human TL-4 gene insert encoding human TIE ligand-4 was deposited with the ATCC on Jul. 2, 1996 and designated as "hTL-4" under ATCC Accession No. 98095.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. An isolated nucleic acid molecule comprising a nucleotide sequence encoding a modified TIE-2 ligand, wherein the nucleotide sequence is selected from the group consisting of:
(a) a nucleotide sequence encoding the mature modified TIE-2 ligand as set forth by nucleotides 49–1485 in FIGS. 27A–27C (SEQ ID NO 25); and
(b) a nucleotide sequence that, as a result of the degeneracy of the genetic code, differs from the nucleotide sequence of (a) and which encodes the modified TIE-2 ligand of (a).

2. An isolated nucleic acid molecule, which is modified to encode a serine amino acid residue instead of the cysteine amino acid residue encoded by nucleotides 784–786 set forth in FIGS. 27A–27C (SEQ ID NO 25).

3. The isolated nucleic acid molecule of claim 2, which is further modified to encode a serine amino acid residue instead of the arginine amino acid residue encoded by nucleotides 199–201 set forth in FIGS. 27A–27C (SEQ ID NO 25).

4. The isolated nucleic acid molecule of claim 2, which is further modified to encode a different amino acid residue instead of the cysteine amino acid residue encoded by nucleotides 784–786 set forth in FIGS. 27A–27C (SEQ ID NO 25), wherein the different amino acid residue is selected from the group consisting of glycine, threonine, tyrosine, asparagine and glutamine.

5. The isolated nucleic acid molecule of claim 3, which is further modified to encode a different amino acid residue instead of the arginine amino acid residue encoded by nucleotides 199–201 set forth in FIGS. 27A–27C (SEQ ID NO 25), wherein the different amino acid residue is selected from the group consisting of lysine and histidine.

6. An isolated nucleic acid molecule comprising a nucleotide sequence encoding a modified TIE-2 ligand, wherein the nucleotide sequence is selected from the group consisting of:
 (a) a nucleotide sequence encoding the mature modified TIE-2 ligand as set forth by nucleotides 49–1488 in FIGS. 25A–25C (SEQ ID NO 21); and
 (b) a nucleotide sequence that, as a result of the degeneracy of the genetic code, differs from the nucleotide sequence of (a) and which encodes the modified TIE-2 ligand of (a).

7. An isolated nucleic acid molecule comprising a nucleotide sequence encoding a modified TIE-2 ligand that binds and activates TIE-2 receptor comprising a nucleotide sequence encoding mature TIE-2 ligand 1 protein as set forth in FIGS. 4A–4D (SEQ ID NO 1) which is modified to encode a serine amino acid residue instead of the cysteine amino acid residue at amino acid position 265.

8. An isolated nucleic acid molecule comprising a nucleotide sequence that, as a result of the degeneracy of the genetic code, differs from the nucleotide sequence of claim 7, and which encodes the modified TIE-2 ligand encoded by the nucleotide sequence of claim 7.

* * * * *

```
                     SEQUENCE LISTING (1) GENERAL INFORMATION:

(iii) NUMBER OF SEQUENCES: 28

(2) INFORMATION FOR SEQ ID NO:1:

(i) SEQUENCE CHARACTERISTICS:
        (A) LENGTH: 2149 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 310...1803
        (D) OTHER INFORMATION:
        (A) NAME/KEY: Human TIE-2 ligand 1
        (B) LOCATION: 1...2149
        (D) OTHER INFORMATION:  from clone  gt10 encoding
            htie-2 ligand 1

(xi) SEQUENCE DESCRIPTION: SEQ ID NO:1:

CAGCTGACTC AGGCAGGCTC CATGCTGAAC GGTCACACAG AGAGGAAACA ATAAATCTCA      60

GCTACTATGC AATAAATATC TCAAGTTTTA ACGAAGAAAA ACATCATTGC AGTGAAATAA     120
```

-continued

```
AAAATTTTAA AATTTTAGAA CAAAGCTAAC AAATGGCTAG TTTTCTATGA TTCTTCTTCA    180

AACGCTTTCT TTGAGGGGGA AAGAGTCAAA CAAACAAGCA GTTTTACCTG AAATAAAGAA    240

CTAGTTTTAG AGGTCAGAAG AAAGGAGCAA GTTTTGCGAG AGGCACGGAA GGAGTGTGCT    300

GGCAGTACA ATG ACA GTT TTC CTT TCC TTT GCT TTC CTC GCT GCC ATT CTG    351
          Met Thr Val Phe Leu Ser Phe Ala Phe Leu Ala Ala Ile Leu
          1                 5                  10

ACT CAC ATA GGG TGC AGC AAT CAG CGC CGA AGT CCA GAA AAC AGT GGG    399
Thr His Ile Gly Cys Ser Asn Gln Arg Arg Ser Pro Glu Asn Ser Gly
15              20                  25                  30

AGA AGA TAT AAC CGG ATT CAA CAT GGG CAA TGT GCC TAC ACT TTC ATT    447
Arg Arg Tyr Asn Arg Ile Gln His Gly Gln Cys Ala Tyr Thr Phe Ile
            35                  40                  45

CTT CCA GAA CAC GAT GGC AAC TGT CGT GAG AGT ACG ACA GAC CAG TAC    495
Leu Pro Glu His Asp Gly Asn Cys Arg Glu Ser Thr Thr Asp Gln Tyr
            50                  55                  60

AAC ACA AAC GCT CTG CAG AGA GAT GCT CCA CAC GTG GAA CCG GAT TTC    543
Asn Thr Asn Ala Leu Gln Arg Asp Ala Pro His Val Glu Pro Asp Phe
65              70                  75

TCT TCC CAG AAA CTT CAA CAT CTG GAA CAT GTG ATG GAA AAT TAT ACT    591
Ser Ser Gln Lys Leu Gln His Leu Glu His Val Met Glu Asn Tyr Thr
80              85                  90

CAG TGG CTG CAA AAA CTT GAG AAT TAC ATT GTG GAA AAC ATG AAG TCG    639
Gln Trp Leu Gln Lys Leu Glu Asn Tyr Ile Val Glu Asn Met Lys Ser
95              100                 105                 110

GAG ATG GCC CAG ATA CAG CAG AAT GCA GTT CAG AAC CAC ACG GCT ACC    687
Glu Met Ala Gln Ile Gln Gln Asn Ala Val Gln Asn His Thr Ala Thr
                115                 120                 125

ATG CTG GAG ATA GGA ACC AGC CTC CTC TCT CAG ACT GCA GAG CAG ACC    735
Met Leu Glu Ile Gly Thr Ser Leu Leu Ser Gln Thr Ala Glu Gln Thr
                130                 135                 140

AGA AAG CTG ACA GAT GTT GAG ACC CAG GTA CTA AAT CAA ACT TCT CGA    783
Arg Lys Leu Thr Asp Val Glu Thr Gln Val Leu Asn Gln Thr Ser Arg
            145                 150                 155

CTT GAG ATA CAG CTG CTG GAG AAT TCA TTA TCC ACC TAC AAG CTA GAG    831
Leu Glu Ile Gln Leu Leu Glu Asn Ser Leu Ser Thr Tyr Lys Leu Glu
    160                 165                 170

AAG CAA CTT CTT CAA CAG ACA AAT GAA ATC TTG AAG ATC CAT GAA AAA    879
Lys Gln Leu Leu Gln Gln Thr Asn Glu Ile Leu Lys Ile His Glu Lys
175                 180                 185                 190

AAC AGT TTA TTA GAA CAT AAA ATC TTA GAA ATG GAA GGA AAA CAC AAG    927
Asn Ser Leu Leu Glu His Lys Ile Leu Glu Met Glu Gly Lys His Lys
                195                 200                 205

GAA GAG TTG GAC ACC TTA AAG GAA GAG AAA GAG AAC CTT CAA GGC TTG    975
Glu Glu Leu Asp Thr Leu Lys Glu Glu Lys Glu Asn Leu Gln Gly Leu
                210                 215                 220

GTT ACT CGT CAA ACA TAT ATA ATC CAG GAG CTG GAA AAG CAA TTA AAC    1023
Val Thr Arg Gln Thr Tyr Ile Ile Gln Glu Leu Glu Lys Gln Leu Asn
            225                 230                 235

AGA GCT ACC ACC AAC AAC AGT GTC CTT CAG AAG CAG CAA CTG GAG CTG    1071
Arg Ala Thr Thr Asn Asn Ser Val Leu Gln Lys Gln Gln Leu Glu Leu
        240                 245                 250

ATG GAC ACA GTC CAC AAC CTT GTC AAT CTT TGC ACT AAA GAA GGT GTT    1119
Met Asp Thr Val His Asn Leu Val Asn Leu Cys Thr Lys Glu Gly Val
255                 260                 265                 270

TTA CTA AAG GGA GGA AAA AGA GAG GAA GAG AAA CCA TTT AGA GAC TGT    1167
Leu Leu Lys Gly Gly Lys Arg Glu Glu Glu Lys Pro Phe Arg Asp Cys
                275                 280                 285

GCA GAT GTA TAT CAA GCT GGT TTT AAT AAA AGT GGA ATC TAC ACT ATT    1215
```

```
                                                        -continued

Ala Asp Val Tyr Gln Ala Gly Phe Asn Lys Ser Gly Ile Tyr Thr Ile
            290                 295                 300

TAT ATT AAT AAT ATG CCA GAA CCC AAA AAG GTG TTT TGC AAT ATG GAT    1263
Tyr Ile Asn Asn Met Pro Glu Pro Lys Lys Val Phe Cys Asn Met Asp
305                 310                 315

GTC AAT GGG GGA GGT TGG ACT GTA ATA CAA CAT CGT GAA GAT GGA AGT    1311
Val Asn Gly Gly Gly Trp Thr Val Ile Gln His Arg Glu Asp Gly Ser
    320                 325                 330

CTA GAT TTC CAA AGA GGC TGG AAG GAA TAT AAA ATG GGT TTT GGA AAT    1359
Leu Asp Phe Gln Arg Gly Trp Lys Glu Tyr Lys Met Gly Phe Gly Asn
335                 340                 345                 350

CCC TCC GGT GAA TAT TGG CTG GGG AAT GAG TTT ATT TTT GCC ATT ACC    1407
Pro Ser Gly Glu Tyr Trp Leu Gly Asn Glu Phe Ile Phe Ala Ile Thr
                355                 360                 365

AGT CAG AGG CAG TAC ATG CTA AGA ATT GAG TTA ATG GAC TGG GAA GGG    1455
Ser Gln Arg Gln Tyr Met Leu Arg Ile Glu Leu Met Asp Trp Glu Gly
            370                 375                 380

AAC CGA GCC TAT TCA CAG TAT GAC AGA TTC CAC ATA GGA AAT GAA AAG    1503
Asn Arg Ala Tyr Ser Gln Tyr Asp Arg Phe His Ile Gly Asn Glu Lys
        385                 390                 395

CAA AAC TAT AGG TTG TAT TTA AAA GGT CAC ACT GGG ACA GCA GGA AAA    1551
Gln Asn Tyr Arg Leu Tyr Leu Lys Gly His Thr Gly Thr Ala Gly Lys
    400                 405                 410

CAG AGC AGC CTG ATC TTA CAC GGT GCT GAT TTC AGC ACT AAA GAT GCT    1599
Gln Ser Ser Leu Ile Leu His Gly Ala Asp Phe Ser Thr Lys Asp Ala
415                 420                 425                 430

GAT AAT GAC AAC TGT ATG TGC AAA TGT GCC CTC ATG TTA ACA GGA GGA    1647
Asp Asn Asp Asn Cys Met Cys Lys Cys Ala Leu Met Leu Thr Gly Gly
                435                 440                 445

TGG TGG TTT GAT GCT TGT GGC CCC TCC AAT CTA AAT GGA ATG TTC TAT    1695
Trp Trp Phe Asp Ala Cys Gly Pro Ser Asn Leu Asn Gly Met Phe Tyr
            450                 455                 460

ACT GCG GGA CAA AAC CAT GGA AAA CTG AAT GGG ATA AAG TGG CAC TAC    1743
Thr Ala Gly Gln Asn His Gly Lys Leu Asn Gly Ile Lys Trp His Tyr
        465                 470                 475

TTC AAA GGG CCC AGT TAC TCC TTA CGT TCC ACA ACT ATG ATG ATT CGA    1791
Phe Lys Gly Pro Ser Tyr Ser Leu Arg Ser Thr Thr Met Met Ile Arg
    480                 485                 490

CCT TTA GAT TTT TGA AAG CGCA ATGTCAGAAG CGATTATGAA AGCAACAAAG AAAT C1848
Pro Leu Asp Phe
495

CGGAGAAGCT GCCAGGTGAG AAACTGTTTG AAAACTTCAG AAGCAAACAA TATTGTCTCC     1908

CTTCCAGCAA TAAGTGGTAG TTATGTGAAG TCACCAAGGT TCTTGACCGT GAATCTGGAG     1968

CCGTTTGAGT TCACAAGAGT CTCTACTTGG GGTGACAGTG CTCACGTGGC TCGACTATAG     2028

AAAACTCCAC TGACTGTCGG GCTTTAAAAA GGGAAGAAAC TGCTGAGCTT GCTGTGCTTC     2088

AAACTACTAC TGGACCTTAT TTTGGAACTA TGGTAGCCAG ATGATAAATA TGGTTAATTT     2148

C                                                                      2149

(2) INFORMATION FOR SEQ ID NO:2:

(i) SEQUENCE CHARACTERISTICS:
            (A) LENGTH: 498 amino acids
            (B) TYPE: amino acid
            (C) STRANDEDNESS: single
            (D) TOPOLOGY: linear (ii) MOLECULE TYPE: protein (v) FRAGMENT TYPE: internal
```

(ix) FEATURE:
    (A) NAME/KEY: Human TIE-2 ligand 1
    (B) LOCATION: 1...498
    (D) OTHER INFORMATION: from clone gt10 encoding htie-2 ligand 1

(xi) SEQUENCE DESCRIPTION: SEQ ID NO:2:

```
Met Thr Val Phe Leu Ser Phe Ala Phe Leu Ala Ala Ile Leu Thr His
 1               5                  10                  15

Ile Gly Cys Ser Asn Gln Arg Arg Ser Pro Glu Asn Ser Gly Arg Arg
             20                  25                  30

Tyr Asn Arg Ile Gln His Gly Gln Cys Ala Tyr Thr Phe Ile Leu Pro
             35                  40                  45

Glu His Asp Gly Asn Cys Arg Glu Ser Thr Thr Asp Gln Tyr Asn Thr
 50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
             85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
            115                 120                 125

Glu Ile Gly Thr Ser Leu Leu Ser Gln Thr Ala Glu Gln Thr Arg Lys
130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
            165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
            195                 200                 205

Leu Asp Thr Leu Lys Glu Glu Lys Glu Asn Leu Gln Gly Leu Val Thr
210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
            245                 250                 255

Thr Val His Asn Leu Val Asn Leu Cys Thr Lys Glu Gly Val Leu Leu
            260                 265                 270

Lys Gly Gly Lys Arg Glu Glu Glu Lys Pro Phe Arg Asp Cys Ala Asp
            275                 280                 285

Val Tyr Gln Ala Gly Phe Asn Lys Ser Gly Ile Tyr Thr Ile Tyr Ile
290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
            325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
            355                 360                 365

Arg Gln Tyr Met Leu Arg Ile Glu Leu Met Asp Trp Glu Gly Asn Arg
```

```
                370                375                380
Ala Tyr Ser Gln Tyr Asp Arg Phe His Ile Gly Asn Glu Lys Gln Asn
385                 390                395                 400

Tyr Arg Leu Tyr Leu Lys Gly His Thr Gly Thr Ala Gly Lys Gln Ser
                405                410                 415

Ser Leu Ile Leu His Gly Ala Asp Phe Ser Thr Lys Asp Ala Asp Asn
                420                425                430

Asp Asn Cys Met Cys Lys Cys Ala Leu Met Leu Thr Gly Gly Trp Trp
            435                440                445

Phe Asp Ala Cys Gly Pro Ser Asn Leu Asn Gly Met Phe Tyr Thr Ala
    450                455                460

Gly Gln Asn His Gly Lys Leu Asn Gly Ile Lys Trp His Tyr Phe Lys
465                 470                475                 480

Gly Pro Ser Tyr Ser Leu Arg Ser Thr Thr Met Met Ile Arg Pro Leu
                485                490                495

Asp Phe (2) INFORMATION FOR SEQ ID NO:3:

(i) SEQUENCE CHARACTERISTICS:
        (A) LENGTH: 2146 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 310...1800
        (D) OTHER INFORMATION:
        (A) NAME/KEY: Human TIE-2 ligand 1
        (B) LOCATION: 1...2146
        (D) OTHER INFORMATION: from T98G clone (xi) SEQUENCE DESCRIPTION: SEQ ID NO:3:

CAGCTGACTC AGGCAGGCTC CATGCTGAAC GGTCACACAG AGAGGAAACA ATAAATCTCA     60

GCTACTATGC AATAAATATC TCAAGTTTTA ACGAAGAAAA ACATCATTGC AGTGAAATAA    120

AAAATTTTAA AATTTTAGAA CAAAGCTAAC AAATGGCTAG TTTTCTATGA TTCTTCTTCA    180

AACGCTTTCT TGAGGGGGA AAGAGTCAAA CAAACAAGCA GTTTTACCTG AAATAAAGAA     240

CTAGTTTTAG AGGTCAGAAG AAAGGAGCAA GTTTTGCGAG AGGCACGGAA GGAGTGTGCT    300

GGCAGTACA ATG ACA GTT TTC CTT TCC TTT GCT TTC CTC GCT GCC ATT CTG    351
          Met Thr Val Phe Leu Ser Phe Ala Phe Leu Ala Ala Ile Leu
           1               5                  10

ACT CAC ATA GGG TGC AGC AAT CAG CGC CGA AGT CCA GAA AAC AGT GGG      399
Thr His Ile Gly Cys Ser Asn Gln Arg Arg Ser Pro Glu Asn Ser Gly
15               20                 25                 30

AGA AGA TAT AAC CGG ATT CAA CAT GGG CAA TGT GCC TAC ACT TTC ATT      447
Arg Arg Tyr Asn Arg Ile Gln His Gly Gln Cys Ala Tyr Thr Phe Ile
                35                 40                 45

CTT CCA GAA CAC GAT GGC AAC TGT CGT GAG AGT ACA ACA GAC CAG TAC      495
Leu Pro Glu His Asp Gly Asn Cys Arg Glu Ser Thr Thr Asp Gln Tyr
            50                 55                 60

AAC ACA AAC GCT CTG CAG AGA GAT GCT CCA CAC GTG GAA CCG GAT TTC      543
Asn Thr Asn Ala Leu Gln Arg Asp Ala Pro His Val Glu Pro Asp Phe
        65                 70                 75

TCT TCC CAG AAA CTT CAA CAT CTG GAA CAT GTG ATG GAA AAT TAT ACT      591
Ser Ser Gln Lys Leu Gln His Leu Glu His Val Met Glu Asn Tyr Thr
    80                 85                 90
```

```
CAG TGG CTG CAA AAA CTT GAG AAT TAC ATT GTG GAA AAC ATG AAG TCG        639
Gln Trp Leu Gln Lys Leu Glu Asn Tyr Ile Val Glu Asn Met Lys Ser
 95             100                 105                 110

GAG ATG GCC CAG ATA CAG CAG AAT GCA GTT CAG AAC CAC ACG GCT ACC        687
Glu Met Ala Gln Ile Gln Gln Asn Ala Val Gln Asn His Thr Ala Thr
                115                 120                 125

ATG CTG GAG ATA GGA ACC AGC CTC CTC TCT CAG ACT GCA GAG CAG ACC        735
Met Leu Glu Ile Gly Thr Ser Leu Leu Ser Gln Thr Ala Glu Gln Thr
            130                 135                 140

AGA AAG CTG ACA GAT GTT GAG ACC CAG GTA CTA AAT CAA ACT TCT CGA        783
Arg Lys Leu Thr Asp Val Glu Thr Gln Val Leu Asn Gln Thr Ser Arg
        145                 150                 155

CTT GAG ATA CAG CTG CTG GAG AAT TCA TTA TCC ACC TAC AAG CTA GAG        831
Leu Glu Ile Gln Leu Leu Glu Asn Ser Leu Ser Thr Tyr Lys Leu Glu
    160                 165                 170

AAG CAA CTT CTT CAA CAG ACA AAT GAA ATC TTG AAG ATC CAT GAA AAA        879
Lys Gln Leu Leu Gln Gln Thr Asn Glu Ile Leu Lys Ile His Glu Lys
175                 180                 185                 190

AAC AGT TTA TTA GAA CAT AAA ATC TTA GAA ATG GAA GGA AAA CAC AAG        927
Asn Ser Leu Leu Glu His Lys Ile Leu Glu Met Glu Gly Lys His Lys
                195                 200                 205

GAA GAG TTG GAC ACC TTA AAG GAA GAG AAA GAG AAC CTT CAA GGC TTG        975
Glu Glu Leu Asp Thr Leu Lys Glu Glu Lys Glu Asn Leu Gln Gly Leu
            210                 215                 220

GTT ACT CGT CAA ACA TAT ATA ATC CAG GAG CTG GAA AAG CAA TTA AAC       1023
Val Thr Arg Gln Thr Tyr Ile Ile Gln Glu Leu Glu Lys Gln Leu Asn
        225                 230                 235

AGA GCT ACC ACC AAC AAC AGT GTC CTT CAG AAG CAG CAA CTG GAG CTG       1071
Arg Ala Thr Thr Asn Asn Ser Val Leu Gln Lys Gln Gln Leu Glu Leu
    240                 245                 250

ATG GAC ACA GTC CAC AAC CTT GTC AAT CTT TGC ACT AAA GAA GTT TTA       1119
Met Asp Thr Val His Asn Leu Val Asn Leu Cys Thr Lys Glu Val Leu
255                 260                 265                 270

CTA AAG GGA GGA AAA AGA GAG GAA GAG AAA CCA TTT AGA GAC TGT GCA       1167
Leu Lys Gly Gly Lys Arg Glu Glu Glu Lys Pro Phe Arg Asp Cys Ala
                275                 280                 285

GAT GTA TAT CAA GCT GGT TTT AAT AAA AGT GGA ATC TAC ACT ATT TAT       1215
Asp Val Tyr Gln Ala Gly Phe Asn Lys Ser Gly Ile Tyr Thr Ile Tyr
            290                 295                 300

ATT AAT AAT ATG CCA GAA CCC AAA AAG GTG TTT TGC AAT ATG GAT GTC       1263
Ile Asn Asn Met Pro Glu Pro Lys Lys Val Phe Cys Asn Met Asp Val
        305                 310                 315

AAT GGG GGA GGT TGG ACT GTA ATA CAA CAT CGT GAA GAT GGA AGT CTA       1311
Asn Gly Gly Gly Trp Thr Val Ile Gln His Arg Glu Asp Gly Ser Leu
    320                 325                 330

GAT TTC CAA AGA GGC TGG AAG GAA TAT AAA ATG GGT TTT GGA AAT CCC       1359
Asp Phe Gln Arg Gly Trp Lys Glu Tyr Lys Met Gly Phe Gly Asn Pro
335                 340                 345                 350

TCC GGT GAA TAT TGG CTG GGG AAT GAG TTT ATT TTT GCC ATT ACC AGT       1407
Ser Gly Glu Tyr Trp Leu Gly Asn Glu Phe Ile Phe Ala Ile Thr Ser
                355                 360                 365

CAG AGG CAG TAC ATG CTA AGA ATT GAG TTA ATG GAC TGG GAA GGG AAC       1455
Gln Arg Gln Tyr Met Leu Arg Ile Glu Leu Met Asp Trp Glu Gly Asn
            370                 375                 380

CGA GCC TAT TCA CAG TAT GAC AGA TTC CAC ATA GGA AAT GAA AAG CAA       1503
Arg Ala Tyr Ser Gln Tyr Asp Arg Phe His Ile Gly Asn Glu Lys Gln
        385                 390                 395

AAC TAT AGG TTG TAT TTA AAA GGT CAC ACT GGG ACA GCA GGA AAA CAG       1551
Asn Tyr Arg Leu Tyr Leu Lys Gly His Thr Gly Thr Ala Gly Lys Gln
```

```
                        400                 405                 410
AGC AGC CTG ATC TTA CAC GGT GCT GAT TTC AGC ACT AAA GAT GCT GAT           1599
Ser Ser Leu Ile Leu His Gly Ala Asp Phe Ser Thr Lys Asp Ala Asp
415                 420                 425                 430

AAT GAC AAC TGT ATG TGC AAA TGT GCC CTC ATG TTA ACA GGA GGA TGG           1647
Asn Asp Asn Cys Met Cys Lys Cys Ala Leu Met Leu Thr Gly Gly Trp
                435                 440                 445

TGG TTT GAT GCT TGT GGC CCC TCC AAT CTA AAT GGA ATG TTC TAT ACT           1695
Trp Phe Asp Ala Cys Gly Pro Ser Asn Leu Asn Gly Met Phe Tyr Thr
                450                 455                 460

GCG GGA CAA AAC CAT CGA AAA CTG AAT GGG ATA AAG TGG CAC TAC TTC           1743
Ala Gly Gln Asn His Arg Lys Leu Asn Gly Ile Lys Trp His Tyr Phe
                465                 470                 475

AAA GGG CCC AGT TAC TCC TTA CGT TCC ACA ACT ATG ATG ATT CGA CCT           1791
Lys Gly Pro Ser Tyr Ser Leu Arg Ser Thr Thr Met Met Ile Arg Pro
                480                 485                 490

TTA GAT TTT TGA AAGCGCA ATGTCAGAAG CGATTATGAA AGCAACAAAG AAATCCGGA        1849
Leu Asp Phe
495

GAAGCTGCCA GGTGAGAAAC TGTTTGAAAA CTTCAGAAGC AAACAATATT GTCTCCCTTC         1909

CACCAATAAG TGGTAGTTAT GTGAAGTCAC CAAGGTTCTT GACCGTGAAT CTGGAGCCGT         1969

TTGAGTTCAC AAGAGTCTCT ACTTGGGGTG ACAGTGCTCA CGTGGCTCGA CTATAGAAAA         2029

CTCCACTGAC TGTCGGGCTT TAAAAAGGGA AGAAACTGCT GAGCTTGCTG TGCTTCAAAC         2089

TACTACTGGA CCTTATTTTG GAACTATGGT AGCCAGATGA TAAATATGGT TAATTTC            2146

(2) INFORMATION FOR SEQ ID NO:4:

(i) SEQUENCE CHARACTERISTICS:
        (A) LENGTH: 497 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Human TIE-2 ligand 1
        (B) LOCATION: 1...2146
        (D) OTHER INFORMATION: from T98G clone (xi) SEQUENCE DESCRIPTION: SEQ ID NO:4:

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
                35                  40                  45

Glu His Asp Gly Asn Cys Arg Glu Ser Thr Thr Asp Gln Tyr Asn Thr
50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
                100                 105                 110

Ala Gln Ile Gln Gln Asn Ala Val Gln Asn His Thr Ala Thr Met Leu
                115                 120                 125
```

-continued

```
Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Val Leu Leu Lys
            260                 265                 270

Gly Gly Lys Arg Glu Glu Lys Pro Phe Arg Asp Cys Ala Asp Val
        275                 280                 285

Tyr Gln Ala Gly Phe Asn Lys Ser Gly Ile Tyr Thr Ile Tyr Ile Asn
    290                 295                 300

Asn Met Pro Glu Pro Lys Lys Val Phe Cys Asn Met Asp Val Asn Gly
305                 310                 315                 320

Gly Gly Trp Thr Val Ile Gln His Arg Glu Asp Gly Ser Leu Asp Phe
                325                 330                 335

Gln Arg Gly Trp Lys Glu Tyr Lys Met Gly Phe Gly Asn Pro Ser Gly
            340                 345                 350

Glu Tyr Trp Leu Gly Asn Glu Phe Ile Phe Ala Ile Thr Ser Gln Arg
        355                 360                 365

Gln Tyr Met Leu Arg Ile Glu Leu Met Asp Trp Glu Gly Asn Arg Ala
    370                 375                 380

Tyr Ser Gln Tyr Asp Arg Phe His Ile Gly Asn Glu Lys Gln Asn Tyr
385                 390                 395                 400

Arg Leu Tyr Leu Lys Gly His Thr Gly Thr Ala Gly Lys Gln Ser Ser
                405                 410                 415

Leu Ile Leu His Gly Ala Asp Phe Ser Thr Lys Asp Ala Asp Asn Asp
            420                 425                 430

Asn Cys Met Cys Lys Cys Ala Leu Met Leu Thr Gly Gly Trp Trp Phe
        435                 440                 445

Asp Ala Cys Gly Pro Ser Asn Leu Asn Gly Met Phe Tyr Thr Ala Gly
    450                 455                 460

Gln Asn His Arg Lys Leu Asn Gly Ile Lys Trp His Tyr Phe Lys Gly
465                 470                 475                 480

Pro Ser Tyr Ser Leu Arg Ser Thr Thr Met Met Ile Arg Pro Leu Asp
                485                 490                 495

Phe
```

(2) INFORMATION FOR SEQ ID NO:5:

(i) SEQUENCE CHARACTERISTICS:
        (A) LENGTH: 2282 base pairs
        (B) TYPE: nucleic acid
        (C) STRANDEDNESS: single (D) TOPOLOGY: linear (ii) MOLECULE TYPE: DNA (ix) FEATURE:
        (A) NAME/KEY: Coding Sequence
        (B) LOCATION: 357...1844
        (D) OTHER INFORMATION:
        (A) NAME/KEY: Human TIE-2 ligand 2
        (B) LOCATION: 1...2282
        (D) OTHER INFORMATION: from clone pBluescript KS
            encoding human TIE 2 ligand 2

(xi) SEQUENCE DESCRIPTION: SEQ ID NO:5:

```
GAATTCCTGG GTTGGTGTTT ATCTCCTCCC AGCCTTGAGG GAGGGAACAA CACTGTAGGA     60

TCTGGGGAGA GAGGAACAAA GGACCGTGAA AGCTGCTCTG TAAAAGCTGA CACAGCCCTC    120

CCAAGTGAGC AGGACTGTTC TTCCCACTGC AATCTGACAG TTTACTGCAT GCCTGGAGAG    180

AACACAGCAG TAAAAACCAG GTTTGCTACT GGAAAAAGAG GAAAGAGAAG ACTTTCATTG    240

ACGGACCCAG CCATGGCAGC GTAGCAGCCC TGCGTTTCAG ACGGCAGCAG CTCGGGACTC    300

TGGACGTGTG TTTGCCCTCA AGTTTGCTAA GCTGCTGGTT TATTACTGAA GAAAGA ATG    359
                                                               Met
                                                                 1

TGG CAG ATT GTT TTC TTT ACT CTG AGC TGT GAT CTT GTC TTG GCC GCA     407
Trp Gln Ile Val Phe Phe Thr Leu Ser Cys Asp Leu Val Leu Ala Ala
          5                  10                  15

GCC TAT AAC AAC TTT CGG AAG AGC ATG GAC AGC ATA GGA AAG AAG CAA     455
Ala Tyr Asn Asn Phe Arg Lys Ser Met Asp Ser Ile Gly Lys Lys Gln
         20                  25                  30

TAT CAG GTC CAG CAT GGG TCC TGC AGC TAC ACT TTC CTC CTG CCA GAG     503
Tyr Gln Val Gln His Gly Ser Cys Ser Tyr Thr Phe Leu Leu Pro Glu
 35                  40                  45

ATG GAC AAC TGC CGC TCT TCC TCC AGC CCC TAC GTG TCC AAT GCT GTG     551
Met Asp Asn Cys Arg Ser Ser Ser Ser Pro Tyr Val Ser Asn Ala Val
 50                  55                  60                  65

CAG AGG GAC GCG CCG CTC GAA TAC GAT GAC TCG GTG CAG AGG CTG CAA     599
Gln Arg Asp Ala Pro Leu Glu Tyr Asp Asp Ser Val Gln Arg Leu Gln
                 70                  75                  80

GTG CTG GAG AAC ATC ATG GAA AAC AAC ACT CAG TGG CTA ATG AAG CTT     647
Val Leu Glu Asn Ile Met Glu Asn Asn Thr Gln Trp Leu Met Lys Leu
             85                  90                  95

GAG AAT TAT ATC CAG GAC AAC ATG AAG AAA GAA ATG GTA GAG ATA CAG     695
Glu Asn Tyr Ile Gln Asp Asn Met Lys Lys Glu Met Val Glu Ile Gln
        100                 105                 110

CAG AAT GCA GTA CAG AAC CAG ACG GCT GTG ATG ATA GAA ATA GGG ACA     743
Gln Asn Ala Val Gln Asn Gln Thr Ala Val Met Ile Glu Ile Gly Thr
    115                 120                 125

AAC CTG TTG AAC CAA ACA GCT GAG CAA ACG CGG AAG TTA ACT GAT GTG     791
Asn Leu Leu Asn Gln Thr Ala Glu Gln Thr Arg Lys Leu Thr Asp Val
130                 135                 140                 145

GAA GCC CAA GTA TTA AAT CAG ACC ACG AGA CTT GAA CTT CAG CTC TTG     839
Glu Ala Gln Val Leu Asn Gln Thr Thr Arg Leu Glu Leu Gln Leu Leu
                150                 155                 160

GAA CAC TCC CTC TCG ACA AAC AAA TTG GAA AAA CAG ATT TTG GAC CAG     887
Glu His Ser Leu Ser Thr Asn Lys Leu Glu Lys Gln Ile Leu Asp Gln
            165                 170                 175

ACC AGT GAA ATA AAC AAA TTG CAA GAT AAG AAC AGT TTC CTA GAA AAG     935
Thr Ser Glu Ile Asn Lys Leu Gln Asp Lys Asn Ser Phe Leu Glu Lys
        180                 185                 190

AAG GTG CTA GCT ATG GAA GAC AAG CAC ATC ATC CAA CTA CAG TCA ATA     983
Lys Val Leu Ala Met Glu Asp Lys His Ile Ile Gln Leu Gln Ser Ile
```

-continued

|  |  |  |  |  |  |  |  |  |  |  |  |  |  |  |  |
|---|---|---|---|---|---|---|---|---|---|---|---|---|---|---|---|
|  | 195 |  |  |  | 200 |  |  |  |  | 205 |  |  |  |  |  |
| AAA | GAA | GAG | AAA | GAT | CAG | CTA | CAG | GTG | TTA | GTA | TCC | AAG | CAA | AAT | TCC | 1031 |
| Lys | Glu | Glu | Lys | Asp | Gln | Leu | Gln | Val | Leu | Val | Ser | Lys | Gln | Asn | Ser |
| 210 |  |  |  |  | 215 |  |  |  |  | 220 |  |  |  |  | 225 |
| ATC | ATT | GAA | GAA | CTA | GAA | AAA | AAA | ATA | GTG | ACT | GCC | ACG | GTG | AAT | AAT | 1079 |
| Ile | Ile | Glu | Glu | Leu | Glu | Lys | Lys | Ile | Val | Thr | Ala | Thr | Val | Asn | Asn |
|  |  |  |  |  | 230 |  |  |  |  | 235 |  |  |  |  | 240 |
| TCA | GTT | CTT | CAA | AAG | CAG | CAA | CAT | GAT | CTC | ATG | GAG | ACA | GTT | AAT | AAC | 1127 |
| Ser | Val | Leu | Gln | Lys | Gln | Gln | His | Asp | Leu | Met | Glu | Thr | Val | Asn | Asn |
|  |  |  |  | 245 |  |  |  |  | 250 |  |  |  |  | 255 |  |
| TTA | CTG | ACT | ATG | ATG | TCC | ACA | TCA | AAC | TCA | GCT | AAG | GAC | CCC | ACT | GTT | 1175 |
| Leu | Leu | Thr | Met | Met | Ser | Thr | Ser | Asn | Ser | Ala | Lys | Asp | Pro | Thr | Val |
|  |  |  | 260 |  |  |  |  | 265 |  |  |  |  | 270 |  |  |
| GCT | AAA | GAA | GAA | CAA | ATC | AGC | TTC | AGA | GAC | TGT | GCT | GAA | GTA | TTC | AAA | 1223 |
| Ala | Lys | Glu | Glu | Gln | Ile | Ser | Phe | Arg | Asp | Cys | Ala | Glu | Val | Phe | Lys |
| 275 |  |  |  |  | 280 |  |  |  |  | 285 |  |  |  |  |  |
| TCA | GGA | CAC | ACC | ACA | AAT | GGC | ATC | TAC | ACG | TTA | ACA | TTC | CCT | AAT | TCT | 1271 |
| Ser | Gly | His | Thr | Thr | Asn | Gly | Ile | Tyr | Thr | Leu | Thr | Phe | Pro | Asn | Ser |
| 290 |  |  |  |  | 295 |  |  |  |  | 300 |  |  |  |  | 305 |
| ACA | GAA | GAG | ATC | AAG | GCC | TAC | TGT | GAC | ATG | GAA | GCT | GGA | GGA | GGC | GGG | 1319 |
| Thr | Glu | Glu | Ile | Lys | Ala | Tyr | Cys | Asp | Met | Glu | Ala | Gly | Gly | Gly | Gly |
|  |  |  |  | 310 |  |  |  |  | 315 |  |  |  |  | 320 |  |
| TGG | ACA | ATT | ATT | CAG | CGA | CGT | GAG | GAT | GGC | AGC | GTT | GAT | TTT | CAG | AGG | 1367 |
| Trp | Thr | Ile | Ile | Gln | Arg | Arg | Glu | Asp | Gly | Ser | Val | Asp | Phe | Gln | Arg |
|  |  |  | 325 |  |  |  |  | 330 |  |  |  |  | 335 |  |  |
| ACT | TGG | AAA | GAA | TAT | AAA | GTG | GGA | TTT | GGT | AAC | CCT | TCA | GGA | GAA | TAT | 1415 |
| Thr | Trp | Lys | Glu | Tyr | Lys | Val | Gly | Phe | Gly | Asn | Pro | Ser | Gly | Glu | Tyr |
|  |  | 340 |  |  |  |  | 345 |  |  |  |  | 350 |  |  |  |
| TGG | CTG | GGA | AAT | GAG | TTT | GTT | TCG | CAA | CTG | ACT | AAT | CAG | CAA | CGC | TAT | 1463 |
| Trp | Leu | Gly | Asn | Glu | Phe | Val | Ser | Gln | Leu | Thr | Asn | Gln | Gln | Arg | Tyr |
| 355 |  |  |  |  | 360 |  |  |  |  | 365 |  |  |  |  |  |
| GTG | CTT | AAA | ATA | CAC | CTT | AAA | GAC | TGG | GAA | GGG | AAT | GAG | GCT | TAC | TCA | 1511 |
| Val | Leu | Lys | Ile | His | Leu | Lys | Asp | Trp | Glu | Gly | Asn | Glu | Ala | Tyr | Ser |
| 370 |  |  |  |  | 375 |  |  |  |  | 380 |  |  |  |  | 385 |
| TTG | TAT | GAA | CAT | TTC | TAT | CTC | TCA | AGT | GAA | GAA | CTC | AAT | TAT | AGG | ATT | 1559 |
| Leu | Tyr | Glu | His | Phe | Tyr | Leu | Ser | Ser | Glu | Glu | Leu | Asn | Tyr | Arg | Ile |
|  |  |  |  | 390 |  |  |  |  | 395 |  |  |  |  | 400 |  |
| CAC | CTT | AAA | GGA | CTT | ACA | GGG | ACA | GCC | GGC | AAA | ATA | AGC | AGC | ATC | AGC | 1607 |
| His | Leu | Lys | Gly | Leu | Thr | Gly | Thr | Ala | Gly | Lys | Ile | Ser | Ser | Ile | Ser |
|  |  |  | 405 |  |  |  |  | 410 |  |  |  |  | 415 |  |  |
| CAA | CCA | GGA | AAT | GAT | TTT | AGC | ACA | AAG | GAT | GGA | GAC | AAC | GAC | AAA | TGT | 1655 |
| Gln | Pro | Gly | Asn | Asp | Phe | Ser | Thr | Lys | Asp | Gly | Asp | Asn | Asp | Lys | Cys |
|  |  | 420 |  |  |  |  | 425 |  |  |  |  | 430 |  |  |  |
| ATT | TGC | AAA | TGT | TCA | CAA | ATG | CTA | ACA | GGA | GGC | TGG | TGG | TTT | GAT | GCA | 1703 |
| Ile | Cys | Lys | Cys | Ser | Gln | Met | Leu | Thr | Gly | Gly | Trp | Trp | Phe | Asp | Ala |
|  | 435 |  |  |  |  | 440 |  |  |  |  | 445 |  |  |  |  |
| TGT | GGT | CCT | TCC | AAC | TTG | AAC | GGA | ATG | TAC | TAT | CCA | CAG | AGG | CAG | AAC | 1751 |
| Cys | Gly | Pro | Ser | Asn | Leu | Asn | Gly | Met | Tyr | Tyr | Pro | Gln | Arg | Gln | Asn |
| 450 |  |  |  |  | 455 |  |  |  |  | 460 |  |  |  |  | 465 |
| ACA | AAT | AAG | TTC | AAC | GGC | ATT | AAA | TGG | TAC | TAC | TGG | AAA | GGC | TCA | GGC | 1799 |
| Thr | Asn | Lys | Phe | Asn | Gly | Ile | Lys | Trp | Tyr | Tyr | Trp | Lys | Gly | Ser | Gly |
|  |  |  |  | 470 |  |  |  |  | 475 |  |  |  |  | 480 |  |
| TAT | TCG | CTC | AAG | GCC | ACA | ACC | ATG | ATG | ATC | CGA | CCA | GCA | GAT | TTC | TAAA C | 1849 |
| Tyr | Ser | Leu | Lys | Ala | Thr | Thr | Met | Met | Ile | Arg | Pro | Ala | Asp | Phe |
|  |  |  | 485 |  |  |  |  | 490 |  |  |  |  | 495 |  |  |

ATCCCAGTCC ACCTGAGGAA CTGTCTCGAA CTATTTTCAA AGACTTAAGC CCAGTCACT  1909

GAAAGTCACG GCTGCGCACT GTGTCCTCTT CCACCACAGA GGGCGTGTGC TCGGTGCTGA  1969

CGGGACCCAC ATGCTCCAGA TTAGAGCCTG TAAACTTTAT CACTTAAACT TGCATCACTT  2029

```
AACGGACCAA AGCAAGACCC TAAACATCCA TAATTGTGAT TAGACAGAAC ACCTATGCAA    2089

AGATGAACCC GAGGCTGAGA ATCAGACTGA CAGTTTACAG ACGCTGCTGT CACAACCAAG    2149

AATGTTATGT GCAAGTTTAT CAGTAAATAA CTGGAAAACA GAACACTTAT GTTATACAAT    2209

ACAGATCATC TTGGAACTGC ATTCTTCTGA GCACTGTTTA TACACTGTGT AAATACCCAT    2269

ATGTCCTGAA TTC                                                       2282
```

(2) INFORMATION FOR SEQ ID NO:6:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: Human TIE-2 ligand 2
        (B) LOCATION: 1...496
        (D) OTHER INFORMATION: from clone pBluescript KS
            encoding human TIE 2 ligand 2

(xi) SEQUENCE DESCRIPTION: SEQ ID NO:6:

```
Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
 50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255
```

```
Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
            290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
            370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
            405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
            485                 490                 495

(2) INFORMATION FOR SEQ ID NO:7:

(i) SEQUENCE CHARACTERISTICS:
        (A) LENGTH: 478 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Mature TL1 protein
        (B) LOCATION: 1...478
        (D) OTHER INFORMATION:

(xi) SEQUENCE DESCRIPTION: SEQ ID NO:7:

Asn Gln Arg Arg Ser Pro Glu Asn Ser Gly Arg Arg Tyr Asn Arg Ile
1               5                   10                  15

Gln His Gly Gln Cys Ala Tyr Thr Phe Ile Leu Pro Glu His Asp Gly
            20                  25                  30

Asn Cys Arg Glu Ser Thr Thr Asp Gln Tyr Asn Thr Asn Ala Leu Gln
            35                  40                  45

Arg Asp Ala Pro His Val Glu Pro Asp Phe Ser Ser Gln Lys Leu Gln
            50                  55                  60

His Leu Glu His Val Met Glu Asn Tyr Thr Gln Trp Leu Gln Lys Leu
65                  70                  75                  80
```

-continued

```
Glu Asn Tyr Ile Val Glu Asn Met Lys Ser Glu Met Ala Gln Ile Gln
                85                  90                  95
Gln Asn Ala Val Gln Asn His Thr Ala Thr Met Leu Glu Ile Gly Thr
            100                 105                 110
Ser Leu Leu Ser Gln Thr Ala Glu Gln Thr Arg Lys Leu Thr Asp Val
        115                 120                 125
Glu Thr Gln Val Leu Asn Gln Thr Ser Arg Leu Glu Ile Gln Leu Leu
    130                 135                 140
Glu Asn Ser Leu Ser Thr Tyr Lys Leu Glu Lys Gln Leu Leu Gln Gln
145                 150                 155                 160
Thr Asn Glu Ile Leu Lys Ile His Glu Lys Asn Ser Leu Leu Glu His
                165                 170                 175
Lys Ile Leu Glu Met Glu Gly Lys His Lys Glu Leu Asp Thr Leu
            180                 185                 190
Lys Glu Glu Lys Glu Asn Leu Gln Gly Leu Val Thr Arg Gln Thr Tyr
        195                 200                 205
Ile Ile Gln Glu Leu Glu Lys Gln Leu Asn Arg Ala Thr Thr Asn Asn
    210                 215                 220
Ser Val Leu Gln Lys Gln Gln Leu Glu Leu Met Asp Thr Val His Asn
225                 230                 235                 240
Leu Val Asn Leu Cys Thr Lys Glu Gly Val Leu Leu Lys Gly Gly Lys
                245                 250                 255
Arg Glu Glu Glu Lys Pro Phe Arg Asp Cys Ala Asp Val Tyr Gln Ala
            260                 265                 270
Gly Phe Asn Lys Ser Gly Ile Tyr Thr Ile Tyr Ile Asn Asn Met Pro
        275                 280                 285
Glu Pro Lys Lys Val Phe Cys Asn Met Asp Val Asn Gly Gly Gly Trp
    290                 295                 300
Thr Val Ile Gln His Arg Glu Asp Gly Ser Leu Asp Phe Gln Arg Gly
305                 310                 315                 320
Trp Lys Glu Tyr Lys Met Gly Phe Gly Asn Pro Ser Gly Glu Tyr Trp
                325                 330                 335
Leu Gly Asn Glu Phe Ile Phe Ala Ile Thr Ser Gln Arg Gln Tyr Met
            340                 345                 350
Leu Arg Ile Glu Leu Met Asp Trp Glu Gly Asn Arg Ala Tyr Ser Gln
        355                 360                 365
Tyr Asp Arg Phe His Ile Gly Asn Glu Lys Gln Asn Tyr Arg Leu Tyr
    370                 375                 380
Leu Lys Gly His Thr Gly Thr Ala Gly Lys Gln Ser Ser Leu Ile Leu
385                 390                 395                 400
His Gly Ala Asp Phe Ser Thr Lys Asp Ala Asp Asn Asp Asn Cys Met
                405                 410                 415
Cys Lys Cys Ala Leu Met Leu Thr Gly Gly Trp Trp Phe Asp Ala Cys
            420                 425                 430
Gly Pro Ser Asn Leu Asn Gly Met Phe Tyr Thr Ala Gly Gln Asn His
        435                 440                 445
Gly Lys Leu Asn Gly Ile Lys Trp His Tyr Phe Lys Gly Pro Ser Tyr
    450                 455                 460
Ser Leu Arg Ser Thr Thr Met Met Ile Arg Pro Leu Asp Phe
465                 470                 475
```

(2) INFORMATION FOR SEQ ID NO:8:

(i) SEQUENCE CHARACTERISTICS:

(A) LENGTH: 480 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Mature TL2 protein
        (B) LOCATION: 1...480
        (D) OTHER INFORMATION:

(xi) SEQUENCE DESCRIPTION: SEQ ID NO:8:

```
Ala Ala Tyr Asn Asn Phe Arg Lys Ser Met Asp Ser Ile Gly Lys Lys
  1               5                  10                  15

Gln Tyr Gln Val Gln His Gly Ser Cys Ser Tyr Thr Phe Leu Leu Pro
             20                  25                  30

Glu Met Asp Asn Cys Arg Ser Ser Ser Pro Tyr Val Ser Asn Ala
         35                  40                  45

Val Gln Arg Asp Ala Pro Leu Glu Tyr Asp Asp Ser Val Gln Arg Leu
     50                  55                  60

Gln Val Leu Glu Asn Ile Met Glu Asn Asn Thr Gln Trp Leu Met Lys
 65                  70                  75                  80

Leu Glu Asn Tyr Ile Gln Asp Asn Met Lys Lys Glu Met Val Glu Ile
                 85                  90                  95

Gln Gln Asn Ala Val Gln Asn Gln Thr Ala Val Met Ile Glu Ile Gly
             100                 105                 110

Thr Asn Leu Leu Asn Gln Thr Ala Glu Gln Thr Arg Lys Leu Thr Asp
             115                 120                 125

Val Glu Ala Gln Val Leu Asn Gln Thr Thr Arg Leu Glu Leu Gln Leu
     130                 135                 140

Leu Glu His Ser Leu Ser Thr Asn Lys Leu Glu Lys Gln Ile Leu Asp
145                 150                 155                 160

Gln Thr Ser Glu Ile Asn Lys Leu Gln Asp Lys Asn Ser Phe Leu Glu
                 165                 170                 175

Lys Lys Val Leu Ala Met Glu Asp Lys His Ile Ile Gln Leu Gln Ser
             180                 185                 190

Ile Lys Glu Glu Lys Asp Gln Leu Gln Val Leu Val Ser Lys Gln Asn
         195                 200                 205

Ser Ile Ile Glu Glu Leu Glu Lys Lys Ile Val Thr Ala Thr Val Asn
210                 215                 220

Asn Ser Val Leu Gln Lys Gln Gln His Asp Leu Met Glu Thr Val Asn
225                 230                 235                 240

Asn Leu Leu Thr Met Met Ser Thr Ser Asn Ser Ala Lys Asp Pro Thr
                 245                 250                 255

Val Ala Lys Glu Glu Gln Ile Ser Phe Arg Asp Cys Ala Glu Val Phe
             260                 265                 270

Lys Ser Gly His Thr Thr Asn Gly Ile Tyr Thr Leu Thr Phe Pro Asn
         275                 280                 285

Ser Thr Glu Glu Ile Lys Ala Tyr Cys Asp Met Glu Ala Gly Gly Gly
     290                 295                 300

Gly Trp Thr Ile Ile Gln Arg Arg Glu Asp Gly Ser Val Asp Phe Gln
305                 310                 315                 320

Arg Thr Trp Lys Glu Tyr Lys Val Gly Phe Gly Asn Pro Ser Gly Glu
                 325                 330                 335

Tyr Trp Leu Gly Asn Glu Phe Val Ser Gln Leu Thr Asn Gln Gln Arg
                 340                 345                 350
```

```
Tyr Val Leu Lys Ile His Leu Lys Asp Trp Glu Gly Asn Glu Ala Tyr
        355                 360                 365

Ser Leu Tyr Glu His Phe Tyr Leu Ser Ser Glu Glu Leu Asn Tyr Arg
        370                 375                 380

Ile His Leu Lys Gly Leu Thr Gly Thr Ala Gly Lys Ile Ser Ser Ile
385                 390                 395                 400

Ser Gln Pro Gly Asn Asp Phe Ser Thr Lys Asp Gly Asp Asn Asp Lys
                405                 410                 415

Cys Ile Cys Lys Cys Ser Gln Met Leu Thr Gly Gly Trp Trp Phe Asp
                420                 425                 430

Ala Cys Gly Pro Ser Asn Leu Asn Gly Met Tyr Tyr Pro Gln Arg Gln
        435                 440                 445

Asn Thr Asn Lys Phe Asn Gly Ile Lys Trp Tyr Tyr Trp Lys Gly Ser
450                 455                 460

Gly Tyr Ser Leu Lys Ala Thr Thr Met Met Ile Arg Pro Ala Asp Phe
465                 470                 475                 480

(2) INFORMATION FOR SEQ ID NO:9:

(i) SEQUENCE CHARACTERISTICS:
        (A) LENGTH: 1849 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 47...1573
        (D) OTHER INFORMATION:
        (A) NAME/KEY: TIE ligand-3
        (B) LOCATION: 1...1849
        (D) OTHER INFORMATION: The fibrinogen-like
            domain starts at position 929.

(xi) SEQUENCE DESCRIPTION: SEQ ID NO:9:

CTGTCCTGGT ACCTGACAAG ACCACCTCAC CACCACTTGG TCTCAG ATG CTC TGC          55
                                                  Met Leu Cys
                                                   1

CAG CCA GCT ATG CTA CTA GAT GGC CTC CTC CTG CTG GCC ACC ATG GCT       103
Gln Pro Ala Met Leu Leu Asp Gly Leu Leu Leu Leu Ala Thr Met Ala
        5                   10                  15

GCA GCC CAG CAC AGA GGG CCA GAA GCC GGT GGG CAC CGC CAG ATT CAC       151
Ala Ala Gln His Arg Gly Pro Glu Ala Gly Gly His Arg Gln Ile His
20              25                  30                  35

CAG GTC CGG CGT GGC CAG TGC AGC TAC ACC TTT GTG GTG CCG GAG CCT       199
Gln Val Arg Arg Gly Gln Cys Ser Tyr Thr Phe Val Val Pro Glu Pro
            40                  45                  50

GAT ATC TGC CAG CTG GCG CCG ACA GCG GCG CCT GAG GCT TTG GGG GGC       247
Asp Ile Cys Gln Leu Ala Pro Thr Ala Ala Pro Glu Ala Leu Gly Gly
            55                  60                  65

TCC AAT AGC CTC CAG AGG GAC TTG CCT GCC TCG AGG CTG CAC CTA ACA       295
Ser Asn Ser Leu Gln Arg Asp Leu Pro Ala Ser Arg Leu His Leu Thr
        70                  75                  80

GAC TGG CGA GCC CAG AGG GCC CAG CGG GCC CAG CGT GTG AGC CAG CTG       343
Asp Trp Arg Ala Gln Arg Ala Gln Arg Ala Gln Arg Val Ser Gln Leu
    85                  90                  95

GAG AAG ATA CTA GAG AAT AAC ACT CAG TGG CTG CTG AAG CTG GAG CAG       391
Glu Lys Ile Leu Glu Asn Asn Thr Gln Trp Leu Leu Lys Leu Glu Gln
100                 105                 110                 115
```

```
TCC ATC AAG GTG AAC TTG AGG TCA CAC CTG GTG CAG GCC CAG CAG GAC         439
Ser Ile Lys Val Asn Leu Arg Ser His Leu Val Gln Ala Gln Gln Asp
            120                 125                 130

ACA ATC CAG AAC CAG ACA ACT ACC ATG CTG GCA CTG GGT GCC AAC CTC         487
Thr Ile Gln Asn Gln Thr Thr Thr Met Leu Ala Leu Gly Ala Asn Leu
            135                 140                 145

ATG AAC CAG ACC AAA GCT CAG ACC CAC AAG CTG ACT GCT GTG GAG GCA         535
Met Asn Gln Thr Lys Ala Gln Thr His Lys Leu Thr Ala Val Glu Ala
            150                 155                 160

CAG GTC CTA AAC CAG ACA TTG CAC ATG AAG ACC CAA ATG CTG GAG AAC         583
Gln Val Leu Asn Gln Thr Leu His Met Lys Thr Gln Met Leu Glu Asn
    165                 170                 175

TCA CTG TCC ACC AAC AAG CTG GAG CGG CAG ATG CTG ATG CAG AGC CGA         631
Ser Leu Ser Thr Asn Lys Leu Glu Arg Gln Met Leu Met Gln Ser Arg
180                 185                 190                 195

GAG CTG CAG CGG CTG CAG GGT CGC AAC AGG GCC CTG GAG ACC AGG CTG         679
Glu Leu Gln Arg Leu Gln Gly Arg Asn Arg Ala Leu Glu Thr Arg Leu
                200                 205                 210

CAG GCA CTG GAA GCA CAA CAT CAG GCC CAG CTT AAC AGC CTC CAA GAG         727
Gln Ala Leu Glu Ala Gln His Gln Ala Gln Leu Asn Ser Leu Gln Glu
            215                 220                 225

AAG AGG GAA CAA CTG CAC AGT CTC CTG GGC CAT CAG ACC GGG ACC CTG         775
Lys Arg Glu Gln Leu His Ser Leu Leu Gly His Gln Thr Gly Thr Leu
            230                 235                 240

GCT AAC CTG AAG CAC AAT CTG CAC GCT CTC AGC AGC AAT TCC AGC TCC         823
Ala Asn Leu Lys His Asn Leu His Ala Leu Ser Ser Asn Ser Ser Ser
245                 250                 255

CTG CAG CAG CAG CAG CAG CAA CTG ACG GAG TTT GTA CAG CGC CTG GTA         871
Leu Gln Gln Gln Gln Gln Gln Leu Thr Glu Phe Val Gln Arg Leu Val
260                 265                 270                 275

CGG ATT GTA GCC CAG GAC CAG CAT CCG GTT TCC TTA AAG ACA CCT AAG         919
Arg Ile Val Ala Gln Asp Gln His Pro Val Ser Leu Lys Thr Pro Lys
                280                 285                 290

CCA GTG TTC CAG GAC TGT GCA GAG ATC AAG CGC TCC GGG GTT AAT ACC         967
Pro Val Phe Gln Asp Cys Ala Glu Ile Lys Arg Ser Gly Val Asn Thr
            295                 300                 305

AGC GGT GTC TAT ACC ATC TAT GAG ACC AAC ATG ACA AAG CCT CTC AAG        1015
Ser Gly Val Tyr Thr Ile Tyr Glu Thr Asn Met Thr Lys Pro Leu Lys
            310                 315                 320

GTG TTC TGT GAC ATG GAG ACT GAT GGA GGT GGC TGG ACC CTC ATC CAG        1063
Val Phe Cys Asp Met Glu Thr Asp Gly Gly Gly Trp Thr Leu Ile Gln
325                 330                 335

CAC CGG GAG GAT GGA AGC GTA AAT TTC CAG AGG ACC TGG GAA GAA TAC        1111
His Arg Glu Asp Gly Ser Val Asn Phe Gln Arg Thr Trp Glu Glu Tyr
340                 345                 350                 355

AAA GAG GGT TTT GGT AAT GTG GCC AGA GAG CAC TGG CTG GGC AAT GAG        1159
Lys Glu Gly Phe Gly Asn Val Ala Arg Glu His Trp Leu Gly Asn Glu
                360                 365                 370

GCT GTG CAC CGC CTC ACC AGC AGA ACG GCC TAC TTG CTA CGC GTG GAA        1207
Ala Val His Arg Leu Thr Ser Arg Thr Ala Tyr Leu Leu Arg Val Glu
            375                 380                 385

CTG CAT GAC TGG GAA GGC CGC CAG ACC TCC ATC CAG TAT GAG AAC TTC        1255
Leu His Asp Trp Glu Gly Arg Gln Thr Ser Ile Gln Tyr Glu Asn Phe
            390                 395                 400

CAG CTG GGC AGC GAG AGG CAG CGG TAC AGC CTC TCT GTG AAT GAC AGC        1303
Gln Leu Gly Ser Glu Arg Gln Arg Tyr Ser Leu Ser Val Asn Asp Ser
            405                 410                 415

AGC AGT TCA GCA GGG CGC AAG AAC AGC CTG GCT CCT CAG GGC ACC AAG        1351
Ser Ser Ser Ala Gly Arg Lys Asn Ser Leu Ala Pro Gln Gly Thr Lys
420                 425                 430                 435
```

-continued

```
TTC AGC ACC AAA GAC ATG GAC AAT GAT AAC TGC ATG TGT AAA TGT GCT      1399
Phe Ser Thr Lys Asp Met Asp Asn Asp Asn Cys Met Cys Lys Cys Ala
                440                 445                 450

CAG ATG CTG TCT GGA GGG TGG TGG TTT GAT GCC TGT GGC CTC TCC AAC      1447
Gln Met Leu Ser Gly Gly Trp Trp Phe Asp Ala Cys Gly Leu Ser Asn
            455                 460                 465

CTC AAT GGC ATC TAC TAT TCA GTT CAT CAG CAC TTG CAC AAG ATC AAT      1495
Leu Asn Gly Ile Tyr Tyr Ser Val His Gln His Leu His Lys Ile Asn
            470                 475                 480

GGC ATC CGC TGG CAC TAC TTC CGA GGC CCC AGC TAC TCA CTG CAC GGC      1543
Gly Ile Arg Trp His Tyr Phe Arg Gly Pro Ser Tyr Ser Leu His Gly
        485                 490                 495

ACA CGC ATG ATG CTG AGG CCA ATG GGT GCC TGA CACACAG CCCTGCAGAG AC T  1596
Thr Arg Met Met Leu Arg Pro Met Gly Ala
500                 505

GATGCCGTAG GAGGATTCTC AACCCAGGTG ACTCTGTGCA CGCTGGGCCC TGCCCAGAAA    1656

TCAGTGCCCA GGGCTCATCT TGACATTCTG GAACATCGGA ACCAGCTTAC CTTGCCCCTG    1716

AATTACAAGA ATTCACCTGC CTCCCTGTTG CCCTCTAATT GTGAAATTGC TGGGTGCTTG    1776

AAGGCACCTG CCTCTGTTGG AACCATACTC TTTCCCCCTC CTGCTGCATG CCCGGGAATC    1836

CCTGCCATGA ACT                                                       1849
```

(2) INFORMATION FOR SEQ ID NO:10:

(i) SEQUENCE CHARACTERISTICS:
        (A) LENGTH: 509 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: TIE ligand-3
        (B) LOCATION: 1...509
        (D) OTHER INFORMATION:

(xi) SEQUENCE DESCRIPTION: SEQ ID NO:10:

```
Met Leu Cys Gln Pro Ala Met Leu Leu Asp Gly Leu Leu Leu Leu Ala
1               5                   10                  15

Thr Met Ala Ala Ala Gln His Arg Gly Pro Glu Ala Gly Gly His Arg
            20                  25                  30

Gln Ile His Gln Val Arg Arg Gly Gln Cys Ser Tyr Thr Phe Val Val
        35                  40                  45

Pro Glu Pro Asp Ile Cys Gln Leu Ala Pro Thr Ala Ala Pro Glu Ala
    50                  55                  60

Leu Gly Gly Ser Asn Ser Leu Gln Arg Asp Leu Pro Ala Ser Arg Leu
65                  70                  75                  80

His Leu Thr Asp Trp Arg Ala Gln Arg Ala Gln Arg Ala Gln Arg Val
                85                  90                  95

Ser Gln Leu Glu Lys Ile Leu Glu Asn Asn Thr Gln Trp Leu Leu Lys
            100                 105                 110

Leu Glu Gln Ser Ile Lys Val Asn Leu Arg Ser His Leu Val Gln Ala
        115                 120                 125

Gln Gln Asp Thr Ile Gln Asn Gln Thr Thr Thr Met Leu Ala Leu Gly
    130                 135                 140

Ala Asn Leu Met Asn Gln Thr Lys Ala Gln Thr His Lys Leu Thr Ala
```

```
                    145                 150                 155                 160
        Val Glu Ala Gln Val Leu Asn Gln Thr Leu His Met Lys Thr Gln Met
                        165                 170                 175

Leu Glu Asn Ser Leu Ser Thr Asn Lys Leu Glu Arg Gln Met Leu Met
                        180                 185                 190

Gln Ser Arg Glu Leu Gln Arg Leu Gln Gly Arg Asn Arg Ala Leu Glu
                        195                 200                 205

Thr Arg Leu Gln Ala Leu Glu Ala Gln His Gln Ala Gln Leu Asn Ser
                        210                 215                 220

Leu Gln Glu Lys Arg Glu Gln Leu His Ser Leu Leu Gly His Gln Thr
        225                 230                 235                 240

Gly Thr Leu Ala Asn Leu Lys His Asn Leu His Ala Leu Ser Ser Asn
                        245                 250                 255

Ser Ser Ser Leu Gln Gln Gln Gln Gln Leu Thr Glu Phe Val Gln
                        260                 265                 270

Arg Leu Val Arg Ile Val Ala Gln Asp Gln His Pro Val Ser Leu Lys
                        275                 280                 285

Thr Pro Lys Pro Val Phe Gln Asp Cys Ala Glu Ile Lys Arg Ser Gly
                        290                 295                 300

Val Asn Thr Ser Gly Val Tyr Thr Ile Tyr Glu Thr Asn Met Thr Lys
        305                 310                 315                 320

Pro Leu Lys Val Phe Cys Asp Met Glu Thr Asp Gly Gly Gly Trp Thr
                        325                 330                 335

Leu Ile Gln His Arg Glu Asp Gly Ser Val Asn Phe Gln Arg Thr Trp
                        340                 345                 350

Glu Glu Tyr Lys Glu Gly Phe Gly Asn Val Ala Arg Glu His Trp Leu
                        355                 360                 365

Gly Asn Glu Ala Val His Arg Leu Thr Ser Arg Thr Ala Tyr Leu Leu
                        370                 375                 380

Arg Val Glu Leu His Asp Trp Glu Gly Arg Gln Thr Ser Ile Gln Tyr
        385                 390                 395                 400

Glu Asn Phe Gln Leu Gly Ser Glu Arg Gln Arg Tyr Ser Leu Ser Val
                        405                 410                 415

Asn Asp Ser Ser Ser Ala Gly Arg Lys Asn Ser Leu Ala Pro Gln
                        420                 425                 430

Gly Thr Lys Phe Ser Thr Lys Asp Met Asp Asn Asp Asn Cys Met Cys
                        435                 440                 445

Lys Cys Ala Gln Met Leu Ser Gly Gly Trp Trp Phe Asp Ala Cys Gly
                        450                 455                 460

Leu Ser Asn Leu Asn Gly Ile Tyr Tyr Ser Val His Gln His Leu His
        465                 470                 475                 480

Lys Ile Asn Gly Ile Arg Trp His Tyr Phe Arg Gly Pro Ser Tyr Ser
                        485                 490                 495

Leu His Gly Thr Arg Met Met Leu Arg Pro Met Gly Ala
                        500                 505
```

(2) INFORMATION FOR SEQ ID NO:11:

(i) SEQUENCE CHARACTERISTICS:
        (A) LENGTH: 503 amino acids
        (B) TYPE: amino acid
        (C) STRANDEDNESS: single
        (D) TOPOLOGY: linear (ii) MOLECULE TYPE: protein (ix) FEATURE:
    (A) NAME/KEY: mTL3
    (B) LOCATION: 1...503
    (D) OTHER INFORMATION: mouse TIE ligand-3

(xi) SEQUENCE DESCRIPTION: SEQ ID NO:11:

```
Met Leu Leu Asp Gly Leu Leu Leu Ala Thr Met Ala Ala Gln
 1               5                  10                  15

His Arg Gly Pro Glu Ala Gly Gly His Arg Gln Ile His Gln Val Arg
                 20                  25                  30

Arg Gly Gln Cys Ser Tyr Thr Phe Val Val Pro Glu Pro Asp Ile Cys
             35                  40                  45

Gln Leu Ala Pro Thr Ala Ala Pro Glu Ala Leu Gly Gly Ser Asn Ser
 50                  55                  60

Leu Gln Arg Asp Leu Pro Ala Ser Arg Leu His Leu Thr Asp Trp Arg
 65                  70                  75                  80

Ala Gln Arg Ala Gln Arg Ala Gln Arg Val Ser Gln Leu Glu Lys Ile
                 85                  90                  95

Leu Glu Asn Asn Thr Gln Trp Leu Leu Lys Leu Glu Gln Ser Ile Lys
                100                 105                 110

Val Asn Leu Arg Ser His Leu Val Gln Ala Gln Gln Asp Thr Ile Gln
                115                 120                 125

Asn Gln Thr Thr Thr Met Leu Ala Leu Gly Ala Asn Leu Met Asn Gln
130                 135                 140

Thr Lys Ala Gln Thr His Lys Leu Thr Ala Val Glu Ala Gln Val Leu
145                 150                 155                 160

Asn Gln Thr Leu His Met Lys Thr Gln Met Leu Glu Asn Ser Leu Ser
                165                 170                 175

Thr Asn Lys Leu Glu Arg Gln Met Leu Met Gln Ser Arg Glu Leu Gln
                180                 185                 190

Arg Leu Gln Gly Arg Asn Arg Ala Leu Glu Thr Arg Leu Gln Ala Leu
                195                 200                 205

Glu Ala Gln His Gln Ala Gln Leu Asn Ser Leu Gln Glu Lys Arg Glu
                210                 215                 220

Gln Leu His Ser Leu Leu Gly His Gln Thr Gly Thr Leu Ala Asn Leu
225                 230                 235                 240

Lys His Asn Leu His Ala Leu Ser Ser Asn Ser Ser Ser Leu Gln Gln
                245                 250                 255

Gln Gln Gln Gln Leu Thr Glu Phe Val Gln Arg Leu Val Arg Ile Val
                260                 265                 270

Ala Gln Asp Gln His Pro Val Ser Leu Lys Thr Pro Lys Pro Val Phe
                275                 280                 285

Gln Asp Cys Ala Glu Ile Lys Arg Ser Gly Val Asn Thr Ser Gly Val
                290                 295                 300

Tyr Thr Ile Tyr Glu Thr Asn Met Thr Lys Pro Leu Lys Val Phe Cys
305                 310                 315                 320

Asp Met Glu Thr Asp Gly Gly Gly Trp Thr Leu Ile Gln His Arg Glu
                325                 330                 335

Asp Gly Ser Val Asn Phe Gln Arg Thr Trp Glu Glu Tyr Lys Glu Gly
                340                 345                 350

Phe Gly Asn Val Ala Arg Glu His Trp Leu Gly Asn Glu Ala Val His
                355                 360                 365

Arg Leu Thr Ser Arg Thr Ala Tyr Leu Leu Arg Val Glu Leu His Asp
                370                 375                 380
```

```
Trp Glu Gly Arg Gln Thr Ser Ile Gln Tyr Glu Asn Phe Gln Leu Gly
385                 390                 395                 400

Ser Glu Arg Gln Arg Tyr Ser Leu Ser Val Asn Asp Ser Ser Ser Ser
            405                 410                 415

Ala Gly Arg Lys Asn Ser Leu Ala Pro Gln Gly Thr Lys Phe Ser Thr
            420                 425                 430

Lys Asp Met Asp Asn Asp Asn Cys Met Cys Lys Cys Ala Gln Met Leu
            435                 440                 445

Ser Gly Gly Trp Trp Phe Asp Ala Cys Gly Leu Ser Asn Leu Asn Gly
450                 455                 460

Ile Tyr Tyr Ser Val His Gln His Leu His Lys Ile Asn Gly Ile Arg
465                 470                 475                 480

Trp His Tyr Phe Arg Gly Pro Ser Tyr Ser Ile His Gly Thr Arg Met
                485                 490                 495

Met Leu Arg Pro Met Gly Ala
            500
```

(2) INFORMATION FOR SEQ ID NO:12:

(i) SEQUENCE CHARACTERISTICS:
        (A) LENGTH: 490 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: hTL1
        (B) LOCATION: 1...490
        (D) OTHER INFORMATION: human TIE-2 ligand 1

(xi) SEQUENCE DESCRIPTION: SEQ ID NO:12:

```
Ala Phe Leu Ala Ala Ile Leu Thr His Ile Gly Cys Ser Asn Gln Arg
1               5                   10                  15

Arg Ser Pro Glu Asn Ser Gly Arg Arg Tyr Asn Arg Ile Gln His Gly
            20                  25                  30

Gln Cys Ala Tyr Thr Phe Ile Leu Pro Glu His Asp Gly Asn Cys Arg
            35                  40                  45

Glu Ser Thr Thr Asp Gln Tyr Asn Thr Asn Ala Leu Gln Arg Asp Ala
50                  55                  60

Pro His Val Glu Pro Asp Phe Ser Ser Gln Lys Leu Gln His Leu Glu
65                  70                  75                  80

His Val Met Glu Asn Tyr Thr Gln Trp Leu Gln Lys Leu Glu Asn Tyr
            85                  90                  95

Ile Val Glu Asn Met Lys Ser Glu Met Ala Gln Ile Gln Gln Asn Ala
            100                 105                 110

Val Gln Asn His Thr Ala Thr Met Leu Glu Ile Gly Thr Ser Leu Leu
            115                 120                 125

Ser Gln Thr Ala Glu Gln Thr Arg Lys Leu Thr Asp Val Glu Thr Gln
130                 135                 140

Val Leu Asn Gln Thr Ser Arg Leu Glu Ile Gln Leu Leu Glu Asn Ser
145                 150                 155                 160

Leu Ser Thr Tyr Lys Leu Glu Lys Gln Leu Leu Gln Gln Thr Asn Glu
            165                 170                 175

Ile Leu Lys Ile His Glu Lys Asn Ser Leu Leu Glu His Lys Ile Leu
            180                 185                 190

Glu Met Glu Gly Lys His Lys Glu Glu Leu Asp Thr Leu Lys Glu Glu
```

-continued

```
                195                 200                 205
Lys Glu Asn Leu Gln Gly Leu Val Thr Arg Gln Thr Tyr Ile Ile Gln
        210                 215                 220
Glu Leu Glu Lys Gln Leu Asn Arg Ala Thr Thr Asn Asn Ser Val Leu
225                 230                 235                 240
Gln Lys Gln Gln Leu Glu Leu Met Asp Thr Val His Asn Leu Val Asn
                245                 250                 255
Leu Cys Thr Lys Glu Val Leu Leu Lys Gly Lys Arg Glu Glu Glu
        260                 265                 270
Lys Pro Phe Arg Asp Cys Ala Asp Val Tyr Gln Ala Gly Phe Asn Lys
        275                 280                 285
Ser Gly Ile Tyr Thr Ile Tyr Ile Asn Asn Met Pro Glu Pro Lys Lys
        290                 295                 300
Val Phe Cys Asn Met Asp Val Asn Gly Gly Gly Trp Thr Val Ile Gln
305                 310                 315                 320
His Arg Glu Asp Gly Ser Leu Asp Phe Gln Arg Gly Trp Lys Glu Tyr
                325                 330                 335
Lys Met Gly Phe Gly Asn Pro Ser Gly Glu Tyr Trp Leu Gly Asn Glu
                340                 345                 350
Phe Ile Phe Ala Ile Thr Ser Gln Arg Gln Tyr Met Leu Arg Ile Glu
                355                 360                 365
Leu Met Asp Trp Glu Gly Asn Arg Ala Tyr Ser Gln Tyr Asp Arg Phe
        370                 375                 380
His Ile Gly Asn Glu Lys Gln Asn Tyr Arg Leu Tyr Leu Lys Gly His
385                 390                 395                 400
Thr Gly Thr Ala Gly Lys Gln Ser Ser Leu Ile Leu His Gly Ala Asp
                405                 410                 415
Phe Ser Thr Lys Asp Ala Asp Asn Asp Asn Cys Met Cys Lys Cys Ala
        420                 425                 430
Leu Met Leu Thr Gly Gly Trp Trp Phe Asp Ala Cys Gly Pro Ser Asn
        435                 440                 445
Leu Asn Gly Met Phe Tyr Thr Ala Gly Gln Asn His Gly Lys Leu Asn
        450                 455                 460
Gly Ile Lys Trp His Tyr Phe Lys Gly Pro Ser Tyr Ser Ile Arg Ser
465                 470                 475                 480
Thr Thr Met Met Ile Arg Pro Leu Asp Phe
                485                 490

(2) INFORMATION FOR SEQ ID NO:13:

(i) SEQUENCE CHARACTERISTICS:
        (A) LENGTH: 491 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: chTL1
        (B) LOCATION: 1...491
        (D) OTHER INFORMATION: chicken TIE-2 ligand 1

(xi) SEQUENCE DESCRIPTION: SEQ ID NO:13:

Ala Phe Leu Ala Ala Ile Leu Ala His Ile Gly Cys Thr Thr Gln Arg
1               5                   10                  15
Arg Ser Pro Glu Asn Ser Gly Arg Arg Phe Asn Arg Ile Gln His Gly
            20                  25                  30
```

-continued

```
Gln Cys Thr Tyr Thr Phe Ile Leu Pro Glu Gln Asp Gly Asn Cys Arg
         35                      40                      45
Glu Ser Thr Thr Asp Gln Tyr Asn Thr Asn Ala Leu Gln Arg Asp Ala
 50                      55                      60
Pro His Val Glu Gln Asp Phe Ser Phe Gln Lys Leu Gln His Leu Glu
 65                      70                      75                      80
His Val Met Glu Asn Tyr Thr Gln Trp Leu Gln Lys Leu Glu Ser Tyr
                         85                      90                      95
Ile Val Glu Asn Met Lys Ser Glu Met Ala Gln Leu Gln Gln Asn Ala
                        100                     105                     110
Val Gln Asn His Thr Ala Thr Met Leu Glu Ile Gly Thr Ser Leu Leu
                        115                     120                     125
Ser Gln Thr Ala Glu Gln Thr Arg Lys Leu Thr Asp Val Glu Thr Gln
                        130                     135                     140
Val Leu Asn Gln Thr Ser Arg Leu Glu Ile Gln Leu Leu Glu Asn Ser
145                     150                     155                     160
Leu Ser Thr Tyr Lys Leu Glu Lys Gln Leu Leu Gln Gln Thr Asn Glu
                        165                     170                     175
Ile Leu Lys Ile His Glu Lys Asn Ser Leu Leu Glu His Lys Ile Leu
                        180                     185                     190
Glu Met Glu Glu Arg His Lys Glu Glu Met Asp Thr Leu Lys Glu Glu
                        195                     200                     205
Lys Glu Asn Leu Gln Gly Leu Val Thr Arg Gln Ser Tyr Ile Ile Gln
                        210                     215                     220
Glu Leu Glu Lys Gln Leu Asn Lys Ala Thr Thr Asn Asn Ser Val Leu
225                     230                     235                     240
Gln Lys Gln Gln Leu Glu Leu Met Asp Thr Val His Thr Leu Ile Thr
                        245                     250                     255
Leu Cys Ser Lys Glu Gly Val Leu Leu Lys Asn Ala Lys Arg Glu Glu
                        260                     265                     270
Glu Lys Pro Phe Arg Asp Cys Ala Asp Val Tyr Gln Ala Gly Phe Asn
                        275                     280                     285
Lys Ser Gly Ile Tyr Thr Ile Tyr Ile Asn Asn Val Ser Asp Pro Lys
                        290                     295                     300
Lys Val Phe Cys Asn Met Asp Val Asn Gly Gly Gly Trp Thr Val Ile
305                     310                     315                     320
Gln His Arg Glu Asp Gly Ser Leu Asp Phe Gln Lys Gly Trp Lys Glu
                        325                     330                     335
Tyr Lys Met Gly Phe Gly Ser Pro Ser Gly Glu Tyr Trp Leu Gly Asn
                        340                     345                     350
Glu Phe Ile Phe Ala Ile Thr Ser Gln Arg Gln Tyr Ser Leu Arg Ile
                        355                     360                     365
Glu Leu Met Asp Trp Glu Gly Asn Arg Ala Tyr Ser Gln Tyr Asp Arg
                        370                     375                     380
Phe His Ile Gly Asn Glu Lys Gln Asn Tyr Arg Leu Tyr Leu Lys Gly
385                     390                     395                     400
His Ser Gly Thr Ala Gly Lys Gln Ser Ser Leu Ile Leu His Gly Ala
                        405                     410                     415
Glu Phe Ser Thr Lys Asp Ala Asp Asn Asp Asn Cys Met Cys Lys Cys
                        420                     425                     430
Ala Leu Met Leu Thr Gly Gly Trp Trp Phe Asp Ala Cys Gly Pro Ser
                        435                     440                     445
```

```
Asn Leu Asn Gly Met Phe Tyr Thr Ala Gly Gln Asn His Gly Lys Leu
            450                 455                 460

Asn Gly Ile Lys Trp His Tyr Phe Lys Gly Pro Arg Tyr Ser Ile Arg
465                 470                 475                 480

Ser Thr Thr Met Met Ile Arg Pro Leu Asp Phe
                485                 490

(2) INFORMATION FOR SEQ ID NO:14:

(i) SEQUENCE CHARACTERISTICS:
        (A) LENGTH: 497 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: mTL1
        (B) LOCATION: 1...497
        (D) OTHER INFORMATION: mouse TIE-2 ligand 1

(xi) SEQUENCE DESCRIPTION: SEQ ID NO:14:

Met Thr Val Phe Leu Ser Phe Ala Phe Phe Ala Ala Ile Leu Thr His
1               5                   10                  15

Ile Gly Cys Ser Asn Gln Arg Arg Asn Pro Glu Asn Ser Gly Arg Arg
                20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Thr Thr Asp Gln Tyr Asn Thr
        50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Thr Asn Glu Ile Leu Lys Ile His Glu Lys Asn Ser Leu
            180                 185                 190

Leu Glu His Lys Ile Leu Glu Met Glu Gly Lys His Lys Glu Glu Met
        195                 200                 205

Asp Thr Leu Lys Glu Glu Lys Glu Asn Leu Gln Gly Leu Val Ser Arg
    210                 215                 220

Gln Ser Phe Ile Ile Gln Glu Leu Glu Lys Gln Leu Ser Arg Ala Thr
225                 230                 235                 240

Asn Asn Asn Ser Ile Leu Gln Lys Gln Gln Leu Glu Leu Met Asp Thr
                245                 250                 255

Val His Asn Leu Ile Ser Leu Cys Thr Lys Glu Gly Val Leu Leu Lys
            260                 265                 270

Gly Gly Lys Arg Glu Glu Glu Lys Pro Phe Arg Asp Cys Ala Asp Val
```

```
                    275                 280                 285
Tyr Gln Ala Gly Phe Asn Lys Ser Gly Ile Tyr Thr Ile Tyr Phe Asn
            290                 295                 300

Asn Val Pro Glu Pro Lys Lys Val Phe Cys Asn Met Asp Val Asn Gly
305                 310                 315                 320

Gly Gly Trp Thr Val Ile Gln His Arg Glu Asp Gly Ser Leu Asp Phe
                325                 330                 335

Gln Lys Gly Trp Lys Glu Tyr Lys Met Gly Phe Gly Ser Pro Ser Gly
                340                 345                 350

Glu Tyr Trp Leu Gly Asn Glu Phe Ile Phe Ala Ile Thr Ser Gln Arg
                355                 360                 365

Gln Tyr Met Leu Arg Ile Glu Leu Met Asp Trp Glu Gly Asn Arg Ala
            370                 375                 380

Tyr Ser Gln Tyr Asp Arg Phe His Ile Gly Asn Glu Lys Gln Asn Tyr
385                 390                 395                 400

Arg Leu Tyr Leu Lys Gly His Thr Gly Thr Ala Gly Lys Gln Ser Ser
                405                 410                 415

Leu Ile Leu His Gly Ala Asp Phe Ser Thr Lys Asp Ala Asp Asn Asp
                420                 425                 430

Asn Cys Met Cys Lys Cys Ala Leu Met Leu Thr Gly Gly Trp Trp Phe
            435                 440                 445

Asp Ala Cys Gly Pro Ser Asn Leu Asn Gly Met Phe Tyr Thr Ala Gly
450                 455                 460

Gln Asn His Gly Lys Leu Asn Gly Ile Lys Trp His Tyr Phe Lys Gly
465                 470                 475                 480

Pro Arg Tyr Ser Ile Arg Ser Thr Thr Met Met Ile Arg Pro Leu Asp
                485                 490                 495

Phe (2) INFORMATION FOR SEQ ID NO:15:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: mTL2
        (B) LOCATION: 1...496
        (D) OTHER INFORMATION: mouse TIE-2 ligand 2

(xi) SEQUENCE DESCRIPTION: SEQ ID NO:15:

Met Trp Gln Ile Ile Phe Leu Thr Phe Gly Trp Asp Ala Val Leu Thr
 1               5                  10                  15

Ser Ala Tyr Ser Asn Phe Arg Lys Ser Val Asp Ser Thr Gly Arg Arg
                20                  25                  30

Arg Tyr Arg Ile Gln Asn Gly Pro Cys Ala Tyr Thr Phe Leu Leu Pro
            35                  40                  45

Glu Thr Asp Ser Gly Arg Ser Ser Ser Thr Tyr Met Thr Asn Ala
 50                 55                  60

Val Gln Arg Asp Ala Pro Pro Asp Tyr Glu Asp Ser Val Gln Ser Leu
65                  70                  75                  80

Gln Leu Leu Glu Asn Val Met Glu Asn Tyr Thr Gln Trp Leu Met Lys
                85                  90                  95
```

```
Leu Glu Asn Tyr Ile Gln Asp Asn Met Lys Lys Glu Met Ala Glu Ile
                100                 105                 110
Gln Gln Asn Val Val Gln Asn His Thr Ala Val Met Ile Glu Ile Gly
            115                 120                 125
Thr Ser Leu Leu Ser Gln Thr Ala Glu Gln Thr Arg Lys Leu Thr Asp
        130                 135                 140
Val Glu Thr Gln Val Leu Asn Gln Thr Thr Arg Leu Glu Leu Gln Leu
145                 150                 155                 160
Leu Gln His Ser Ile Ser Thr Tyr Lys Leu Glu Lys Gln Ile Leu Asp
                165                 170                 175
Gln Thr Ser Glu Ile Asn Lys Ile His Asn Lys Asn Ser Phe Leu Glu
            180                 185                 190
Gln Lys Val Leu Asp Met Glu Gly Lys His Ser Glu Met Gln Thr
        195                 200                 205
Met Lys Glu Gln Lys Asp Glu Leu Gln Val Leu Val Ser Lys Gln Ser
210                 215                 220
Ser Val Ile Asp Glu Leu Glu Lys Lys Leu Val Thr Ala Thr Val Asn
225                 230                 235                 240
Asn Ser Leu Leu Gln Lys Gln His Asp Leu Met Asp Thr Val Asn
            245                 250                 255
Ser Leu Leu Thr Met Met Ser Ser Pro Asn Ser Lys Ser Ser Leu Ala
        260                 265                 270
Ile Arg Arg Glu Glu Gln Thr Thr Phe Arg Asp Cys Ala Asp Val Phe
        275                 280                 285
Lys Ala Gly Leu Thr Lys Ser Gly Ile Tyr Thr Leu Thr Phe Pro Asn
        290                 295                 300
Ser Pro Glu Glu Ile Lys Ala Tyr Cys Asn Met Asp Val Gly Gly Gly
305                 310                 315                 320
Gly Trp Thr Val Ile Gln His Arg Glu Asp Gly Ser Leu Asp Phe Gln
                325                 330                 335
Lys Gly Trp Lys Glu Tyr Lys Met Gly Phe Gly Asn Pro Leu Gly Glu
            340                 345                 350
Tyr Trp Leu Gly Asn Glu Phe Ile Ser Gln Ile Thr Gly Gln His Arg
        355                 360                 365
Tyr Val Leu Lys Ile Gln Leu Lys Asp Trp Glu Gly Asn Glu Ala His
370                 375                 380
Ser Leu Tyr Asp His Phe Tyr Ile Ala Gly Glu Glu Ser Asn Tyr Arg
385                 390                 395                 400
Ile His Leu Thr Gly Leu Thr Gly Thr Ala Ala Lys Ile Ser Ser Ile
                405                 410                 415
Ser Gln Pro Gly Ser Asp Phe Ser Thr Lys Asp Ser Asp Asn Asp Lys
            420                 425                 430
Cys Ile Cys Lys Cys Ser Leu Met Leu Thr Gly Gly Trp Trp Phe Asp
        435                 440                 445
Ala Cys Gly Pro Ser Asn Leu Asn Gly Gln Phe Tyr Pro Gln Lys Gln
        450                 455                 460
Asn Thr Asn Lys Phe Asn Gly Ile Lys Trp Tyr Trp Lys Gly Ser
465                 470                 475                 480
Gly Tyr Ser Ile Lys Ala Thr Thr Met Met Ile Arg Pro Ala Asp Phe
                485                 490                 495
```

(2) INFORMATION FOR SEQ ID NO:16:

(i) SEQUENCE CHARACTERISTICS:

(A) LENGTH: 496 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: hTL2
        (B) LOCATION: 1...496
        (D) OTHER INFORMATION: human TIE-2 ligand 2

(xi) SEQUENCE DESCRIPTION: SEQ ID NO:16:

```
Met Trp Gln Ile Val Phe Phe Thr Leu Ser Cys Asp Ala Val Leu Thr
 1               5                  10                  15

Ala Ala Tyr Asn Asn Phe Arg Lys Ser Met Asp Ser Ile Gly Lys Lys
            20                  25                  30

Arg Tyr Arg Ile Gln His Gly Ser Cys Ala Tyr Thr Phe Leu Leu Pro
        35                  40                  45

Glu Met Asp Asn Gly Arg Ser Ser Ser Thr Tyr Val Thr Asn Ala
 50                  55                  60

Val Gln Arg Asp Ala Pro Pro Glu Tyr Glu Asp Ser Val Gln Ser Leu
65                  70                  75                  80

Gln Leu Leu Glu Asn Val Met Glu Asn Tyr Thr Gln Trp Leu Met Lys
            85                  90                  95

Leu Glu Asn Tyr Ile Gln Asp Asn Met Lys Lys Glu Met Ala Glu Ile
                100                 105                 110

Gln Gln Asn Ala Val Gln Asn His Thr Ala Val Met Ile Glu Ile Gly
            115                 120                 125

Thr Ser Leu Leu Ser Gln Thr Ala Glu Gln Thr Arg Lys Leu Thr Asp
130                 135                 140

Val Glu Thr Gln Val Leu Asn Gln Thr Thr Arg Leu Glu Leu Gln Leu
145                 150                 155                 160

Leu Gln His Ser Ile Ser Thr Tyr Lys Leu Glu Lys Gln Ile Leu Asp
                165                 170                 175

Gln Thr Ser Glu Ile Asn Lys Ile His Asp Lys Asn Ser Phe Leu Glu
            180                 185                 190

Lys Lys Val Leu Asp Met Glu Asp Lys His Ile Ile Glu Met Gln Thr
            195                 200                 205

Ile Lys Glu Glu Lys Asp Glu Leu Gln Val Leu Val Ser Lys Gln Asn
210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Asp Thr Val Asn
                245                 250                 255

Asn Leu Leu Thr Met Met Ser Thr Ser Asn Ser Ala Lys Asp Ser Thr
            260                 265                 270

Val Ala Arg Glu Glu Gln Ile Ser Phe Arg Asp Cys Ala Asp Val Phe
            275                 280                 285

Lys Ala Gly His Thr Lys Asn Gly Ile Tyr Thr Leu Thr Phe Pro Asn
            290                 295                 300

Ser Pro Glu Glu Ile Lys Ala Tyr Cys Asn Met Asp Ala Gly Gly Gly
305                 310                 315                 320

Gly Trp Thr Ile Ile Gln Arg Arg Glu Asp Gly Ser Leu Asp Phe Gln
                325                 330                 335

Lys Gly Trp Lys Glu Tyr Lys Val Gly Phe Gly Ser Pro Ser Gly Glu
            340                 345                 350
```

```
Tyr Trp Leu Gly Asn Glu Phe Ile Ser Gln Ile Thr Asn Gln Gln Arg
        355                 360                 365

Tyr Val Leu Lys Ile His Leu Lys Asp Trp Glu Gly Asn Glu Ala Tyr
        370                 375                 380

Ser Leu Tyr Asp His Phe Tyr Ile Ser Gly Glu Glu Leu Asn Tyr Arg
385                 390                 395                 400

Ile His Leu Lys Gly Leu Thr Gly Thr Ala Ala Lys Ile Ser Ser Ile
                405                 410                 415

Ser Gln Pro Gly Asn Asp Phe Ser Thr Lys Asp Gly Asp Asn Asp Lys
                420                 425                 430

Cys Ile Cys Lys Cys Ser Leu Met Leu Thr Gly Gly Trp Trp Phe Asp
        435                 440                 445

Ala Cys Gly Pro Ser Asn Leu Asn Gly Met Phe Tyr Pro Gln Arg Gln
        450                 455                 460

Asn Thr Asn Lys Phe Asn Gly Ile Lys Trp Tyr Tyr Trp Lys Gly Ser
465                 470                 475                 480

Gly Tyr Ser Ile Lys Ala Thr Thr Met Met Ile Arg Pro Ala Asp Phe
                485                 490                 495
```

(2) INFORMATION FOR SEQ ID NO:17:

(i) SEQUENCE CHARACTERISTICS:
        (A) LENGTH: 1512 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...1509
        (D) OTHER INFORMATION:
        (A) NAME/KEY: TIE ligand-4
        (B) LOCATION: 1...1512
        (D) OTHER INFORMATION:

(xi) SEQUENCE DESCRIPTION: SEQ ID NO:17:

```
ATG CTC TCC CAG CTA GCC ATG CTG CAG GGC AGC CTC CTC CTT GTG GTT      48
Met Leu Ser Gln Leu Ala Met Leu Gln Gly Ser Leu Leu Leu Val Val
1               5                   10                  15

GCC ACC ATG TCT GTG GCT CAA CAG ACA AGG CAG GAG GCG GAT AGG GGC      96
Ala Thr Met Ser Val Ala Gln Gln Thr Arg Gln Glu Ala Asp Arg Gly
                20                  25                  30

TGC GAG ACA CTT GTA GTC CAG CAC GGC CAC TGT AGC TAC ACC TTC TTG     144
Cys Glu Thr Leu Val Val Gln His Gly His Cys Ser Tyr Thr Phe Leu
            35                  40                  45

CTG CCC AAG TCT GAG CCC TGC CCT CCG GGG CCT GAG GTC TCC AGG GAC     192
Leu Pro Lys Ser Glu Pro Cys Pro Pro Gly Pro Glu Val Ser Arg Asp
        50                  55                  60

TCC AAC ACC CTC CAG AGA GAA TCA CTG GCC AAC CCA CTG CAC CTG GGG     240
Ser Asn Thr Leu Gln Arg Glu Ser Leu Ala Asn Pro Leu His Leu Gly
65              70                  75                  80

AAG TTG CCC ACC CAG CAG GTG AAA CAG CTG GAG CAG GCA CTG CAG AAC     288
Lys Leu Pro Thr Gln Gln Val Lys Gln Leu Glu Gln Ala Leu Gln Asn
                85                  90                  95

AAC ACG CAG TGG CTG AAG AAG CTA GAG AGG GCC ATC AAG ACG ATC TTG     336
Asn Thr Gln Trp Leu Lys Lys Leu Glu Arg Ala Ile Lys Thr Ile Leu
            100                 105                 110

AGG TCG AAG CTG GAG CAG GTC CAG CAG CAA ATG GCC CAG AAT CAG ACG     384
Arg Ser Lys Leu Glu Gln Val Gln Gln Gln Met Ala Gln Asn Gln Thr
```

|     |     |     |     |     |     |     |     |     |     |     |     |     |     |      |
|-----|-----|-----|-----|-----|-----|-----|-----|-----|-----|-----|-----|-----|-----|------|
|     |     | 115 |     |     |     | 120 |     |     |     |     | 125 |     |     |      |
| GCC | CCC | ATG | CTA | GAG | CTG | GGC | ACC | AGC | CTC | CTG | AAC | CAG | ACC | ACT GCC | 432 |
| Ala | Pro | Met | Leu | Glu | Leu | Gly | Thr | Ser | Leu | Leu | Asn | Gln | Thr | Thr Ala |     |
|     | 130 |     |     |     |     | 135 |     |     |     |     | 140 |     |     |      |
| CAG | ATC | CGC | AAG | CTG | ACC | GAC | ATG | GAG | GCT | CAG | CTC | CTG | AAC | CAG ACA | 480 |
| Gln | Ile | Arg | Lys | Leu | Thr | Asp | Met | Glu | Ala | Gln | Leu | Leu | Asn | Gln Thr |     |
| 145 |     |     |     |     | 150 |     |     |     |     | 155 |     |     |     | 160  |
| TCA | AGA | ATG | GAT | GCC | CAG | ATG | CCA | GAG | ACC | TTT | CTG | TCC | ACC | AAC AAG | 528 |
| Ser | Arg | Met | Asp | Ala | Gln | Met | Pro | Glu | Thr | Phe | Leu | Ser | Thr | Asn Lys |     |
|     |     |     |     | 165 |     |     |     |     | 170 |     |     |     | 175 |      |
| CTG | GAG | AAC | CAG | CTG | CTG | CTA | CAG | AGG | CAG | AAG | CTC | CAG | CAG | CTT CAG | 576 |
| Leu | Glu | Asn | Gln | Leu | Leu | Leu | Gln | Arg | Gln | Lys | Leu | Gln | Gln | Leu Gln |     |
|     |     |     | 180 |     |     |     |     | 185 |     |     |     |     | 190 |      |
| GGC | CAA | AAC | AGC | GCG | CTC | GAG | AAG | CGG | TTG | CAG | GCC | CTG | GAG | ACC AAG | 624 |
| Gly | Gln | Asn | Ser | Ala | Leu | Glu | Lys | Arg | Leu | Gln | Ala | Leu | Glu | Thr Lys |     |
|     |     | 195 |     |     |     |     | 200 |     |     |     |     | 205 |     |      |
| CAG | CAG | GAG | GAG | CTG | GCC | AGC | ATC | CTC | AGC | AAG | AAG | GCG | AAG | CTG CTG | 672 |
| Gln | Gln | Glu | Glu | Leu | Ala | Ser | Ile | Leu | Ser | Lys | Lys | Ala | Lys | Leu Leu |     |
|     | 210 |     |     |     |     | 215 |     |     |     |     | 220 |     |     |      |
| AAC | ACG | CTG | AGC | CGC | CAG | AGC | GCC | GCC | CTC | ACC | AAC | ATC | GAG | CGC GGC | 720 |
| Asn | Thr | Leu | Ser | Arg | Gln | Ser | Ala | Ala | Leu | Thr | Asn | Ile | Glu | Arg Gly |     |
| 225 |     |     |     | 230 |     |     |     |     | 235 |     |     |     |     | 240  |
| CTG | CGC | GGT | GTC | AGG | CAC | AAC | TCC | AGC | CTC | CTG | CAG | GAC | CAG | CAG CAC | 768 |
| Leu | Arg | Gly | Val | Arg | His | Asn | Ser | Ser | Leu | Leu | Gln | Asp | Gln | Gln His |     |
|     |     |     |     | 245 |     |     |     |     | 250 |     |     |     | 255 |      |
| AGC | CTG | CGC | CAG | CTG | CTG | GTG | TTG | TTG | CGG | CAC | CTG | GTG | CAA | GAA AGG | 816 |
| Ser | Leu | Arg | Gln | Leu | Leu | Val | Leu | Leu | Arg | His | Leu | Val | Gln | Glu Arg |     |
|     |     |     | 260 |     |     |     |     | 265 |     |     |     |     | 270 |      |
| GCT | AAC | GCC | TCG | GCC | CCG | GCC | TTC | ATA | ATG | GCA | GGT | GAG | CAG | GTG TTC | 864 |
| Ala | Asn | Ala | Ser | Ala | Pro | Ala | Phe | Ile | Met | Ala | Gly | Glu | Gln | Val Phe |     |
|     |     | 275 |     |     |     |     | 280 |     |     |     |     | 285 |     |      |
| CAG | GAC | TGT | GCA | GAG | ATC | CAG | CGC | TCT | GGG | GCC | AGT | GCC | AGT | GGT GTC | 912 |
| Gln | Asp | Cys | Ala | Glu | Ile | Gln | Arg | Ser | Gly | Ala | Ser | Ala | Ser | Gly Val |     |
|     | 290 |     |     |     |     | 295 |     |     |     |     | 300 |     |     |      |
| TAC | ACC | ATC | CAG | GTG | TCC | AAT | GCA | ACG | AAG | CCC | AGG | AAG | GTG | TTC TGT | 960 |
| Tyr | Thr | Ile | Gln | Val | Ser | Asn | Ala | Thr | Lys | Pro | Arg | Lys | Val | Phe Cys |     |
| 305 |     |     |     | 310 |     |     |     |     | 315 |     |     |     |     | 320  |
| GAC | CTG | CAG | AGC | AGT | GGA | GGC | AGG | TGG | ACC | CTC | ATC | CAG | CGC | CGT GAG | 1008 |
| Asp | Leu | Gln | Ser | Ser | Gly | Gly | Arg | Trp | Thr | Leu | Ile | Gln | Arg | Arg Glu |     |
|     |     |     |     | 325 |     |     |     |     | 330 |     |     |     | 335 |      |
| AAT | GGC | ACC | GTG | AAT | TTT | CAG | CGG | AAC | TGG | AAG | GAT | TAC | AAA | CAG GGC | 1056 |
| Asn | Gly | Thr | Val | Asn | Phe | Gln | Arg | Asn | Trp | Lys | Asp | Tyr | Lys | Gln Gly |     |
|     |     |     | 340 |     |     |     |     | 345 |     |     |     |     | 350 |      |
| TTC | GGA | GAC | CCA | GCT | GGG | GAG | CAC | TGG | CTG | GGC | AAT | GAA | GTG | GTG CAC | 1104 |
| Phe | Gly | Asp | Pro | Ala | Gly | Glu | His | Trp | Leu | Gly | Asn | Glu | Val | Val His |     |
|     |     | 355 |     |     |     |     | 360 |     |     |     |     | 365 |     |      |
| CAG | CTC | ACC | AGA | AGG | GCA | GCC | TAC | TCT | CTG | CGT | GTG | GAG | CTG | CAA GAC | 1152 |
| Gln | Leu | Thr | Arg | Arg | Ala | Ala | Tyr | Ser | Leu | Arg | Val | Glu | Leu | Gln Asp |     |
|     | 370 |     |     |     |     | 375 |     |     |     |     | 380 |     |     |      |
| TGG | GAA | GGC | CAC | GAG | GCC | TAT | GCC | CAG | TAC | GAA | CAT | TTC | CAC | CTG GGC | 1200 |
| Trp | Glu | Gly | His | Glu | Ala | Tyr | Ala | Gln | Tyr | Glu | His | Phe | His | Leu Gly |     |
| 385 |     |     |     | 390 |     |     |     |     | 395 |     |     |     |     | 400  |
| AGT | GAG | AAC | CAG | CTA | TAC | AGG | CTT | TCT | GTG | GTC | GGG | TAC | AGC | GGC TCA | 1248 |
| Ser | Glu | Asn | Gln | Leu | Tyr | Arg | Leu | Ser | Val | Val | Gly | Tyr | Ser | Gly Ser |     |
|     |     |     |     | 405 |     |     |     |     | 410 |     |     |     | 415 |      |
| GCA | GGG | CGC | CAG | AGC | AGC | CTG | GTC | CTG | CAG | AAC | ACC | AGC | TTT | AGC ACC | 1296 |
| Ala | Gly | Arg | Gln | Ser | Ser | Leu | Val | Leu | Gln | Asn | Thr | Ser | Phe | Ser Thr |     |
|     |     |     | 420 |     |     |     |     | 425 |     |     |     |     | 430 |      |
| CTT | GAC | TCA | GAC | AAC | GAC | CAC | TGT | CTC | TGC | AAG | TGT | GCC | CAG | GTG ATG | 1344 |

```
Leu Asp Ser Asp Asn Asp His Cys Leu Cys Lys Cys Ala Gln Val Met
        435                 440                 445

TCT GGA GGG TGG TGG TTT GAC GCC TGT GGC CTG TCA AAC CTC AAC GGC    1392
Ser Gly Gly Trp Trp Phe Asp Ala Cys Gly Leu Ser Asn Leu Asn Gly
    450                 455                 460

GTC TAC TAC CAC GCT CCC GAC AAC AAG TAC AAG ATG GAC GGC ATC CGC    1440
Val Tyr Tyr His Ala Pro Asp Asn Lys Tyr Lys Met Asp Gly Ile Arg
465                 470                 475                 480

TGG CAC TAC TTC AAG GGC CCC AGC TAC TCA CTG CGT GCC TCT CGC ATG    1488
Trp His Tyr Phe Lys Gly Pro Ser Tyr Ser Leu Arg Ala Ser Arg Met
                485                 490                 495

ATG ATA CGG CCT TTG GAC ATC TAA                                    1512
Met Ile Arg Pro Leu Asp Ile
                500
```

(2) INFORMATION FOR SEQ ID NO:18:

(i) SEQUENCE CHARACTERISTICS:
        (A) LENGTH: 503 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: TIE ligand-4
        (B) LOCATION: 1...503
        (D) OTHER INFORMATION:

(xi) SEQUENCE DESCRIPTION: SEQ ID NO:18:

```
Met Leu Ser Gln Leu Ala Met Leu Gln Gly Ser Leu Leu Leu Val Val
1               5                   10                  15

Ala Thr Met Ser Val Ala Gln Gln Thr Arg Gln Glu Ala Asp Arg Gly
            20                  25                  30

Cys Glu Thr Leu Val Val Gln His Gly His Cys Ser Tyr Thr Phe Leu
        35                  40                  45

Leu Pro Lys Ser Glu Pro Cys Pro Pro Gly Pro Glu Val Ser Arg Asp
    50                  55                  60

Ser Asn Thr Leu Gln Arg Glu Ser Leu Ala Asn Pro Leu His Leu Gly
65                  70                  75                  80

Lys Leu Pro Thr Gln Gln Val Lys Gln Leu Glu Gln Ala Leu Gln Asn
                85                  90                  95

Asn Thr Gln Trp Leu Lys Lys Leu Glu Arg Ala Ile Lys Thr Ile Leu
            100                 105                 110

Arg Ser Lys Leu Glu Gln Val Gln Gln Gln Met Ala Gln Asn Gln Thr
        115                 120                 125

Ala Pro Met Leu Glu Leu Gly Thr Ser Leu Leu Asn Gln Thr Thr Ala
    130                 135                 140

Gln Ile Arg Lys Leu Thr Asp Met Glu Ala Gln Leu Leu Asn Gln Thr
145                 150                 155                 160

Ser Arg Met Asp Ala Gln Met Pro Glu Thr Phe Leu Ser Thr Asn Lys
                165                 170                 175

Leu Glu Asn Gln Leu Leu Leu Gln Arg Gln Lys Leu Gln Gln Leu Gln
            180                 185                 190

Gly Gln Asn Ser Ala Leu Glu Lys Arg Leu Gln Ala Leu Glu Thr Lys
        195                 200                 205

Gln Gln Glu Glu Leu Ala Ser Ile Leu Ser Lys Lys Ala Lys Leu Leu
```

```
            210                 215                 220
Asn Thr Leu Ser Arg Gln Ser Ala Ala Leu Thr Asn Ile Glu Arg Gly
225                 230                 235                 240

Leu Arg Gly Val Arg His Asn Ser Ser Leu Leu Gln Asp Gln Gln His
                    245                 250                 255

Ser Leu Arg Gln Leu Leu Val Leu Leu Arg His Leu Val Gln Glu Arg
                260                 265                 270

Ala Asn Ala Ser Ala Pro Ala Phe Ile Met Ala Gly Glu Gln Val Phe
                275                 280                 285

Gln Asp Cys Ala Glu Ile Gln Arg Ser Gly Ala Ser Ala Ser Gly Val
    290                 295                 300

Tyr Thr Ile Gln Val Ser Asn Ala Thr Lys Pro Arg Lys Val Phe Cys
305                 310                 315                 320

Asp Leu Gln Ser Ser Gly Gly Arg Trp Thr Leu Ile Gln Arg Arg Glu
                325                 330                 335

Asn Gly Thr Val Asn Phe Gln Arg Asn Trp Lys Asp Tyr Lys Gln Gly
                340                 345                 350

Phe Gly Asp Pro Ala Gly Glu His Trp Leu Gly Asn Glu Val Val His
                355                 360                 365

Gln Leu Thr Arg Arg Ala Ala Tyr Ser Leu Arg Val Glu Leu Gln Asp
    370                 375                 380

Trp Glu Gly His Glu Ala Tyr Ala Gln Tyr Glu His Phe His Leu Gly
385                 390                 395                 400

Ser Glu Asn Gln Leu Tyr Arg Leu Ser Val Val Gly Tyr Ser Gly Ser
                405                 410                 415

Ala Gly Arg Gln Ser Ser Leu Val Leu Gln Asn Thr Ser Phe Ser Thr
                420                 425                 430

Leu Asp Ser Asp Asn Asp His Cys Leu Cys Lys Cys Ala Gln Val Met
                435                 440                 445

Ser Gly Gly Trp Trp Phe Asp Ala Cys Gly Leu Ser Asn Leu Asn Gly
                450                 455                 460

Val Tyr Tyr His Ala Pro Asp Asn Lys Tyr Lys Met Asp Gly Ile Arg
465                 470                 475                 480

Trp His Tyr Phe Lys Gly Pro Ser Tyr Ser Leu Arg Ala Ser Arg Met
                485                 490                 495

Met Ile Arg Pro Leu Asp Ile
                500

(2) INFORMATION FOR SEQ ID NO:19:

(i) SEQUENCE CHARACTERISTICS:
        (A) LENGTH: 1497 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...1494
        (D) OTHER INFORMATION:
        (A) NAME/KEY: 1N1C2F (chimera 1)
        (B) LOCATION: 1...1497
        (D) OTHER INFORMATION:
        (A) NAME/KEY: Other
        (B) LOCATION: 1...60
        (D) OTHER INFORMATION: Putative leader sequence is
            encoded by nucleotides 1-60
```

(xi) SEQUENCE DESCRIPTION: SEQ ID NO:19:

```
ATG ACA GTT TTC CTT TCC TTT GCT TTC CTC GCT GCC ATT CTG ACT CAC        48
Met Thr Val Phe Leu Ser Phe Ala Phe Leu Ala Ala Ile Leu Thr His
 1               5                  10                  15

ATA GGG TGC AGC AAT CAG CGC CGA AGT CCA GAA AAC AGT GGG AGA AGA        96
Ile Gly Cys Ser Asn Gln Arg Arg Ser Pro Glu Asn Ser Gly Arg Arg
                 20                  25                  30

TAT AAC CGG ATT CAA CAT GGG CAA TGT GCC TAC ACT TTC ATT CTT CCA       144
Tyr Asn Arg Ile Gln His Gly Gln Cys Ala Tyr Thr Phe Ile Leu Pro
             35                  40                  45

GAA CAC GAT GGC AAC TGT CGT GAG AGT ACG ACA GAC CAG TAC AAC ACA       192
Glu His Asp Gly Asn Cys Arg Glu Ser Thr Thr Asp Gln Tyr Asn Thr
         50                  55                  60

AAC GCT CTG CAG AGA GAT GCT CCA CAC GTG GAA CCG GAT TTC TCT TCC       240
Asn Ala Leu Gln Arg Asp Ala Pro His Val Glu Pro Asp Phe Ser Ser
 65                  70                  75                  80

CAG AAA CTT CAA CAT CTG GAA CAT GTG ATG GAA AAT TAT ACT CAG TGG       288
Gln Lys Leu Gln His Leu Glu His Val Met Glu Asn Tyr Thr Gln Trp
                 85                  90                  95

CTG CAA AAA CTT GAG AAT TAC ATT GTG GAA AAC ATG AAG TCG GAG ATG       336
Leu Gln Lys Leu Glu Asn Tyr Ile Val Glu Asn Met Lys Ser Glu Met
                100                 105                 110

GCC CAG ATA CAG CAG AAT GCA GTT CAG AAC CAC ACG GCT ACC ATG CTG       384
Ala Gln Ile Gln Gln Asn Ala Val Gln Asn His Thr Ala Thr Met Leu
            115                 120                 125

GAG ATA GGA ACC AGC CTC CTC TCT CAG ACT GCA GAG CAG ACC AGA AAG       432
Glu Ile Gly Thr Ser Leu Leu Ser Gln Thr Ala Glu Gln Thr Arg Lys
        130                 135                 140

CTG ACA GAT GTT GAG ACC CAG GTA CTA AAT CAA ACT TCT CGA CTT GAG       480
Leu Thr Asp Val Glu Thr Gln Val Leu Asn Gln Thr Ser Arg Leu Glu
145                 150                 155                 160

ATA CAG CTG CTG GAG AAT TCA TTA TCC ACC TAC AAG CTA GAG AAG CAA       528
Ile Gln Leu Leu Glu Asn Ser Leu Ser Thr Tyr Lys Leu Glu Lys Gln
                165                 170                 175

CTT CTT CAA CAG ACA AAT GAA ATC TTG AAG ATC CAT GAA AAA AAC AGT       576
Leu Leu Gln Gln Thr Asn Glu Ile Leu Lys Ile His Glu Lys Asn Ser
            180                 185                 190

TTA TTA GAA CAT AAA ATC TTA GAA ATG GAA GGA AAA CAC AAG GAA GAG       624
Leu Leu Glu His Lys Ile Leu Glu Met Glu Gly Lys His Lys Glu Glu
        195                 200                 205

TTG GAC ACC TTA AAG GAA GAG AAA GAG AAC CTT CAA GGC TTG GTT ACT       672
Leu Asp Thr Leu Lys Glu Glu Lys Glu Asn Leu Gln Gly Leu Val Thr
210                 215                 220

CGT CAA ACA TAT ATA ATC CAG GAG CTG GAA AAG CAA TTA AAC AGA GCT       720
Arg Gln Thr Tyr Ile Ile Gln Glu Leu Glu Lys Gln Leu Asn Arg Ala
225                 230                 235                 240

ACC ACC AAC AAC AGT GTC CTT CAG AAG CAG CAA CTG GAG CTG ATG GAC       768
Thr Thr Asn Asn Ser Val Leu Gln Lys Gln Gln Leu Glu Leu Met Asp
                245                 250                 255

ACA GTC CAC AAC CTT GTC AAT CTT TGC ACT AAA GAA GGT GTT TTA CTA       816
Thr Val His Asn Leu Val Asn Leu Cys Thr Lys Glu Gly Val Leu Leu
            260                 265                 270

AAG GGA GGA AAA AGA GAG GAA GAG AAA CCA TTT AGA GAC TGT GCT GAA       864
Lys Gly Gly Lys Arg Glu Glu Glu Lys Pro Phe Arg Asp Cys Ala Glu
        275                 280                 285

GTA TTC AAA TCA GGA CAC ACC ACA AAT GGC ATC TAC ACG TTA ACA TTC       912
Val Phe Lys Ser Gly His Thr Thr Asn Gly Ile Tyr Thr Leu Thr Phe
    290                 295                 300

CCT AAT TCT ACA GAA GAG ATC AAG GCC TAC TGT GAC ATG GAA GCT GGA       960
```

```
Pro Asn Ser Thr Glu Glu Ile Lys Ala Tyr Cys Asp Met Glu Ala Gly
305                 310                 315                 320

GGA GGC GGG TGG ACA ATT ATT CAG CGA CGT GAG GAT GGC AGC GTT GAT    1008
Gly Gly Gly Trp Thr Ile Ile Gln Arg Arg Glu Asp Gly Ser Val Asp
                325                 330                 335

TTT CAG AGG ACT TGG AAA GAA TAT AAA GTG GGA TTT GGT AAC CCT TCA    1056
Phe Gln Arg Thr Trp Lys Glu Tyr Lys Val Gly Phe Gly Asn Pro Ser
                340                 345                 350

GGA GAA TAT TGG CTG GGA AAT GAG TTT GTT TCG CAA CTG ACT AAT CAG    1104
Gly Glu Tyr Trp Leu Gly Asn Glu Phe Val Ser Gln Leu Thr Asn Gln
                355                 360                 365

CAA CGC TAT GTG CTT AAA ATA CAC CTT AAA GAC TGG GAA GGG AAT GAG    1152
Gln Arg Tyr Val Leu Lys Ile His Leu Lys Asp Trp Glu Gly Asn Glu
370                 375                 380

GCT TAC TCA TTG TAT GAA CAT TTC TAT CTC TCA AGT GAA GAA CTC AAT    1200
Ala Tyr Ser Leu Tyr Glu His Phe Tyr Leu Ser Ser Glu Glu Leu Asn
385                 390                 395                 400

TAT AGG ATT CAC CTT AAA GGA CTT ACA GGG ACA GCC GGC AAA ATA AGC    1248
Tyr Arg Ile His Leu Lys Gly Leu Thr Gly Thr Ala Gly Lys Ile Ser
                405                 410                 415

AGC ATC AGC CAA CCA GGA AAT GAT TTT AGC ACA AAG GAT GGA GAC AAC    1296
Ser Ile Ser Gln Pro Gly Asn Asp Phe Ser Thr Lys Asp Gly Asp Asn
                420                 425                 430

GAC AAA TGT ATT TGC AAA TGT TCA CAA ATG CTA ACA GGA GGC TGG TGG    1344
Asp Lys Cys Ile Cys Lys Cys Ser Gln Met Leu Thr Gly Gly Trp Trp
                435                 440                 445

TTT GAT GCA TGT GGT CCT TCC AAC TTG AAC GGA ATG TAC TAT CCA CAG    1392
Phe Asp Ala Cys Gly Pro Ser Asn Leu Asn Gly Met Tyr Tyr Pro Gln
450                 455                 460

AGG CAG AAC ACA AAT AAG TTC AAC GGC ATT AAA TGG TAC TAC TGG AAA    1440
Arg Gln Asn Thr Asn Lys Phe Asn Gly Ile Lys Trp Tyr Tyr Trp Lys
465                 470                 475                 480

GGC TCA GGC TAT TCG CTC AAG GCC ACA ACC ATG ATG ATC CGA CCA GCA    1488
Gly Ser Gly Tyr Ser Leu Lys Ala Thr Thr Met Met Ile Arg Pro Ala
                485                 490                 495

GAT TTC TAA                                                        1497
Asp Phe
```

(2) INFORMATION FOR SEQ ID NO:20:

(i) SEQUENCE CHARACTERISTICS:
        (A) LENGTH: 498 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: 1N1C2F (chimera 1)
        (B) LOCATION: 1...498
        (D) OTHER INFORMATION:

(xi) SEQUENCE DESCRIPTION: SEQ ID NO:20:

```
Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
                35                  40                  45
```

-continued

```
Glu His Asp Gly Asn Cys Arg Glu Ser Thr Thr Asp Gln Tyr Asn Thr
 50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                     85                  90                  95

Leu Gln Lys Leu Glu Asn Tyr Ile Val Glu Asn Met Lys Ser Glu Met
                100                 105                 110

Ala Gln Ile Gln Gln Asn Ala Val Gln Asn His Thr Ala Thr Met Leu
                115                 120                 125

Glu Ile Gly Thr Ser Leu Leu Ser Gln Thr Ala Glu Gln Thr Arg Lys
                130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
                180                 185                 190

Leu Leu Glu His Lys Ile Leu Glu Met Glu Gly Lys His Lys Glu Glu
                195                 200                 205

Leu Asp Thr Leu Lys Glu Glu Lys Glu Asn Leu Gln Gly Leu Val Thr
210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
                260                 265                 270

Lys Gly Gly Lys Arg Glu Glu Lys Pro Phe Arg Asp Cys Ala Glu
                275                 280                 285

Val Phe Lys Ser Gly His Thr Thr Asn Gly Ile Tyr Thr Leu Thr Phe
290                 295                 300

Pro Asn Ser Thr Glu Glu Ile Lys Ala Tyr Cys Asp Met Glu Ala Gly
305                 310                 315                 320

Gly Gly Gly Trp Thr Ile Ile Gln Arg Arg Glu Asp Gly Ser Val Asp
                325                 330                 335

Phe Gln Arg Thr Trp Lys Glu Tyr Lys Val Gly Phe Gly Asn Pro Ser
                340                 345                 350

Gly Glu Tyr Trp Leu Gly Asn Glu Phe Val Ser Gln Leu Thr Asn Gln
                355                 360                 365

Gln Arg Tyr Val Leu Lys Ile His Leu Lys Asp Trp Glu Gly Asn Glu
                370                 375                 380

Ala Tyr Ser Leu Tyr Glu His Phe Tyr Leu Ser Ser Glu Glu Leu Asn
385                 390                 395                 400

Tyr Arg Ile His Leu Lys Gly Leu Thr Gly Thr Ala Gly Lys Ile Ser
                405                 410                 415

Ser Ile Ser Gln Pro Gly Asn Asp Phe Ser Thr Lys Asp Gly Asp Asn
                420                 425                 430

Asp Lys Cys Ile Cys Lys Cys Ser Gln Met Leu Thr Gly Gly Trp Trp
                435                 440                 445

Phe Asp Ala Cys Gly Pro Ser Asn Leu Asn Gly Met Tyr Tyr Pro Gln
450                 455                 460

Arg Gln Asn Thr Asn Lys Phe Asn Gly Ile Lys Trp Tyr Tyr Trp Lys
```

```
                465                  470                  475                  480
Gly Ser Gly Tyr Ser Leu Lys Ala Thr Thr Met Met Ile Arg Pro Ala
                         485                  490                  495

Asp Phe
```

(2) INFORMATION FOR SEQ ID NO:21:

(i) SEQUENCE CHARACTERISTICS:
        (A) LENGTH: 1491 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...1488
        (D) OTHER INFORMATION:
        (A) NAME/KEY: 2N2C1F (chimera 2)
        (B) LOCATION: 1...1491
        (D) OTHER INFORMATION:
        (A) NAME/KEY: Other
        (B) LOCATION: 1...48
        (D) OTHER INFORMATION: Putative leader sequence is
            encoded by nucleotides 1-48

(xi) SEQUENCE DESCRIPTION: SEQ ID NO:21:

```
ATG TGG CAG ATT GTT TTC TTT ACT CTG AGC TGT GAT CTT GTC TTG GCC         48
Met Trp Gln Ile Val Phe Phe Thr Leu Ser Cys Asp Leu Val Leu Ala
1                   5                  10                  15

GCA GCC TAT AAC AAC TTT CGG AAG AGC ATG GAC AGC ATA GGA AAG AAG         96
Ala Ala Tyr Asn Asn Phe Arg Lys Ser Met Asp Ser Ile Gly Lys Lys
                20                  25                  30

CAA TAT CAG GTC CAG CAT GGG TCC TGC AGC TAC ACT TTC CTC CTG CCA        144
Gln Tyr Gln Val Gln His Gly Ser Cys Ser Tyr Thr Phe Leu Leu Pro
            35                  40                  45

GAG ATG GAC AAC TGC CGC TCT TCC TCC AGC CCC TAC GTG TCC AAT GCT        192
Glu Met Asp Asn Cys Arg Ser Ser Ser Ser Pro Tyr Val Ser Asn Ala
    50                  55                  60

GTG CAG AGG GAC GCG CCG CTC GAA TAC GAT GAC TCG GTG CAG AGG CTG        240
Val Gln Arg Asp Ala Pro Leu Glu Tyr Asp Asp Ser Val Gln Arg Leu
65                  70                  75                  80

CAA GTG CTG GAG AAC ATC ATG GAA AAC AAC ACT CAG TGG CTA ATG AAG        288
Gln Val Leu Glu Asn Ile Met Glu Asn Asn Thr Gln Trp Leu Met Lys
                85                  90                  95

CTT GAG AAT TAT ATC CAG GAC AAC ATG AAG AAA GAA ATG GTA GAG ATA        336
Leu Glu Asn Tyr Ile Gln Asp Asn Met Lys Lys Glu Met Val Glu Ile
                100                 105                 110

CAG CAG AAT GCA GTA CAG AAC CAG ACG GCT GTG ATG ATA GAA ATA GGG        384
Gln Gln Asn Ala Val Gln Asn Gln Thr Ala Val Met Ile Glu Ile Gly
            115                 120                 125

ACA AAC CTG TTG AAC CAA ACA GCT GAG CAA ACG CGG AAG TTA ACT GAT        432
Thr Asn Leu Leu Asn Gln Thr Ala Glu Gln Thr Arg Lys Leu Thr Asp
    130                 135                 140

GTG GAA GCC CAA GTA TTA AAT CAG ACC ACG AGA CTT GAA CTT CAG CTC        480
Val Glu Ala Gln Val Leu Asn Gln Thr Thr Arg Leu Glu Leu Gln Leu
145                 150                 155                 160

TTG GAA CAC TCC CTC TCG ACA AAC AAA TTG GAA AAA CAG ATT TTG GAC        528
Leu Glu His Ser Leu Ser Thr Asn Lys Leu Glu Lys Gln Ile Leu Asp
                165                 170                 175

CAG ACC AGT GAA ATA AAC AAA TTG CAA GAT AAG AAC AGT TTC CTA GAA        576
Gln Thr Ser Glu Ile Asn Lys Leu Gln Asp Lys Asn Ser Phe Leu Glu
                180                 185                 190
```

```
AAG AAG GTG CTA GCT ATG GAA GAC AAG CAC ATC ATC CAA CTA CAG TCA         624
Lys Lys Val Leu Ala Met Glu Asp Lys His Ile Ile Gln Leu Gln Ser
        195                 200                 205

ATA AAA GAA GAG AAA GAT CAG CTA CAG GTG TTA GTA TCC AAG CAA AAT         672
Ile Lys Glu Glu Lys Asp Gln Leu Gln Val Leu Val Ser Lys Gln Asn
        210                 215                 220

TCC ATC ATT GAA GAA CTA GAA AAA AAA ATA GTG ACT GCC ACG GTG AAT         720
Ser Ile Ile Glu Glu Leu Glu Lys Lys Ile Val Thr Ala Thr Val Asn
225                 230                 235                 240

AAT TCA GTT CTT CAA AAG CAG CAA CAT GAT CTC ATG GAG ACA GTT AAT         768
Asn Ser Val Leu Gln Lys Gln Gln His Asp Leu Met Glu Thr Val Asn
                245                 250                 255

AAC TTA CTG ACT ATG ATG TCC ACA TCA AAC TCA GCT AAG GAC CCC ACT         816
Asn Leu Leu Thr Met Met Ser Thr Ser Asn Ser Ala Lys Asp Pro Thr
            260                 265                 270

GTT GCT AAA GAA GAA CAA ATC AGC TTC AGA GAC TGT GCA GAT GTA TAT         864
Val Ala Lys Glu Glu Gln Ile Ser Phe Arg Asp Cys Ala Asp Val Tyr
                275                 280                 285

CAA GCT GGT TTT AAT AAA AGT GGA ATC TAC ACT ATT TAT ATT AAT AAT         912
Gln Ala Gly Phe Asn Lys Ser Gly Ile Tyr Thr Ile Tyr Ile Asn Asn
        290                 295                 300

ATG CCA GAA CCC AAA AAG GTG TTT TGC AAT ATG GAT GTC AAT GGG GGA         960
Met Pro Glu Pro Lys Lys Val Phe Cys Asn Met Asp Val Asn Gly Gly
305                 310                 315                 320

GGT TGG ACT GTA ATA CAA CAT CGT GAA GAT GGA AGT CTA GAT TTC CAA        1008
Gly Trp Thr Val Ile Gln His Arg Glu Asp Gly Ser Leu Asp Phe Gln
                325                 330                 335

AGA GGC TGG AAG GAA TAT AAA ATG GGT TTT GGA AAT CCC TCC GGT GAA        1056
Arg Gly Trp Lys Glu Tyr Lys Met Gly Phe Gly Asn Pro Ser Gly Glu
                340                 345                 350

TAT TGG CTG GGG AAT GAG TTT ATT TTT GCC ATT ACC AGT CAG AGG CAG        1104
Tyr Trp Leu Gly Asn Glu Phe Ile Phe Ala Ile Thr Ser Gln Arg Gln
            355                 360                 365

TAC ATG CTA AGA ATT GAG TTA ATG GAC TGG GAA GGG AAC CGA GCC TAT        1152
Tyr Met Leu Arg Ile Glu Leu Met Asp Trp Glu Gly Asn Arg Ala Tyr
        370                 375                 380

TCA CAG TAT GAC AGA TTC CAC ATA GGA AAT GAA AAG CAA AAC TAT AGG        1200
Ser Gln Tyr Asp Arg Phe His Ile Gly Asn Glu Lys Gln Asn Tyr Arg
385                 390                 395                 400

TTG TAT TTA AAA GGT CAC ACT GGG ACA GCA GGA AAA CAG AGC AGC CTG        1248
Leu Tyr Leu Lys Gly His Thr Gly Thr Ala Gly Lys Gln Ser Ser Leu
                405                 410                 415

ATC TTA CAC GGT GCT GAT TTC AGC ACT AAA GAT GCT GAT AAT GAC AAC        1296
Ile Leu His Gly Ala Asp Phe Ser Thr Lys Asp Ala Asp Asn Asp Asn
                420                 425                 430

TGT ATG TGC AAA TGT GCC CTC ATG TTA ACA GGA GGA TGG TGG TTT GAT        1344
Cys Met Cys Lys Cys Ala Leu Met Leu Thr Gly Gly Trp Trp Phe Asp
            435                 440                 445

GCT TGT GGC CCC TCC AAT CTA AAT GGA ATG TTC TAT ACT GCG GGA CAA        1392
Ala Cys Gly Pro Ser Asn Leu Asn Gly Met Phe Tyr Thr Ala Gly Gln
450                 455                 460

AAC CAT GGA AAA CTG AAT GGG ATA AAG TGG CAC TAC TTC AAA GGG CCC        1440
Asn His Gly Lys Leu Asn Gly Ile Lys Trp His Tyr Phe Lys Gly Pro
465                 470                 475                 480

AGT TAC TCC TTA CGT TCC ACA ACT ATG ATG ATT CGA CCT TTA GAT TTT T     1489
Ser Tyr Ser Leu Arg Ser Thr Thr Met Met Ile Arg Pro Leu Asp Phe
                485                 490                 495

GA                                                                    1491
```

(2) INFORMATION FOR SEQ ID NO:22:

(i) SEQUENCE CHARACTERISTICS:
        (A) LENGTH: 496 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: 2N2C1F (chimera 2)
        (B) LOCATION: 1...496
        (D) OTHER INFORMATION:

(xi) SEQUENCE DESCRIPTION: SEQ ID NO:22:

```
Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
 50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
            85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
            165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
        210                 215                 220

Ser Ile Ile Glu Glu Leu Glu Lys Lys Ile Val Thr Ala Thr Val Asn
225                 230                 235                 240

Asn Ser Val Leu Gln Lys Gln His Asp Leu Met Glu Thr Val Asn
            245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Asp Val Tyr
        275                 280                 285

Gln Ala Gly Phe Asn Lys Ser Gly Ile Tyr Thr Ile Tyr Ile Asn Asn
        290                 295                 300

Met Pro Glu Pro Lys Lys Val Phe Cys Asn Met Asp Val Asn Gly Gly
305                 310                 315                 320
```

```
Gly Trp Thr Val Ile Gln His Arg Glu Asp Gly Ser Leu Asp Phe Gln
            325                 330                 335

Arg Gly Trp Lys Glu Tyr Lys Met Gly Phe Gly Asn Pro Ser Gly Glu
            340                 345                 350

Tyr Trp Leu Gly Asn Glu Phe Ile Phe Ala Ile Thr Ser Gln Arg Gln
            355                 360                 365

Tyr Met Leu Arg Ile Glu Leu Met Asp Trp Glu Gly Asn Arg Ala Tyr
        370                 375                 380

Ser Gln Tyr Asp Arg Phe His Ile Gly Asn Glu Lys Gln Asn Tyr Arg
385                 390                 395                 400

Leu Tyr Leu Lys Gly His Thr Gly Thr Ala Gly Lys Gln Ser Ser Leu
            405                 410                 415

Ile Leu His Gly Ala Asp Phe Ser Thr Lys Asp Ala Asp Asn Asp Asn
            420                 425                 430

Cys Met Cys Lys Cys Ala Leu Met Leu Thr Gly Gly Trp Trp Phe Asp
            435                 440                 445

Ala Cys Gly Pro Ser Asn Leu Asn Gly Met Phe Tyr Thr Ala Gly Gln
            450                 455                 460

Asn His Gly Lys Leu Asn Gly Ile Lys Trp His Tyr Phe Lys Gly Pro
465                 470                 475                 480

Ser Tyr Ser Leu Arg Ser Thr Met Met Ile Arg Pro Leu Asp Phe
            485                 490                 495

(2) INFORMATION FOR SEQ ID NO:23:

(i) SEQUENCE CHARACTERISTICS:
        (A) LENGTH: 1500 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...1497
        (D) OTHER INFORMATION:
        (A) NAME/KEY: 1N2C2F (chimera 3)
        (B) LOCATION: 1...1500
        (D) OTHER INFORMATION:
        (A) NAME/KEY: Other
        (B) LOCATION: 1...60
        (D) OTHER INFORMATION: Putative leader sequence is
            encoded by nucleotides 1-60

(xi) SEQUENCE DESCRIPTION: SEQ ID NO:23:

ATG ACA GTT TTC CTT TCC TTT GCT TTC CTC GCT GCC ATT CTG ACT CAC      48
Met Thr Val Phe Leu Ser Phe Ala Phe Leu Ala Ala Ile Leu Thr His
 1               5                  10                  15

ATA GGG TGC AGC AAT CAG CGC CGA AGT CCA GAA AAC AGT GGG AGA AGA      96
Ile Gly Cys Ser Asn Gln Arg Arg Ser Pro Glu Asn Ser Gly Arg Arg
             20                  25                  30

TAT AAC CGG ATT CAA CAT GGG CAA TGT GCC TAC ACT TTC ATT CTT CCA     144
Tyr Asn Arg Ile Gln His Gly Gln Cys Ala Tyr Thr Phe Ile Leu Pro
         35                  40                  45

GAA CAC GAT GGC AAC TGT CGT GAG AGT ACG ACA GAC CAG TAC AAC ACA     192
Glu His Asp Gly Asn Cys Arg Glu Ser Thr Thr Asp Gln Tyr Asn Thr
     50                  55                  60

AAC GCT CTG CAG AGA GAT GCT CCA CAC GTG GAA CCG GAT GAC TCG GTG     240
Asn Ala Leu Gln Arg Asp Ala Pro His Val Glu Pro Asp Asp Ser Val
 65                  70                  75                  80
```

-continued

| | |
|---|---|
| CAG AGG CTG CAA GTG CTG GAG AAC ATC ATG GAA AAC AAC ACT CAG TGG<br>Gln Arg Leu Gln Val Leu Glu Asn Ile Met Glu Asn Asn Thr Gln Trp<br>                              85                             90                         95 | 288 |
| CTA ATG AAG CTT GAG AAT TAT ATC CAG GAC AAC ATG AAG AAA GAA ATG<br>Leu Met Lys Leu Glu Asn Tyr Ile Gln Asp Asn Met Lys Lys Glu Met<br>             100                         105                     110 | 336 |
| GTA GAG ATA CAG CAG AAT GCA GTA CAG AAC CAG ACG GCT GTG ATG ATA<br>Val Glu Ile Gln Gln Asn Ala Val Gln Asn Gln Thr Ala Val Met Ile<br>           115                       120                         125 | 384 |
| GAA ATA GGG ACA AAC CTG TTG AAC CAA ACA GCT GAG CAA ACG CGG AAG<br>Glu Ile Gly Thr Asn Leu Leu Asn Gln Thr Ala Glu Gln Thr Arg Lys<br>130                         135                         140 | 432 |
| TTA ACT GAT GTG GAA GCC CAA GTA TTA AAT CAG ACC ACG AGA CTT GAA<br>Leu Thr Asp Val Glu Ala Gln Val Leu Asn Gln Thr Thr Arg Leu Glu<br>145                         150                         155                     160 | 480 |
| CTT CAG CTC TTG GAA CAC TCC CTC TCG ACA AAC AAA TTG GAA AAA CAG<br>Leu Gln Leu Leu Glu His Ser Leu Ser Thr Asn Lys Leu Glu Lys Gln<br>                        165                         170                     175 | 528 |
| ATT TTG GAC CAG ACC AGT GAA ATA AAC AAA TTG CAA GAT AAG AAC AGT<br>Ile Leu Asp Gln Thr Ser Glu Ile Asn Lys Leu Gln Asp Lys Asn Ser<br>                         180                         185                     190 | 576 |
| TTC CTA GAA AAG AAG GTG CTA GCT ATG GAA GAC AAG CAC ATC ATC CAA<br>Phe Leu Glu Lys Lys Val Leu Ala Met Glu Asp Lys His Ile Ile Gln<br>         195                         200                         205 | 624 |
| CTA CAG TCA ATA AAA GAA GAG AAA GAT CAG CTA CAG GTG TTA GTA TCC<br>Leu Gln Ser Ile Lys Glu Glu Lys Asp Gln Leu Gln Val Leu Val Ser<br>       210                        215                         220 | 672 |
| AAG CAA AAT TCC ATC ATT GAA GAA CTA GAA AAA AAA ATA GTG ACT GCC<br>Lys Gln Asn Ser Ile Ile Glu Glu Leu Glu Lys Lys Ile Val Thr Ala<br>225                         230                         235                     240 | 720 |
| ACG GTG AAT AAT TCA GTT CTT CAA AAG CAG CAA CAT GAT CTC ATG GAG<br>Thr Val Asn Asn Ser Val Leu Gln Lys Gln Gln His Asp Leu Met Glu<br>                         245                         250                     255 | 768 |
| ACA GTT AAT AAC TTA CTG ACT ATG ATG TCC ACA TCA AAC TCA GCT AAG<br>Thr Val Asn Asn Leu Leu Thr Met Met Ser Thr Ser Asn Ser Ala Lys<br>                         260                         265                     270 | 816 |
| GAC CCC ACT GTT GCT AAA GAA GAA CAA ATC AGC TTC AGA GAC TGT GCT<br>Asp Pro Thr Val Ala Lys Glu Glu Gln Ile Ser Phe Arg Asp Cys Ala<br>       275                        280                         285 | 864 |
| GAA GTA TTC AAA TCA GGA CAC ACC ACA AAT GGC ATC TAC ACG TTA ACA<br>Glu Val Phe Lys Ser Gly His Thr Thr Asn Gly Ile Tyr Thr Leu Thr<br>         290                        295                     300 | 912 |
| TTC CCT AAT TCT ACA GAA GAG ATC AAG GCC TAC TGT GAC ATG GAA GCT<br>Phe Pro Asn Ser Thr Glu Glu Ile Lys Ala Tyr Cys Asp Met Glu Ala<br>305                       310                         315                     320 | 960 |
| GGA GGA GGC GGG TGG ACA ATT ATT CAG CGA CGT GAG GAT GGC AGC GTT<br>Gly Gly Gly Gly Trp Thr Ile Ile Gln Arg Arg Glu Asp Gly Ser Val<br>                       325                         330                     335 | 1008 |
| GAT TTT CAG AGG ACT TGG AAA GAA TAT AAA GTG GGA TTT GGT AAC CCT<br>Asp Phe Gln Arg Thr Trp Lys Glu Tyr Lys Val Gly Phe Gly Asn Pro<br>                       340                         345                     350 | 1056 |
| TCA GGA GAA TAT TGG CTG GGA AAT GAG TTT GTT TCG CAA CTG ACT AAT<br>Ser Gly Glu Tyr Trp Leu Gly Asn Glu Phe Val Ser Gln Leu Thr Asn<br>               355                         360                     365 | 1104 |
| CAG CAA CGC TAT GTG CTT AAA ATA CAC CTT AAA GAC TGG GAA GGG AAT<br>Gln Gln Arg Tyr Val Leu Lys Ile His Leu Lys Asp Trp Glu Gly Asn<br>       370                       375                         380 | 1152 |
| GAG GCT TAC TCA TTG TAT GAA CAT TTC TAT CTC TCA AGT GAA GAA CTC<br>Glu Ala Tyr Ser Leu Tyr Glu His Phe Tyr Leu Ser Ser Glu Glu Leu<br>385                       390                         395                     400 | 1200 |

```
AAT TAT AGG ATT CAC CTT AAA GGA CTT ACA GGG ACA GCC GGC AAA ATA    1248
Asn Tyr Arg Ile His Leu Lys Gly Leu Thr Gly Thr Ala Gly Lys Ile
                    405                 410                 415

AGC AGC ATC AGC CAA CCA GGA AAT GAT TTT AGC ACA AAG GAT GGA GAC    1296
Ser Ser Ile Ser Gln Pro Gly Asn Asp Phe Ser Thr Lys Asp Gly Asp
                420                 425                 430

AAC GAC AAA TGT ATT TGC AAA TGT TCA CAA ATG CTA ACA GGA GGC TGG    1344
Asn Asp Lys Cys Ile Cys Lys Cys Ser Gln Met Leu Thr Gly Gly Trp
            435                 440                 445

TGG TTT GAT GCA TGT GGT CCT TCC AAC TTG AAC GGA ATG TAC TAT CCA    1392
Trp Phe Asp Ala Cys Gly Pro Ser Asn Leu Asn Gly Met Tyr Tyr Pro
        450                 455                 460

CAG AGG CAG AAC ACA AAT AAG TTC AAC GGC ATT AAA TGG TAC TAC TGG    1440
Gln Arg Gln Asn Thr Asn Lys Phe Asn Gly Ile Lys Trp Tyr Tyr Trp
465                 470                 475                 480

AAA GGC TCA GGC TAT TCG CTC AAG GCC ACA ACC ATG ATG ATC CGA CCA    1488
Lys Gly Ser Gly Tyr Ser Leu Lys Ala Thr Thr Met Met Ile Arg Pro
                485                 490                 495

GCA GAT TTC TAA                                                    1500
Ala Asp Phe
```

(2) INFORMATION FOR SEQ ID NO:24:

(i) SEQUENCE CHARACTERISTICS:
        (A) LENGTH: 499 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: 1N2C2F (chimera 3)

(xi) SEQUENCE DESCRIPTION: SEQ ID NO:24:

```
Met Thr Val Phe Leu Ser Phe Ala Phe Leu Ala Ala Ile Leu Thr His
 1               5                  10                  15

Ile Gly Cys Ser Asn Gln Arg Arg Ser Pro Glu Asn Ser Gly Arg Arg
                20                  25                  30

Tyr Asn Arg Ile Gln His Gly Gln Cys Ala Tyr Thr Phe Ile Leu Pro
                35                  40                  45

Glu His Asp Gly Asn Cys Arg Glu Ser Thr Thr Asp Gln Tyr Asn Thr
        50                  55                  60

Asn Ala Leu Gln Arg Asp Ala Pro His Val Glu Pro Asp Asp Ser Val
65                  70                  75                  80

Gln Arg Leu Gln Val Leu Glu Asn Ile Met Glu Asn Asn Thr Gln Trp
                85                  90                  95

Leu Met Lys Leu Glu Asn Tyr Ile Gln Asp Asn Met Lys Lys Glu Met
                100                 105                 110

Val Glu Ile Gln Gln Asn Ala Val Gln Asn Gln Thr Ala Val Met Ile
            115                 120                 125

Glu Ile Gly Thr Asn Leu Leu Asn Gln Thr Ala Glu Gln Thr Arg Lys
        130                 135                 140

Leu Thr Asp Val Glu Ala Gln Val Leu Asn Gln Thr Thr Arg Leu Glu
145                 150                 155                 160

Leu Gln Leu Leu Glu His Ser Leu Ser Thr Asn Lys Leu Glu Lys Gln
                165                 170                 175
```

```
Ile Leu Asp Gln Thr Ser Glu Ile Asn Lys Leu Gln Asp Lys Asn Ser
            180                 185                 190

Phe Leu Glu Lys Lys Val Leu Ala Met Glu Asp Lys His Ile Ile Gln
            195                 200                 205

Leu Gln Ser Ile Lys Glu Glu Lys Asp Gln Leu Gln Val Leu Val Ser
            210                 215                 220

Lys Gln Asn Ser Ile Ile Glu Glu Leu Glu Lys Lys Ile Val Thr Ala
225                 230                 235                 240

Thr Val Asn Asn Ser Val Leu Gln Lys Gln His Asp Leu Met Glu
            245                 250                 255

Thr Val Asn Asn Leu Leu Thr Met Met Ser Thr Ser Asn Ser Ala Lys
            260                 265                 270

Asp Pro Thr Val Ala Lys Glu Glu Gln Ile Ser Phe Arg Asp Cys Ala
            275                 280                 285

Glu Val Phe Lys Ser Gly His Thr Thr Asn Gly Ile Tyr Thr Leu Thr
            290                 295                 300

Phe Pro Asn Ser Thr Glu Glu Ile Lys Ala Tyr Cys Asp Met Glu Ala
305                 310                 315                 320

Gly Gly Gly Gly Trp Thr Ile Ile Gln Arg Arg Glu Asp Gly Ser Val
            325                 330                 335

Asp Phe Gln Arg Thr Trp Lys Glu Tyr Lys Val Gly Phe Gly Asn Pro
            340                 345                 350

Ser Gly Glu Tyr Trp Leu Gly Asn Glu Phe Val Ser Gln Leu Thr Asn
            355                 360                 365

Gln Gln Arg Tyr Val Leu Lys Ile His Leu Lys Asp Trp Glu Gly Asn
            370                 375                 380

Glu Ala Tyr Ser Leu Tyr Glu His Phe Tyr Leu Ser Ser Glu Glu Leu
385                 390                 395                 400

Asn Tyr Arg Ile His Leu Lys Gly Leu Thr Gly Thr Ala Gly Lys Ile
            405                 410                 415

Ser Ser Ile Ser Gln Pro Gly Asn Asp Phe Ser Thr Lys Asp Gly Asp
            420                 425                 430

Asn Asp Lys Cys Ile Cys Lys Cys Ser Gln Met Leu Thr Gly Gly Trp
            435                 440                 445

Trp Phe Asp Ala Cys Gly Pro Ser Asn Leu Asn Gly Met Tyr Tyr Pro
450                 455                 460

Gln Arg Gln Asn Thr Asn Lys Phe Asn Gly Ile Lys Trp Tyr Tyr Trp
465                 470                 475                 480

Lys Gly Ser Gly Tyr Ser Leu Lys Ala Thr Thr Met Met Ile Arg Pro
            485                 490                 495

Ala Asp Phe (2) INFORMATION FOR SEQ ID NO:25:

(i) SEQUENCE CHARACTERISTICS:
        (A) LENGTH: 1488 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 1...1485
        (D) OTHER INFORMATION:
        (A) NAME/KEY: 2N1C1F (chimera 4)
        (B) LOCATION: 1...1488
```

(D) OTHER INFORMATION:
(A) NAME/KEY: Other
(B) LOCATION: 1...48
(D) OTHER INFORMATION: Putative leader sequence (xi) SEQUENCE DESCRIPTION: SEQ ID NO:25:

| | | | | | | | | | | | | | | | | |
|---|---|---|---|---|---|---|---|---|---|---|---|---|---|---|---|---|
| ATG | TGG | CAG | ATT | GTT | TTC | TTT | ACT | CTG | AGC | TGT | GAT | CTT | GTC | TTG | GCC | 48 |
| Met | Trp | Gln | Ile | Val | Phe | Phe | Thr | Leu | Ser | Cys | Asp | Leu | Val | Leu | Ala | |
| 1 | | | | 5 | | | | | 10 | | | | | 15 | | |
| GCA | GCC | TAT | AAC | AAC | TTT | CGG | AAG | AGC | ATG | GAC | AGC | ATA | GGA | AAG | AAG | 96 |
| Ala | Ala | Tyr | Asn | Asn | Phe | Arg | Lys | Ser | Met | Asp | Ser | Ile | Gly | Lys | Lys | |
| | | | | 20 | | | | | 25 | | | | | 30 | | |
| CAA | TAT | CAG | GTC | CAG | CAT | GGG | TCC | TGC | AGC | TAC | ACT | TTC | CTC | CTG | CCA | 144 |
| Gln | Tyr | Gln | Val | Gln | His | Gly | Ser | Cys | Ser | Tyr | Thr | Phe | Leu | Leu | Pro | |
| | | 35 | | | | | 40 | | | | | 45 | | | | |
| GAG | ATG | GAC | AAC | TGC | CGC | TCT | TCC | TCC | AGC | CCC | TAC | GTG | TCC | AAT | GCT | 192 |
| Glu | Met | Asp | Asn | Cys | Arg | Ser | Ser | Ser | Ser | Pro | Tyr | Val | Ser | Asn | Ala | |
| 50 | | | | | 55 | | | | | 60 | | | | | | |
| GTG | CAG | AGG | GAC | GCG | CCG | CTC | GAA | TAC | GAT | TTC | TCT | TCC | CAG | AAA | CTT | 240 |
| Val | Gln | Arg | Asp | Ala | Pro | Leu | Glu | Tyr | Asp | Phe | Ser | Ser | Gln | Lys | Leu | |
| 65 | | | | | 70 | | | | | 75 | | | | | 80 | |
| CAA | CAT | CTG | GAA | CAT | GTG | ATG | GAA | AAT | TAT | ACT | CAG | TGG | CTG | CAA | AAA | 288 |
| Gln | His | Leu | Glu | His | Val | Met | Glu | Asn | Tyr | Thr | Gln | Trp | Leu | Gln | Lys | |
| | | | | 85 | | | | | 90 | | | | | 95 | | |
| CTT | GAG | AAT | TAC | ATT | GTG | GAA | AAC | ATG | AAG | TCG | GAG | ATG | GCC | CAG | ATA | 336 |
| Leu | Glu | Asn | Tyr | Ile | Val | Glu | Asn | Met | Lys | Ser | Glu | Met | Ala | Gln | Ile | |
| | | | | 100 | | | | | 105 | | | | | 110 | | |
| CAG | CAG | AAT | GCA | GTT | CAG | AAC | CAC | ACG | GCT | ACC | ATG | CTG | GAG | ATA | GGA | 384 |
| Gln | Gln | Asn | Ala | Val | Gln | Asn | His | Thr | Ala | Thr | Met | Leu | Glu | Ile | Gly | |
| | | | | 115 | | | | | 120 | | | | | 125 | | |
| ACC | AGC | CTC | CTC | TCT | CAG | ACT | GCA | GAG | CAG | ACC | AGA | AAG | CTG | ACA | GAT | 432 |
| Thr | Ser | Leu | Leu | Ser | Gln | Thr | Ala | Glu | Gln | Thr | Arg | Lys | Leu | Thr | Asp | |
| | | 130 | | | | | 135 | | | | | 140 | | | | |
| GTT | GAG | ACC | CAG | GTA | CTA | AAT | CAA | ACT | TCT | CGA | CTT | GAG | ATA | CAG | CTG | 480 |
| Val | Glu | Thr | Gln | Val | Leu | Asn | Gln | Thr | Ser | Arg | Leu | Glu | Ile | Gln | Leu | |
| 145 | | | | | 150 | | | | | 155 | | | | | 160 | |
| CTG | GAG | AAT | TCA | TTA | TCC | ACC | TAC | AAG | CTA | GAG | AAG | CAA | CTT | CTT | CAA | 528 |
| Leu | Glu | Asn | Ser | Leu | Ser | Thr | Tyr | Lys | Leu | Glu | Lys | Gln | Leu | Leu | Gln | |
| | | | | 165 | | | | | 170 | | | | | 175 | | |
| CAG | ACA | AAT | GAA | ATC | TTG | AAG | ATC | CAT | GAA | AAA | AAC | AGT | TTA | TTA | GAA | 576 |
| Gln | Thr | Asn | Glu | Ile | Leu | Lys | Ile | His | Glu | Lys | Asn | Ser | Leu | Leu | Glu | |
| | | | | 180 | | | | | 185 | | | | | 190 | | |
| CAT | AAA | ATC | TTA | GAA | ATG | GAA | GGA | AAA | CAC | AAG | GAA | GAG | TTG | GAC | ACC | 624 |
| His | Lys | Ile | Leu | Glu | Met | Glu | Gly | Lys | His | Lys | Glu | Glu | Leu | Asp | Thr | |
| | | 195 | | | | | 200 | | | | | 205 | | | | |
| TTA | AAG | GAA | GAG | AAA | GAG | AAC | CTT | CAA | GGC | TTG | GTT | ACT | CGT | CAA | ACA | 672 |
| Leu | Lys | Glu | Glu | Lys | Glu | Asn | Leu | Gln | Gly | Leu | Val | Thr | Arg | Gln | Thr | |
| 210 | | | | | 215 | | | | | 220 | | | | | | |
| TAT | ATA | ATC | CAG | GAG | CTG | GAA | AAG | CAA | TTA | AAC | AGA | GCT | ACC | ACC | AAC | 720 |
| Tyr | Ile | Ile | Gln | Glu | Leu | Glu | Lys | Gln | Leu | Asn | Arg | Ala | Thr | Thr | Asn | |
| 225 | | | | | 230 | | | | | 235 | | | | | 240 | |
| AAC | AGT | GTC | CTT | CAG | AAG | CAG | CAA | CTG | GAG | CTG | ATG | GAC | ACA | GTC | CAC | 768 |
| Asn | Ser | Val | Leu | Gln | Lys | Gln | Gln | Leu | Glu | Leu | Met | Asp | Thr | Val | His | |
| | | | | 245 | | | | | 250 | | | | | 255 | | |
| AAC | CTT | GTC | AAT | CTT | TGC | ACT | AAA | GAA | GGT | GTT | TTA | CTA | AAG | GGA | GGA | 816 |
| Asn | Leu | Val | Asn | Leu | Cys | Thr | Lys | Glu | Gly | Val | Leu | Leu | Lys | Gly | Gly | |
| | | | | 260 | | | | | 265 | | | | | 270 | | |
| AAA | AGA | GAG | GAA | GAG | AAA | CCA | TTT | AGA | GAC | TGT | GCA | GAT | GTA | TAT | CAA | 864 |
| Lys | Arg | Glu | Glu | Glu | Lys | Pro | Phe | Arg | Asp | Cys | Ala | Asp | Val | Tyr | Gln | |
| | | 275 | | | | | 280 | | | | | 285 | | | | |

```
GCT GGT TTT AAT AAA AGT GGA ATC TAC ACT ATT TAT ATT AAT AAT ATG    912
Ala Gly Phe Asn Lys Ser Gly Ile Tyr Thr Ile Tyr Ile Asn Asn Met
    290                 295                 300

CCA GAA CCC AAA AAG GTG TTT TGC AAT ATG GAT GTC AAT GGG GGA GGT    960
Pro Glu Pro Lys Lys Val Phe Cys Asn Met Asp Val Asn Gly Gly Gly
305                 310                 315                 320

TGG ACT GTA ATA CAA CAT CGT GAA GAT GGA AGT CTA GAT TTC CAA AGA   1008
Trp Thr Val Ile Gln His Arg Glu Asp Gly Ser Leu Asp Phe Gln Arg
                325                 330                 335

GGC TGG AAG GAA TAT AAA ATG GGT TTT GGA AAT CCC TCC GGT GAA TAT   1056
Gly Trp Lys Glu Tyr Lys Met Gly Phe Gly Asn Pro Ser Gly Glu Tyr
            340                 345                 350

TGG CTG GGG AAT GAG TTT ATT TTT GCC ATT ACC AGT CAG AGG CAG TAC   1104
Trp Leu Gly Asn Glu Phe Ile Phe Ala Ile Thr Ser Gln Arg Gln Tyr
        355                 360                 365

ATG CTA AGA ATT GAG TTA ATG GAC TGG GAA GGG AAC CGA GCC TAT TCA   1152
Met Leu Arg Ile Glu Leu Met Asp Trp Glu Gly Asn Arg Ala Tyr Ser
    370                 375                 380

CAG TAT GAC AGA TTC CAC ATA GGA AAT GAA AAG CAA AAC TAT AGG TTG   1200
Gln Tyr Asp Arg Phe His Ile Gly Asn Glu Lys Gln Asn Tyr Arg Leu
385                 390                 395                 400

TAT TTA AAA GGT CAC ACT GGG ACA GCA GGA AAA CAG AGC AGC CTG ATC   1248
Tyr Leu Lys Gly His Thr Gly Thr Ala Gly Lys Gln Ser Ser Leu Ile
                405                 410                 415

TTA CAC GGT GCT GAT TTC AGC ACT AAA GAT GCT GAT AAT GAC AAC TGT   1296
Leu His Gly Ala Asp Phe Ser Thr Lys Asp Ala Asp Asn Asp Asn Cys
            420                 425                 430

ATG TGC AAA TGT GCC CTC ATG TTA ACA GGA GGA TGG TGG TTT GAT GCT   1344
Met Cys Lys Cys Ala Leu Met Leu Thr Gly Gly Trp Trp Phe Asp Ala
        435                 440                 445

TGT GGC CCC TCC AAT CTA AAT GGA ATG TTC TAT ACT GCG GGA CAA AAC   1392
Cys Gly Pro Ser Asn Leu Asn Gly Met Phe Tyr Thr Ala Gly Gln Asn
    450                 455                 460

CAT GGA AAA CTG AAT GGG ATA AAG TGG CAC TAC TTC AAA GGG CCC AGT   1440
His Gly Lys Leu Asn Gly Ile Lys Trp His Tyr Phe Lys Gly Pro Ser
465                 470                 475                 480

TAC TCC TTA CGT TCC ACA ACT ATG ATG ATT CGA CCT TTA GAT TTT TGA   1488
Tyr Ser Leu Arg Ser Thr Thr Met Met Ile Arg Pro Leu Asp Phe
                485                 490                 495
```

(2) INFORMATION FOR SEQ ID NO:26:

(i) SEQUENCE CHARACTERISTICS:
        (A) LENGTH: 495 amino acids
        (B) TYPE: amino acid
        (C) STRANDEDNESS: single
        (D) TOPOLOGY: linear (ii) MOLECULE TYPE: protein (v) FRAGMENT TYPE: internal (ix) FEATURE:
        (A) NAME/KEY: 2N1C1F (chimera 4)
        (B) LOCATION: 1...495
        (D) OTHER INFORMATION:

(xi) SEQUENCE DESCRIPTION: SEQ ID NO:26:

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
```

-continued

```
              35                  40                  45
Glu Met Asp Asn Cys Arg Ser Ser Ser Pro Tyr Val Ser Asn Ala
             50                  55                  60
Val Gln Arg Asp Ala Pro Leu Glu Tyr Asp Phe Ser Ser Gln Lys Leu
 65                  70                  75                  80
Gln His Leu Glu His Val Met Glu Asn Tyr Thr Gln Trp Leu Gln Lys
                 85                  90                  95
Leu Glu Asn Tyr Ile Val Glu Asn Met Lys Ser Glu Met Ala Gln Ile
                100                 105                 110
Gln Gln Asn Ala Val Gln Asn His Thr Ala Thr Met Leu Glu Ile Gly
            115                 120                 125
Thr Ser Leu Leu Ser Gln Thr Ala Glu Gln Thr Arg Lys Leu Thr Asp
            130                 135                 140
Val Glu Thr Gln Val Leu Asn Gln Thr Ser Arg Leu Glu Ile Gln Leu
145                 150                 155                 160
Leu Glu Asn Ser Leu Ser Thr Tyr Lys Leu Glu Lys Gln Leu Leu Gln
                165                 170                 175
Gln Thr Asn Glu Ile Leu Lys Ile His Glu Lys Asn Ser Leu Leu Glu
            180                 185                 190
His Lys Ile Leu Glu Met Glu Gly Lys His Lys Glu Glu Leu Asp Thr
            195                 200                 205
Leu Lys Glu Glu Lys Glu Asn Leu Gln Gly Leu Val Thr Arg Gln Thr
210                 215                 220
Tyr Ile Ile Gln Glu Leu Glu Lys Gln Leu Asn Arg Ala Thr Thr Asn
225                 230                 235                 240
Asn Ser Val Leu Gln Lys Gln Leu Glu Leu Met Asp Thr Val His
            245                 250                 255
Asn Leu Val Asn Leu Cys Thr Lys Glu Gly Val Leu Leu Lys Gly Gly
            260                 265                 270
Lys Arg Glu Glu Glu Lys Pro Phe Arg Asp Cys Ala Asp Val Tyr Gln
            275                 280                 285
Ala Gly Phe Asn Lys Ser Gly Ile Tyr Thr Ile Tyr Ile Asn Asn Met
            290                 295                 300
Pro Glu Pro Lys Lys Val Phe Cys Asn Met Asp Val Asn Gly Gly Gly
305                 310                 315                 320
Trp Thr Val Ile Gln His Arg Glu Asp Gly Ser Leu Asp Phe Gln Arg
                325                 330                 335
Gly Trp Lys Glu Tyr Lys Met Gly Phe Gly Asn Pro Ser Gly Glu Tyr
                340                 345                 350
Trp Leu Gly Asn Glu Phe Ile Phe Ala Ile Thr Ser Gln Arg Gln Tyr
            355                 360                 365
Met Leu Arg Ile Glu Leu Met Asp Trp Glu Gly Asn Arg Ala Tyr Ser
            370                 375                 380
Gln Tyr Asp Arg Phe His Ile Gly Asn Glu Lys Gln Asn Tyr Arg Leu
385                 390                 395                 400
Tyr Leu Lys Gly His Thr Gly Thr Ala Gly Lys Gln Ser Ser Leu Ile
                405                 410                 415
Leu His Gly Ala Asp Phe Ser Thr Lys Asp Ala Asp Asn Asp Asn Cys
            420                 425                 430
Met Cys Lys Cys Ala Leu Met Leu Thr Gly Gly Trp Trp Phe Asp Ala
            435                 440                 445
Cys Gly Pro Ser Asn Leu Asn Gly Met Phe Tyr Thr Ala Gly Gln Asn
450                 455                 460
```

-continued

```
His Gly Lys Leu Asn Gly Ile Lys Trp His Tyr Phe Lys Gly Pro Ser
465                 470                 475                 480

Tyr Ser Leu Arg Ser Thr Thr Met Met Ile Arg Pro Leu Asp Phe
                485                 490                 495
```

(2) INFORMATION FOR SEQ ID NO:27:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: hTL4atg
        (B) LOCATION: 1...47
        (D) OTHER INFORMATION: PCR primer
        (A) NAME/KEY: Other
        (B) LOCATION: 1...20
        (D) OTHER INFORMATION: "tail" sequences added to
            PCR primer to facilitate cloning
            of the amplified PCR fragments (xi) SEQUENCE DESCRIPTION: SEQ ID NO:27:

```
GCATGCTATC TCGAGCCACC ATGCTCTCCC AGCTAGCCAT GCTGCAG                47
```

(2) INFORMATION FOR SEQ ID NO:28:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: hTL4not
        (B) LOCATION: 1...55
        (D) OTHER INFORMATION: PCR Primer
        (A) NAME/KEY: Other
        (B) LOCATION: 1...28
        (D) OTHER INFORMATION: "tail" sequence added to the
            PCR primers to facilitate cloning
            of the amplified PCR fragments (xi) SEQUENCE DESCRIPTION: SEQ ID NO:28:

```
GTGTCGACGC GGCCGCTCTA GATCAGACTT AGATGTCCAA AGGCCGTATC ATCAT        55
```